United States Patent
Geigle et al.

(10) Patent No.: US 11,731,945 B2
(45) Date of Patent: Aug. 22, 2023

(54) REDOX-ACTIVE COMPOUNDS AND USES THEREOF

(71) Applicant: CMBLU PROJEKT AG, Alzenau (DE)

(72) Inventors: Peter Geigle, Alzenau (DE); Jan Hartwig, Alzenau (DE); Evgeny Larionov, Hanau (DE); Eduard Baal, Offenbach (DE)

(73) Assignee: CMBLU Energy AG, Alzenau (DE)

( * ) Notice: Subject to any disclaimer, the term of this patent is extended or adjusted under 35 U.S.C. 154(b) by 0 days.

(21) Appl. No.: 17/267,923

(22) PCT Filed: Aug. 14, 2019

(86) PCT No.: PCT/EP2019/071887
§ 371 (c)(1),
(2) Date: Feb. 11, 2021

(87) PCT Pub. No.: WO2020/035548
PCT Pub. Date: Feb. 20, 2020

(65) Prior Publication Data
US 2021/0253540 A1    Aug. 19, 2021

(30) Foreign Application Priority Data

Aug. 14, 2018 (WO) ................. PCT/EP2018/072075

(51) Int. Cl.
*C07D 241/46* (2006.01)
*H01M 8/18* (2006.01)

(52) U.S. Cl.
CPC ............ *C07D 241/46* (2013.01); *H01M 8/18* (2013.01)

(58) Field of Classification Search
CPC .................................................. C07D 241/46
See application file for complete search history.

(56) References Cited

U.S. PATENT DOCUMENTS

| | | | | | |
|---|---|---|---|---|---|
| 2,667,486 | A  * | 1/1954 | Cain | ................... | C07D 475/08 544/260 |
| 2017/0062842 | A1* | 3/2017 | Huang | ................. | C07D 241/46 |
| 2018/0006336 | A1* | 1/2018 | Odom | ............... | H01M 10/4235 |
| 2018/0085744 | A1* | 3/2018 | Helms | ..................... | C08J 5/2256 |
| 2018/0366757 | A1* | 12/2018 | Wei | ...................... | C07D 241/46 |
| 2023/0095542 | A1* | 3/2023 | Geigle | .................... | H01M 8/18 429/108 |
| 2023/0097730 | A1* | 3/2023 | Geigle | ................. | H01M 50/46 429/105 |

FOREIGN PATENT DOCUMENTS

| | | |
|---|---|---|
| CN | 106518792 | 3/2017 |
| EP | 2078720 | 7/2009 |
| JP | 2016122519 | 7/2016 |
| KR | 20180079881 | 7/2018 |
| WO | WO1997029237 | 8/1997 |
| WO | WO2011045561 | 4/2011 |
| WO | WO2016144909 | 9/2016 |
| WO | WO-2016144909 A1 * | 9/2016 .......... H01M 8/0289 |

OTHER PUBLICATIONS

J. Winsberg et al., 1 ACS Energy Letters, 976-980 (2016) (Year: 2016).*
A. Hollas et al., Nature Energy (2018) (Year: 2018).*
K Wedge et al., Scientific Reports (2016) (Year: 2016).*
K. Lin et al., Nature Energy (2016) (Year: 2016).*
Auri A. Linden et al: "Preparation and Redox Properties ofN , N , N-1,3,5-Trialkylated Flavin Derivatives and Their Activity as Redox Catalysts", Chemistry—A European Journal, vol. 11, No. 1, Jan. 1, 2005 (Jan. 1, 2005), pp. 112-119, XP055663930.
Cees G. Van Schagen et al: "A Comparative 13 C-NMR. Study on Various Reduced Flavins", Helvetica Chimica Acta, vol. 63, No. 8, Dec. 10, 1980 (Dec. 10, 1980), pp. 2187-2201, XP055663954.
Guirado Antonio et al: "First synthesis and biological evaluation of 4-amino-2-aryl-6,9-dichlorobenzo[g]pteridi nes as inhibitors of TNF-[alpha] and", European Journal of Medicinal Chemistry, Elsevier, Amsterdam, NL, vol. 66, May 24, 2013 (May 24, 2013), pp. 269-275, XP028685915.
Hong, J. et al.; "Neutral Red and Ferroin as Reversible and Rapid RedoxMaterials for Redoy Flow Batteries", Chemsuschem, May 2, 2018, oages 1866-1872, XP002790901.
Hugo Cerecetto et al.: "Anti-T. cruzi Agents: Our Experience in the Evaluation of More than Five Hundred Compounds", Mini Reviews in Medicinal Chemistry, vol. 8, No. 13, Nov. 1, 2008 (Nov. 1, 2008), pp. 1355-1383, XP055663948.
Kaixiang Lin et al: "A redox-flow battery with an alloxazine-based organic electrolyte", Nature Energy, vol. 1, No. 9, Sep. 1, 2016 (Sep. 1, 2016), XP055599338.
Lee, M. et al.; "Multi-electron redox phenazine for ready-tochargeorganic batteries", Green Chemistry, vol. 19, May 8, 2017, pp. 2980-2985, XP002790900.
Michael H. Palmer et al: "The electronic structure of flavin derivatives", Journal of Molecular Structure., vol. 66, Sep. 1, 1980 (Sep. 1, 1980), pp. 243-263, XP055663939.
Schutsyer, W. et al., "Chemicals from lignin: an interplay of lignocellulose fractionation, depolymerisation, and upgrading", Chemical Society Reviews, vol. 47, No. 3, Jan. 1, 2018, pp. 852-908, XP055664139.
Takuya Sakai et al: "Comparison of riboflavin-derived flavinium salts applied to catalytic H 2 0 2 oxidations", Organic & Biomolecular Chemistry, vol. 16, No. 21, Jan. 1, 2018 (Jan. 1, 2018), pp. 3999-4007, XP055663937.
Thomas J. Bardos et al: "Synthesis of Deoxyalloxazines (Benzopteridines) I", Journal of the American Chemical Society, vol. 79, No. 17, Sep. 1, 1957 (Sep. 1, 1957), pp. 4704-4708, XP05566395.

(Continued)

*Primary Examiner* — Alexander R Pagano
(74) *Attorney, Agent, or Firm* — McDonnell Boehnen Hulbert & Berghoff LLP

(57) ABSTRACT

The present invention relates to novel lignin-derived compounds and compositions comprising the same and their use as redox flow battery electrolytes. The invention further provides a method for preparing said compounds and compositions as well as a redox flow battery comprising said compounds and compositions. Additionally, an assembly for carrying out the inventive method is provided.

24 Claims, 5 Drawing Sheets

(56) References Cited

OTHER PUBLICATIONS

Ueda T et al: "Reaction of lumichrome or 2-thiolumichrome with alkylamines", Journal of Heterocyclic Chemistry, Wiley-Blackwell Publishing, Inc, US, vol. 28, Jan. 1, 1991 (Jan. 1, 1991), pp. 1485-1490, XP002330036.
Winsberg, Jan et al.; "TEMPO/Phenazine Combi-Molecule: A Redox-Active Material for Symmetric Aqueous Redox-Flow Batteries", ACS Energy Letters, vol. 1, No. 5, Oct. 17, 2016, pp. 976-980, XP055561791.
Yeh, M C et al., "Synthesis of polyphilic hexaazatrinaphthylenes and mesomorphic properties", Tetrahedron, Elsevier Science Publishers, Amsterdam, NL, vol. 66, No. 46, Nov. 13, 2010, pp. 8888-8892; XP027427563.
Yu Ding et al: "Molecular engineering of organic electroactive materials for redox flow batteries", Chemical Society Reviews, vol. 47, No. 1, Jan. 1, 2018 (Jan. 1, 2018), pp. 69-103, XP055663903.
Zakzeski Joseph et al., "The Catalytic Valorization of Lignin for the Production of Renewable Chemicals", Chemical Reviews, vol. 110, No. 6, Jun. 9, 2010, pp. 3552-3599, XP055075650.
International Search Report for International application No. PCT/EP2019/071887 dated Feb. 18, 2020.
Written Opinion for International application No. PCT/EP2019/071887 dated Feb. 18, 2020.

\* cited by examiner

REDOX-ACTIVE COMPOUNDS AND USES THEREOF

This application is the U.S. National Stage Application of International Application No.: PCT/EP2019/071887, filed Aug. 14, 2019, which is a continuation of International Application No.: PCT/EP2018/072075, filed Aug. 14, 2018, the disclosures of each of which are explicitly incorporated by reference herein in their entirety.

In recent years, concerns resulting from environmental consequences of exploiting fossil fuels as the main energy sources have led to an increasing prominence of renewable-energy systems (e.g., solar- and wind-based systems). The intermittent nature of such renewable energy sources however makes it difficult to fully integrate these energy sources into electrical power grids and distribution networks. A solution to this problem are large-scale electrical energy storage (EES) systems, which are also vital for the smart grid and distributed power generation development. Another important application of EES is electrification of on-ground transportation, as the replacement of traditional combustion engines with hybrid, plug-in hybrid, and pure electric vehicles (EVs) allows for reduction of carbon emissions and fuel savings (Soloveichik G. L. Chem. Rev. 2015, 115, 11533-11558).

The U.S. Department of Energy has identified four major challenges to the widespread implementation of EES: cost, reliability and safety, equitable regulatory environments, and industry acceptance. The development of novel EES technologies capable of resolving these challenges is critical (Soloveichik G. L. Chem. Rev. 2015, 115, 11533-11558). Redox-flow batteries (RFBs)—first developed by NASA during the energy crisis of the 1970's and currently entering a period of renaissance—are among the most promising scalable EES technologies. RFBs are electrochemical systems that can repeatedly store and convert electrical energy to chemical energy and vice versa when needed. Redox reactions are employed to store energy in the form of a chemical potential in liquid electrolyte solutions which flow through a battery of electrochemical cells during charge and discharge. The stored electrochemical energy can be converted to electrical energy upon discharge with concomitant reversal of the opposite redox reactions.

RFBs usually include a positive electrode (cathode) and a negative electrode (anode) in separated cells and separated by an ion-exchange membrane, and two circulating electrolyte solutions, positive and negative electrolyte flow streams, generally referred to as the "catholyte" and "anolyte", respectively. Energy conversion between electrical energy and chemical potential occurs instantly at the electrodes, once the electrolyte solutions begin to flow through the cell. During discharge, electrons are released via an oxidation reaction from a high chemical potential state on the anode of the battery and subsequently move through an external circuit. Finally, the electrons are accepted via a reduction reaction at a lower chemical potential state on the cathode of the battery. Redox-flow batteries can be recharged by inversing the flow of the redox fluids and applying current to the electrochemical reactor.

The capacity and energy of redox flow batteries is determined by the total amount of redox active species for a set system available in the volume of electrolyte solution, whereas their current (power) depends on the number of atoms or molecules of the active chemical species that are reacted within the redox flow battery cell as a function of time. Redox-flow batteries thus have the advantage that their capacity (energy) and their current the (power) can be readily separated, and therefore readily up-scaled. Thus, capacity (energy) can be increased by increasing the number or size of the electrolyte tanks whereas the current (power) is controlled by controlling the number and size of the current collectors. Since energy and power of RFB systems are independent variables, RFBs are inherently well suitable for large applications, since they scale-up in a more cost-effective manner than other batteries. Moreover, RFBs provide a unique design flexibility as the required capacities for any application can be provided using tailor-made energy and power modules.

A well-established example of an RFB is the vanadium redox flow battery, which contains redox couples exclusively based on vanadium cations. Nevertheless, there is also a wide range of less commonly used inorganic flow cell chemistries, including the polysulfide-bromide battery (PSB). The wide-scale utilization of RFBs using inorganic redox materials is presently still limited by availability and costs of the redox materials. That holds even more so, whenever the redox materials are based on redox-active transition metals such as vanadium, and/or require precious-metal electrocatalysts. Toxicity (and associated health and environmental risks) of inorganic redox materials (such as vanadium salts or bromine) further limits applicability of inorganic RFBs for energy storage. That holds in particular when applying distributed, modular energy generation technologies that use (intermittent) "green power", such as wind, photovoltaic, or hydroelectric power. Also, the incorporated materials may constitute overheating, fire or explosion risks.

In view of the disadvantages of RFBs based on inorganic redox species, RFBs were envisaged with different organic compounds. Novel organic redox active species for large-scale use in redox flow batteries should preferably be inexpensive, with high solubility and redox potential, and exhibit fast electrode kinetics. In early 2014, Huskinson et al. developed a metal-free flow battery based on 9,10-anthraquinone-2,7-disulphonic acid (AQDS) (Huskinson et al. Nature 2014, 505, 195-198 and WO 2014/052682 A2). Yang et al. reported on an organic redox flow battery with 1,2-benzoquinone-3,5-disulfonic acid (BQDS) as the catholyte, while AQDS or anthraquinone-2-sulfonic acid (AQS) was used as the anolyte (Yang et al. J. Electrochem. Soc. 2014, 161, A1371-A1380). However, sheer volume of needed energy storage demands millions of tons of active materials. To date, only a smaller number of organic chemicals are produced worldwide at such a scale (e.g., methanol, acetic acid, and phenol). Based on scale and availability, the "ideal" redox flow battery for large-scale deployment should be aqueous and use highly soluble multi-electron (i.e. highly energy dense) redox active species that are readily available and inexpensive as electrolytes. Derivatized anthra- and benzoquinones suggested as electrolytes by Huskinson et al. and Yang et al. are commercially available; however, costly and elaborate manufacture of any of them severely limits their broad-range, large-scale employment.

In summary, despite recent advantages in the development of rechargeable batteries, a long-felt need exists for safe, inexpensive, easy-to-use, reliable and efficient technologies for energy storage that enables diversification of energy supply and optimization of the energy grid, including increased penetration and utilization of renewable energies. By to their unique ability to decouple power and capacity functions, redox flow batteries are at least in principle well suitable for large scale energy storage applications. However, development efforts have not yet achieved large-scale employment of RFBs.

Moreover, existing redox flow batteries suffer from the reliance on battery chemistries that result in high costs of active materials and system engineering, low cell and system performance (e.g. round trip energy efficiency), poor cycle life and toxicity. Thus, there remains a need for novel electroactive redox materials, which are readily available at low cost and exhibit reduced toxicity. Preferably, such electrolytes further provide for a high energy density, a high operating potential, increased cell output voltage and extended lifetime. Accordingly, there is a need in the art for improved redox flow battery chemistries and systems.

It is the object of the present invention to comply with the above needs.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments, should not be construed to limit the present invention to only explicitly described embodiments. This present description should be understood to support and encompass embodiments, which combine the explicitly described embodiments, with any number of the disclosed and/or preferred features. Furthermore, any permutations and combinations of all described features in this application shall be considered supported by the description of the present application, unless it is understood otherwise.

Throughout this specification and the claims which follow, unless the context requires otherwise, the term "comprise", and variations such as "comnprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Unless denoted otherwise,

The term "alkyl" refers to the radical of saturated hydrocarbon groups, including linear (i.e. straight-chain) alkyl groups, branched-chain alkyl groups, cyclo-alkyl (alicyclic) groups, alkyl-substituted cyclo-alkyl groups, and cyclo-alkyl-substituted alkyl groups.

Preferably, an alkyl group contains less than 30 carbon atoms, more preferably from 1 to 10 carbon atoms ("$C_{1-10}$alkyl"), from 1 to 9 carbon atoms ("$C_{1-9}$alkyl"), from 1 to 8 carbon atoms ("$C_{1-8}$alkyl"), from 1 to 7 carbon atoms ("$C_{1-7}$ alkyl"), or from 1 to 6 carbon atoms ("$C_{1-6}$alkyl"). In some embodiments, an alkyl group has 1 to 5 carbon atoms ("$C_{1-5}$ alkyl"). In some embodiments, an alkyl group may contain 1 to 4 carbon atoms ("$C_{1-4}$ alkyl"), from 1 to 3 carbon atoms ("$C_{1-3}$ alkyl"), or from 1 to 2 carbon atoms ("$C_{1-2}$ alkyl").

Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like.

Unless otherwise specified, each instance of an alkyl group is independently unsubstituted (an "unsubstituted alkyl") or substituted (a "substituted alkyl") with one or more substituents (e.g., halogen, such as F).

In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. Compounds described herein contemplates any and all such combinations in order to arrive at a stable compound. Heteroatoms such as nitrogen may have hydrogen substituents and/or any suitable substituent as described herein which satisfy the valencies of the heteroatoms and results in the formation of a stable moiety. Compounds described herein are not intended to be limited in any manner by the exemplary substituents described herein.

In certain embodiments, the alkyl group is an unsubstituted $C_{1-10}$ alkyl (such as unsubstituted $C_{1-6}$alkyl, e.g., —$CH_3$(Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tent-butyl (tent-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$alkyl, e.g., —$CF_3$, Bn).

Exemplary substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety, or a $G^a$ group as defined herein.

Substituents may themselves be substituted. For instance, the substituents of a "substituted alkyl" may include both substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls may be further substituted with alkyls, alkenyls, alkoxys, alkylthios, aminoalkyls, carbonyl-substituted alkyls, —$CF_3$, —CN, and the like.

The term "haloalkyl" refers a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group as defined herein, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent hydrocarbon chain. Unless otherwise specified, each instance of a heteroalkyl group is independently unsubstituted (an "unsubstituted heteroalkyl") or substituted (a "substituted heteroalkyl") with one or more substituents as defined herein.

The term "carbocyclyl" or "carbocyclic" refers to a radical of a non-aromatic cyclic hydrocarbon group having preferably from 3 to 14 ring carbon atoms ("$C_{3-14}$ carbocyclyl") and zero heteroatoms in the non-aromatic ring system. Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents as defined herein.

The term "heterocyclyl" or "heterocyclic" refers to a radical of a preferably 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment may be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and may be saturated or may contain one or more carbon-carbon double or triple bonds. Heterocyclyl polycyclic ring systems may include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents as defined herein.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) preferably having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as defined herein.

The term "heteroaryl" refers to a radical of a preferably 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment may be a carbon or nitrogen atom, as valency permits. Heteroaryl polycyclic ring systems may include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

A group is optionally substituted unless expressly provided otherwise. The term "optionally substituted" refers to a group which may be substituted or unsubstituted as defined herein.

The term "aliphatic group" refers to a straight-chain, branched-chain, or cyclic non-aromatic saturated or unsaturated hydrocarbon group and includes as alkyl groups, alkenyl groups, and alkynyl groups.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to group of formula —OR, wherein R is an alkyl group, as defined herein. Exemplary alkoxyl groups include methoxy, ethoxy, propyloxy, tert-butoxy and the like.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" refers to a group which contains a carbon atom connected with a double bond to an oxygen or a sulfur atom. Examples of moieties which contain a carbonyl include aldehydes, ketones, carboxylic acids, amides, esters, anhydrides, etc.

The term "ester" refers to groups or molecules which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "carbonyl" includes groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups are also included as well as other combinations of carbonyl groups bound to heteroatoms (e.g., nitrogen, oxygen, sulfur, etc. as well as carbon atoms), such as thiocarbonyl, thiocarboxylic acid and thiolformate. Furthermore, the heteroatom can be further substituted with one or more alkyl, alkenyl, alkynyl, aryl, aralkyl, acyl, etc. moieties.

The term "ether" refers to groups or molecules which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" refers to groups or molecules which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "amine" or "amino" includes compounds where a nitrogen atom is covalently bonded to at least one carbon atom or heteroatom. The term "alkyl amino" includes groups and compounds where the nitrogen is bound to at least one additional alkyl group. The term "dialkyl amino" includes groups where the nitrogen atom is bound to at least two additional alkyl groups. The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amine" or "amino" in particular refers to a —NH$_2$ group, preferably including any of its protonation states, such as —NH$_3$+.

The term "amide" or "aminocarboxy" includes compounds or moieties which contain a nitrogen atom which is bound to the carbon atom of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "nitro" refers to a —NO$_2$ group.

The term "halo" or "halogen" refers to fluorine (fluoro, —F), chlorine (chloro, —Cl), bromine (bromo, —Br), or iodine (iodo, —I) groups.

The term "thiol" or "sulfhydryl" refers to a —SH group.

The term "hydroxyl" refers to a —OH group, preferably including all of its protonation states, such as —O$^+$.

The term "sulfonyl" refers to a —SO$_3$H group, preferably including all of its protonation states, such as -SO$_3^-$.

The term "phosphoryl" refers to a —PO$_3$H$_2$ group, preferably including all of its protonation states, such as —PO$_3$H$^-$ and —PO$_3^{2-}$.

The term "phosphonyl" refers to a —PO$_3$R$_2$ group, wherein each R is H or alkyl, provided at least one R is alkyl, as defined herein, preferably including all of its protonation states, such as —PO$_3$R$^-$.

The term "oxo" refers to a =O group.

The term "carboxyl" refers to a —COOH group, preferably including all of its protonation states, such as —COO$^-$.

The term "oxy" refers to a —O group.

The term "quinone" refers to a class of cyclic organic compounds that include fully conjugated —C(=O)— groups and carbon-carbon double bonds. In one example, the term "quinone" refers to organic compounds that are formally derived from aromatic compounds by replacement of an even number of —CH= groups with —C(=O)— groups with the double bonds rearranged as necessary to provide a fully conjugated cyclic dione, tetra-one, or hexa-one structure. The term inter alia covers substituted and unsubstituted quinones derived from mono-, di- and trihydroaromatic systems comprising 1 to 3 fused carbon cyclic rings in both their oxidized ("quinone") and reduced ("hydroquinone") forms.

The term "conjugated" when referring to two functional groups (having a double bond) means that the two groups are part of a connected system of p-orbital delocalized electrons with alternating single and multiple bonds. The two groups also include a degree of unsaturation. For example, conjugated groups may include multiple double bonds or aromatic groups (e.g., phenyl) between the groups. Moreover, if the two groups adjacent, the groups are also conjugated.

The term "standard electrode potential" means the electrical potential (i.e., the voltage developed) of a reversible electrode at standard state in which solutes are at an effective concentration of 1 mol/liter, the activity for each pure solid, pure liquid, or for water (solvent) is 1, the pressure of each gaseous reagent is 1 atm., and the temperature is 25° C. Standard electrode potentials are reduction potentials.

The present invention provides novel compounds, compositions comprising the same and their unprecedented use in various applications, inter alia as redox active species in redox flow batteries. Means and methods for preparing said compounds and compositions are also provided. The inventive compounds may advantageously be obtained from lignin, crude oil, coal or pure organic substances. In particular, lignin derivatives produced as waste or by-products of the pulping industry have previously largely been unexploited and can be valorized by the methods of the present invention.

The inventive compounds are preferably low molecular weight aromatic compounds obtained by (1) providing a starting material, preferably selected from lignocellulosic material, crude oil, coal or pure organic substances; (2) isolating modified lignin-derived components from said starting material; (3) chemically decomposing said modified lignin-derived components to obtain decomposition products comprising or consisting of precursor compounds; (4) providing said precursor compounds; (5) subjecting said precursor compounds to a condensation reaction, thereby obtaining condensation products characterized by General Formula (1)-(6) herein; (6) modifying said condensation products by introducing one or more substituents of interest; thereby obtaining a compound or a composition according to the present invention.

Step (6) of the inventive method may advantageously serve to introduce substituents into the condensation products which act as functional groups capable of increasing the solubility and/or the electrochemical properties of the resulting compounds or compositions according to the present invention.

The inventive compounds and compositions may be used various applications, inter alia as electrolytes for redox flow battery applications.

Advantageously, the present invention inter alia allows the valorization of lignocellulosic material, which is currently discarded as waste material of the pulping industry. According to the present invention, useful compounds and compositions may be obtained from lignin by using byproducts of the pulping process as starting material for the subsequent generation of useful compounds and compositions comprising the same. That approach preferably has the advantage of reducing energy consumption and employing renewable resources. The inventive method may advantageously be employed to provide, ideally within an integrated plant, the inventive compounds and compositions.

These compounds and compositions may advantageously be used as redox active compounds in redox flow batteries, which were previously (economically) amenable by non-renewable sources only, or can be employed in various other applications.

Furthermore, the inventors further discovered that compositions comprising or (essentially) consisting of mixtures of a plurality of at least 2 of the inventive compounds exhibit favourable electrochemical properties and are useful, e.g., as redox flow battery electrolytes as well. Advantageously, the present invention thus provides compositions which are directly obtainable from lignin (or crude oil, coal, pure organic substances) processing as "ready-to-use" products, and in particular as electrolytes (or slurry, solids) in redox flow batteries. The invention thus surprisingly opens up unprecedented possibilities to obtain effective redox flow battery electrolytes at large scale and low cost by exploiting mass by-products of the pulping industry (or other feedstock materials).

Accordingly, in a first aspect, the present invention relates to novel compounds and compositions. In a further aspect, the invention provides methods for preparing said compounds and compositions. Said methods preferably comprise the general method steps (1)-(6) as indicated above. In a particular aspect, the present invention features a method for preparing the inventive compounds and compositions from lignin.

Redox Active Compounds and Compositions

The inventive method provides novel compounds and compositions. Said compounds and compositions are preferably redox active. Preferably, the term "redox active" refers to the capability of a compound (or a composition comprising the same) to participate in a redox reaction. Such "redox active" compounds typically have energetically accessible levels that allow redox reactions to alter their charge state, whereby electrons are either removed (oxidation-yielding an oxidized form of the compound) from atoms of the compound being oxidized or transferred to the compound being reduced (reduction-yielding a reduced from of the compound). A "redox active" compound may thus be understood as a chemical compound, which may form a pair of an oxidizing and a reducing agent, i.e. a redox pair.

The inventive method preferably provides redox active compounds and compositions, which may preferably be derived from lignin or other sources such as crude oil, coal or pure organic substances, and which are particularly envisaged as redox flow battery electrolytes. The inventive compounds and compositions may also referred to as "target compounds" or "target compositions" herein. The compounds and compositions of the invention may preferably be obtained from lignin (or alternatively from crude oil, coal or pure organic substances) by using the methods disclosed herein. Preferred, optionally lignin-derived, compounds in accordance with the invention include substituted low molecular weight organic, preferably aromatic, compounds, in particular phenazines, N-substituted phenazines, alloxazines, N-substituted alloxazines, benzopteridines, and N-substituted benzopteridines and derivatives thereof.

In the following, the term "low molecular weight" may be abbreviated as "lmw".

Compounds

In a first aspect, the present invention provides compounds characterized by any one of General Formulas (1)-(6):

General Formula (1):

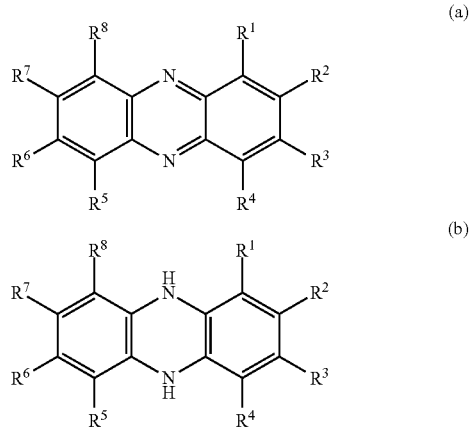

General Formula (2):

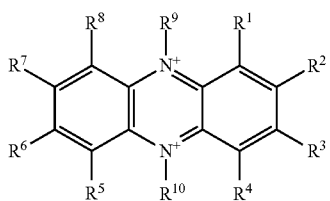
(a)

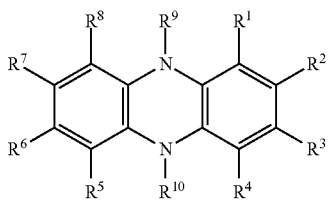
(b)

General Formula (3):

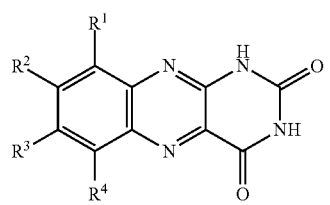
(a)

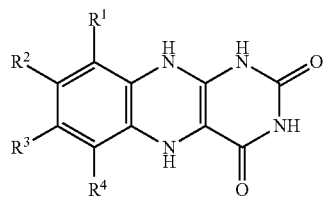
(b)

General Formula (4):

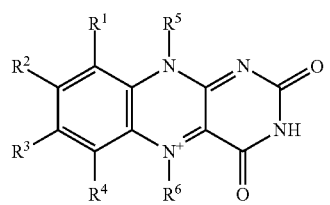
(a)

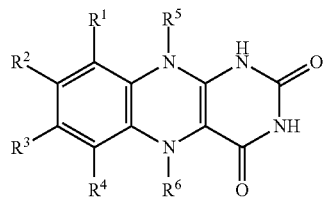
(b)

General Formula (5):

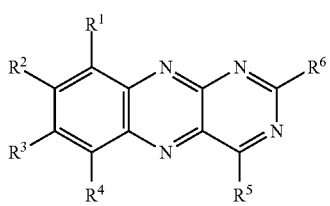
(a)

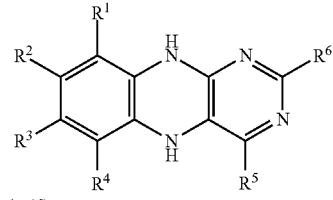
(b)

General Formula (6):

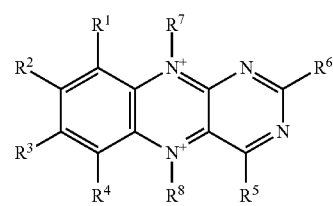
(a)

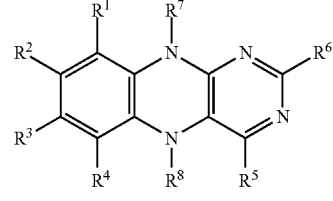
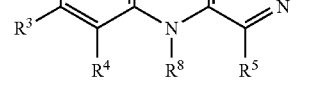
(b)

wherein,
each $R^1$-$R^8$ in General Formula (1),
each $R^1$-$R^{10}$ in General Formula (2),
each $R^1$-$R^4$ in General Formula (3),
each $R^1$-$R^6$ in General Formula (4),
each $R^1$-$R^6$ in General Formula (5), and
each $R^1$-$R^8$ in General Formula (6)
is independently selected from —H, -Alkyl, -AlkylG$^a$, -Aryl, —SO$_3$H, —SO$_3^-$, —PO$_3$H$_2$, —OH, —OG$^a$, —SH, -Amine, —NH$_2$, —CHO, —COOH, —COOG$^a$, —CN, —CONH$_2$, —CONHG$^a$, —CONG$^a{}_2$, -Heteroaryl, -Heterocycyl, NOG$^a$, —N$^+$OG$^a$, —F, —Cl, and —Br, or are joined together to form a saturated or unsaturated carbocycle;
wherein each G$^a$ is independently selected from —H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3{}^+$, —NHG$^b$, —NG$^b{}_2$, —NG$^b{}_3{}^+$, —CHO, —COOH, —COOAlkyl, —CN, —CONH$_2$, —CONHAlkyl, —CONAlkyl$_2$, -Heteroaryl, Heterocycyl, —NOG$^b$, —N$^+$OAlkyl, —F, —Cl, and —Br;
wherein each G$^b$ is independently selected from —H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3{}^+$, —CHO, —COOH, —COOAlkyl, —CN, —CONH$_2$, —CONHAlkyl, —CONAlkyl$_2$, -Heteroaryl, Heterocycyl, —N$^+$OAlkyl, —F, —Cl, and Br.

Preferably,
each $R^1$-$R^8$ in General Formula (1),
each $R^1$-$R^{10}$ in General Formula (2),
each $R^1$-$R^4$ in General Formula (3),
each $R^1$-$R^6$ in General Formula (4),
each $R^1$-$R^6$ in General Formula (5), and
each $R^1$-$R^8$ in General Formula (6)
may be independently selected from —H, -Alkyl, -AlkylG$^a$, —SO$_3$H, —SO$_3^-$, —OG$^a$, and —COOH, wherein each $G^a$ is independently selected from
—H, -Alkyl, -AlkylG$^a$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b{}_2$, —NG$^b{}_3{}^+$, —CHO, —COOH, —COOAlkyl, —CN, —CONH$_2$, —CONHAlkyl, —CONAlkyl$_2$, -Heteroaryl, Heterocycyl, —NOG$^b$, —N$^+$OAlkyl, —F, —Cl, and —Br;
wherein each $G^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, Heterocycyl, —N$^+$OAlkyl, —F, —Cl, and —Br.

Alternatively,
"alkyl" is selected from linear, branched or cyclic —$C_nH_{2n-o}$ and —$C_nH_{2n-o-m}G^a{}_m$;
"aryl" is selected from —$C_6H_5$, —$C_{10}H_7$, $C_{13}H_8$, $C_{14}H_9$, —$C_6H_{5-m}G^a{}_m$, —$C_{10}H_{7-m}G^a{}_m$, $C_{13}H_{8-m}G^a{}_m$, $C_{14}H_{9-m}G^a{}_m$;
"heteroaryl" is selected from —$C_{5-p}N_pH_{5-p-q}G^a{}_q$, —$C_{6-p}N_pH_{5-p-q}G^a{}_q$, —$C_{7-p}N_pH_{7-p-q}G^a{}_q$, —$C_{8-p}N_pH_{6-p-q}G^a{}_q$, —$C_{9-p}N_pH_{7-p}$-$G^a{}_q$, —$C_{10-p}N_pH_{7-p-q}G^a{}_q$, —$C_4OH_{3-q}G^a{}_q$, —$C_6OH_{5-q}G^a{}_q$, —$C_7OH_{4-q}G^a{}_q$, —$C_6O_2H_{3-q}G^a{}_q$, —$C_8OH_{5-q}G^a{}_q$, —$C_4SH_{3-q}G^a{}_q$, —$C_6SH_{5-q}G^a{}_q$, —$C_7SH_{4-q}G^a{}_q$, —$C_6S_2H_{3-q}G^a{}_q$, —$C_8SH_{5-q}G^a{}_q$, —$C_3ON_pH_{3-p-q}G^a{}_q$, —$C_6ON_pH_{5-p-q}G^a{}_q$, —$C_7ON_pH_{4-p-q}G^a{}_q$, —$C_6O_2N_pH_{3-p-q}G^a{}_q$, —$C_8ON_pH_{5-p-q}G^a{}_q$, —$C_3SN_pH_{3-p-q}G^a{}_q$, —$C_6SN_pH_{5-p-q}G^a{}_q$, —$C_7SN_pH_{4-p-q}G^a{}_q$, —$C_6S_2N_pH_{3-p-q}G^a{}_q$, —$C_6OSN_pH_{3-p-q}G^a{}_q$, —$C_8SN_pH_{5-p-q}G^a{}_q$, —$C_{5-p}N_p{}^+H_{6-p-q}G^a{}_q$, —$C_{6-p}N_p{}^+H_{6-p-q}G^a{}_q$, —$C_{7-p}N_p{}^+H_{8-p-q}G^a{}_q$, —$C_{8-p}N_p{}^+H_{7-p-q}G^a{}_q$, —$C_{9-p}N_p{}^+H_{8-p-q}G^a{}_q$, —$C_{10-p}N_p{}^+H_{8-p-q}G^a{}_q$, —$C_3ON_p{}^+H_{4-p-q}G^a{}_q$, —$C_6ON_p{}^+H_{6-p-q}G^a{}_q$, —$C_7ON_p{}^+H_{5-p-q}G^a{}_q$, —$C_6O_2N_p{}^+H_{4-p-q}G^a{}_q$, —$C_8ON_p{}^+H_{6-p-q}G^a{}_q$, —$C_3SN_p{}^+H_{6-p-q}G^a{}_q$, —$C_6SN_p{}^+H_{6-p-q}G^a{}_q$, —$C_7SN_p{}^+H_{5-p-q}G^a{}_q$, —$C_6S_2N_p{}^+H_{4-p-q}G^a{}_q$, —$C_6OSN_p{}^+H_{4-p-q}G^a{}_q$, —$C_8SN_p{}^+H_{6-p-q}G^a{}_q$,
"heterocyclyl" is selected from —$C_{5-p}N_pH_{8-o-p-q}G^a{}_q$, —$C_{6-p}N_pH_{10-o-p-q}G^a{}_q$, —$C_{7-p}N_pH_{12-o-p-q}G^a{}_q$, —$C_{8-p}N_pH_{14-o-p-q}G^a{}_q$, —$C_{9-p}N_pH_{16-o-p-q}G^a{}_q$, —$C_{10-p}N_pH_{18-o-p-q}G^a{}_q$, —$C_{5-p}O_pH_{8-o-2p-q}G^a{}_q$, —$C_{6-p}O_pH_{10-o-2p-q}G^a{}_q$, —$C_{7-p}O_pH_{12-o-2p-q}G^a{}_q$, —$C_{8-p}O_pH_{14-o-2p-q}G^a{}_q$, —$C_{9-p}O_pH_{16-o-2p-q}G^a{}_q$, —$C_{10-p}O_pH_{18-o-2p-q}G^a{}_q$, —$C_{5-p}S_pH_{8-o-2p-q}G^a{}_q$, —$C_{6-p}S_pH_{10-o-2p-q}G^a{}_q$, —$C_{7-p}S_pH_{12-o-2p-q}G^a{}_q$, —$C_{8-p}S_pH_{14-o-2p-q}G^a{}_q$, —$C_{9-p}S_pH_{16-o-2p-q}G^a{}_q$, —$C_{10-p}S_pH_{18-o-2p-q}G^a{}_q$, —$C_{5-p}O_lN_pH_{8-o-p-2l-q}G^a{}_q$, —$C_{6-p}O_lN_pH_{10-o-p-2l-q}G^a{}_q$, —$C_{7-p}O_lN_pH_{12-o-p-2l-q}G^a{}_q$, —$C_{8-p}O_lN_pH_{14-o-p-2l-q}G^a{}_q$, —$C_{9-p}O_lN_pH_{16-o-p-2l-q}G^a{}_q$, —$C_{10-p}O_lN_pH_{18-o-p-2l-q}G^a{}_q$, —$C_{5-p}S_lN_pH_{8-o-p-2l-q}G^a{}_q$, —$C_{6-p}S_lN_pH_{10-o-p-2l-q}G^a{}_q$, —$C_{7-p}S_lN_pH_{12-o-p-2l-q}G^a{}_q$, —$C_{8-p}S_lN_pH_{14-o-p-2l-q}G^a{}_q$, —$C_{9-p}S_lN_pH_{16-o-2l-q}G^a{}_q$, —$C_{10-p}S_lN_pH_{18-o-p-2l-q}G^a{}_q$; and/or
"amine" is selected from —$C_sH_{2s}$—NH$_2$, —$C_sH_{2s}$—NHG$^a$, —$C_nH_{2s}$-NG$^a{}_2$, —$C_sH_{2s}$-NG$^a{}_3{}^+$,
wherein
l=1, 2, 3, 4,
n=1, 2, 3, 4, 5, 6, 7, 8, 9, 10, more preferably n=1, 2, 3, 4, 5, 6, most preferably n=1, 2, 3 or 4,
m=1, 2, 3, 4, 5, 6, 7, 8, 9, 10, more preferably m=1, 2, 3, 4, most preferably m=1 or 2,
o=-1, 2, 3, 5, 7, 9,
p=1, 2, 3, 4, 5, 6, more preferably p=3, 4, 5 or 6,
q=1, 2, 3, 4, 5, more preferably q=1, 2 or 3,
s=1, 2, 3, 4, 5 or 6;

wherein $G^a$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b{}_2$, —NG$^b{}_3{}^+$, —CHO, —COOH, —COOAlkyl, —CN, —CONH$_2$, —CONHAlkyl, —CONAlkyl$_2$, -Heteroaryl, -Heterocycyl, —NOG$^b$, —N$^+$OAlkyl, —F, —Cl, and —Br;
wherein each $G^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

In some embodiments, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is each independently not selected from —SH, —NOG$^a$ and —N$^+$OG$^a$.

In some embodiments, each $G^a$ in any one of General Formulas (1)-(6) is each independently not selected from —OOH, —OOAlkyl, —SH, —NOG$^b$ and —N$^+$OAlkyl, wherein G$^b$ is as defined above.

In some embodiments, each $G^b$ in any one of General Formulas (1)-(6) is each independently not selected from —OOH, —OOAlkyl, —SH, and —N$^+$OAlkyl.

The inventive compounds may be referred to as "substituted low molecular weight aromatic target compounds" herein.

The inventive compounds according to General Formula (1) may preferably be classified as phenazines. The inventive compounds according to General Formula (2) may preferably be classified as N-substituted phenazines. The inventive compounds according to General Formula (3) may preferably be classified as alloxazines. The inventive compounds according to General Formula (4) may preferably be classified as N-substituted alloxazines. The inventive compounds according to General Formula (5) may preferably be classified as benzopteridines. The inventive compounds according to General Formula (6) may preferably be classified as N-substituted benzopteridines.

Particularly preferred compounds according to the present invention may be characterized by General Formula (1), (3) or (4) as defined above.

Substituents

The compounds according to the present invention are preferably substituted and include one or more substituents as described herein below. The presence of certain substituents may, e.g., improve the solubility, electrochemical properties and/or stability of the inventive compounds.

The compounds according to the present invention may include at least one substituent selected from:
—H, -Alkyl, -AlkylG$^a$, -Aryl, —SO$_3$H, —SO$_3^-$, —PO$_3$H$_2$, —OH, —OG$^a$, —SH, -Amine, —NH$_2$, —CHO, —COOH, —COOG$^a$, —CN, —CONH$_2$, —CONHG$^a$, —CONG$^a{}_2$, -Heteroaryl, -Heterocycyl, —NOG$^a$, —N$^+$OG$^a$, —F, —Cl, and —Br, or may be joined together to form a saturated or unsaturated carbocycle;
wherein each $G^a$ is independently selected from
—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b{}_2$, —NG$^b{}_3{}^+$, —CHO, —COOH, —COOAlkyl, —CN, —CONH$_2$, —CONHAlkyl, —CONAlkyl$_2$, -Heteroaryl, -Heterocycyl, —NOG$^b$, —N$^+$OAlkyl, —F, —Cl, and —Br;

wherein each $G^b$ is independently selected from
—H, -Alkyl, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —CONAlkyl$_2$, -Heteroaryl, -Heterocycyl, —$N^+OAlkyl$, —F, —Cl, and —Br.

More preferably, the compounds according to the present invention may include at least one substituent selected from —H, -Alkyl, -AlkylG$^a$, —$SO_3H$/—$SO_3^-$, —$OG^a$, and —COOH,
wherein each $G^a$ is independently selected from
—H, -Alkyl, -AlkylG$^b$, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —$NHG^b$, —$NG^b_2$, —$NG^b_3{}^+$, —CHO, —COOH, —COOAlkyl, —CN, —$CONH_2$, —CONHAlkyl, —CONAlkyl$_2$, -Heteroaryl, -Heterocycyl, —$NOG^b$, —$N^+OAlkyl$, —F, —Cl, and —Br;
wherein each $G^b$ is independently selected from
—H, -Alkyl, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —CONAlkyl$_2$, -Heteroaryl, -Heterocycyl, —$N^+OAlkyl$, —F, —Cl, and —Br.

In some embodiments, the substituents may each independently not be —SH, —$NOG^a$ and —$N^+OG^a$, wherein $G^a$ is as defined above. In some embodiments, in the above substituent definitions, each $G^a$ is independently not selected from —OOH, —OOAlkyl, —SH, —$NOG^b$ and —$N^+OAlkyl$, wherein $G^b$ is as defined above. In some embodiments, in the above substituent definitions, each $G^b$ is independently not selected from —OOH, —OOAlkyl, —SH, and —$N^+OAlkyl$.

Preferably, "alkyl", "aryl", "heteroaryl", "heterocyclyl" and "amine" are as defined above.

Alternatively,
"alkyl" may be selected from linear, branched or cyclic —$C_nH_{2n-o}$ and —$CH_{2n-o-m}G^a_m$;
"aryl" may be selected from —$C_6H_5$, —$C_{10}H_7$, $C_{13}H_8$, $C_{14}H_9$, —$C_6H_{5-m}G^a_m$, —$C_{10}H_{7-m}G^a_m$, $C_{13}H_{8-m}G^a_m$, $C_{14}H_{9-m}G^a_m$;
"heteroaryl" may be selected from —$C_{5-p}N_pH_{5-p-q}G^a_q$, —$C_{6-p}N_pH_{5-p-q}G^a_q$, —$C_{7-p}N_pH_{7-p-q}G^a_q$, —$C_{8-p}N_p$ $H_{6-p-q}G^a_q$, —$C_{9-p}N_pH_{7-p-q}G^a_q$, —$C_{10-p}N_pH_{7-p-q}G^a_q$, —$C_4OH_{3-q}G^a_q$, —$C_6OH_{5-q}G^a_q$, —$C_7OH_{4-q}G^a_q$, —$C_6O_2H_{3-q}G^a_q$, —$C_8OH_{5-q}G^a_q$, —$C_4SH_{3-q}G^a_q$, —$C_6SH_{5-q}G^a_q$, —$C_7SH_{4-q}G^a_q$, —$C_6S_2H_{3-q}G^a_q$, —$C_8SH_{5-q}G^a_q$, —$C_3ON_pH_{3-p-q}G^a_q$, —$C_6ON_p$ $H_{5-p-q}G^a_q$, —$C_7ON_pH_{4-p-q}G^a_q$, —$C_6O_2N_pH_{3-p-q}G^a_q$, —$C_8ON_pH_{5-p-q}G^a_q$, —$C_3SN_pH_{3-p-q}G^a_q$, —$C_6SN_p$ $H_{5-p-q}G^a_q$, —$C_7SN_pH_{4-p-q}G^a_q$, —$C_6S_2N_pH_{3-p-q}G^a_q$, —$C_6OSN_pH_{3-p-q}G^a_q$, —$C_8SN_pH_{5-p-q}G^a_q$, —$C_{5-p}N_p{}^+$ $H_{6-p-q}G^a_q$, —$C_{6-p}N_p{}^+H_{6-p-q}G^a_q$, —$C_{7-p}N_pH_{8-p-q}G^a_q$, —$C_{8-p}N_p{}^+H_{7-p-q}G^a_q$, —$C_{9-p}N_pH_{8-p-q}G^a_q$, —$C_{10-p}N_p{}^+$ $H_{8-p-q}G^a_q$, —$C_3ON_p{}^+H_{4-p-q}G^a_q$, —$C_7ON_p{}^+H_{6-p-q}G^a_q$, —$C_7ON_p{}^+H_{5-p-q}G^a_q$, —$C_6O_2N_p{}^+H_{4-p-q}G^a_q$, —$C_8ON_p{}^+H_{6-p-q}G^a_q$, —$C_3SN_p{}^+H_{4-p-q}G^a_q$, —$C_6SN_p{}^+$ $H_{6-p-q}G^a_q$, —$C_7SN_p{}^+H_{5-p-q}G^a_q$, —$C_6S_2N_p{}^+H_{4-p-q}G^a_q$, —$C_6OSN_p{}^+NH_{4-p-q}G^a_q$, —$C_8SN_p{}^+H_{6-p-q}G^a_q$;
"heteroaryl" may be selected from —$C_{5-p}N_pH_{8-o-p-q}G^a_q$, —$C_{6-p}N_pH_{10-o-p-q}G^a_q$, —$C_{7-p}N_pH_{12-o-p-q}G^a_q$, —$C_{8-p}$ $N_pH_{14-o-p-q}G^a_q$, —$C_{9-p}N_pH_{16-o-p-q}G^a_q$, —$C_{10-p}N_p$ $H_{18-o-p-q}G^a_q$, —$C_5O_pH_{8-2p-q}G^a_q$, —$C_{6-p}O_p$ $H_{10-o-2p-q}G^a_q$, —$C_7O_pH_{12-o-2p-q}G^a_q$, —$C_{8-p}O_p$ $H_{14-o-2p-q}G^a_q$, —$C_9O_pH_{16-o-2p-q}G^a_q$, —$C_{10-p}O_p$ $H_{18-o-2p-q}G^a_q$, —$C_{5-p}S_pH_{8-o-2p-q}G^a_q$, —$C_{6-p}S_p$ $H_{10-o-2p-q}G^a_q$, —$C_{7-p}S_pH_{12-o-2p-q}G^a_q$, —$C_{8-p}S_p$ $H_{14-o-2p-q}G^a_q$, —$C_{9-p}S_pH_{16-o-2p-q}G^a_q$, —$C_{10-p}S_p$ $H_{18-o-2p-q}G^a_q$, —$C_{5-p}O_lN_pH_{8-o-p-2l-q}G^a_q$, —$C_{6-p}$ $O_lN_pH_{10-o-p-2l-q}G^a_q$, —$C_{7-p}O_lN_pH_{12-o-p-2l-q}G^a_q$, —$C_{8-p}O_lNH_{14-o-p-2l-}$ $G^a_q$, —$C_{9-p}O_lN_pH_{16-o-p-2l-q}G^a_q$, —$C_{10-p}O_lN_pH_{18-o-p-2l-q}G^a_q$, —$C_{5-p}S_lN_pH_{8-o-p-2l-q}G^a_q$, —$C_{6-p}S_lN_pH_{10-o-p-2l-q}G^a_q$, —$C_{7-p}S_lN_pH_{12-o-p-2l-q}G^a_q$, —$C_{8-p}S_lN_pH_{14-o-p-2l-q}G^a_q$, —$C_{9-p}S_lN_pH_{16-o-p-2l-q}G^a_q$, —$C_{10-p}S_lN_pH_{18-o-p-2l-q}G^a_q$; and/or
"amine" may be selected from —$C_nH_{2n}$—$NH_2$, —$C_nH_{2n}$—$NHG^a$, —$C_nH_{2n}$-$NG^a_2$, —$C_nH_{2n}$-$NG^a_3{}^+$,
wherein
l=1, 2, 3, 4
n=1, 2, 3, 4, 5, 6, 7, 8, 9, 10, more preferably n=1, 2, 3, 4, 5, 6, most preferably n=1, 2, 3 or 4
m=1, 2, 3, 4, 5, 6, 7, 8, 9, 10, more preferably m=1, 2, 3, 4, most preferably m=1 or 2
o=−1, 2, 3, 5, 7, 9
p=1, 2, 3, 4, 5, 6, more preferably p=3, 4, 5 or 6
q=1, 2, 3, 4, 5, more preferably q=1, 2 or 3,
s=1, 2, 3, 4, 5 or 6;
each $G^a$ is independently selected from
—H, -Alkyl, -AlkylG$^b$, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —$NHG^b$, —$NG^b_2$, —$NG^b_3{}^+$, —CHO, —COOH, —COOAlkyl, —CN, —$CONH_2$, —CONHAlkyl, —CONAlkyl$_2$, -Heteroaryl, -Heterocycyl, —$NOG^b$, —$N^+OAlkyl$, —F, —Cl, and Br;
wherein each $G^b$ is independently selected from
—H, -Alkyl, -Aryl, —$SO_3H$, —$SO_3^-$, —$PO_3H_2$, —OH, —OAlkyl, —OOH, —OOAlkyl, —SH, —SAlkyl, —$NH_2$, —NHAlkyl, —$NAlkyl_2$, —$NAlkyl_3^+$, —CHO, —COOH, —COOAlkyl, —CN, —$CONH_2$, —CONHAlkyl, —CONAlkyl$_2$, -Heteroaryl, -Heterocycyl, —$N^+OAlkyl$, —F, —Cl, and —Br.

In some embodiments, in the above substituent definitions, each $G^a$ is independently not selected from —OOH, —OOAlkyl, —SH, —$NOG^b$ and —$N^+OAlkyl$, wherein $G^b$ is as defined elsewhere herein. In some embodiments, in the above substituent definitions, each $G^b$ is independently not selected from —OOH, —OOAlkyl, —SH, and —$N^+OAlkyl$.

Preferably, the compounds according to the present invention comprise 2-5 substituents as defined above, wherein said 2-5 substituents are preferably not selected from —H. More preferably, the compounds according to the present invention comprise 3-4 substituents as defined above, wherein said 3-4 substituents are preferably not selected from —H.

Accordingly, in some embodiments, the present invention provides compounds wherein 2-5 or 1-5, more preferably 1, 3 or 4 or 3-4 of
$R^1$-$R^8$ in General Formula (1),
$R^1$-$R^{10}$ in General Formula (2),
$R^1$-$R^4$ in General Formula (3),
$R^1$-$R^6$ in General Formula (4),
$R^1$-$R^6$ in General Formula (5), and
$R^1$-$R^8$ in General Formula (6) are independently selected from -Alkyl, -AlkylG$^a$, -Aryl, —$SO_3H$, —$SO_3^-$, —$PO_3H_2$, —OH, —$OG^a$, —SH, -Amine, —$NH_2$, —CHO, —COOH, —$COOG^a$, —CN, —$CONH_2$, —CONHG$^a$, —CONG$^a_2$, -Heteroaryl, -Heterocycyl, $NOG^a$, —$N^+OG^a$, —F, —Cl, and —Br, or are joined together to form a saturated or unsaturated carbocycle, more preferably from —H, -Alkyl, -AlkylG$^a$, —$SO_3H$/—$SO_3^-$, —$OG^a$, and —COOH;

wherein each $G^a$ is independently selected from
—H, -Alkyl, -Alkyl$G^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3^+$, —CHO, —COOH, —COOAlkyl, —CN, —CONH$_2$, —CON-HAlkyl, —CONAlkyl$_2$, -Heteroaryl, -Heterocycyl, —NOG$^b$, —N$^+$OAlkyl, —F, —Cl, and Br;

wherein each $G^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CON-HAlkyl, —CONAlkyl$_2$, -Heteroaryl, Heterocycyl, —N$^+$OAlkyl, —F, —Cl, and Br.

In some embodiments, each $R^1$-$R^8$ in General Formula (1), each $R^1$-$R^{10}$ in General Formula (2), each $R^1$-$R^4$ in General Formula (3), each $R^1$-$R^6$ in General Formula (4), each $R^1$-$R^6$ in General Formula (5), and each $R^1$-$R^8$ in General Formula (6) is independently not selected from —SH, —NOG$^a$ and —N$^+$OG$^a$, wherein $G^a$ is as defined above.

In some embodiments, each G, in any one of General Formulas (1)-(6) is independently not selected from —OOH, —OOAlkyl, —SH, —NOG$^b$ and —N$^+$OAlkyl, wherein $G^b$ is as defined above.

In some embodiments, each $G^b$ in any one of General Formulas (1)-(6) is independently not selected from —OOH, —OOAlkyl, —SH, and —N$^+$OAlkyl.

In some embodiments, the inventive compounds may preferably comprise at least one —SO$_3$H/—SO$_3^-$ group.

In some embodiments, the inventive compounds may preferably comprise at least one hydroxyl group.

In some embodiments, the inventive compounds may preferably comprise at least one alkyl group.

In some embodiments, the inventive compounds may preferably comprise at least one alkyoxy (alkoxy) group.

In some embodiments, the inventive compounds may preferably comprise at least one carboxyl group.

In some embodiments, the inventive compounds may preferably comprise at least one amine group.

More specifically, the present invention provides compounds inventive compounds comprising a —SO$_3$H/—SO$_3^-$ group and at least one other substituent selected from the group consisting of an alkoxy group, e.g. methoxy group, a hydroxyl group and an carboxyl group. In another embodiment, the inventive compounds comprise by their substitution pattern at least one hydroxyl group, preferably two hydroxyl groups, and at least one other substituent selected from the group consisting of an carboxyl group, a —SO$_3$H/—SO$_3^-$ group, and an alkoxy group. In a further preferred embodiment, the inventive compound comprises as substituents at least one alkoxy, e.g. methoxy group, and at least one hydroxyl group. In a further alternative embodiment, the inventive compound comprises as substituents at least one carboxyl group and at least one —SO$_3$H/—SO$_3^-$ group. In a still further embodiment, the inventive compound comprises as substituents at least one —SO$_3$H/—SO$_3^-$ group and at least one hydroxyl group. In a still further embodiment, the inventive compound comprises as substituents at least one —SO$_3$H/—SO$_3^-$ group and at least one alkoxy, e.g. methoxy, group. In a further alternative embodiment, the inventive compound comprises as substituents at least one carboxyl group and at least one hydroxyl group. In a still further embodiment, the inventive compound comprises as substituents at least one —SO$_3$H/—SO$_3^-$ group, at least one hydroxyl and at least one methoxy group. In another preferred embodiment, the inventive compound comprises as substituents at least one —SO$_3$H/—SO$_3^-$ group, at least one hydroxyl and at least one carboxyl group. In a still further preferred embodiment, the inventive compound comprises as substituents at least one alkoxy, e.g. methoxy, group, at least one hydroxyl and at least one carboxyl group. In a preferred embodiment, the inventive compound comprises a methoxy, a hydroxyl and a —SO$_3$H/—SO$_3^-$ group.

In combination with at least one —SO$_3$H/—SO$_3^-$ group, it is also advantageous for the inventive compound to comprise as substituents at least one alkyl group, e.g. a methyl group, specifically two alkyl groups. Any of the above embodiments comprising an —SO$_3$H/—SO$_3^-$ group (and at least one of a carboxyl group, hydroxyl group and/or alkoxy group) may thus also comprise at least one alkyl group, e.g. one or two alkyl groups, specifically one alkyl group.

Preferred compounds of the invention are e.g. selected from:

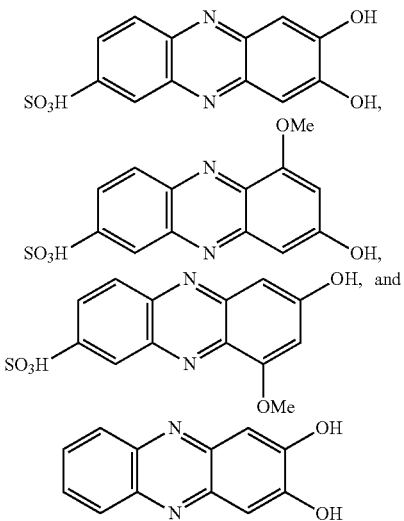

or any combination of two or more of the above.

Other preferred compounds are

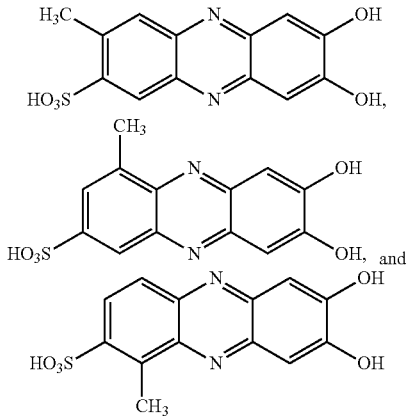

or any combination thereof, in particular a combination of all of the above three compounds each having a methyl group at another position of the phenazine ring system.

Other preferred compounds are

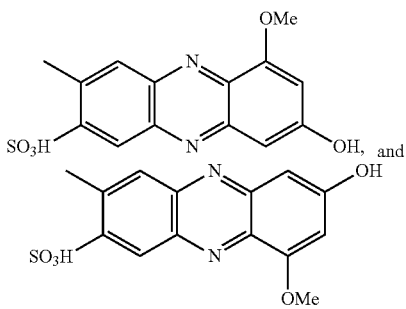

or a combination thereof.

Compositions

In a further aspect, the present invention relates to a composition, preferably an aqueous composition, comprising or (essentially) consisting of the inventive compounds as defined herein. The compositions may comprise or (essentially) consist of at least 1, or a plurality of at least 2, 3, 4, 5 or more of the inventive compounds as defined herein. Unless denoted otherwise, e.g. "two" of the inventive compounds comprised by an inventive composition may represent the oxidized and the reduced from of the (structurally otherwise identical) inventive compound or may represent two structurally distinct inventive compounds.

A composition "comprising" the inventive compounds as defined herein may comprise, in addition to the at least 1, or a plurality of at least 2, 3, 4, 5 or more of the inventive compounds and any suitable additive, e.g. solvents, stabilizers, or the like.

A composition "essentially consisting of" the inventive compounds as defined herein may comprise at least 1, or a plurality of at least 2, 3, 4, 5 or more of the inventive compounds with a minor amount of by-products, impurities or contaminants, preferably in an amount of less than 10%, more preferably less than 5% the overall composition by dry content mass. Said by-products, impurities or contaminants are not compounds as defined herein.

A composition "consisting of" the inventive compounds as defined herein may consist of at least 1, or a plurality of at least 2, 3, 4, 5 or more of the inventive compounds and does not comprise any additives, by-products, impurities or contaminants as defined above. It may be preferred that a composition "consisting of" the inventive compounds is composed exclusively from a plurality of at least 2, 3, 4, 5 or more of the inventive compounds.

The compositions according to the invention may be derived from lignin.

It may be preferred that the compositions according to the invention exhibit a purity of 100%. Put differently, it may be preferred that the compositions according to the invention do not contain any by-products, impurities or contaminants. Such compositions may be particularly useful as redox flow battery electrolytes.

The composition according to the present invention may preferably comprise or (essentially) consist of at least 1, or a plurality of at least 2, 3, 4, 5 or more compounds of the present invention as defined by any one of General Formulas (1)-(6). The compounds may typically cycle between their reduced and oxidized form, as indicated by Sub-Formulas (a) and (b) of each General Formula (1)-(6). By way of example, a composition comprising a compound according to General Formula (1) will typically comprise the compound in its reduced and oxidized form, as indicated by Sub-Formulas (1) (a) and (1) (b). The amount and ratio of oxidized versus reduced forms typically depends on the redox conditions.

Preferably, the inventive composition may comprise or (essentially) consist of a plurality of at least 2, 3, 4, 5 or more compounds of the present invention, each of which is present in its oxidized and reduced form.

Preferably, the plurality of at least 2, 3, 4, 5 or more compounds in the inventive composition differ from each other by their General Formula or by their substitution pattern.

The inventive composition may therefore comprise or (essentially) consist of at least 1 or a plurality of at least 2, 3, 4, 5 or more compounds according to General Formula (1), (2), (3), (4), (5) or (6). Each of the aforementioned compounds may be present in its reduced and/or oxidized form.

Where the inventive composition comprises or (essentially) consists of a plurality of at least 2, 3, 4, 5 or more compounds according to the same General Formula (1), (2), (3), (4), (5), or (6), the compounds may preferably differ from each other by their substitution pattern. In this context, a "substitution pattern" refers to the number, type and distribution of substituents of a particular compound.

The composition according to the present invention may therefore comprise a mixture of compounds as described herein, wherein the compounds differ in terms of their General Formula, or are represented by the same General Formula (1)-(6) and exhibit a different substitution pattern.

For instance, a "different substitution pattern" may refer to a different sulfonation pattern, i.e. different residues R in the General Formulas (1)-(6) represent —SO$_3$H groups.

It may be preferred that the inventive composition may comprise at least two compounds according to the invention selected from:

(a) compounds according to Formula (1) (a) and (b) as defined herein, preferably having different substitution patterns;

(b) compounds according to Formula (2) (a) and (b) as defined herein, preferably having different substitution patterns;

(c) compounds according to Formula (3) (a) and (b) as defined herein, preferably having different substitution patterns;

(d) compounds according to Formula (4) (a) and (b) as defined herein, preferably having different substitution patterns;

(e) compounds according to Formula (5) (a) and (b) as defined herein, preferably having different substitution patterns; and/or (f) compounds according to Formula (6) (a) and (b) as defined herein, preferably having different substitution patterns.

Without wishing to be bound by specific theory, the compositions according to the present invention—in particular those comprising or (essentially) consisting of inventive compounds sharing the same General Formula but exhibiting a different substitution pattern—may exhibit favorable electrochemical properties and be particularly useful as, e.g., redox flow battery electrolytes. This is advantageous as it may preferably obviate the need for purification steps after the substitution reaction has been performed. Rather, the inventive compositions comprising mixtures of the compounds according to the invention may be "ready to use" (e.g., as redox flow battery electrolytes") after "batch" substitution reactions.

Starting Materials

As indicated above, the compositions and compounds described throughout the present specification (including both precursor and target compositions/compounds) may be "lignin-derived" ("derived from lignin"). Thus, compositions and compounds can advantageously be obtained from lignin or lignin derivatives that typically occur as by-products of the pulping industry. It is however also conceivable to provide suitable precursor (and ultimately target) compounds from fossil resources, including crude oil and coal, or from pure organic substances.

"Lignin" is generally understood herein as wood-derived heterogeneous phenolic macromolecule or, rather, a group of phenolic macromolecules of plant origin, which is or are composed of different monomeric building blocks. Hence, it is understood to be a natural copolymer. More specifically, lignin may be generally defined as an amorphous three-dimensional polymer, which is mainly and naturally composed of phenolic building blocks. Lignin in its "native" state, i.e. as part of the natural lignocellulosic material, is the starting material of the inventive method for any "modified lignin" and, subsequently, any "lignin-derived" compositions or compounds as described herein as product of the inventive methods.

Lignin typically comprises p-coumaryl, coniferyl and sinapyl alcohol as the phenolic building blocks, which are linked (randomly) with ether (C—O—C) bonds, such as "beta-O-4", "4-O-5" and, to a less frequent extent, "1-O-4". The most frequently seen covalent linkage in natural softwood and hardwood lignin is typically the "beta-O-4" bond, which accounts, e.g., for approximately 45-50% of all bonds in spruce and up to 60% in birch. Additionally, carbon-carbon (C—C) linkages may occur in natural lignin, such as "5-5", "beta-5", "beta-beta" and "beta-1", amongst which the "5-5" linkage is the most frequently seen C—C linkage, in particular in softwood, such as spruce. Typical linkages as "beta-O-4", "4-O-5" and "5-5" are depicted in the following:

β-O-4

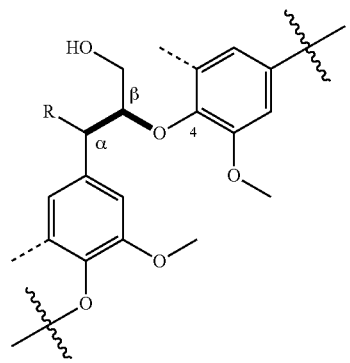

4-O-5

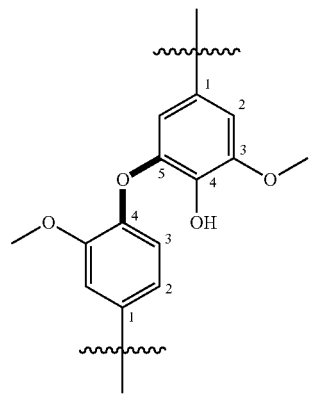

5-5

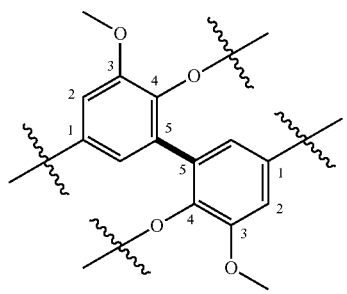

A "building block" as a base unit (derived from lignin) as used herein may preferably be understood as an organic moiety, which comprises at least one bond to covalently link said building block to another building block of the same or different chemical structure to form a plurality of covalently associated building blocks. Preferably, a building block according to the present invention is a "phenolic building block", i.e. any moiety comprising a six-membered aromatic ring, covalently functionalized by at least one hydroxyl group (—OH). Hence, the lignin "building block" is typically characterized by a monocyclic, typically an aromatic moiety, with the monocycle typically being substituted at least one position. Typically, each lignin building block exhibits a carbocyclic monocycle with one or two substituents acting as linkers to another building block and one or two substituents, which do not exhibit any linking function. A building block corresponds to a "monomer". A "dimer" as used herein typically comprises two such building blocks, which are covalently linked. Thus, the dimer is typically characterized by two isolated monocyclic moieties covalently linked by a linker group or by a bond (biphenylic ring system). Biphenylic ring systems (as a characteristic moiety of dimers) occur with lower frequency in plant lignin, in some plants (e.g. in spruce) with higher frequency. More generally, any such dimeric compounds belong to the class of bicycles.

A larger plurality of any such covalently connected or linked building blocks forms typically the larger 3-dimensional lignin structure. In the context of the present invention, a "polymer" refers to a natural lignin molecule as it occurs in plants, e.g. as part of lignocellulosic material. The lignin polymer is typically a copolymer of distinct building blocks. Natural lignin's "building block" corresponds to a "monomer". Accordingly, a building block typically is a (repeating) structural part of the natural polymer lignin. The (phenolic) building block has typically 9 carbon atoms ($C_9$) or, less frequently seen, 8 carbon atoms ($C_8$). Typically, the building blocks have a molecular weight of about 130 to 300 Da, preferably of 150 to 250 Da, more preferably of 160 to 190 Da. Preferably, their basic monomeric $C_9$ or $C_8$ structure is not altered in the course of the natural lignin modifying process by e.g. pulping. Such building blocks may serve as the basic unit in their chemistry, providing aromatic organic target compounds according to the present invention.

As used herein, the term "lignin-derived" has the broadest meaning with regard to any lignin, which underwent one or more process steps, from process step (1) onwards, according to the present invention. Therein, a "derived" material has to be understood as a chemical derivative. A "lignin-derived" material may be of any molecular weight smaller than the natural lignin polymer, including a small molecule, i.e. a low molecular weight compound as used herein. In this regard, both "modified lignin-derived components" and "lignin-derived compounds" according to the present invention are lignin-derived material. Accordingly, a "lignin-derived" modified lignin-derived component or a (target or precursor) compound as defined herein, is a (macro-)molecule, which corresponds to or is derived from a (monomeric) building block of natural lignin or is a homo- or heterodimer of such (monomeric) building blocks. Such compounds are derived from natural lignin via its modification in step (1.2) onwards, which provides the fraction of modified lignin-derived components as intermediates of the inventive method. Subsequently, a chemical decomposition step (3) provides lignin-derived low molecular weight precursor compounds that are subsequently processed to yield lignin-derived compounds and compositions according to the invention.

In a further aspect, the present invention provides a method for producing compounds and compositions according to the present invention from lignin, fossil resources (such as crude oil or coal) or pure substances. An inventive method for preparing the inventive compounds and compositions from lignin is described in greater detail in the following. Such methods for preparing a compound or a composition comprising or (essentially) consisting of the same, preferably according to the invention comprise the following steps:

(1) providing a starting material;
(2) optionally subjecting said starting material to a process suitable to obtain at least one low molecular weight precursor compound;
(3) isolating and optionally modifying at least one low molecular weight precursor compound; thereby obtaining at least one low molecular weight aromatic precursor compound;
(4) subjecting said at least one low molecular weight precursor compound to a condensation reaction, ring expansion or 3-ring formation reaction, thereby obtaining a condensation product, an aromatic or aliphatic multi-ring system;
(5) optionally, subjecting said condensation product to a modification reaction, preferably wherein one or more substituents are introduced into said condensation product, or to a transformation reaction of an aliphatic compound into a multi-ring aromatic system, to obtain at least one substituted low molecular weight aromatic compound or a composition comprising the same or (essentially) consisting thereof; wherein said starting material is preferably selected from lignocellulosic material, crude oil, coal or pure organic substances.

More specifically, the method involves starting material being lignocellulosic material, wherein said method comprises the followings steps:

(1) subjecting lignocellulosic material to a pulping process; thereby obtaining modified lignin-derived components;
(2) isolating said modified lignin-derived components;
(3) subjecting said modified lignin-derived components to a chemical decomposition step; thereby obtaining decomposition products comprising or consisting of at least one low molecular weight precursor compound;
(4) isolating at least one low molecular weight precursor compound; thereby obtaining at least one low molecular weight precursor compound or aromatic precursor compound;
(4') optionally modifying said low molecular weight aromatic precursor compound, thereby obtaining at least one low molecular weight compound or at least one low molecular weight aromatic compound;
(5) subjecting said at least one low molecular weight aromatic (precursor) compound or said at least one low molecular weight (precursor) compound to a condensation reaction, ring expansion or 3-ring formation reaction to obtain at least one condensation product; and
(6) optionally, subjecting said at least one condensation product to a modification reaction, preferably wherein one or more substituents are introduced into said at least one precursor compound or condensation product, or to a transformation reaction of an aliphatic compound into a multi-ring aromatic system; thereby obtaining at least one substituted low molecular weight aromatic compound or a composition comprising the same or (essentially) consisting thereof.

Preparation of Compounds and Compositions from Lignocellulosic Material

The lignin-derived compounds and compositions according to the present invention are preferably obtained by a process comprising the following steps:

In a first step (1), lignocellulosic material is subjected to a pulping process; yielding modified lignin-derived components. Said modified lignin-derived components are isolated in a second step (2) and in a third step (3) subjected to chemical decomposition; whereby decomposition products comprising or consisting of at least one low molecular weight lignin-derived precursor compound are obtained. In a fourth step (4), precursor compounds are provided before being subjected to a condensation (step (5)) and further modification reactions (step (6)) to yield the inventive compounds and/or compositions.

Each single step of the inventive method leading to the provision of the desired target compound or composition are discussed in greater detail below.

Step (1): Pulping of Lignocellulosic Material and Provision of Modified Lignin-Derived Components By step (1) of the inventive method, lignocellulosic material is subjected to a pulping process to yield modified lignin-derived components. That step typically involves the following sub-steps: Provision of lignocellulosic material (1.1), pulping of said lignocellulosic material (1.2) and separating the pulp from the resulting modified lignin-derived components (1.3).

Sub-Step (1.1): Provision of Lignocellulosic Material

In step (1.1) of the inventive method, lignocellulosic material is provided. Preferably, said lignocellulosic material is chopped.

"Lignocellulosic material", understood to be the starting material for the method of the present invention, may be provided as any form of plant biomass, which naturally comprises cellulose, lignin and hemicellulose. Therein, cellulose (a polysaccharide consisting of a linear chain of several hundred to many thousands of beta(1→4) linked D-glucose units) typically forms a scaffold of fiber together with hemicellulose. Lignin (as defined above) is typically embedded within this scaffold, typically without being covalently linked to cellulose and/or hemicellulose. "Hemicellulose" is any of several heteropolymeric polysaccharides, which include xylan, glucuronoxylan, arabinoxylan, glucomannan, and xyloglucan. It is typically present along with cellulose in almost all plant cell walls. In contrast to cellulose, hemicellulose usually has a random, amorphous structure with little strength.

The lignocellulosic material may be derived from any appropriate plant origin, e.g. wood, fiber crops or waste paper origin. In case waste paper is used as starting material for the inventive method, such waste paper is typically of lower paper quality, such as newspaper paper. It usually comprises higher amounts of residual lignin, while higher quality paper is typically lignin-free. Field crop fiber or agricultural residues (instead of wood fiber) may be preferred as being of more sustainable nature. However, wood is the preferred renewable source, with about 90 percent of pulp originating from wood plantations or reforested areas. Non-wood fiber sources may be employed by the inventive method as well (as far as it is for global pulp production), for a variety of reasons, including seasonal availability, problems with chemical recovery, brightness of the pulp etc. Non-wood pulp processing, however, usually requires more water and energy than wood pulp pressing.

Lignocellulosic material of known and invariant character is preferred, such that the inventive method's downstream products remain essentially unaltered, preferably provided in the form of chopped lignocellulosic material, e.g. in the form of wood chips. "Chopped" lignocellulosic material is understood—by the present invention—to be advantageously mechanically processed starting from plant material of natural origin, such that it is chopped to smaller pieces. Said lignocellulosic material is typically processed by any form of grinding, crushing and/or milling, which results in smaller pieces of the lignocellulosic material, i.e. the chopped lignocellulosic material, which is preferred in the context of the present invention. It may be preferred to employ lignocellulosic material with a lignin content of at least 15%, more preferred of at least 20%, most preferred of 20 to 35%.

The lignocellulosic material used as a starting material is preferably provided in the form of woodchips. "Woodchips" are understood as a medium-sized solid material made by cutting, or chipping, larger pieces of wood. Characteristic values (such as water content, ash content, particle size distribution, bulk density, nitrogen content, chlorine content) are preferably chosen such that they fulfil generally accepted provisions, such as the European Standard EN 14961. Wood chips as typically used for chemical pulping processes are preferably used for the inventive method as well as they are usually relatively uniform in size and substantially free of bark. The optimum size may vary with the wood species. Preferred sizes of the main fraction are about 3 to 45 mm with a fine fraction, defined as particles below 1 mm, of preferably less than 5%. Common wood chips used in pulp production, which are preferred in the method of the present invention, are on average 12-25 mm (0.47-0.98 in) long and 2-10 mm (0.079-0.394 in) thick. Damage of the wood fibers is preferably avoided, as fibers free of physical defects are advantageous for the pulp properties. As the method of the present invention shares the same starting material as the pulping process, the starting material should satisfy the requirements of both the inventive method as a whole and the pulping process. For roundwood it is most common to use disk chippers. Therein, "roundwood" is understood as industrial roundwood, which is commonly defined, e.g., in the FAO Forest Products Yearbook to include all industrial wood (e.g. sawlogs and veneer logs, pulpwood and other industrial roundwood) and marketed forms, such as chips, particles or wood residues.

Accordingly, the lignocellulosic material may preferably be derivable of wood of low silica and resin content, more preferably derivable from northern woods, more preferably be derivable from the group consisting of beech, pine, birch, eucalyptus, grasses and spruce, wherein the lignocellulosic material is preferably chopped, and wherein the lignocellulosic material is more preferably provided in the form of woodchips.

Sub-Step (1.2): Pulping

In sub-step (1.2) of the inventive method, lignocellulosic material (preferably as provided in step (1.1)) is subjected to a pulping process. Thereby, the lignocellulosic material is preferably subjected to (a) a Kraft process or (b) a sulfite process as described herein. A "pulping process" is understood in the context of the present invention as process of chemically and/or mechanically disjoining cellulose fibres from other constituents of the lignocellulosic starting material of the pulping process, such as any wood, fibre crops or waste paper. Said pulping process preferably yields pulp and modified lignin-derived components. "Pulp" is understood herein to essentially comprise a mixture of (preferably pure/enriched) cellulosic fibrous material, which does not contain lignin or lignin-derived components or contains only minor residual amounts of lignin components (e.g. as impurities of the cellulosic fibrous material).

In contrast to pulping processes employed for manufacturing of pulp (wherein modified lignin-derived components are generally considered by-products), the inventive method aims to valorize lignin and lignin derivatives by providing useful lignin-derived redox active species. Thus, in the inventive method, modified lignin-derived components are considered intermediates whereas pulp is the by-product.

The "pulping process" (also referred to as "pulp and/or paper manufacturing process") is typically a commercially established process for the production of pulp and/or paper in a pulp and/or paper manufacturing plant. A pulping process provides the preferably pure cellulosic fibrous material (pulp). Being typically in the form of fibres, pulp is usually not dissolved, but dispersed or suspended in the liquid employed in the pulping process. Due to its fibrous form, pulp is typically separated by sub-step (1.3) of the inventive method as fibrous material, preferably by mechanical means, such as sieves and/or centrifuges, from the method's process stream, which contains the (preferably dissolved, suspended and/or dispersed) fraction of lignin-derived material and which is further processed by step (2).

It is typically the aim of any "pulping process" to allow disintegration of wood into fibrous cellulosic material, lignin and hemicellulose products. This is achieved by breaking covalent bonds of 3-dimensional polymeric lignin macromolecules. Carbon to carbon (C—C) bonds are more stable than oxygen-carbon bonds (C—O) under conditions typically applied for bond breaking by the "cooking" sub-step of the inventive method. Thus, cleavage of oxygen-carbon bonds is the most prevalent and important reaction in any typical pulping process described herein as sub-step (1.2). Thereby, cooking under alkaline conditions in the Kraft process, under acidic conditions in the sulfite process and in organic solvents in the organosolv process allows to break oxygen-carbon bonds of lignin. Typically, any such reaction of sub-step (1.2) produces modified products characterized by phenolic hydroxyl groups due to cleavage of natural lignin's aryl-alkyl-ether bonds. The modified lignin-derived components as modified products of the pulping process, i.e. "the modified lignin-derived components", are of lower molecular size than the polymeric lignin starting material (natural lignin). Furthermore, such lower molecular weight lignin-derived polymers are usually more soluble or dispersible than natural lignin in the process stream leaving the pulping process of sub-step (1.2). From that process stream non-dissolved or non-dispersed pulp, which usually is the target product of any commercial pulping process, may readily be separated from dissolved and/or suspended modified lignin-derived components (as realized by sub-step (1.3) of the inventive method).

The present invention is characterized by the advantage that it may readily employ by its sub-step (1.2) existing plants for pulp production. It is characterized by enabling commercial use of lignin (in the art typically regarded as the major undesired by-product of pulp production) to provide lignin-derived substituted low molecular weight aromatic compounds as redox flow battery electrolytes. If required, the present invention may also use a smaller portion of the lignin-derived fraction of sub-step (1.2) as energy source either for the pulp production or for further downstream steps. The present invention is, however, unprecedented, as it enables lignin (as abundantly available and renewable natural material) to become the starting material for the provision of a large diversity of organic compounds usable in redox flow batteries.

Distinct pulping processes may be used as a matter of choice to provide feedstocks for obtaining the lignin-derived components as intermediates of the method of the present invention. The pulping process separates the principle components of the lignocellulosic material, degrades the polymers to smaller compounds and occasionally causes other chemical transformation, depending from the method employed.

The employed pulping processes may preferably be those overly used in the pulp and paper industries (i.e., Kraft or sulfite process) or other processes such as organosolv. Each process type has its advantages and disadvantages. The choice of the employed pulping process of the inventive method may depend on the type of lignin-derived components which are subsequently processed into valuable target compounds. The choice of the particular pulping process may thereby determine the target compositions and compounds obtainable by the inventive method.

Accordingly, the pulping process of sub-step (1.2) may preferably be selected from the group consisting of Kraft process, sulfite process, organosolv process, and lignin pyrolysis process. Other processes for separating lignin and cellulose components from lignocellulosic starting material (as described herein and known in the art) may also be used for the reaction of sub-step (1.2) to arrive at a (modified) lignin-derived fraction. The Kraft process or, alternatively, the sulfite process are particularly preferred pulping processes employed in sub-step (1.2) for the method of the invention.

Both the Kraft process (a) and the sulfite process (b) are widely known from the afore-mentioned applications and are applied accordingly by the inventive method. They allow to separate cellulosic fibrous material (pulp), which is the target material in the production of pulp and/or paper, from other non-cellulosic wood components, in particular lignin or, rather, the (modified) lignin-derived components. For the inventive method, "pulp" is neither a target product nor an intermediate. Rather, the target of sub-step (1.2) is the provision of lignin as the other major wood component, preferably in its modified, advantageously soluble form ("modified lignin-derived components"). Typically, the present invention processes modified lignin-derived components, such as "Kraft lignin", "sulfonated Kraft lignin" or "lignosulfonate", upon separation of the cellulose fraction, as an intermediate of the inventive method.

(a) Kraft Process

The "Kraft process" is by far the most prevalent pulping process worldwide. It is typically a high pH pulping process in aqueous solution (typically aqueous sodium hydroxide) containing one or more of salt or non-salt agents selected from sulfide, sulfhydryl and polysulfide. It usually further comprises a sulfate salt. Accordingly, the Kraft process (a) is typically a higher pH pulping process in the presence of an aqueous solution containing one or more of salt or non-salt agents selected from the group consisting of sulfide, sulfhydryl and polysulfide. One or more sulfate salt(s) is/are typically added as well.

Despite the sulfides employed, relatively little sulfur is typically contained in the product stream following pulping. The Kraft process is versatile in terms of the lignocellulosic starting material, which is treated in aqueous solution at elevated temperature and pressure. It is energy efficient and recycles most of the employed reactive agents, such as reactive agents required for the pulping process. Said process yields "Kraft lignin". Typically, the modified lignin-derived components (Kraft lignin) have a molecular weight of about 2.000 to 5.000 Da, preferably 2.000 to 3.000 Da. They may be components of the natural 3-D lignin polymers, potentially further chemically functionalized by the introduction of additional functional groups and linkages (e.g. stilbenes). The process chemistry surrounding Kraft process including a description of the ways in which lignin linkages are disrupted during the process are described in Chakar and Ragauskas Ind Crops Prod 2004, 20, 131. Gierer et al. (Wood Sci Technol. 1985, 19, 289 and Wood Sci Technol. 1986, 20, 1) describes the structural changes that occur to lignin as a result of chemical bleaching during the Kraft process.

The Kraft process may be carried out as sub-step (1.2) alternative (a) according to the inventive method. The Kraft process may preferably comprise the sub-steps of (i) optionally pre-steaming the (preferably chopped) lignocellulosic material, wherein the (preferably chopped) lignocellulosic material is advantageously wetted and preheated with steam, (ii) adding (preferably chopped) lignocellulosic material to an aqueous alkaline solution comprising Kraft pulping agents, one or more of the agents preferably selected from the group consisting of a sulfide salt, a sulfhydryl agent (in particular a sulfhydryl compound or salt), a polysulfide salt (and, typically, at least one sulfate salt is additionally comprised by the alkaline solution as well), (iii) cooking the (preferably chopped) lignocellulosic material, which is provided (e.g. suspended and/or dispersed)) in said aqueous alkaline solution, and (iv) optionally sulfonating the lignocellulosic material in the presence, e.g. of sulfuric acid solution and/or sulfur trioxide.

Step (i): Pre-Steaming

By optional sub-step (i) of the Kraft process, preferably chopped lignocellulosic material (such as woodchips) may be pre-treated with hot steam. Thereby, preferably chopped lignocellulosic material is wetted and heated, which typically renders it more susceptible to adsorb treatment solutions as applied by subsequent sub-step (ii). Cavities of fresh wood are filled with fluids and/or air. Steam pre-treatment causes the air to expand. About 25% of the air and/or other fluids naturally occupying the cavities is thereby expelled from these cavities.

Step (ii): Addition of Kraft Pulping Agents

By sub-step (ii) of the applied Kraft process, the optionally pre-treated, i.e. pre-steamed and pre-heated, preferably chopped lignocellulosic material is treated, preferably at elevated temperatures, with an aqueous alkaline solution ("treatment solution"). Typically, the lignocellulosic material is added to the treatment solution. Said solution typically comprises at least one chemically reactive agent for the Kraft process to operate. The treatment solution may be a liquor known in the art as "white liquor". The employed reactive agents may adjust the pH and/or provide nucleophilic sulfide ($S^{2-}$) and/or bisulfide ($HS^-$) ions and/or moieties. Typically, said treatment solution comprises a mixture of chemically reactive agents generally used for Kraft pulping to provide nucleophilic sulfide and/or bisulfide ion or moiety for rupturing the embedment of lignin in the cellulose scaffold of natural lignin. The reactive sulfur containing agents are usually provided as (dissolved) salts, but they may also be provided as non-salt agents, e.g. as (dissolved) organic compounds, which comprise one or more sulphur or sulphur-based chemical functionalities. Generally, any suitable reactive agent known in the art for use in the impregnation and cooking step of the Kraft process may be employed according to the present invention. Other than the sulfur containing reagents, further agents added to the solution in step (1.2) in lower amounts are typically one or more of sodium carbonate, sodium sulfate, sodium thiosulfate, sodium chloride, and calcium carbonate.

Preferably, either of the sulfide and/or sulfate salt comprised in the alkaline solution used in the Kraft process according to (a) is a salt with a cationic counter ion preferably selected from the group consisting of sodium, calcium, magnesium and ammonium. The sulfhydryl and/or polysulfide agent employed by the Kraft process according to (a) is preferably an organic, non-salt agent.

By sub-step (ii) of the Kraft process, the preferably chopped lignocellulosic material is typically initially saturated with the aqueous alkaline solution, e.g. with the fresh ("white liquor") treatment solution or with its recycled equivalent ("black liquor"). The step is preferably designated as the "impregnation step", which may be performed before the chopped lignocellulosic material is forwarded to the vessel for the cooking process (sub-step (iii)) to occur within the vessel. For sub-step (ii), the preferably chopped lignocellulosic material is typically not exposed to elevated temperatures (corresponding to the cooking temperature), but just "pre-treated". Accordingly, the material is not or only gently heated for that pre-treatment step.

Additional reactive agents may be added to the treatment solution to improve the Kraft impregnation of e.g. the employed wood chips with the cooking liquor. Anthraquinone may be used as such an additive. It typically acts as a redox catalyst by oxidizing cellulose and reducing lignin. It protects cellulose from its degradation and makes the lignin component of the starting material more water-soluble. Further, an emulsion breaker may be added in an optional soap separation step to expedite and improve the separation of soap from the cooking liquors by flocculation, once they have been used. Soap, such as rosin soap, generally forms as by-product of the Kraft process. The soap typically floats at the surface of the aqueous liquid and has to be skimmed off. The collected soap may be further processed to tall oil. Advantageously, defoamers may be employed to remove eventually formed foam and foster the pulp production process. Drainage of washing equipment gives cleaner pulp. Dispersing agents, detackifiers and/or complexing agents preferably allow to keep the process vessels cleaner and to reduce the number of maintenance operations. Fixation agents may be used to allow finely dispersed material to be deposited on the fibres, thereby allowing such material to be readily eliminated.

Generally, aqueous alkaline solution ("liquor") used for impregnation may be applied for the cooking step as well. Hence, the aqueous alkaline solution (treatment solution) used for impregnation in sub-step (ii) in the Kraft process—and likewise the corresponding aqueous acidic solution for the sulfite process—is defined as "cooking liquor" in sub-step (iii). By impregnation in sub-step (ii), the treatment solution (or "cooking liquor") preferably penetrates into the capillary structure of the chopped lignocellulosic material, such that initial reactions with the wood components start at low temperature conditions. Intensive impregnation supports the provision of a homogeneous cook and low rejects. Thereby, a larger portion of lignin is yielded as soluble "Kraft lignin". Usually, about 40-60% of all alkaline pulping liquor is consumed for the continuous type Kraft process in its initial impregnation step.

Preferably, the pH of the aqueous alkaline solution in sub-step (ii) of the Kraft process according to (a) is >10. More preferably, the pH in sub-step (ii) of the Kraft process according to (a) is >12. The temperature of the aqueous alkaline solution in sub-step (ii) of the Kraft process according to (a) is typically less than 100° C., e.g. in the range from 70° C. to 90° C.

Step (iii): Cooking

By sub-step (iii) of the Kraft process according to (a) of the inventive method, the pre-treated (impregnated) preferably chopped lignocellulosic material is cooked in said aqueous alkaline treatment solution as required. The cooking period may depend on the reaction conditions, i.e. the pH, pressure and temperature, and may further depend on the type and strength of the employed chopped lignocellulosic material. For Kraft processing, the material is cooked for several hours, e.g. 3 to 9 hours. Essentially, the Kraft process breaks natural lignin's internal ether bonds by nucleophilic attack of sulfide ($S^{2-}$) and/or bisulfide ($HS^-$) ions or moieties. The function of sulfide in the Kraft process may be two-fold: It may promote and accelerate the cleavage of ether bonds between neighbouring building blocks of lignin's 3-dimensional polymeric structure and it reduces the extent of undesirable condensation.

Preferably, sub-step (iii) of the Kraft process is carried out in a pressurized vessel ("digester") for at least 2 hours at a temperature of at least 150° C. Under such conditions, pulp and modified lignin-derived components may be separated from each other. Sub-step (iii) of the Kraft process is preferably carried out at a pressure of at least 4 bar in the pressurized vessel, preferably at 5 to 10 bar. A pressurized vessel is typically a digester as it is commonly used in the art of chemical pulping.

It is preferred that sub-step (iii) of the Kraft process is carried out at a temperature of 150 to 190° C., preferably 170 to 180° C. Such temperatures typically provide higher yields (by improved separation of the lignin and the cellulosic fraction) and process efficiency. Increasing the temperatures significantly beyond 200° C., in particular in combination with the applied overpressure may lead to undesired excessive degradation of the lignin and/or the cellulosic fraction and is unfavorable in terms of energy consumption.

Sub-step (iii) of the Kraft process is preferably carried out for 2 to 24 hours, preferably 3 to 5 hours. Such conditions typically enable satisfying yields, while still ensuring overall process efficiency. Under such conditions of the Kraft process, lignin polymers and hemicellulose are sufficiently degraded, such that their lower molecular weight (lower than the starting material's natural lignin and hemicellulose) degradation products are released from the cellulose scaffold as a result of the cooking step. Such lower molecular weight degradation products are typically more soluble in (strongly) basic solution than the polymers of the lignocellulosic starting material.

Sub-step (iii) of the Kraft process may be carried out either in a batch mode or in a continuous mode. For the continuous mode, the lignocellulosic starting material is fed into a digester at a rate, which allows the pulping reaction to be complete by the time the materials exit the reactor. The continuous mode is preferred to ensure higher throughput and improved efficiency. Digesters producing 1.000 tons or more of pulp per day are common and may be used according to the inventive method.

The modified lignin-derived components obtained from sub-step (iii) of the Kraft process are commonly known as "Kraft lignin". These components are essentially unsulfonated or at least less sulfonated than "lignosulfonate" resulting from the sulfite process according to alternative (b) of sub-step (1.2). Typically, they are more soluble in aqueous alkaline solution, preferably at a pH of greater than about 9 and reasonably soluble in strongly polar organic solvents. The average molecular weight of the lignin-derived components is generally between 1.000 and 4.000 Da, preferably 2.000 to 3.000 Da. Usually, the average component of that lignin-derived fraction comprises about 10 to building blocks, preferably 10 to 25 building blocks, and thus, may have a "polymerization degree" of 10 to 35, preferably 10 to 25. The lignin-derived material typically exhibits a polydispersity of between 2 and 4, although it can be as high as 8 or 9. Material of such higher values of polydispersity may be typically employed for industrial grade applications, but does usually not allow its subsequent exploitation as basic material for the provision of a larger variety of organic target compounds as envisaged by the invention. Accordingly, polydispersity of the material obtained by sub-step (iii) of the Kraft process should not go beyond 6, preferably should be less than 5 or from 2 to 5. A "molecular formula" of $C_9H_{8.5}O_{2.1}S_{0.1}(OCH_3)_{0.8}(CO_2H)_{0.2}$ was previously reported for softwood Kraft lignin. About 4% by weight is typically free phenolic hydroxyl. (Lebo, S. E. et al, Lignin, Kirk-Othmer Encyclopedia of Chemical Technology, p. 18 of on-line version, (2001), John Wiley & Sons, Inc.). Kraft process-derived modified lignin-derived components typically also comprise biphenylic moieties, in particular when using lignocellulosic starting material being of spruce origin. Hence, spruce may be the preferred starting material for the inventive method, if dimeric biphenylic target products are desired.

Step (iv): Sulfonation

In order to obtain material from the Kraft process exhibiting an increased water-solubility over a wider pH range, i.e. for acidic and neutral pH milieu, sub-step (iv) may optionally be included into the Kraft process. That sub-step is preferably a sulfonation step. Therein, sulfonating agents known in the art, such as a solution of preferably concentrated sulfuric acid, may be added. Aliphatic side chains are typically sulfonated, e.g. by the introduction of sulfonyl moieties as substituents of side chains of Kraft lignin. Sulfonation may occasionally also affect the aromatic rings of the Kraft lignin components.

By sulfonation of Kraft lignin, sulfonated modified lignin is obtained, which is herein understood as "sulfonated Kraft lignin".

Generally, sulfonation of sub-step (iv) of the Kraft process confers increased solubility and surfactant properties to Kraft lignin. "Sulfonated Kraft lignin" shares characteristic structural or functional properties with "lignosulfonate" of the sulfite process, such as water solubility over a broader pH range. Both, Kraft process-derived "sulfonated Kraft lignin" and sulfite process-derived "lignosulfonate" are referred to as "sulfonated lignin". Kraft process-derived "sulfonated Kraft lignin" and sulfite process-derived "lignosulfonate" are generated under distinct chemical conditions resulting in structural distinct lignin-derived compositions. The average molecular weight of components of "sulfonated Kraft lignin" is typically lower than the average molecular weight of components of "lignosulfonate" resulting from the sulfite process. Accordingly, the molecular weight of the components of sulfonated Kraft lignin may typically be about 1.000 to 4.500 Da, preferably 2.500 to 3.500 Da.

For sulfonation according to sub-step (iv) of the Kraft process, overpressure and/or increased temperature may be applied. After a reaction period of preferably at least two hours, sulfonated Kraft lignin may be recovered, e.g., by water removal or by precipitation, e.g. with excess lime, as calcium lignosulfonates. As sulfonation confers improved water solubility properties to Kraft lignin, it makes such sulfonated lignin-derived material easier to separate in an aqueous environment from insoluble cellulosic material. In standard pulp and/or paper manufacturing plants operating under the Kraft process, additional sulfonation step (iv) (which may also be designated as "postsulfonation" for Kraft lignin) is therefore typically beneficially applied.

Sulfonation sub-step (iv) of the Kraft process is preferably carried out at a temperature below 300° C., more preferably below 200° C. Such elevated temperatures preferably ensure both sufficiently high yields of sulfonated reaction products, while it avoids premature, i.e. uncontrolled thermal degradation of the lignin-derived Kraft lignin material. Thereby, it is ensured that the lower molecular weight (as compared to the natural lignin polymers) aromatic lignin-derived components remain intact (without uncontrolled degradation) for their further processing towards the inventive method's target compounds. Low molecular weight monomeric or dimeric target compounds are obtained by well-controlled decomposition of the modified lignin-derived components in downstream method step (3), followed by subsequent isolation (purification) in step (4). Accordingly, the largest portion of modified lignin-derived components possible resulting from step (2) shall be made available for controlled decomposition in downstream step (3). Otherwise, the yield of the target compound would be unfavorably reduced.

(b) Sulfite Process

Alternatively, the "sulfite process" may be employed in sub-step (1.2), which is the second most prevalent pulping process worldwide. It is typically a low pH pulping process (although it may be conducted between pH 2 and 12) in aqueous solution containing one or more of salt or non-salt agents exhibiting one or more of sulfite or bisulfite groups or anions. For the sulfite process, the lignocellulosic starting material is treated in aqueous solution at elevated temperature and pressure. The process yields "lignosulfonate", which is typically soluble in water and in some highly polar organics and amines. Lignosulfonate is generally more water-soluble than "Kraft lignin". Sulfite pulping is generally less destructive than Kraft pulping, i.e. the natural lignin polymer is degraded to modified lignin-derived components being larger (and in particular exhibiting a higher average molecule weight and higher monomer molecular weights) than the corresponding components in Kraft pulping. Thus, "lignosulfonate" typically has a molecular weight of about 3.000 to 100.000 Da, preferably 5.000 to 20.000 Da.

In contrast to the Kraft process, the sulfite process is referred to as alternative method step (b). The sulfite process may preferably comprise the sub-steps of (i) optionally pre-steaming the (preferably chopped) lignocellulosic material, wherein the (preferably chopped) lignocellulosic material is advantageously wetted and preheated with steam, (ii) adding the (preferably chopped) lignocellulosic material to an aqueous, preferably acidic solution comprising a sulfite and/or bisulfite salt, and (iii) cooking the (preferably chopped) lignocellulosic material, which is provided (e.g. dispersed or and/or suspended) in said aqueous, preferably acidic, solution.

In the sulfite process, the resulting solid cellulose fibres are obtained by using salts of sulfurous acid to separate the lignin fraction from natural lignocellulosic starting material, such as wood chips, e.g. in digesters preferably operating at larger pressure. The salt anions used in the pulping process may either be sulfites ($SO_3^{2-}$), and/or bisulfites ($HSO_3^-$), depending on the pH. At lower pH, i.e. under stronger acidic conditions, such as less than pH 2.5, the sulfite is typically provided as $HSO_3^-$. Counter cations may be sodium ($Na^+$), calcium ($Ca^{2+}$), potassium ($K^+$), magnesium ($Mg^{2+}$) or ammonium ($NH_4^+$). Particularly divalent (e.g. earth alkali) cations, such as calcium and/or magnesium, may be used as the counter cation. Sulfite pulping is preferably carried out under acidic conditions, preferably at a pH below 5, preferably from pH 1.5 to 5 or 1.5 to 4. The (acidic) pH may be adapted depending on the nature of the counter cation for the sulfite (bisulfite) anion. The preferred salt is calcium bisulfite, which may advantageously be employed, if the selected pH value for the sulfite process is 2.5 or less. Higher pH sulfite pulping (at a pH above pH 2.5 or, more specifically, above pH 4) generally employs monovalent ions, such as sodium or ammonium, as counter cations. However, it is not excluded that sulfite pulping may be carried out over a wider pH range, including alkaline conditions of about pH 7 to 12.

Step (i): Pre-Steaming

Optional sub-step (i) of the sulfite process is conducted as is sub-step (i) in the Kraft process (see above). Therefore, preferably chopped lignocellulosic material (such as woodchips) may be pre-treated with hot steam. Thereby, the preferably chopped lignocellulosic material is wetted and heated, which typically renders it more susceptible to adsorb treatment solutions as applied by subsequent sub-step (ii). Cavities of fresh wood are filled with fluids and/or air. Steam pre-treatment causes the air to expand. About 25% of the air and/or other fluids naturally occupying the cavities is thereby expelled from these cavities.

Step (ii): Addition of Sulfite or Bisulfite Salt

In sub-step (ii) of the sulfite process, the lignocellulosic material may be brought into contact with an aqueous, preferably acidic sulfite and/or bisulfite containing solution used as a pulping reactive agent (or "pulping liquor").

The "pulping liquor" used in sub-step (ii) of the sulfite process may be provided as follows: Sulfur may be oxidized (burnt) with the stochiometrically adequate amount of oxygen to yield sulfur dioxide. Sulfur dioxide is preferably added, e.g. as a gas, to water to give Sulfurous acid, which may be further diluted for its use as "pulping liquor".

Preferably, the sulfite or bisulfite salt comprised in the aqueous (preferably acidic) solution in step (ii) of the sulphite process is a salt with a cationic counter ion preferably selected from the group consisting of sodium, calcium, magnesium and ammonium. The preferred salt is calcium bisulfite.

For sub-step (ii) of the sulfite, the pH of the aqueous preferably acidic solution is preferably 1 to 5 and more preferably 1.5 to 4. The temperature of the aqueous (preferably acidic) solution in sub-step (ii) of the sulfite process is also typically less than 100° C., e.g. from 70° C. to 90° C.

Step (iii): Cooking

The lignocellulosic material may be brought into contact with the pulping reactive agents for more than three hours, preferably 4 to 14 hours.

Sub-step (iii) of the sulfite process according to (b) is preferably carried out at a temperature of 120 to 170° C., more preferably at a temperature of 130 to 160° C. The temperature is thus typically above 120° C., preferably ranging from 130 to 160° C., depending on the reactive agents and their concentrations used.

Preferably, cooking in sub-step (iii) of the sulfite process is carried out in a pressurized vessel for at least 3 hours at a temperature of at least 120° C. Under such conditions, pulp and modified lignin-derived components may be separated from each other. Sub-step (iii) of the sulfite process according to (b) is preferably
carried out at a pressure of at least 4 bar in the pressurized vessel, preferably at to 10 bar. A pressurized vessel is typically a digester as it is commonly used in the art of chemical pulping.

Preferably, sub-step (iii) of the sulfite process is carried out for 2 to 24 hours, preferably 4 to 6 hours.

Preferably, sub-step (iii) of the sulfite process is carried out either in a batch mode or in a continuous mode. For the continuous mode, the lignocellulosic starting material is fed into a digester at a rate, which allows the pulping reaction to be complete by the time the materials exit the reactor. The continuous mode is preferred to ensure higher throughput and improved efficiency. Digesters producing 1.000 tons or more of pulp per day are common and may be used according to the inventive method.

The modified lignin-derived components resulting from the sulfite process are generally designated as "lignosulfonate". Due to the nature of the sulfite process, "lignosulfonate" typically contains significant amounts of sulfur-based moieties (typically in the form of sulfonate groups), for example, in the aliphatic side chains of the modified lignin-derived components.

"Lignosulfonate" is thus a complex (heterogeneous) mixture of modified lignin-derived components, i.e. water-soluble anionic lignin-derived polyelectrolytes, which carry —$SO_3H$ functional groups. Lignosulfonate typically exhibits by its heterogeneous components a broad molecular weight range (broader than observed for Kraft lignin). Lignosulfonate is polydisperse with a polydispersity being typically higher than that of the Kraft process (about 4 to 9). As the sulfite process is less destructive than Kraft pulping, it does not degrade lignin to the same extent as the Kraft process. Thus, sulfite process-derived lignosulfonate typically has a higher average molecular weight than Kraft lignin as described herein. A maximum molecular weight of 140.000 Da is reported for softwood lignosulfonates, while maximum values for hardwoods are usually lower, e.g. lower than 50.000 Da. The typical range of the molecular weight for lignosulfonate polymers is about 5.000 to 50.000 Da, preferably about 5.000 to 20.000 Da (Brogdon, B. N., Dimmel, D. R. J. Wood Chem. Technol. 1996, 16, 297). Usually, it comprises about 10 to 300 building blocks, preferably 20 to 200, most preferably 25 to 150 building blocks, and thus, may have a "polymerization degree" of 10 to 300, preferably 20 to 200, most preferably of to 150. It typically exhibits a higher sulfur content (about 3% to 8% w/w) than (unsulfonated) Kraft lignin (having a sulfur content of typically less than 1% w/w).

Lignosulfonates are used in the art as low-value chemicals in tanning leather, making concrete, drilling mud and drywall, such as binders or additives for building material.

Sulfite process-derived lignosulfonates are typically soluble in water over essentially the entire pH range. Sulfite process-derived lignosulfonate may also be soluble in highly polar organic and amine solvents. Its approximate "molecular formulas" are described as $C_9H_{8.5}O_{2.5}(OCH_3)_{0.85}(SO_3H)_{0.4}$ for softwood or as $C_9H_{7.5}O_{2.5}(OCH_3)_{1.39}(SO_3H)_{0.6}$ for hardwood, respectively, as starting material for sulfite process-derived lignosulfonate. Sulfite process-derived lignosulfonate may comprise biphenylic moieties for some of the components of the larger number of components representing the "lignosulfonate" fraction. That holds specifically for lignocellulosic material of spruce origin. Hence, spruce may be the preferred starting material for the inventive method, if biphenylic precursor or target compounds are desired.

(c) Alternative Methods
Organosolv Process

As a further alternative, the "organosolv process" is typically carried out by treatment of wood or bagasse with various organic solvents. "Bagasse" is the fibrous residue that remains once plant material (such as sugar cane) has been crushed and juice or sap have been extracted. The "Alcell process" is one of the most well-known organosolv processes. It finally involves dissolution of lignin in either ethanol or ethanol/water mixtures. The advantage of the organosolv process is that it allows to automatically generate separate process streams of cellulose, hemicelluloses, and lignin. Thereby, all components of the lignocellulosic biomass starting material may be individually processed. That process is generally considered as environmentally attractive, as it does not employ aggressive reactive agents (e.g. sulfides) and harsh conditions used in the more common Kraft or sulfite processes. The organosolv process typically yields organosolv lignin as the modified lignin-derived components, which may be employed in further downstream reaction steps of the present invention. Organosolv lignin is therefore typically low in sulfur content. It has a low molecular weight of about 1.000 to 2.000 Da. It is typically also of higher purity than the lignin-derived components obtained from other pulping processes. A disadvantage of the organosolv process are the costs of solvent recovery.

Steam Explosion Process

Another pulping process, which may be employed by the present invention, is the "steam explosion process" involving steam impregnation under pressure followed by rapid pressure release, which separates the lignocellulosic constituents. Covalent linkages of 3D lignin are ruptured as well, such that a complex mixture of lignin derived fragments is obtained. Typically, wood or bagasse is exposed to steam at overpressure and elevated temperature, such as a total pressure of 1.38 to 3.45 MPa and a temperature from about 180° C. to about 230° C. for about 1-20 min before rapid pressure release. The molecular weight distribution of the lignin fragments obtained by the steam explosion process is typically similar to the organosolv process. In addition, the process uses no sulfur, and separating the process streams is also possible.

Pyrolysis

Pyrolysis of lignocellulosic material (as a further alternative of sub-step (1.2)) generally leads to pyrolyzed lignin-derived fragments, which may also be considered as modified lignin-derived components to be employed by the present invention. The pyrolysis process typically involves relatively high temperatures, typically at least 600 K, such as between 720 and 750 K. No waste other than flue gas and ash is produced by that process, whereas increased energy consumption is required to fuel the process. Pyrolysis lignin exhibits structural characteristics significantly different from lignin components obtained from other "pulping processes". It involves $C_8$— rather than $C_9$ building blocks, potentially allowing for unique downstream reactions according to the present invention. Thereby, specific aromatic hydrocarbons are made available as target compounds, which are not available via other processes.

Other Methods

Several other methods for isolating (modified) lignin from wood or plant biomass or starting material are described in the art as well, including the "ammonia fibre explosion" (AFEX) process and the "hot water process", which may also be employed as sub-step (1.2), which are described in further detail by Bozell et al. (Top Value Added Candidates from Biomass. Volume II: Results of Screening for Potential Candidates from Biorefinery: Lignin; Pacific Northwest National Laboratory: Richland, Wash., 2007) and Kamm et al. (Biorefineries—Industrial Processes and Products; VCH: Weinheim, Germany, 2006; Vol. 2). Finally, the "dilute acid process" as a further option for sub-step (1.2) of the inventive method may ensure effective separation of lignin from other biomass components. It may, however, provide lower yields. Corrosion of equipment (due to the acidic environment) may also be an issue. The "alkaline oxidation process" may use $O_2$ or $H_2O_2$ to degrade lignin. However, the process may suffer from slower delignification rates. The dilute acid process and alkaline oxidation process may both provide modified lignin-derived components with similar molecular weight (distributions) as organosolv lignin.

Lignin-Derived Components

Generally, modified lignin-derived components, such as (sulfonated) "Kraft lignin" and/or "lignosulfonate", are typically dissolved or dispersed in the consumed pulping liquor, once processed according to sub-step (1.2). Said liquor (process stream leaving step (1.2)) usually also comprises most of the hemicellulose and/or its hydrolysis products (poly-, oligo and/or monosaccharides) in dissolved form.

The lignin-derived fraction of any pulping process is preferably forwarded to separation sub-step (1.3) for its further processing towards the low molecular weight target compound. In particular, "Kraft lignin" upon application of sub-steps (i) to (iii) of the Kraft process according to (a), or "lignosulfonate" upon application of the sulfite process according to (b) or "sulfonated Kraft lignin" upon application of sub-steps (i) to (iv) of the Kraft process according to (a) may be employed for further processing by sub-step (1.3).

Further downstream, the method of the present invention thus typically employs the steps of separating pulp in sub-step (1.3) from the process stream and, subsequently, isolating the fraction of modified lignin-derived components in step (2) from other components being present in the process stream.

Sub-Step (1.3): Pulp Separating Step

In step (1.3), the pulp obtained in sub-step (1.2) is separated in a pulp separating step from the process stream obtainable from the pulping process in sub-step (1.2), to provide a substantially pulp-free process stream.

Hereby, the process stream of sub-step (1.2) is converted to (i) an essentially pulp-free stream with enriched fractions of modified lignin-derived components, hemicellulose and/or fragments of any thereof and/or inorganic material, and (ii) pulp, which is understood herein to essentially comprise a mixture of (enriched) cellulose fibrous material.

The pulp fraction may be separated by sub-step (1.3) as dry matter or as a pulp containing stream. Sub-step (1.3) may be carried out by any suitable separation method preferably selected from the group consisting of blowing, sieving, countercurrent flow, centrifugation, filtration, washing, stripping, ion-exchange, or any combination thereof. Separation of the pulp from the process stream is more preferably carried out by blowing, sieving and/or washing. The pulp or pulp containing stream is further processed according to state-of-the-art technologies for, e.g., manufacturing paper. The stream(s) containing the fraction of modified lignin-derived components is subjected to step (2) of the inventive method for isolation of said modified lignin-derived components.

As used herein, a "stream" "or process stream" is generally understood as a liquid medium comprising intermediates of the inventive method resulting from the preceding method step, which serve as starting (process) material for the subsequent method step. Generally, the stream includes its components dissolved, suspended or dispersed in said liquid medium. Distinct fractions of the (process) stream may be obtained reflecting components of homogenous nature, which may be isolated by fractionation from the process stream.

A "fraction" may represent a part of a whole or, more generally, any number of (equal) parts. In particular, a fraction is understood herein to be a part of a (process) stream according to the present invention, which typically comprises at least two different fractions.

Accordingly, different fractions may be organic matter comprising (residual) cellulosic material and non-cellulosic material such as modified lignin-derived components (e.g. Kraft lignin or lignosulfonate) and hemicelluloses. Further, fractions of a stream according to the present invention may be inorganic reactive agents, which are required to run the process, e.g. inorganic buffer salts. Another fraction, typically the largest both in terms of volume and mass, is the solvent/dispersant. The solvent usually is an aqueous solvent/dispersant from the pulping process, which may be diluted or concentrated in the steps following sub-step (1.2), which is herein understood to form a part of the total dry mass carried in the stream according to the present invention. A particularly important fraction of the stream in the context of the present invention is the fraction of modified lignin-derived components.

As a derivative of natural lignin, the "modified lignin-derived component" is a lignin molecule, which underwent a pulping process, such as "Kraft lignin" or "lignosulfonate". A "modified lignin-derived component" typically has a lower molecular weight than natural lignin, from which it is derived. However, the "modified lignin-derived component" is larger than the low molecular weight lignin-derived compound, preferably having a molecular weight of at least 1.000 Da. The nature (and the actual molecular weight) of the "modified lignin-derived component" may vary largely depending, e.g., on the starting material, on the (pulping) method, by which the modified lignin-derived component is obtained, and on the reaction conditions applied by the inventive method. However, it is common to the modified lignin-derived components that they are composed of C8 or C9 building blocks after, e.g., a pulping process, as they occur in natural lignin.

It follows from natural lignin's complex and somewhat random chemical structure that lignin-derived components, such as products of the pulping process, are typically heterogeneous. The pulping process provides a larger variety of lignin-derived components, which may typically contain from 8 to 150 building blocks. Moreover, lignin-derived components of the same number of building blocks are also diverse in terms of their chemical nature, as they reflect individual portions of the heterogeneous natural lignin polymer. That chemical and structural heterogeneity of lignin-derived material obtained from e.g. the pulping process traditionally impeded the preparation of homogeneous and/or high quality products by prior art methods, such that adequate economic exploitation of lignin-derived material was difficult to achieve in the art. That prior art issue is overcome by the inventive method.

Pulping processes, nevertheless, typically yield "modified" lignin-derived components based on $C_8$ or $C_9$ building blocks, wherein some or all of the building blocks may be modified. Modifications preferably occur at the linking groups of those building blocks of natural lignin, which are dissociated by the pulping process, and/or at substitution sites of the building blocks, in particular at the aromatic ring system of a building block, e.g. by side chain modification or e.g. by sulfonation. Accordingly, the molecular weight of the modified building blocks of lignin-derived components may typically be slightly higher than the molecular weight of the building blocks of the natural lignin polymer.

Typically, "modified lignin-derived components" as used herein are present as a fraction of a (process) "stream". Such a stream may comprise residual or waste material and the solvent and/or dispersant from which the intermediate of interest is preferably isolated. Typically, the solvent and/or dispersant accounts for at least 50% (w/w) of the total weight of material forwarded as a "stream" to the next method step, or at least 60% (w/w), preferably for at least 70% (w/w), or at least 80% (w/w). The solvent and/or dispersant is typically an aqueous medium, but may alternatively be an organic solvent, depending on the pulping process. Generally, the stream flows unidirectionally, from the preceding method step to the more downstream method steps. Valves, pumps and/or gravity-assisted means may typically be employed to facilitate the required flow of the stream downwards to the final step of the method of the present invention.

Typically, upon pulping, the lignin in the lignocellulosic material is broken into smaller molecules, which are more soluble in the pulping liquid. Cellulose is degraded to a minor degree, although individual cellulose fibres may detach from the chopped lignocellulosic material during the pulping process and dissolve rather in the pulping liquid than natural lignin. As a consequence, a residual cellulosic scaffold remains. However, to a varying degree, cellulose fibres are also present in the liquid in dispersed form, i.e. not in the larger scaffold structure of fibres.

In sub-step (1.3) of the inventive method, preferably both the scaffold and the dispersed cellulose fibres are separated from the process stream. A preferred way of separating the cellulose which is present in the scaffolds, is "blowing" the cellulose scaffold of the chopped lignocellulosic material, which underwent the pulping of sub-step (1.2), into a collection tank ("blow tank"). The residual cellulosic scaffolds may be blown into a blow tank that usually operates at atmospheric pressure. This blowing typically releases steam and volatiles. Volatiles are understood herein as organic chemicals that have a high vapour pressure at ordinary room temperature. Typically, they are characterized by an individual oder. The volatile fraction may be condensed and collected. When employing "northern softwoods" as the starting material for the present invention, the volatile fraction typically encompasses raw turpentine.

The pulp separation in sub-step (1.3) may preferably further comprise to separating cellulose from the liquid, which was not blown out as part of the blown out residual cellulosic scaffold, e.g. the dispersed cellulose fibres. The pulp separation according to sub-step (1.3) may encompass distinct sieves or screens and/or centrifugal separation. The sieves are typically arranged in a multistage cascade-like assembly. By such an arrangement, considerable amounts of pulp is preferably captured, and thus, separated from the process stream containing the fraction of interest according to the inventive method, i.e. the fraction of modified lignin-derived components.

The process stream (optionally subject to blowing, sieving and/or filtration) may also undergo one or more washing steps to separate pulp. Thereby, (residual) dispersed cellulose fibres are separated from the process stream. Usually, a pulp mill encompasses 3-5 washing stages in series. Pulp washing as used herein is typically carried out by pulp washers using counter-current flow in between two subsequent stages such that the pulp moves in the opposite direction to the flow of washing water. While the washing water becomes a part of the process stream comprising the target modified lignin according to the present invention, cellulose is effectively separated and ready for conventional use such as paper production. Various techniques may be involved in pulp washing, such as thickening/dilution, displacement and diffusion. The washing equipment may comprise, for example, pressure diffusers, atmospheric diffusers, vacuum drum washers, drum displacers and wash presses.

Said pulp separation step or steps may provide an essentially pulp-free process stream as a result of sub-step (1.3). Therein, the essentially pulp-free process stream, which contains the modified lignin-derived components, may be provided as one single process stream (a) or may be partitioned in at least two (partial) process streams (b) in a further stream separation step.

By said stream separation step, the sum of the flow rates of the partial streams is typically equal to the flow rate prior to the stream separation step. The flow rate of each of the two or more partial streams may correspond to e.g. up to 50%, 33%, and 25% etc. of the flow rate of the initial pulp-free process stream prior to the division. Alternatively, one of the partial streams may exhibit a higher flow rate than the other partial stream(s). Typical percentile ratios of flow rates may be 5:95, 10:90, 15:85, 20:80, 25:75, 30:70, 35:65, 40:60 and 55:45. When dividing e.g. into three partial streams, each process stream may have a flow rate corresponding to one third of the flow rate of the stream. Alternatively, one or two partial streams may have a flow rate higher or lower than the third stream, provided that the sum of the flow rates of the partial streams preferably equals the flow rate of the initial stream. Thereby, e.g. modified lignin-derived components comprised in all partial streams may be simultaneously supplied to (conventional) combustion as an energy source, to further processing according to the inventive method and, e.g., to storage facilities, e.g. a container. Hence, said stream division may provide a "buffer capacity" depending on the status of the plant and the turnover of the method as a whole, which adds versatility and efficiency to the method, preferably without generating extra waste.

Separating the stream for further processing in downstream steps may be carried out by technical means known in the field of fluid process technology. Preferably, the separation means are adjustable in such a way, that defined portions of the single process stream according to (a) may be mechanically divided into two or more, three or more or four or more partial streams. The means for dividing may be selected from a flap, hatch, clack, lid, valve, damper or shutter or a combination thereof. Said means may operate electrically and/or hydraulically. Alternatively, the stream may be divided into partial streams by vacuum and/or pressurized gas, i.e. portions of the stream may be sucked or blown into two or more passages. Therein, a passage is understood as any form of duct, which passes the respective stream to its next stage. The dividing means and/or of the passages conducting the partial process streams are typically made of non-corroding metal, preferably coated or non-coated stainless steel.

The essentially pulp-free stream, which is herein forwarded for its further processing in step (2), is commonly designated as "black liquor" (due to its color), when applying the Kraft process or "brown liquor", when applying the sulfite process in step (1.2). It typically comprises modified lignin-derived components and random fragments thereof (i.e. lignin-derived molecules formed during the pulping process, but having a lower molecular weight than the typical modified lignin-derived components) and hydrolysis products of hemicellulose. Hemicellulose is typically hydrolysed in any pulping process, e.g. in acidic or alkaline medium, yielding smaller pieces of hemicellulose such as poly- or oligosaccharide fragments or even mono- or disaccharides thereof, which are all usually dissolved in the pulping liquid and/or the process stream. Further, (in)organic salts as residual components of the reactive agents used for the pulping process may be comprised in the essentially pulp-free process stream, such as sodium carbonate and/or sodium sulfate.

Step (2): Isolation of Modified Lignin-Derived Components

After the pulping process according to sub-step (1.2), the fraction of modified lignin-derived components comprised either in the single process stream provided by sub-step (1.3(a)) or in at least one of the at least two (partial) process streams provided by sub-step (1.3(b)) is isolated from the process stream(s) and its/their other components (e.g. hemicellulose and/or hydrolysis products thereof). Dividing the product stream into partial product streams adds flexibility to the control of the yield envisaged for the fractions comprised in the essentially pulp-free process stream. Modified lignin-derived components are thus either isolated from the single process stream (obtained from 1.3(a)) or from at least one of the at least two partial process streams (obtained from 1.3(b)) Therefore, by alternative (b), isolation of the fraction of modified lignin-derived components is applied to one or more of the partial streams provided at the stage of sub-step 1.3(b).

In other words, isolation of modified lignin-derived components as described below may be accomplished from a single process stream obtained from sub-step (1.3 (a)) or from one of several (partial) process streams obtained from sub-step (1.3(b). Several process streams are provided from the single process stream of (1.3(a)) by separating (or dividing) said process stream into two or more (partial) streams. This allows to control the amount of the modified lignin-derived components further processed according to the inventive method. Hence, stream separation is a tool to fine tune the inventive method when determining its flow rate and turnover of the process. By dividing the stream into two or more partial streams, supply of modified lignin-derived components either to downstream process steps (3) and (4) may be controlled as well.

Modified lignin-derived components present in either a single process stream or in two or more (partial) process streams obtained from sub-step (1.3) are isolated from said process stream(s) as described below.

Isolation, i.e. controlled removal, of the fraction of modified lignin-derived components from the process stream(s) may be controlled by the isolation means applied, e.g. by the parameters applied (e.g. the amount of precipitation agent, pH, extraction or filtration characteristics. Isolation may be applied to all or part of the partial process streams (if present). Typically, the essentially pulp-free process stream provided by sub-step (1.3) is divided into two partial process streams (1.3(b)), with one of them subjected to isolation of the fraction of modified lignin-derived components from the process stream and the other partial process streams being used for combustion and/or other uses.

In particular, the fraction of modified lignin-derived components may be isolated from the solvent and/or dispersant of the process stream, such that the fraction of modified lignin-derived components may be obtained as dry matter. It may then be re-dissolved in a suitable solvent or dispersed in a suitable dispersant, e.g. an aqueous solvent or dispersant, to be further processed in the subsequent method step. Alternatively, the fraction of modified lignin-derived components may be enriched, e.g. by reducing the solvent and/or dispersant content of the fraction of modified lignin-derived components, such that a concentrated solution or dispersion is provided.

Isolation of step (2) may be carried out by any appropriate means employed in the field of solid-fluid or fluid-fluid separation. The isolation may, for example, involve filtration, extraction, counter current flow separation and precipitation. Any technology may be used according to step (2) of the invention to control the amount of isolated modified lignin-derived components, which may then be subjected to further processing.

Step (2), i.e. isolation of the fraction of modified lignin-derived components from other (e.g. hemicellulosic) components in the process stream, may preferably be carried out by filtration including ultra- and/or nanofiltration, extraction, countercurrent flow, stripping, ion-exchange, precipitation by di- or multivalent cations, such as calcium cations (which may e.g. be provided as calcium hydroxide), precipitation by $CO_2$ in acidic solution, or any combination of thereof.

(a) Filtration

Preferably, isolation is carried out by any type of extraction or filtration, preferably ultrafiltration and/or nanofiltration.

"Filtration" is hereby understood as a physical purification or enrichment method involving membrane technology by permeable membranes. Membranes are characterized by their nominal pore size. It typically describes the maximum pore size distribution. As that parameter provides only vague information about the retention capacity of the membrane, the "cut-off" is typically used as the parameter to characterize separation properties of membrane-associated filtration. The exclusion limit or "cut-off" of the membrane is usually specified in the form of NMWC (nominal molecular weight cut-off, or MWCO, molecular weight cut off, with units in Dalton). It is commonly defined as the minimum molecular weight of a globular molecule that is retained to 90% by the membrane. In practice, the MWCO of the membrane should be at least 20% lower than the molecular weight of the molecule that is to be separated. For example, a 1 kDa filter is suitable to let pass a small molecule with a molecular weight of, e.g., 500 Da, while the larger modified lignin-derived components of a molecular weight of, e.g., 2.000 Da are not able to pass.

Preferably, filtration is used herein to isolate, in step (2), the dispersed or suspended modified lignin-derived components obtained in step (1). The filter cut-off is set in such a way, that it is suitable to discriminate the molecular weight of the target modified lignin-derived components and of other components in the process stream. The other components may be larger (e.g. residual natural lignin and/or fragments thereof having a higher molecular weight than the modified lignin-derived components) or smaller (e.g. reactive agents of the pulping process, hydrolyzed hemicellulose) than the target components. If the target modified lignin-derived components are of a larger molecular weight than all other components in the process stream, the filter is selected to have a cut off such that the target components are typically retained in the filter. Otherwise, if other components are larger—in terms of molecular weight—than the modified lignin-derived components, the cut-off may typically be selected such that the target components may typically be found in the filtrate.

Typically, the filtration in isolation step (2) may be a combination of (different) filtration steps. Therein, for example, in one step the cut off of the filter is selected to be higher than the molecular weight of the modified lignin-derived components. Accordingly, other components with a higher molecular weight are kept in the filter and the modified-lignin-derived components remain in the filtrate, i.e. in the residual process stream. In another step, the residual process stream may be subjected to a second filtration, wherein the cut-off is selected to be lower than the molecular weight of the modified lignin-derived components. Accordingly, the target modified lignin-derived components are retained in the filter and, thereby, isolated from the residual process stream. Thereby, the target components may be obtained as dry matter and may subsequently be dissolved for further processing.

The more the different fractions within the process stream differ in terms of their molecular weight, the more effective may the isolation by filtration be carried out. For example, as the Kraft process typically yields modified lignin-derived components (Kraft lignin) of lower molecular weight than the sulfite process, filtration may be very preferred to separate Kraft lignin from lignin-derived material of higher molecular weight, such as non-modified or re-polymerized lignin-derived material or other debris in step (2).

Ultrafiltration and/or (depending on the size of the lignin-derived components to be isolated) nanofiltration may be preferably employed in step (2). Ultrafiltration typically employs a pore size of 2-100 nm and a molecular weight cut-off value of about 5 kDa. Nanofiltration typically refers to a filtration mode based on a pore size of 1-2 nm and a molecular weight cut-off value of 0.1-5 kDa. Accordingly, ultrafiltration is typically employed to separate or isolate larger lignin-derived components (e.g. larger than 5.000 Da, larger than 8.000 Da or larger than 10.000 Da) from the process stream (containing components of whatever e.g. the lignin-derived fraction or residual cellulosic fraction or the hemicellulosic fraction of a molecular weight of less than 5.000 Da). That isolated larger molecular weight fraction may be subject to further separation in order to separate larger isolated components of distinct fractions, e.g. to isolate the lignin-derived components from residual cellulosic degradation products or hemicellulosic components. The isolated lignin-derived fraction of the molecular weight retained by the chosen cut-off value of the ultrafiltration device may then be further processed in step (3).

Also, the remaining components of the lignin-derived fraction in the process stream having a molecular weight lower than the cut-off level chosen for initial ultrafiltration may be isolated from other components in the process stream. E.g. the (partial) process stream may be subjected to another filtration step with a lower cut-off level than chosen for the initial ultrafiltration step, e.g. by additional lower cut-off level ultrafiltration and/or nanofiltration. Thereby, the lignin-derived components of a molecular weight lower than the cut-off-level of the first filtration step and larger than the cut-off level of the second filtration step may be isolated. That retained lignin-derived fraction may be subject to further isolation to separate the lignin-derived component fraction from components of similar size of other fractions (e.g. from hemicellulosic degradation products of similar size). Accordingly, the inventive method may be set up such that components of the lignin-derived fraction are isolated, which fall within the individually desired smaller molecular weight range of e.g. between 1.000, 2.000, 3.000, 4.000, 5.000 or 6.000 Da (cut-off level of the second filtration step) and 5.000, 6.000, 8.000 or 10.000 Da (cut-off level of the first filtration step). Thereby or by any other method known in the art to separate by molecular weight or by other physico-chemical parameters, a more homogeneous lignin-derived fraction may be forwarded to decomposition step (3).

Accordingly, two ultrafiltration steps or ultrafiltration and nanofiltration, respectively, may e.g. be combined to arrive at a modified lignin-derived fraction of a defined molecular weight range (e.g. 5.000 to 10.000 or 1.000 to 5.000 Da, respectively for Kraft lignin). Whenever isolation from the process stream of the sulfite process-derived lignosulfonate is concerned, such isolation may preferably be performed by employing suitable isolation methods, e.g. as described by Lebo et al. (Lebo, Stuart E. Jr.; Gargulak, Jerry D.; McNally, Timothy J. (2001). "Lignin". Kirk-Othmer Encyclopedia of Chemical Technology. Kirk Othmer Encyclopedia of Chemical Technology. John Wiley & Sons, Inc.), which is incorporated herein by reference. "Lignosulfonate" (due to the larger molecular weight of its components) will preferably be based on two ultrafiltration steps resulting e.g. in a molecular weight range of the isolated lignin-derived components of between 6.000 Da and 15.000 Da or 8.000 Da and 12.000 Da.

Ultra- and/or nanofiltration typically employ membranes, which are preferably tubular membranes exposing solvent resistance, i.e. which are preferably resistant at high and low pH values. Ultra- and/or nanofiltration is typically performed at elevated pressure, preferably above about 2 bar, more preferably at about 3 bar or above, even more preferably at about 4 bar or above, most preferably at about 5 bar. Higher pressures may also be applied, e.g. above 10 bar, such as 10-15 bar. Further, the applied temperature for the filtration step is typically higher than room temperature (25° C.) to facilitate isolation of the fraction of modified lignin-derived components. Usually, the temperature is chosen such that degradation of the components to be isolated is essentially avoided. The temperature may be at least 40° C., preferably at least 50° C., most preferably about 60-65° C.

Hence, the preferred membrane's cut-off size of the employed ultra- or nanofiltration in step (2) may depend on the expected molecular weight of the target modified lignin-derived components. For example, Kraft lignin being of a relatively small molecular weight may require a membrane cut-off of about 2 to kDa or from 2 to 8 kDa, while larger lignosulfonate may require a membrane cut-off of about 5 to 50 kDa or even up to 100 kDa. Typically, the cut-off size for membranes to isolate lignosulfonate may be about 1 to 20 kDa.

If ultra- and/or nanofiltration is applied, it is preferably preceded by a pre-filtration step to separate larger debris, e.g. insoluble or poorly soluble polymers and/or fragments thereof. Thereby, efficiency may be increased as excessive blockade of the ultra- and/or nanofiltration membrane may be avoided, when isolating the fraction of modified lignin-derived components. Accordingly, the pre-filter typically has a larger pore size and/or molecular weight cut-off than the ultra- and/or nanofiltration membrane.

Whether filtration is applied by step (2) or not may depend on whether the modified lignin-derived components are dissolved in the fluid phase or suspended as solid components. Filtration is preferably used for separation of suspended or dispersed solid, i.e. preferably dispersed particles of a size of about >1 µm. By filtration, oversize solid particles are typically retained by the membrane with the yield depending on the character of the modified lignin components, their particle size and the filter's cut off.

Preferably, isolation step (2) thus comprises filtration and/or extraction, preferably ultrafiltration and/or nanofiltration by an ultrafiltration and/or nanofiltration cell, preferably having a pre-filtration section. Filtration in step (2) is preferably carried out in a ultrafiltration and/or nanofiltration cell comprising at least one molecular weight cut-off unit, preferably at least two molecular weight cut-off units, wherein the at least one molecular weight cut-off unit has a cut-off level preferably of 0.5 kDa to 2 kDa.

(b) Extraction

Alternatively, extraction e.g. by means of an organic solvent, may be performed. As used herein, "extraction" is typically a separation process comprising the separation of a desired substance from its environment. It may include liquid-liquid extraction and/or solid phase extraction. Extraction may use two immiscible phases to separate dissolved modified lignin-derived components from the original phase into another. By extraction, organic compounds are extracted by an organic solvent from the aqueous phase. Common solvents for extraction are classified by their polarity from ethyl acetate (lowest polarity) to water (highest polarity):ethyl acetate<acetone<ethanol< methanol<acetone:water (7:3)<ethanol:water (8:2)<methanol:water (8:2)<water, in the order of the Hildebrand solubility parameter. The solution containing the extracted fraction (i.e. the components) may be dried, e.g. by using a centrifugal evaporator or a freeze-drier.

For example, Kraft lignin may be extracted by step (2) from the process stream, if less soluble in an aqueous medium than in appropriate organic solvents (such as methanol, ethanol, acetone and aqueous mixtures thereof known in the art).

Alternative extraction techniques may include supercritical carbon dioxide extraction, ultrasonic extraction, heat reflux extraction, microwave-assisted extraction, instant controlled pressure drop extraction (DIC), and perstraction. Amongst them, perstraction may be preferred. Typically, "perstraction" includes two liquid phases, with only one phase including a solvent for extraction. Perstraction may advantageously be more gentle, faster and cheaper than traditional biphasic extraction techniques. "Stripping" may be employed as another gentle extraction alternative, which allows the fraction of modified lignin-derived components may be isolated from the process stream. "Stripping" is generally a physical separation process, wherein one or more components are removed from a liquid stream by a vapor stream. In industrial applications, the liquid and vapor streams may be employed co-currently or flow countercurrent. Stripping is usually carried out in either a packed or trayed column.

(c) Countercurrent Exchange

Isolation of the fraction of modified lignin-derived components in step (2) may generally be achieved by countercurrent flow, with the flow forwarded in opposite directions. For the inventive method the concentration of dissolved modified lignin-derived components along the concentration gradient may be envisaged. The counter-current exchange method may maintain the gradient of the two flows essentially stable for the entire contact zone. Hence, countercurrent flow is particularly suitable to isolate dissolved modified lignin-derived components and may be less preferred for dispersed modified lignin-derived components.

(d) Precipitation

Further, precipitation may be employed as an isolation method to allow a solid fraction to be isolated from solution. Precipitation may also be employed to control the amount of precipitated modified lignin (within a given time window) by the choice of the added amount of precipitation agent and/or the pH. Preferably, precipitation according to step (2) (d) may be conducted by means of the addition of a cation, preferably a di- or multivalent cation, most preferably of calcium.

Precipitation according to step (2)(d) may be in particular preferred for lignosulfonate or, equivalently, for sulfonated Kraft lignin. Precipitation by pH is less preferred, e.g. for lignosulfonate, as it is generally soluble in water over the entire pH range and may not be readily isolated by pH modification. However, precipitation by calcium salt addition may be preferred. E.g., excess lime (i.e. a calcium-containing inorganic material, in which carbonates, oxides and hydroxides typically predominate) may be added to the process stream, such that calcium lignosulfonate may precipitate. This process is generally known as Howard process. It is the most straight-forward recovery method known. Typically, up to 95% of the stream's lignosulfonate may be isolated by precipitation. Modified lignin resulting from the Kraft process ("Kraft lignin") may be sulfonated in step (1) and thereafter subjected to, e.g., lime precipitation.

The remainder of modified lignin-derived components, which are not further employed by the present invention, may be channeled to the paper manufacturing process or may serve for other applications such as energy provision, or may be stored for later use or may be discarded.

Step (3): Chemical Decomposition

The isolated fraction of modified lignin-derived components of step (2) is subjected to chemical decomposition by step (3), wherein chemical decomposition step (3) may be carried out by (a) oxidative cracking of the modified lignin-derived components, preferably in the presence of a suitable catalyst comprising a metal or a metalloid component. Alternatively, chemical decomposition step (3) may be enabled (b) by reductive cracking of the modified lignin-derived components, preferably in the presence of a suitable catalyst comprising a metal or a metalloid component. The terms "oxidative cracking" and "cracking and oxidizing" may be used interchangeably herein. The terms "reductive cracking" and "cracking and reducing" may be used interchangeably herein. Alternatively, the modified lignin-derived components may be subjected to (c) electro-oxidation, preferably in alkaline or acidic solution, or (d) to any other suitable decomposition method, e.g. "non redox cracking" of the modified lignin-derived components, optionally in the presence of a heterogeneous or homogeneous catalyst comprising a metal ion or a metalloid component. The term "chemical decomposition" refers to the fact that the modified lignin-derived components are chemically decomposed, i.e. with regard to their chemical structure. "Chemical decomposition" thus preferably disrupts or alters chemical bonds, preferably covalent chemical bonds.

Any one of steps (3)(a)-(c) is envisaged to provide a lignin-derived composition comprising at least one low molecular weight lignin-derived compound.

In step (3) of the inventive method, the isolated fraction of modified lignin-derived components of step (2) are subjected to a chemical (and optionally physical) decomposition step. The reaction may allow to convert the fraction of modified lignin-derived components of higher molecular weight to lower molecular weight compounds characterized by structural elements or units of the initial lignin polymer. Step (3) corresponds to a decomposition reaction of the modified lignin-derived components resulting in a heterogeneous ensemble of preferably low molecular weight compounds of typically aromatic nature.

Disruption of the modified lignin-derived components into smaller subunits by chemical decomposition is an important step for lignin valorization. The smaller subunits may preferably resemble the desired target compounds, and may expose various functional groups on the aromatic rings to further catalytic transformation e.g. in step (6) of the inventive method.

"Chemical decomposition" is typically understood as the provision of a plurality of lower molecular weight compounds by chemical and/or physical degradation of higher molecular weight starting material. Typically, such a reaction yields compounds comprising fragments or moieties of the higher molecular weight starting material. Chemical decomposition may be studied by chemical analysis, e.g. by mass spectrometry, gravimetric analysis, and thermogravimetric analysis. Preferably, decomposition according to the inventive method is carried out by catalytic reaction, or alternatively, electrolytically. Thermal decomposition may be employed as well according to the invention, but is less preferred, as it usually yields an even broader spectrum of diverse low molecular weight lignin-derived compounds. A larger fraction of these compounds following decomposition is of aromatic nature reflecting aromatic ring systems of the building blocks of the natural lignin polymer provided in step (1).

Decomposition may result in a heterogeneous ensemble of lignin-derived products comprising (modified) lignin-derived building blocks, i.e. "monomers" or "dimers", preferably biphenylic dimers. Preferably, the resulting modified lignin-derived products herein essentially consist of monomers and dimers, i.e. the resulting lignin-derived products of step (2) do preferably not comprise larger (oligomeric) modified lignin-derived fragments but only modified lignin-derived monomers and dimers. Higher molecular weight modified lignin-derived components converted by step (3), preferably chemically modified lignin polymers (such as lignosulfonate and Kraft lignin), decompose in a controllable manner at elevated temperatures, preferably below the pyrolytic temperature of, e.g. 1000° C., such as at least 300° C., preferably at least 400° C., more preferably 400 to 500° C. and in the presence of a suitable catalyst (e.g. in a oxidative cracking/reductive cracking reaction) and/or when subjected to electro-oxidation.

"Chemical decomposition" may comprise (alternative (a)) oxidative cracking of the modified lignin-derived components isolated in step (2). Typically, such decomposition is carried out in the presence of a homogeneous metal ion-based or a metalloid-based catalyst. By alternative (b), reductive cracking is applied to decompose the modified lignin-derived components in the presence of a heterogeneous metal ion-based or metalloid-based catalyst. By alternative (c), said step is characterized by electro-oxidation of the modified lignin-derived components in alkaline or acidic solution.

"Cracking" is preferably a catalytic reaction to break or dissociate larger molecules into their smaller fragments by dissociation of covalent bonds of the larger molecule. Generally, "cracking" describes any type of molecular dissociation under the influence of, e.g., heat, catalysts, electric currents and/or solvents.

Originally, the term "cracking" is typically used to refer to reactions developed for petrochemistry to disrupt larger e.g. gasoil molecules into smaller gasoline molecules and olefins. In that context, "cracking" makes use of a reactor and a regenerator for regenerating the catalytic material. Therein, starting material may be injected into preferably hot, fluidized catalysts. The resulting vapor-phase products may be separated from the catalytic materials and fractionated into various product or product fragment fractions by condensation. The catalyst is typically introduced into a regenerator, wherein air or oxygen is preferably used to separate any residual components by an oxidation reaction, such that the surface of the catalyst is freed from any by-products, which are formed as a result of the cracking process. The hot regenerated catalyst may then be recycled to the reactor to complete its cycle. Isolated modified lignin-derived components derived from step (2) may be subjected to "cracking" conditions according to this definition as well, although the term "cracking" is preferably and typically to be understood as "oxidative cracking" or "reductive cracking" as defined above. "Cracking" of the isolated fraction modified lignin-derived components, e.g. Kraft lignin or lignosulfonates, is therefore preferably understood as the reaction underlying the decomposition according to step (3) (a) or (b).

Cracking kinetics and the products of that reaction are typically dependent on the temperature and/or the catalysts applied. In addition, the ensemble of products resulting from cracking is dependent on the nature of the lignin-derived fraction used as starting material for the decomposition reaction. Accordingly, the fraction of modified lignin-derived components, e.g. Kraft lignin or lignosulfonate, may be subjected by step (3) to a catalytic reaction at a temperature significantly lower than pyrolytic temperature or to electric current, preferably by electro-oxidation.

"Oxidation" is involved in the decomposition reaction according to step (3(a)). As used herein, "oxidation" refers to any reaction, which includes loss of electrons. In particular, "oxidation" may include the introduction of oxygen or oxygen-containing functional groups, e.g. a hydroxyl group. For the method of the present invention, aromatic ring systems are typically functionalized by an oxygen-containing functional group and/or by the substitution of a hydroxyl group by an oxo group. Oxidation is typically achieved by an oxidizing agent, which is capable of removing electron(s) from a chemical species, e.g. by transferring (electronegative) oxygen or oxygen-containing groups to said species.

"Catalysis" is involved in step (3(a)) and (3(b)). It typically allows to enhance the kinetics of a chemical reaction by the presence of a catalyst lowering the activation energy.

Preferred catalysts for oxidizing of the (modified) lignin-derived components in step (3(a)) are catalysts comprising metal ions, such as salts with catalytically active cations. Alternatively, (metal or metalloid) coordination complexes may be employed. In general, a "coordination complex" is typically known in chemistry to consist of a central atom, which may be a metallic or metalloid atom, e.g. a metal ion or a metalloid ion. It is called the coordination center. The surrounding sphere of bound molecules or ions is known as ligands or complexing agents. Alternatively, catalysts may be of metalloid character including coordination complexes, with a metalloid atom as the coordination center, such as boron. In particular, catalysts used according to step (3(a)) are homogeneous catalysts, but may also be heterogeneous catalysts. Generally, homogeneous catalysis is based on catalytic reactions with the catalyst being in the same phase as the reactant(s). More specifically, a homogeneous catalyst is dissolved for catalysis in the solution.

(a) Oxidative Cracking of Modified Lignin-Derived Components

Preferably, step (3) involves (a) oxidative cracking of the modified lignin-derived components.

Preferably, step (3(a)) may comprise oxidizing the modified lignin derived-components, preferably in the presence of a heterogeneous or homogeneous catalyst or a combination of catalysts. Step (3(a)) is typically carried out in the presence of an oxidizing agent such as air, $O_2$ or $H_2O_2$ and preferably a catalyst or a mixture of catalysts, which is/are preferably of heterogeneous nature, e.g. with regard to a cracking reaction, but may also be of homogeneous nature.

Heterogenous catalysts of interest for step (3) (a) of the inventive method include $TiO_2$, $Pt/TiO_2$, $Fe(III)/TiO_2$, $Pd/Al_2O_3$, $Ni/MgO$, $CH_3ReO_3$, Cu—Ni, Cu—Mn, Cu—Co—Mn, Cu—Fe—Mn, Cu—Ni—Ce/$Al_2O_3$, Cu—Mn/$Al_2O_3$.

Homogenous catalysts of interest for step (3) (a) of the inventive method may be selected from the following, non-limiting examples of suitable catalysts.

Homogenous catalysts applicable in step (3) (a) of the inventive method may include metalloporphyrins, including catalysts formed from the metalation of the porphyrin with transition metal salts. Metalloporphyrins of interest as catalysts in step (3)(a) of the inventive method include Mn(TSPc)Cl, Fe(TSPc)C, Fe(TFSPP)Cl, CoTSPc, FeTSPc, Rh(TSPP), Fe(TF$_5$PP)Cl and Mn(TSPP)Cl. Crestini and Tagliatesta provide an extensive review on the oxidation of lignin using metalloporphyrin complexes (cf. Crestini and Tagliatesta. The Porphyrin Handbook; Kadish, K. M., Smith, K. M., Guilard, R. Eds.; Academic Press: San Diego, Calif., 2003; Vol. 11, p 161).

Homogenous catalysts applicable in step (3)(a) of the inventive method include Schiff-base catalysts, especially metallosalen catalysts. These are emerging as promising oxidation catalysts of lignin and modified lignin-derived components. The term "salen" refers to [N,N'-bis(salicylidene)ethane-1,2-diaminato]. Metallosalen catalysts of interest as catalysts in step (3)(a) of the inventive method include Co(salen), [(pyr}Co(salen)], Cu-, Fe-, and Mn-triphenylphosphonium-decorated salen complexes, Co-sulphosalen, Co(salen)/SBA-15, and [Co(N-Me salpr)].

Homogenous catalysts applicable in step (3)(a) of the inventive method include nonporphyrinic or Schiff base catalysts, including metallo-TAML (tetraamido macrocyclic ligand), -DTNE (1,2-bis-(4,7-dimethyl-1,4,7-triazacyclonon-1-yl)ethane) and -TACN (1,4,7,-trimethyl-1,4,7-triazacyclononane) catalysts. The metal may for instance be selected from iron or manganese. Catalysts of use in step (3)(a) of the inventive method in this regard include Mn(IV)—Me$_4$DTNE and Mn(IV)—Me$_4$TACN.

Homogenous catalysts applicable in step (3)(a) of the inventive method include polyoxometalates (POMs), as reviewed in detail by Gaspar et al. Green Chem. 2007, 9, 717. Polyoxometalates consist of both primary and secondary heteroatoms, where the former typically determines the structure and the latter, typically transition metal ions, may be substituted without change of structure. Thereby, secondary heteroatoms can be replaced by ions conferring desirable redox characteristics. POMs of interest as catalysts in step (3)(a) of the inventive method include SiW$_{11}$Mn(II), BW$_{11}$Co(II), PW$_{11}$Ru(IV), heteropolyanion-5-Mn(II), alpha-[SiVW$_{10}$O$_{40}$]$^{5-}$, Na$_{5(+1.9)}$[SiV$_{1(-0.1)}$MoW$_{10(+0.1)}$], LaMnO$_3$, LaCoO$_3$, H$_2$MoO$_4$ and Fe$_2$(MoO$_4$)$_3$. POMs may be utilized as catalysts in conjunction of O$_2$ or H$_2$O$_2$ as oxidants.

Homogenous catalysts applicable in step (3)(a) of the inventive method include simple metal salt-based catalysts. These may typically utilized in conjunction with O$_2$ as oxidant. Metal salt-based catalysts of interest as catalysts in step (3)(a) of the inventive method include Co(OAc)$_2$/Mn(OAc)$_2$, Co(OAc)$_2$/Mn(OAc)$_2$/HBr, Co(OAc)$_2$/Zr(OAc)$_4$/HBr, Mn(OAc)$_2$, CuSO$_4$, CuSO$_4$/FeCl$_3$, Cu(OH)$_2$, FeCl$_3$, Fe$_2$O$_3$, NaBr 2,2,6,6-tetramethylpiperidine-1-oxyl-radical (TEMPO), CuO, and CoO.

Homogenous catalysts applicable in step (3)(a) of the inventive method further include miscellaneous catalysts, including hexacyanoruthenate(II)), Ru/CN)$_6$$^{4+}$, tris-(4,4'-dimetyl-2,2'-bipyridine)iron(II) and [Cu(phen)(OH)$_2$].

In principle, step (3)(a) of the inventive method can be performed with any of the aforementioned homogenous catalysts.

Preferably, the employed catalyst may comprise a metal ion, preferably selected from Co(II), Cu(II), Fe(II) and Fe(III), more preferably Fe(III). Alternatively, the catalyst may comprise a metalloid element. The "metalloid element" and/or the metal ion is/are preferably provided as coordination complex or, alternatively, as a salt. In such a coordination complex, a metalloid element or metal ion forms the coordination center. Typically, a "metalloid" is a chemical element with metallic and non-metallic properties. Metalloid may be any element selected from boron, silicon, germanium, arsenic, antimony, tellurium, aluminum, and selenium. A metalloid may have a metallic appearance, it is typically brittle and only a fair conductor of electricity. Chemically, it may behave mostly like a non-metal. Metalloid comprising agents are particularly useful as catalysts. Preferably, the metalloid catalyst comprises the metalloids B(III), Si(IV) and/or Al(II). The metalloid catalyst may preferably be a boron catalyst, comprising preferably B(III). As an example: When using a boron catalyst, step (3 (a)) may be a hydroboration-oxidation reaction, which is preferably a two-step organic reaction. It converts, e.g., an alkene into a neutral alcohol by the net addition of water to the double bond. The hydrogen and hydroxyl group are preferably added in syn addition providing an alcohol in cis stereochemistry. Hydroboration-oxidation typically reflects an anti-Markovnikov reaction, with the hydroxyl group being attached to the less-substituted carbon.

More preferably, the homogeneous catalyst in step (3)(a) is selected from the group consisting of a salt, a coordination complex, a zeolite, a polyoxometalate, and a combination of any of them. Any such catalysts preferably comprises a metal ion selected from Co(I), Cu(II), Fe(II) and Fe(III), most preferably Fe(III).

It is preferred that oxidative cracking according to step (3)(a)) may be performed in the presence of a metal catalyst, in particular a Cu(II) or Fe(III) containing catalyst. Alternatively, a Co(II) comprising catalyst may be employed. The catalyst is preferably a heterogeneous catalyst, but may also be a homogeneous catalyst. The metal catalyst, in particular the Cu(II) or Fe (II) containing catalyst, is preferably a (metal or metalloid) salt. The oxidative cracking reaction is preferably carried out under elevated temperature and/or pressure conditions.

The reaction of step (3)(a) may be carried out at a temperature of 30 to 400° C., preferably 100 to 350° C. The temperature chosen for that reaction is selected such that it is significantly lower than pyrolytic temperatures, e.g. lower than 1000° C. or 800° C. or lower than 500° C. By such a lower temperature reaction, the reaction products are typically less diverse than by a purely pyrolytic reaction (or pyrolytic decomposition).

For example, the solution comprising the fraction of modified lignin-derived components of step (2), e.g. lignosulfonate, is made alkaline, preferably by adjusting the pH value to at least 9. The medium may preferably also be acidic. The metal and/or metalloid catalyst, in particular the Fe(III) containing catalyst, may be added thereafter to that solution. Said catalyst comprising solution may be heated to a temperature of at least 150° C., preferable to a temperature of 150 to 300° C., more preferably 160-170° C. The pressure may be set to an overpressure of at least 5 atm, preferably from 10 to 12 atm. When applying such temperature and pressure conditions, cracking occurs and oxidizing may typically take place simultaneously due to the air's oxygen as oxidizing agent.

In contrast to employing air as oxidizing agent, step (3)(a)) employing a metal and/or metalloid catalyst, in particular the Fe(III) containing catalyst, may be conducted in an oxygen enriched environment, more preferably under increased pressure, in particular increased oxygen partial pressure. Said pressure may—preferably under alkaline conditions—be at least 3 bar p(O$_2$), more preferably 4 to 5 bar p(O$_2$). Under acidic conditions, the p(O$_2$) may advantageously be at least 10 bar, sometimes at least 20 bar. Further advantageously, an alcohol, preferably methanol, may be added to the reaction to avoid re-polymerisation of the lignin-derived components.

The alcohol may be added in an amount of at least 5%, preferably at least 10%, more preferably at least 20%, even more preferably at least 30%, even more preferably at least 40%, even more preferably at least 50%, even more preferably at least 60%, even more preferably at least 70%, most preferably at least 80% with respect to the total reaction volume.

The alcohol, in particular methanol, may be recovered before or after isolation/purification of the target compound in step (4) of the inventive method. In the recovery step, the alcoholic ingredient, in particular methanol, is preferably recovered by heating and vaporization. The recovery step is preferably performed after isolation step (4) of the inventive method.

Oxidative cracking is preferably carried out in a single reaction vessel, preferably simultaneously. The temperature is preferably at least 150° C., more preferably at least 170° C. The reaction may be carried out in solution under constant stirring, e.g. above 500, 600, 700, 800, 900 or 1.000 rpm. Said oxidation in the presence of an oxygen environment may be performed in a fluidized bed reactor, particularly a reactor comprising a sand bed. Under such conditions, the temperature may be set to at least 250° C., preferably to at least 300° C. Thereby, the oxidation rate may advantageously be increased. Upon application of a fluidized bed reactor, less desired or undesired by-products other than the target aromatic or phenolic compounds are preferably less frequently observed, which is preferred for step (3) of the inventive method.

In accordance with the above, step (3) (a) oxidative cracking of the modified lignin-derived components is preferably carried out in the presence of an oxidizing agent and a heterogeneous or homogeneous catalyst comprising (a) a metal ion selected from Co(II), Cu(II), Fe(II) and Fe(III); or (b) a metalloid component selected from B(II), Si(IV) and Al(III) preferably at a temperature of 30-400° C., more preferably 100-350° C. Preferred homogenous catalysts employed in step (3)(a) include those selected from the group consisting of a salt, a coordination complex, a zeolite and a polyoxometalate comprising a metal ion selected from Co(II), Cu(I), Fe(II) and Fe(II).

(b) Reductive Cracking of Modified Lignin-Derived Components

In the alternative, decomposition in step (3) may be carried out by reductive cracking the fraction of modified lignin-derived components isolated in step (2), which is typically conducted in the presence of a reducing agent (alternative (b)) and a suitable catalyst. By alternative step (3)(b), the fraction of modified lignin-derived components is therefore reduced, typically by addition of a reducing agent. A "reducing agent" is understood as an agent which "donates" electron(s) to another chemical species (electron donor).

The reducing agent is preferably hydrogen or an alcohol as H-donor. Such a reaction under reducing conditions typically also requires a suitable catalyst.

Heterogenous catalysts applicable for reductive cracking according to step (3)(b) of the inventive method include, without limitation, Cu·CrO, Raney Ni, Rh, Pd·FeS, Co—Mo, Ni—Mo, Co—Mo—P, $Fe_2O_3$, Mo, Ni—Mo—P, $Mo_2N$, Ni—W, Rh—Co, Ni—Cu, NiO—$MoO_3$, $MoO_3Ru$, M or M—Mo (wherein M is selected from Co, Cu, Ir, Ru, Pd, Fe, Rh, Pt or Ni). Optionally, the Support (i.e. a material to which the catalyst is affixed) may be selected from carbon, $Al_2O_3$, $TiO_2$, $SiO_2$—$Al_2O_3$, $Zr_2$, $CeO_2$, zeolite, MgO or nothing.

A homogeneous catalyst may, however, alternatively be employed in step (3)(b) of the inventive method. Suitable homogenous catalysts include (1,5-hexadiene)RhCl dimer, colloidal rhodium, [(1,5-$C_6H_{10}$)RhCl]2, rhodium nanoparticles, [($C_6H_6$)$Ru_4H_{41}$]$Cl_2$, [(Ru($C_3H_5$)Cl(TPPDS)$_2$], $NaBH_4+I_2$, and $RuCl_2(PPh_3)_3$.

Preferably, a heterogeneous catalyst comprising, e.g., a metal selected from nickel, platinum, palladium, ruthenium, rhenium and gold may be employed. The catalyst is preferably provided on the surface of a support material preferably selected from the group consisting of active carbon, silica, titaniumoxide and/or aluminumoxide. Thereby, the lignin-derived components may be subject to e.g. hydrogen based "lysis" by cleavage of carbon-carbon or carbon-heteroatom single bonds (hydrogenolysis).

The catalyst typically employed by step (3)(b) is a heterogeneous catalyst, which is defined as a catalyst provided in another phase, typically in solid or gaseous phase, than the reactant(s), which are typically provided in solution. A homogeneous catalyst may, however, alternatively be employed. For the present method, the modified lignin-derived components are typically provided in solution and the catalyst is usually provided as solid matter. Generally, heterogeneous catalysis provides the advantage that reaction products may readily be separated from the catalyst component. Advantageously, heterogeneous catalysts are usually more stable and decompose more slowly than homogeneous catalysts. They may be recycled.

For example, reductive cracking of the fraction of modified lignin-derived components isolated in step (2) may be carried out by means of a catalyst comprising nickel, e.g. supported on activated carbon (Ni/C). Therein, a fragmentation-hydrogenolysis process of the modified lignin into lower molecular weight lignin-derived target compounds, e.g. di- or monomeric phenolic target compounds, in alcoholic solvents over nickel-based catalysts may be performed. This reaction involves hydrogenolysis of modified lignin components into di- or monomeric phenolic compounds over nickel catalysts, wherein alcohol is preferably the source of active hydrogen as the reducing agent.

In an alternative example, the fraction of modified lignin-derived components from step (2) may be preferably cracked and reduced in the presence of Ruthenium deposited on a carbon catalyst (Ru/C) in preferably an organic solvent, such as methanol, under a reducing atmosphere, such as an $H_2$ atmosphere, preferably at elevated temperatures. Such a reaction preferably provides, other than residual carbohydrate pulp, lignin oil. The resulting phenol-rich lignin oil typically consist more than 50% (w/w) of phenolic monomers as target compounds of the present invention (mainly) and 10% to 25%, preferably less than 20% (w/w) of phenolic dimers. The obtainable target compounds by that reaction (or alternative reactions) are one or more of syringol, in particular 4-n-propylsyringol, 4-ethylphenol, and guaiacol, in particular 4-ethylguaiacol and 4-n-propylguaiacol.

Alternatively, steps (1) (degradation) and (3) (decomposition) may be combined, which does preferably not require step (2). The combined degradation/decomposition reaction (steps (1) and (3) combined) mode of the inventive method may preferably, but not necessarily be carried out by employing step (3)(b) according to the inventive method. Therein, the natural lignocellulosic material provided in step (1) may be delignified through simultaneous solvolysis and catalytic hydrogenolysis of the lignin material in one single step. Combined solvolysis and catalytic hydrogenolysis may preferably be carried out in the presence of Ruthenium preferably deposited on a carbon catalyst (Ru/C), preferably in an organic solvent, such as methanol, under a reducing atmosphere, such as an $H_2$ atmosphere. The reaction is preferably carried out at elevated temperatures. The resulting product of combined solvolysis and catalytic hydrogenolysis may be further processed as described herein to obtain a purified fraction of low molecular weight aromatic lignin-derived (mono- or dimeric) compounds.

In accordance with the above, step (3) (b) reductive cracking of the modified lignin-derived components is preferably carried out in the presence of a reducing agent, preferably hydrogen or a hydrogen donating alcohol, and a heterogeneous catalyst comprising a metal selected from nickel, platinum, palladium, ruthenium, rhenium and gold, preferably provided on the surface of a support material, preferably selected from the group consisting of active carbon, silica, titaniumoxide and aluminumoxide.

Further advantageously, an alcohol, preferably methanol, may be added to the reaction to avoid re-polymerisation of the lignin-derived components.

(c) Electro-Oxidation of Modified Lignin-Derived Components

Finally, decomposition in step (3) may be carried out by electro-oxidation (alternative (c)).

With regard to step (3)(c), "electro-oxidation" is understood as oxidation at the surface of an electrode and/or in an electrical (electrochemical) cell. Specifically, "electro-oxidation" is defined as an electrochemical process, wherein the oxidation reaction occurs by applying an electric field between two electrodes, e.g. a working electrode and a counter electrode, for the oxidation reaction to take place. Preferably, any such electrical cell employed by step (3(c) is a single galvanic cell or a flow cell. A flow cell is characterized by the ionic solution (electrolyte) passing continuously or batch-wise through the cell. The ionic solution is typically stored in separate storage tanks.

The "working electrode" (electrode in an electrochemical system, on which the reaction of interest takes place) is cathodic or anodic, respectively, depending on whether the reaction on the electrode is reduction or oxidation. Common working electrodes may comprise inert metals, such as gold, silver or platinum, or inert carbon, such as glassy carbon or pyrolytic carbon, or mercury drop and film electrodes. The working electrode employed by the present invention may alternatively also be a nickel or nickel alloy electrode. The counter electrode may be a platinum electrode, in particular whenever the working electrode is a nickel electrode. The electrodes may be, for example, sintered electrodes, which preferably benefit from extended life time and show a higher oxidation capacity than other technologies. Electro-oxidation may be advantageous, as it provides instant operation on demand ("on/off"). Further, no aggressive chemicals are required, and reaction temperatures may be kept low. As the large diversity of by-products is avoided, it allows to efficiently produce lower molecular weight aromatic lignin-derived target compounds. As compared to thermal decomposition methods, energy consumption is reduced.

The electro-oxidation reaction may preferably performed in strong alkaline solution of at least pH 10, and preferably, constant current is applied. Preferred is electro-oxidation carried out galvanostatically at pH 10 to 14. Preferably, the solution comprising the modified lignin-derived components, e.g. lignosulfonate, acts as anolyte and, typically, NaOH solution as catholyte. In general, an anolyte is the part of the electrolyte, which is under direct influence of the anode upon electrolysis. Correspondingly, a catholyte is the part of the electrolyte, which is under direct influence of the cathode upon electrolysis. Alternatively, electro-oxidation may preferably also be carried out under acidic conditions. Further, the modified lignin-derived components in solution may serve as anolyte and catholyte at the same time. Advantageously, no (semi-permeable) membrane is required for the inventive method. In terms of the electrolyte, no specific electrolyte is required, if the reaction is carried out in acidic or alkaline medium. Alternatively or additionally, a salt or distinct salts, preferably an alkali salt, may be added to the electrolyte, e.g. a sodium salt, preferably sodium sulfate.

In accordance with the above, step (3) alternative (c) electrooxidation is preferably carried out galvanostatically, preferably at a pH from pH 1 to 14.

Electro-oxidation may also directly yield the target compounds. In such cases, the isolation/purification step (4) may be omitted.

(d) Other Methods

Chemical decomposition in step (3) of the inventive method may also be accomplished using other methods as described herein.

Enzymatic decomposition according to step (3) (d) of the inventive method may be accomplished by contacting the modified lignin-derived components with suitable enzymes (or organisms producing the same, in particular fungi) under appropriate conditions. Enzymes of interest in this regard include inter alia oxidases, peroxidases and hydrolytic enzymes, e.g. derived from *Phaerochaete chrososporium* or *Pycnoporus cinnabarinus*.

Photooxidation according to step (3) alternative (d) may involve subjecting the modified lignin-derived components to visible or UV light, typically with a wavelength of up to 500 nm.

Alternatively, step (3)(d) of the inventive method may comprise chemical decomposition in ionic liquids. Ionic liquids are composed of ionic organic/inorganic salts that are liquid at low temperature (<100° C.). They typically have low vapour pressures, are chemically and thermally stable and are able to dissolve in a wide range of compounds. Various decomposition reactions can be carried out in ionic liquids, for instance acetylation, acid hydrolysis, heat treatment, acylation of enzymatic treatment as described above. Ionic liquids of interest for the decomposition of the lignin-derived components of the invention include those comprising alkylsulfonates, lactates, acetates, chlorides or phosphates as anions. One of the most important advantages of some ionic liquids (e.g. 1-H-3-Methylimidazolium chloride, 1-ethyl-3-imidazolium chloride) is their ability to act as both an acidic catalyst and a solvent. Such ionic liquids may be particularly preferred. Ionic liquids may be used in conjunction with suitable transition metal catalysts (e.g. 1-ethyl-3-methylimidazolium diethylphosphate and $CoCl_2$ 6 $H_2O$, 1-ethyl-3-methylimidazolium trifluoromethylsulfonate and $Mn(NO_3)_2$) which may promote the decomposition of modified lignin-derived components.

Optionally, the above-mentioned alternatives may be combined with each other. E.g., a synergistic combination of photo-electrocatalysis using a three-electrode iridium oxide system coupled with UV light may be employed. A combination of enzyme-based approaches and ionic liquid is described above.

Step (4): Provision of Precursor Compounds

Step (4) of the inventive method includes the provision of precursor compounds from the decomposition products obtained in step (3) of the inventive method.

Step (4) of the inventive method may include any suitable means to provide useful precursor compounds that can subsequently be reacted to obtain the inventive compounds and compositions.

Preferably, step (4) of the inventive method may include an isolation step (4.1), and optionally further at least one oxidation step (4.2), modification step (4.3), and/or transformation step (4.4).

Step (4) of the inventive method preferably yields precursor compounds which may subsequently be reacted to obtain the compounds and compositions according to the present invention.

Precursor Compounds

Preferably, precursor compounds are aromatic.

Preferably, precursor compounds are low molecular weight compounds. Preferably, precursor may exhibit a molecular weight of less than 1.000 Da, preferably less than 700 Da, more preferably less than 500 Da, most preferably of about 100 to 500 Da, e.g. 200 to 400 Da. Preferably, precursor compounds may exhibit a size in the order of 10-9 m or less.

Precursor compounds may be based on a monomer or, alternatively, a homo- or heterodimer of the polymeric natural lignin, as obtainable from the pulping step of the inventive method. Said monomers may essentially correspond to the (repetitive) building blocks of polymeric natural lignin. Said monomers may be aromatic.

Preferably, precursor compounds are selected from monocyclic phenolic derivatives. More preferably, precursor compounds may comprise one single benzene-derived (substituted) aromatic ring system. Put differently, precursor compounds preferably include carbocyclic benzene or its benzene derivatives, such as phenolic derivatives.

Alternatively, but less preferred, precursor compounds may be dimeric or trimeric. Such dimeric or trimeric precursor compounds may include two or more ring systems directly connected by a bond, and form bi- and multicyclic (annulated) aromatic systems. Alternatively, two monomeric moieties containing an aromatic ring system each may be connected by a linker group, e.g. an aliphatic linker group, to form a homo- or heterodimer, typically a heterodimer. A heterodimer exhibits two aromatic ring systems with individual (distinct) substitution patterns. It may be preferred for the dimer to represent the basic chemical structure of two (substituted) aromatic ring systems directly linked by a bond to form a bi-phenylic ring system. Precursor compounds comprising two aromatic ring systems may thus preferably form a biphenylic moiety. Preferably, the one or more carbocyclic ring(s) of the precursor compounds may be monocyclic.

Preferably, the aromatic ring(s) of the precursor compounds are substituted in at least one, preferably in at least two positions by a functional group, wherein the at least one functional group is preferably alkoxy or hydroxyl. Therein, a monocyclic precursor compound is typically substituted in at least two positions by a functional group, wherein the functional group is preferably alkoxy or hydroxyl. A precursor compound having two ring systems, in particular a biphenylic compound, is typically substituted in at least one position per aromatic ring by a functional group. Preferably, each ring system exhibits its individual substitution pattern being different from the other substitution pattern of the other ring system. Preferably, the at least one functional group is alkoxy or hydroxyl.

Preferably, precursor compounds may be characterized by General Formula (Ia) or (Ib):

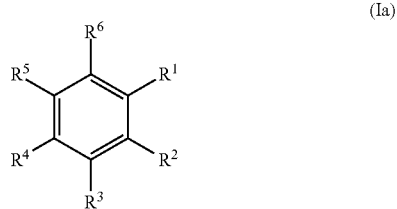

(Ia)

wherein
each of $R^1$-$R^5$ is independently selected from hydrogen; hydroxy; carboxy; amino; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; optionally substituted aryl; esters; oxo or carbonyl;
and $R^6$ is selected from the group consisting of hydrogen; hydroxy; amino; linear or branched, optionally substituted, $C_{1-6}$ carboxyl; linear or branched, optionally substituted, $C_{1-6}$ aldehyde; and linear or branched, optionally substituted, $C_{1-6}$ alcohol.

Alternatively, the at least one lignin-derived lmw aromatic precursor compound may be characterized by general Formula (Ib):

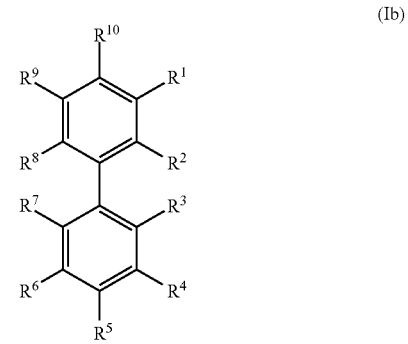

(Ib)

wherein
each of $R^1$-$R^9$ is independently selected from hydrogen; hydroxy; carboxy; amino; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; optionally substituted aryl; esters; oxo or carbonyl; wherein $R^5$ is preferably hydroxy or optionally substituted $C_{1-6}$ alkoxy; and
$R^{10}$ is selected from the group consisting of hydrogen; hydroxy; linear or branched, optionally substituted, $C_{1-6}$ carboxyl; linear or branched, optionally substituted, $C_{1-6}$ aldehyde; and linear or branched, optionally substituted, $C_{1-6}$ alcohol.

The precursor compounds may selected from the group consisting of phenolic derivatives of biphenyl, benzylalcohol, benzaldehydes and benzoic acid, preferably derivatives of p-hydroxy benzylalcohol, p-hydroxy benzaldehydes and p-hydroxy benzoic acid or esters thereof, or more preferably vanillin, guaiacol, eugenol, syringol, phenol, syringaldehyde, vanillic acid or esters thereof and/or a derivative of any of the above, and/or a combination of the above.

Precursor compounds of the invention may preferably be such compounds, which are phenazine precursor compounds, in particular monomers with at least one nitrogen containing substituent, e.g. amino, nitroso or nitro, e.g. selected from Formula Ia, wherein each of $R^1$-$R^6$ in General Formula I a is independently selected from hydrogen; hydroxy; carboxy; amino; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy; linear or branched, optionally substituted, $C_{1-6}$ aldehyde; carboxylic acids; optionally substituted aryl; esters; oxo; or carbonyl, wherein at least one of $R^1$, $R^3$ or $R^5$ is hydroxy, amino or linear or branched, optionally substituted, $C_{1-6}$ alkoxy or $C_{1-6}$ carboxyalkoxy; and wherein $R^6$ is preferably selected from the group consisting of hydrogen; hydroxy; linear or branched, optionally substituted, $C_{1-6}$ carboxyl; linear or branched $C_{1-6}$ aldehyde; and linear or branched, optionally substituted, $C_{1-6}$ alcohol.

Exemplary precursor compounds according to the present invention may be selected from the following compounds and their corresponding esters:

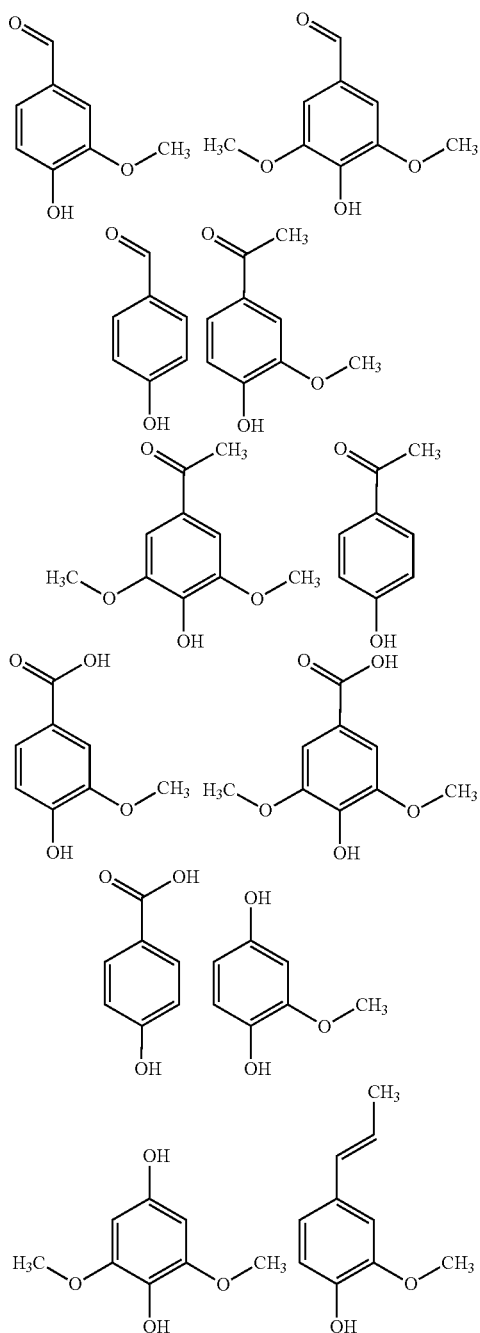

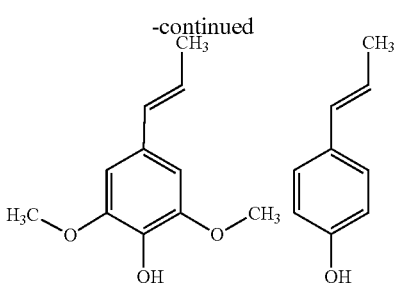

Monomeric precursor compounds containing one aromatic ring are typically derived from a monomer of the modified lignin-derived component.

Less preferred dimeric precursor compounds containing two aromatic rings, which form a biphenylic system, are obtainable by choosing the appropriate lignocellulosic starting material, which encompasses such moieties, e.g. from spruce. Such a biphenylic system typically comprises phenylbenzene or 1,1'-biphenyl as essential chemical structure. Biphenylic moieties are typically formed by 5-5-linkage of natural lignin monomers. Such a bond occurs more frequently in softwood than in hardwood. For example, spruce may comprise more than 15%, preferably more than 20%, even more preferred more than 25% biphenylic moieties among its phenyl-propane units making up its natural lignin. Whenever biphenylic precursor compounds are envisaged, it may be preferred to use spruce wood as a lignocellulosic starting material in step (1) of the inventive method.

The precursor compounds described herein are preferably isolated and optionally modified and/or further purified to yield further precursor compounds that give rise to the inventive compounds.

Particularly preferred precursor compounds include o-phenylenediamine, benzoquinone and 2-hydroxy- or 2-alkoxyphenol precursor compounds. Said precursor compounds may optionally be substituted, i.e. comprise one or more substituents as, e.g., defined in the context of the inventive compounds.

The benzoquinone and 2-hydroxy- or 2-alkoxyphenol precursor compounds are preferably obtained as described in PCT/EP2017/000198 and PCT/EP2018/053597. Briefly, precursor compounds are isolated, modified and purified.

The o-phenylenediamine precursor compound is preferably obtained by the transformation of either 2-hydroxyphenols or 2-alkoxyphenols.

Benzoquinone, 2-Hydroxy- or 2-Alkoxyphenol Precursor Compounds

Benzoquinone, 2-hydroxy- or 2-alkoxyphenol precursor compounds are preferably obtained as described in PCT/EP2017/000198 and PCT/EP2018/053597 and herein below.

Isolation of Precursor Compounds (Step 4.1)

In step (4.1) of the inventive method, the precursor compounds are preferably isolated from the decomposition products obtained from chemical decomposition step (3).

Preferably, isolation is accomplished by filtration and/or extraction, preferably filtration. Preferably, isolation yields precursor compounds as defined above.

Isolation preferably separates the desired precursor compounds from other components, in particular impurities, contaminants or by-products of pulping and/or chemical decomposition, e.g. fragments other than the monomeric or dimeric precursor compounds.

"Fragments" of the modified lignin-derived components are typically larger in molecular weight than the monomeric or dimeric precursor compounds, but have typically a lower molecular weight than the modified lignin-derived components obtained by step (2) of the inventive method. Such fragments are typically not understood to be precursor compounds of the inventive method. Instead, they may comprise or consist of tri- or n-mers of the building blocks of the modified lignin-derived components. Such fragments resulting from the decomposition step are typically oligomers being of smaller molecular weight than the modified lignin-derived components obtainable in the pulping process of sub-step (1.2). However, such fragments may vary significantly in size and in their molecular weight, as the lignin-derived components vary.

Filtration may be selected from ultrafiltration and nanofiltration, which may be carried out by an ultrafiltration and/or nanofiltration cell, preferably having a pre-filtration section for increasing the efficiency of the filtration step (e.g. avoidance of membrane blockade, e.g. by higher molecular weight lignin-derived components). Stirred ultrafiltration cells as described by Duval et al. (Holzforschung 2015, 69, 127-134) may be applied as well. Preferably, the ultrafiltration and/or nanofiltration cell comprises at least one molecular weight cut-off unit, preferably at least two molecular weight cut-off units allowing to isolate lignin-derived precursor compounds within a molecular weight range, which reflects the molecular weight of monomeric and dimeric target compounds, e.g. from 150 Da to 1.000 Da or from 150 to 500 Da. Preferably, a cascade of cut-off units (e.g. starting with one or more ultrafiltration cell(s) and one or more subsequent nanofiltration cell(s) with preferably decreasing cut-off values may be employed to fractionate the resulting lignin-derived decomposition products obtained in step (3). The decomposition products obtained in step (3) may usually be fractionated in solution or may be isolated as dried matter and be re-dissolved thereafter, if required.

Preferably, isolation comprises filtration and/or extraction, preferably ultrafiltration and/or nanofiltration by an ultrafiltration and/or nanofiltration cell, preferably having a pre-filtration section. Filtration is preferably carried out in a ultrafiltration and/or nanofiltration cell comprising at least one molecular weight cut-off unit, preferably at least two molecular weight cut-off units, wherein the at least one molecular weight cut-off unit has a cut-off level preferably of 1 kDa to 1.5 kDa.

Preferably, the ultra- and/or nanofiltration may be followed by further purification steps to increase purity of the precursor compounds. For example, diafiltration against water may be used to remove residual sugars and reactive agents from the low molecular weight precursor compound fraction. Alternatively, the precursor compounds can be isolated by extraction, optionally followed by fractional distillation.

Decomposition reactions which are characterized by reaction conditions bearing the risk of re-polymerization of the lignin-derived material to be decomposed are preferably avoided by step (4) of the inventive method. Nevertheless, any such re-polymerized by-products may still result from step (4), which need to be eliminated downstream of the inventive method. Components other than the precursor compounds are either discarded, e.g. for combustion, or recycled by another step of decomposition (e.g. a second decomposition reaction according to step (3)).

By step (4.1), monomeric or dimeric precursor compounds (obtained from the decomposition reaction of, e.g. lignosulfonate, by step (3)) are isolated from the other fragments of the decomposition step (3). Thereby, lignin-derived precursor compounds as described above are obtained. Said lignin-derived precursor compounds may be isolated in the form of a (precursor) composition comprising or preferably (essentially) consisting of said precursor compounds, which (essentially) does not comprise higher molecular weight (aromatic) lignin components and/or preferably from other non-lignin-derived residual components, including e.g. inorganic reactive agents. Preferably, the composition may comprise at least two monomeric precursor compounds. It is less preferred, but also conceivable, that the composition comprises a mixture of monomeric and dimeric precursor compounds.

The precursor compounds isolated by sub-step (4.1) may be further modified according to the present invention. They may e.g. be oxidized or chemically modified by other reactions, which may result in modified substitution patterns. Thus, the precursor compounds isolated by sub-step (4.1) may be subjected to other chemical reactions (sub-steps (4.2, 4.3) and may thereby comprise substituents not occurring in the modified lignin-derived components obtained by step (2). They may, e.g., be of higher or lower oxidation state, they may contain substituents not occurring in natural lignin at all.

Oxidation (Step 4.2)

Optionally, isolated precursor compounds obtained from step (4.1) may be oxidized. Oxidation may also be accomplished after condensation, purification or further modification steps as described herein.

Preferably, oxidation is accomplished in the presence of (i) an oxidizing agent selected from the group consisting of $H_2O_2$, $O_2$ and air, and (ii) a heterogeneous catalyst comprising a metal ion or a metalloid, or performing homogeneous catalysis in the presence of NaOH (in which case, usually no catalyst comprising a metal ion or a metalloid is required).

Preferably, oxidation may be carried out in the presence of Co(I) complexes. For example, (pyr)Co(II)salen may be employed in the presence of $O_2$ at overpressure, e.g. at least 3 bar. Such a reaction may preferably be conducted at room temperature in an organic solvent such as MeOH. Other preferred catalysts are Co(3-methoxysalen) and Co(N—N-Me salpr). In the latter case, the preferred organic solvent may be $CH_2Cl_2$.

Preferably, oxidation provides an oxidized precursor compound selected from a hydroquinone and/or, upon further oxidation, a quinone compound.

Oxidation of monocyclic precursor compounds to hydroquinones: Oxidation of monocyclic precursor compounds preferably yields at least one hydroquinone compound characterized by General Formula II a:

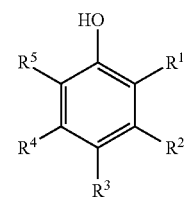

wherein each of $R^1$-$R^5$ is independently selected from hydrogen; hydroxy; amino; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy; linear or branched, optionally substituted, $C_{1-6}$ aldehyde; carboxylic acids; esters; oxo or carbonyl, and wherein one of $R^1$, $R^3$ and $R^5$ is hydroxy;

or, less preferred, by General Formula II b,

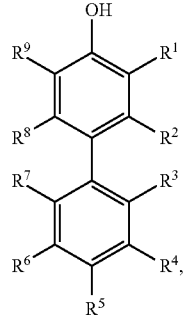

IIb wherein each of $R^1$-$R^9$ is independently selected from hydrogen; hydroxy; amino; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; esters; oxo or carbonyl; and wherein $R^5$ is preferably hydroxy.

The hydroquinone precursor compound may further be purified and/or modified before it is used in a condensation reaction to yield the compounds according to the present invention.

Oxidation of monocyclic precursor compounds to quinones: Alternatively, oxidation may be carried out, typically under harsher reaction conditions, to yield quinone compounds characterized by any of General Formulas III a-d

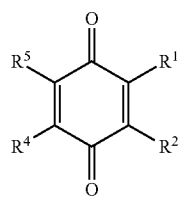

III a wherein each of $R^1$-$R^2$ and $R^1$-$R^5$ is independently selected from hydrogen; amino; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; esters; oxo or carbonyl; or

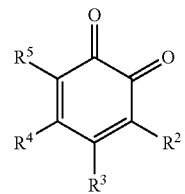

III b wherein each of $R^2$-$R^5$ is independently selected from hydrogen; hydroxy; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy, including methoxy and ethoxy; linear or branched, optionally substituted, $C_{1-6}$ aldehyde; carboxylic acids; esters; oxo or carbonyl; or

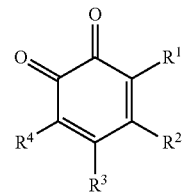

III c wherein each of $R^1$-$R^4$ is independently selected from hydrogen; hydroxy; amino; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; esters; oxo or carbonyl; or, less preferred

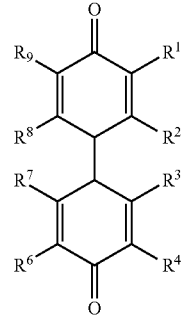

III d wherein each of $R^1$-$R^4$ and $R^6$-$R^9$ is independently selected from hydrogen; hydroxy; amino; carboxy; linear or branched, optionally substituted, $C_{1-6}$ alkyl; linear or branched, optionally substituted, $C_{1-6}$ alkenyl; linear or branched, optionally substituted, $C_{1-6}$ alcohol; linear or branched, optionally substituted, $C_{1-6}$ aminoalkyl; linear or branched, optionally substituted, $C_{1-6}$ carboxyalkyl; linear or branched, optionally substituted, $C_{1-6}$ alkoxy or $C_{1-6}$ carboxyalkoxy, including methoxy and ethoxy; linear or branched, optionally substituted, $C_{1-6}$ aldehyde; carboxylic acids; esters, oxo or carbonyl.

Quinone compounds characterized by any of Formulas III a-d may also be provided by oxidizing the at least one hydroquinone compound according to Formula II a or b as described above, for instance, in the cell stack of a battery or by an oxidant, optionally in the presence of a heterogeneous catalyst. Usually, it is sufficient to provide a hydroquinone compound, which compound is redox active and may be oxidized or a part of the total amount of employed molecules of said hydroquinone compound may become oxidized. It may be preferred to simultaneously accomplish both chemical decomposition of modified lignin-derived components (step (3)) and oxidation of precursor (optionally hydroquinone) compounds (sub-step 4.2). Therein, for example, (cracking and) oxidizing of a modified lignin-derived component (typically alternative (3(a)) or (3(c))) takes place, and instantaneously or concurrently, the component is oxidized to a (hydro-)quinone compound according to the present invention. Further, the step may involve an addition reaction to introduce further substituents of interest under suitable reaction conditions.

Advantageously, said combination of method steps may save time and resources in terms of reactants, reactive agents and/or process equipment and apparatus means. Accordingly, such a combination leads to significant more economic and simple method for producing redox active precursor compounds of renewable origin such as the (hydro-)quinone precursor compounds. Such a combined method step is preferably facilitated by applying electrooxidation of step (3(c)), but catalyst-facilitated oxidation under (3(a)) may also be applied. Electrooxidation is preferred, wherein direct oxidation from a modified lignin such as lignosulfonate to a (hydro-)quinone compound is controlled by the respective set electrochemical conditions. Preferably, the modified lignin is diluted to a concentration below 20% (w/w), preferably below 10% (w/w), more preferably below 5% (w/w), even more preferably below 2% (w/w). The solution may have a pH of 1 to 14. Electrooxidation under acidic conditions is preferred. Alternatively, under alkaline conditions, the preferred pH is at least 11, more preferably at least 13. Electrooxidation is preferably conducted in a flow cell, wherein the flow is at least corresponding to 1 ml/min. preferably 10 ml/min or 50 ml/min, more preferably at least 200 ml/min, but may be up-scaled to significantly higher flows. Electrolysis may typically be conducted galvanostatically, preferably for at least 10 min, preferably at least 30 min, alternatively for at least 1 hour, preferably for at least 4 hours. Most preferred is a time period for conducting electrolysis of at least 30 min, e.g. to save time and resources. Preferably, electrolysis is carried out by applying a current of preferably at least 0.5 mA/cm², more preferably 1 mA/cm², even more preferably at least 5, 10 or 100 mA/cm2.

Purification (Step 4.3)

Preferably, the quinone and hydroquinone precursor compounds obtained from oxidation (step 4.2) may further be subjected to a purification step (4.3) to separate said precursor compounds from impurities, contaminants or by-products by a suitable method, preferably by precipitation, recrystallization, distillation, sublimation, solid phase extraction or fluid-fluid phase extraction.

Preferred precursor compounds obtained from step 4.1, more preferably from step 4.2 or 4.3 are characterized by any one of General Formulas IV, V and V:

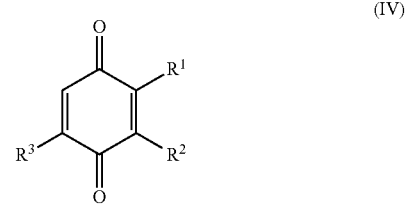

(IV)

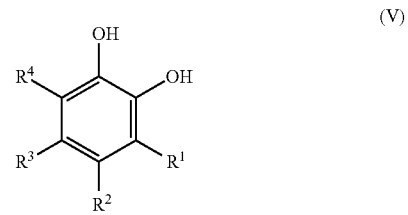

(V)

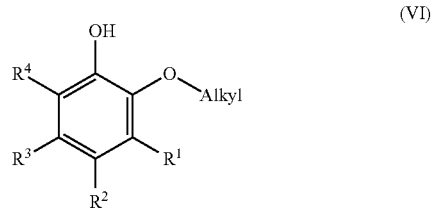

(VI)

wherein
each of $R^1$-$R^3$ in General Formula (IV),
each of $R^1$-$R^4$ in General Formula (V), and
each of $R^1$-$R^4$ in General Formula (VI)
are independently selected from
—H, -Alkyl, -AlkylG$^a$, -Aryl, —SO$_3$H, —SO$_3^-$, —PO$_3$H$_2$, —OH, —OG$^a$, —SH, -Amine, —CHO, —COOH, —COOG$^a$, —CN, —CONH$_2$, —CONHG$^a$, —CONG$^a_2$, -Heteroaryl, -Heterocycyl, NOG$^a$, —N$^+$OG$^a$, —F, —Cl, and —Br, or are joined together to form a saturated or unsaturated carbocycle, more preferably from —H, -Alkyl, —SO$_3$H, —SO$_3^-$, —OG$^a$, and —COOH;

wherein each G$^a$ is independently selected from
—H, -Alkyl, -AlkylG$^a$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3^+$, —CHO, —COOH, —COOAlkyl, —CN, —CONH$_2$, —CONHAlkyl, —CONAlky$_2$, -Heteroaryl, -Heterocycyl, —NOG$^b$, —N$^+$OAlkyl, —F, —Cl, and —Br;

wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

The terms "alkyl", "amine", "heteroalkyl" and "heterocyclyl" are preferably as defined in the context of the inventive compounds as defined by General Formulas (1)-(6).

The precursor compounds according to General Formulas (IV)-(VI) are preferably used to a) obtain further precursor compounds, more preferably o-phenylenediamine, and b) as reaction educts for condensation reactions yielding the inventive compounds.

o-Phenylenediamine Precursor Compounds o-phenylenediamine precursor compounds are preferably obtained from the quinone and hydroquinone precursor compounds obtained from step 4.1, 4.2 or 4.3 of the inventive method.

Transformation (4.4)

Preferably, quinone and hydroquinone precursor compounds obtained from step 4.1, 4.2 or 4.3 of the inventive method are subjected to a transformation reaction to yield o-phenylenediamine precursor compounds according to Reaction Scheme 1:

The precursor compounds may advantageously be obtained from lignin by the inventive method.

Compounds characterized by General Formula (1) or (2) are preferably synthesized by the condensation reaction of a o-phenylenediamine precursor compound with either a benzoquinone or a 2-hydroxy- or 2-alkoxyphenol precursor compound as depicted in Reaction Scheme 2 below. In case of condensation with 2-hydroxy- or 2-alkoxyphenol, the condensation reaction is preferably followed by an oxidation step.

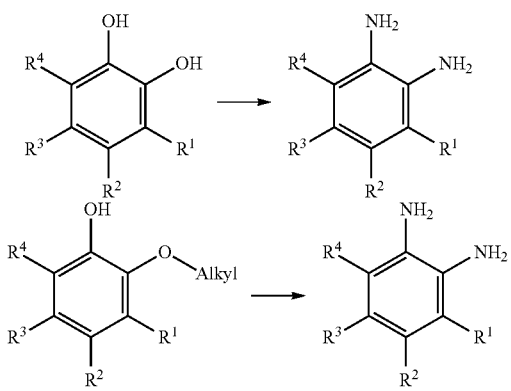

Reaction Scheme 1: Phenylenediamine synthesis form 2-hydroxyphenol (top) and 2-alkoxyphenol (bottom).

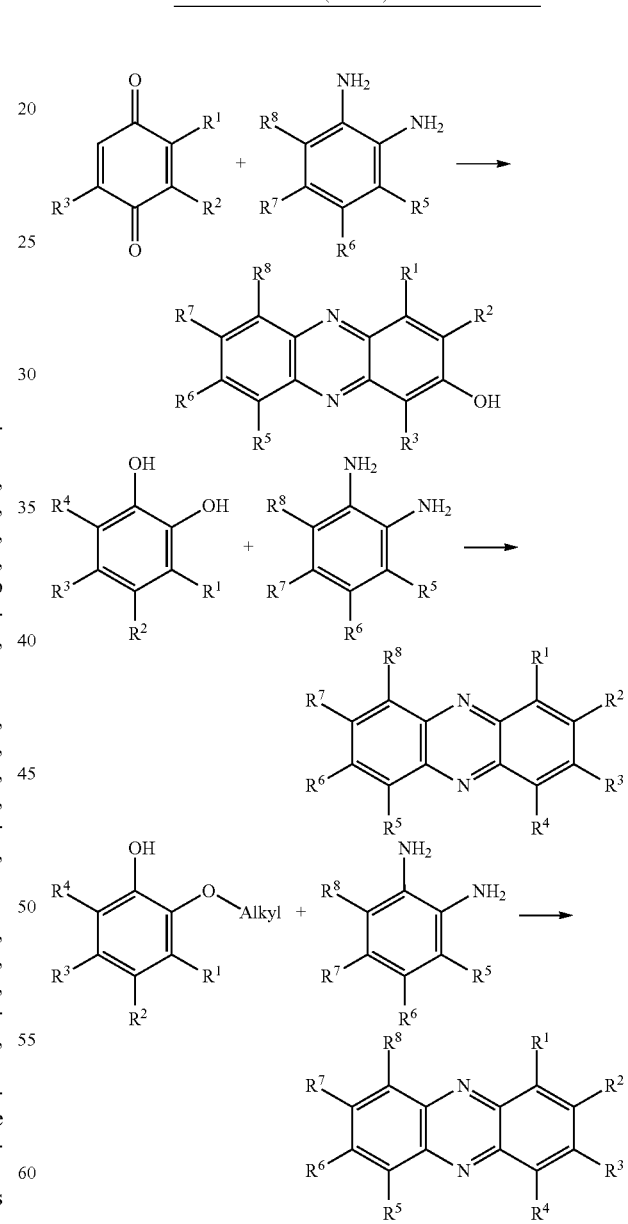

Reaction Scheme 2: Phenazine synthesis from o-phenylenediamine with benzoquinone (top), 2-hydroxphenol (middle) and 2-alkoxypehnol (bottom).

In Reaction Scheme 1, each R substituent is independently selected from

—H, -Alkyl, -AlkylG$^a$, -Aryl, —SO$_3$H, —SO$_3^-$, —PO$_3$H$_2$, —OH, —OG$^a$, —SH, -Amine, —CHO, —COOH, —COOG$^a$, —CN, —CONH$_2$, —CONHG$^a$, —CONG$^a_2$, -Heteroaryl, -Heterocycyl, NOG$^a$, —NOG$^a$, —F, —Cl, and —Br, or are joined together to form a saturated or unsaturated carbocycle, more preferably from —H, -Alkyl, -AlkylG$^a$, —SO$_3$H/—SO$_3^-$, —OG$^a$, and —COOH;

wherein each G$^a$ is independently selected from

—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3{}^+$, —CHO, —COOH, —COOAlkyl, —CN, —CONH$_2$, —CONHAlkyl, —CONAlkyl$_2$, -Heteroaryl, -Heterocycyl, —NOG$^b$, —N$^+$OAlkyl, —F, —Cl, and —Br;

wherein each G$^b$ is independently selected from

—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and Br.

The terms "alkyl", "amine", "heteroalkyl" and "heterocyclyl" are preferably as defined in the context of the inventive compounds as defined by General Formulas (1)-(6).

Preferably, the transformation may be accomplished as described in WO 2012/075053 A2.

Step (5): Condensation

The synthesis of lignin-derived compounds according to any one of General Formulas (1)-(6) can be achieved by a condensation reaction of the precursor compounds described above.

In Reaction Scheme 2, each R substituent is independently selected from

—H, -Alkyl, -AlkylG$^a$, -Aryl, —SO$_3$H, —SO$_3^-$, —PO$_3$H$_2$, —OH, —OG$^a$, —SH, -Amine, —CHO, —COOH, —COOG$^a$, —CN, —CONH$_2$, —CONHG$^a$, —CONG$^a_2$, -Heteroaryl, -Heterocycyl, NOG$^a$, —N$^+$OG$^a$, —F, —Cl, and —Br, or are joined together to form a saturated or unsaturated carbocycle, more preferably from —H, -Alkyl, -AlkylG$^a$, —SO$_3$H/—SO$_3$, —OG$^a$, and —COOH;

wherein each G$^a$ is independently selected from
—H, -Alkyl, -AlkylG$^a$, -Aryl, —SO$_3$H, —SO$_3$, —PO$_3$H$_2$, —OH, —OAlkyl, —OOH, —OOAlkyl, —SH, —SAlkyl, —NH$_2$, —NHAlkyl, —NAlky$_2$, —NAlkyl$_3^+$, —NHG$^b$, —NG$^b_2$, —NG$^b_3{}^+$, —CHO, —COOH, —COOAlkyl, —CN, —CONH$_2$, —CONHAlkyl, —CONAlky$_2$, -Heteroaryl, -Heterocycyl, —NOG$^b$, —N$^+$OAlkyl, —F, —Cl, and —Br;

wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

The terms "alkyl", "amine", "heteroalkyl" and "heterocyclyl" are preferably as defined in the context of the inventive compounds as defined by General Formulas (1)-(6).

Compounds characterized by General Formula (3) or (4) are preferably synthesized by the condensation reaction of a o-phenylenediamine with alloxan as depicted in Reaction Scheme 3 below:

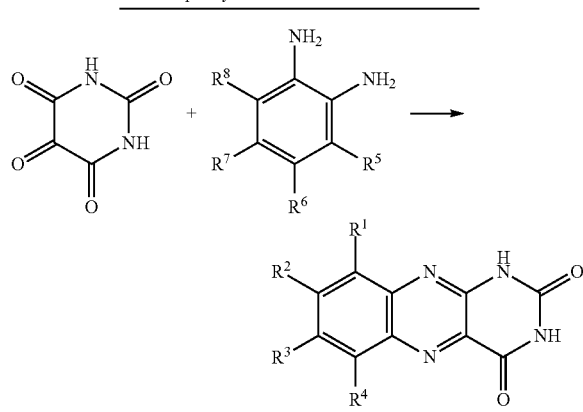

Reaction Scheme 3: Alloxazine synthesis from o-phenylenediamine with Alloxan.

In Reaction Scheme 3, each R substituent is independently selected from
—H, -Alkyl, -AlkylG$^a$, -AlkylG$^a$, -Aryl, —SO$_3$H, —SO$_3^-$, —PO$_3$H$_2$, —OH, —OG$^a$, —SH, -Amine, —CHO, —COOH, —COOG$^a$, —CN, —CONH$_2$, —CONHG$^a$, —CONG$^a_2$, -Heteroaryl, -Heterocycyl, NOG$^a$, —N$^+$OG$^a$, —F, —Cl, and —Br, or are joined together to form a saturated or unsaturated carbocycle, more preferably from —H, -Alkyl, -AlkylG$^a$, —SO$_3$H, —SO$_3$, —OG$^a$, and —COOH;

wherein each G is independently selected from
—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3{}^+$, —CHO, —COOH, —COOAlkyl, —CN, —CONH$_2$, —CONHAlkyl, —CONAlkyl$_2$, -Heteroaryl, Heterocycyl, —NOG$^b$, —N$^+$OAlkyl, —F, —Cl, and —Br;

wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

The terms "alkyl", "amine", "heteroalkyl" and "heterocyclyl" are preferably as defined in the context of the inventive compounds as defined by General Formulas (1)-(6).

After condensation, the obtained condensation products may be subjected to a further purification step to separate said compound(s) from residual compounds, by-products, impurities and contaminants by a suitable method, preferably by precipitation, recrystallization, distillation, sublimation, solid phase extraction or fluid-fluid phase extraction.

The condensation products obtained from step (5) may be the inventive compounds or compositions. Alternatively, the condensation products obtained from step (5) may be subjected to a further modification step (6) to introduce at least one substituent as defined herein and obtain the compounds and compositions according to the present invention.

Step (6): Modification(s)

In step (6) of the inventive method, the condensation products or precursors or mixtures thereof, preferably as obtained from step (5), are modified to preferably introduce at least one substituent as defined herein.

Preferably, "modifying" includes or refers to the introduction of at least one R substituent as defined herein. The term "modification reaction" includes substitution reactions, addition reactions, elimination reactions and rearrangements, with substitution reactions and addition reactions being preferred. In some embodiments, step (6) of the inventive method may include several modification reactions to introduce several, optionally different, substituents as defined herein into the condensation products obtained from step (5).

The condensation products or precursors or mixtures thereof may be transferred to their corresponding oxidized or reduced form prior or subsequent to the modification reaction. Oxidation may be accomplished by the addition of suitable oxidization agents, e.g. selected from air, oxygen or hydrogen peroxide, in combination with or without catalysts. Catalysts may be selected from metal based-catalysts (preferably comprising copper and aluminum), iodine, non-organic and organic acids or other quinones. Reduction may be accomplished by the addition of suitable reduction agents, e.g. selected from hydrogen, sodium dithionate, sodium borohydride, iron, tin(II)-chloride or zinc, in combination with or without catalysts, with hydrogen and sodium dithionate being preferred. Catalysts may be metal based, and may preferably be selected from palladium or nickel.

The condensation products or precursors or mixtures thereof may preferably be modified by substitution and addition reactions. Substitution reactions include any reaction wherein a proton on the aromatic ring is exchanged by a different group, e.g. via an electrophile substitution. Suitable electrophiles may be selected from sulfur trioxide, aldehydes, ketones, esters, lactone, carboxylic acids, anhydrides, imine, carbon dioxide, chlorosulfonic acid, acyl halides, halogens, NO$_2$ and epoxides, preferably carbon dioxide, anhydrides, imines and acyl halides. Addition reactions include any reaction that introduces a new group in the aromatic ring except for protons, preferably via a nucleophile addition on the aromatic ring with subsequent tautomeric rearrangement. Suitable nucleophiles include ammonia, amines, nitrogen containing heterocycles, thiols, alcohols, cyanides and azides, preferably amines, alcohols and nitrogen containing heterocycles.

Reactions can be performed step wise or in several steps in a one pot reaction. The resulting modified condensation products are preferably the compounds or compositions according to the present invention. Said compounds and compositions may preferably exhibit favorable redox properties rendering them useful in a variety of applications.

Preferably, step (6) of the inventive method includes introducing at least one substituent into the condensation products obtained from step (5). Preferably, the at least one substituent may be introduced at a position of the aryl structure other than those characterized by an oxo group. Preferably, the substituent may be directly bound to the aryl structure.

Preferably, the at least one substituent may be selected from -Alkyl, -AlkylG$^a$, -Aryl, —SO$_3$H, —SO$_3^-$, —PO$_3$H$_2$, —OH, —OG$^a$, —SH, -Amine, —CHO, —COOH, —COOG$^a$, —CN, —CONH$_2$, —CONHG$^a$, —CONG$^a_2$, -Heteroaryl, -Heterocycyl, NOG$^a$, —N$^+$OG$^a$, —F, —Cl, and —Br, or substituents may be joined together to form a saturated or unsaturated carbocycle;
wherein each G$^a$ is independently selected from
—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3{}^+$, —CHO, —COOH, —COOAlkyl, —CN, —CONH$_2$, —CONHAlkyl, —CONAlkyl$_2$, -Heteroaryl, -Heterocycyl, —NOG$^b$, —N$^+$OAlkyl, —F, —Cl, and —Br;
wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and Br.

More preferably, the at least one substituent may be selected from -Alkyl, -AlkylG$^a$, SO$_3$H/—SO$_3$, —OG$^a$, and —COOH,
wherein each G$^a$ is independently selected from
—H, -Alkyl, -AlkylG$^a$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b_2$, —NG$^b_3{}^+$, —CHO, —COOH, —COOAlkyl, —CN, —CONH$_2$, —CONHAlkyl, —CONAlkyl$_2$, -Heteroaryl, Heterocycyl, —NOG, —N$^+$OAlkyl, —F, —Cl, and Br;
wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

The terms "alkyl", "amine", "heteroalkyl" and "heterocyclyl" are preferably as defined in the context of the inventive compounds as defined by General Formulas (1)-(6).

In some embodiments, In some embodiments, each substituent is independently not selected from —SH, —NOG$^a$ and —N$^+$OG$^a$, wherein G$^a$ is as defined above.

In some embodiments, in the above substituent definitions, each G$^a$ is independently not selected from —OOH, —OOAlkyl, —SH, —NOG$^b$ and —N$^+$OAlkyl, wherein G$^b$ is as defined above. In some embodiments, in the above substituent definitions, each G$^b$ is independently not selected from —OOH, —OOAlkyl, —SH, and —N$^+$OAlkyl.

By way of example, step (6) of the inventive method may include the sulfonation of the condensation products obtained from step (5). The condensation products may be modified by a further upstream modification reaction before sulfonation and/or may be modified by a further downstream modification reaction after sulfonation. The terms "sulfonation" and "sulfonation reaction" are used herein to refer to a reaction whereby at least one —SO$_3$H/—SO$_3^-$ group is introduced into a condensation product.

Generally, sulfonation may be carried out in the presence of concentrated aqueous sulfuric acid. Alternatively, sulfur trioxide may be mixed with inert gas, such as air, N$_2$ and/or CO$_2$, or complexed with a complexing agent such as pyridine, dioxane, (CH$_3$)$_3$N or DMF. Typically, sulfonation is preferably performed at higher temperatures due to increased resulting yields. Therein, an increased temperature is understood to be at least 50° C., preferably 100° C. However, the temperature shall preferably not decompose the modified condensation product by pyrolysis. Accordingly, the temperature should preferably be lower than 200° C. Separation of the resulting sulfonated condensation product(s) may subsequently be carried out, for example, by filtration or salting out as described herein.

Accordingly, step (6) of the inventive method may thus include the treatment of the condensation product with SO$_3$. To this end, the condensation product(s) may be treated with oleum or SO$_3$ gas. The reaction may be performed under atmospheric pressure or elevated pressure in concentrated sulfuric acid. The reaction may be performed at a temperature of 40-300° C., e.g. at 60-120° C. or 160-180° C. The reaction may be undergone within 1-6 hours, e.g. 3 hours or 4 hours. Subsequently, the reaction mixture may preferably be cooled and neutralized. To this end, the concentrated sulfuric acid may preferably be poured into water and partially neutralized. Calcium hydroxide may be used as a neutralizing agent. The terminative sulfuric acid concentration may be 5-30%, preferably 10-20%. Subsequently, the reaction mixture may be purified. To this end, precipitated sulfates may be filtered off. Subsequently, the resulting mixture may be directly concentrated. To this end, the reaction mixture may be concentrated under reduced pressure to yield a solution of 0.4-1.5 mol/L active material and 10-40% sulfuric acid. Alternatively, the solution may be completely neutralized either with the same or another neutralizing agent and the water may be evaporated under reduced pressure. Additional sulfates that eventually precipitate may be filtered off such that the product precipitates. The remaining water may then be evaporated and the solid is dried to yield a mixture of 30-90% sulfonated product mixed with sulfates. Either process typically yields a crude mixture of differently sulfonated condensation products.

The modification step (6) of the inventive method preferably yields the inventive compounds characterized by any one of General Formulas (1)-(6), or a crude mixture thereof.

The crude mixture may comprise or (essentially) consist a plurality of at least 2, 3, 4, 5 or more compounds according to the present invention. The crude mixture may be the composition of the present invention. The crude mixture may optionally be subjected to at least one further modification step as described herein.

The compounds or compositions obtained from the modification reaction(s) may further be subjected to at least one concentration step.

The compounds or compositions obtained from the modification reaction(s) may further be subjected to at least one purification step. Thereby, modified compounds or compositions method are separated from non-target compounds, impurities, by-products, contaminants and/or decomposed material. Purification may preferably be accomplished by employing an extraction method, preferably precipitation, recrystallization, distillation, sublimation, solid phase extraction or fluid-fluid phase extraction as generally known in the art.

Step (7) Providing Redox Flow Battery Electrolytes and Electrolyte Solutions

Preferably, the inventive method may comprise, optionally after step (5) or (6) a further step (7) of providing the inventive compounds or compositions as redox flow battery electrolytes. Step (7) is described herein as part of the inventive method of valorizing lignin by producing target compounds or compositions therefrom, but is equally applicable to methods that employ crude oil, coal or pure organic substances as a starting material.

Compounds and compositions according to the present invention and optionally obtained by the inventive method are preferably redox active. Preferably, compounds and compositions according to the present invention and optionally obtained by the inventive method are usable or used as redox flow battery electrolytes according to the present invention.

A "(redox flow battery) electrolyte" refers to a substance that is capable of conducting electrical currents via electron transfer in a redox flow battery. Said redox flow battery electrolytes are typically provided as electrolyte solutions. Said "electrolyte solution" may preferably comprises at least one target compound or composition according to the present invention acting as an electrolyte, and at least one solvent. The at least one compound or composition according to the present invention is dissolved or suspended in a suitable solvent. The solvent may preferably be selected from water, methanol, ethanol, dimethylsulfoxide, acetonitrile, acetone and glycol. The electrolyte solution may comprise further additives, including acids, bases, buffers, ionic liquids, stabilizers, and the like.

Compounds and compositions according to the present invention may be used as catholytes and/or anolytes. The term "catholytes" refers to the part or portion of an electrolyte, which is on the cathode side of a redox-flow battery half-cell, whereas the term "anolyte" refers to the part or portion of an electrolyte, which is on the anode side of a redox-flow battery half-cell. It is conceivable to employ the inventive (optionally lignin-derived) target compounds both as catholytes and anolytes in each half-cell (i.e. anode side and cathode side) of the same redox flow battery, thereby providing an "all-organic" redox flow battery. It is however also conceivable to provide the substituted (optionally lignin-derived) target compounds or compositions according to the invention as either catholytes or anolytes in a "half-organic" redox flow battery. Therein, substituted (optionally lignin-derived) target compounds or compositions are utilized either as anolytes (catholytes), whereas the catholyte (anolyte) comprises an inorganic redox active species. Examples for such inorganic redox active species include transition metal ions and halogen ions, such as $VCl_3/VCl_2$, $Br/ClBr_2$, $Cl_2/Cl^-$, $Fe^{2+}/Fe^{3+}$, $Cr^{3+}/Cr^{2+}$, $Ti^{3+}/Ti^{2+}$, $V^{3+}/V^{2+}$, $Zn/Zn^{2+}$, $Br_2/Br^-$, $I^{3-}/I^-$, $VBr_3/VBr_2$, $Ce^{3+}/Ce^{4+}$, $Mn^{2+}/Mn^{3+}$, $Ti^{3+}/Ti^{4+}$, $Cu^+/Cu^{2+}$, $Cu^+/Cu^{2+}$, and others.

Generally, a catholyte is charged when a redox couple is oxidized to a higher one of two oxidation states, and is discharged when reduced to a lower one of the two oxidation state:
Cathode:
(C: Catholyte)

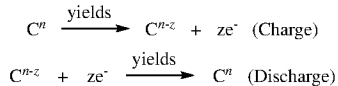

In contrast, an anolyte is charged when a redox couple is reduced to a lower one of two oxidation states, and is discharged when oxidized to a higher one of the two oxidation states:
Anode:

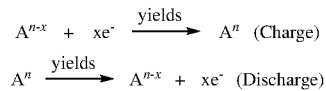

(A: Anolyte)

The standard (redox flow battery) cell potential ($E^o_{cell}$) is the difference in the standard electrode potentials (against the standard hydrogen electrode (SHE)) of the two half-cell reactions of the catholyte and anolyte.

$$E_{cell}^0 = E_{cat}^0 - E_{an}^0 \qquad \text{eq. 1}$$

($E^o_{cell}$=(redox flow battery) cell potential under standard conditions, $E^o_{cat}$: standard reduction potential for the reduction half reaction occurring at the cathode, $E^o_{an}$: standard reduction potential for the oxidation half reaction occurring at the anode).

The Nernst Equation (eq. 2) enables the determination of cell potential under non-standard conditions. It relates the measured cell potential to the reaction quotient and allows the accurate determination of equilibrium constants (including solubility constants).

$$E_{cell} = E_{cell}^0 - \frac{RT}{nF} \ln Q \qquad \text{eq. 2}$$

($E_{cell}$=(redox flow battery) cell potential under non-standard conditions, n=number of electrons transferred in the reaction, F=Faraday constant (96,500 C/mol), T=Temperature and Q=reaction quotient of the redox reaction).

The redox flow battery cell potential thus depends on the concentration and types of reactants (which determines the number of transferred electrons and the reaction quotient). It will be understood that a redox flow battery employing the target compounds or compositions according to the invention as a catholyte and/or anolyte preferably exhibit high (standard) cell potentials. Preferably, the redox flow battery employing (a) target compound(s) or compositions as catholytes and/or anolytes exhibits a cell potential of at least +0.5 V, preferably at least +0.8 V, more preferably at least +1.0 V, or more, typically between +0.5 and +1.5 V, preferably between +0.8 and +1.2 V for the open circuit voltage (OCV) in the fully charged state. Suitable stabilizers can enhance the cell potential to a range typically between +0.5 V and +2.5 V against SHE.

Compounds and compositions according to the present invention, which are envisaged for use as catholytes (accepting electrons in a reduction reaction during discharge) thus preferably exhibit standard reduction potentials (against SHE) $E^0_{cat}$ that are more positive (less negative) than the standard reduction potential for the employed anolyte ($E^0_{an}$). Preferably, target compounds or compositions intended for use as catholytes exhibit positive standard reduction potentials $E^0_{cat}$ of more than 0 V, more preferably of at least +0.5 V, most preferably at least +0.7 V against SHE.

Compounds and compositions according to the present invention, which are envisaged for use as anolytes (donating electrons in an oxidation reaction during discharge) thus preferably exhibit standard reduction potentials (against SHE) $E^0_{an}$ that are more negative (less positive) than the standard reduction potential for the employed catholyte ($E^0_{cat}$). Preferably, target compounds or compositions intended for use as anolytes exhibit standard reduction potentials of less than +0.3 V, preferably +0.1 V or less against SHE.

The standard reduction potential of the redox couple is characteristic of the molecule and its specific substituent groups and is inter alia related to the electronic energy of the molecular orbitals. For instance, $-SO_3H/-SO_3^-$ groups may increase the standard reduction potential, which is consistent with the lowering of molecular orbital energies by electro-withdrawing groups.

While the equilibrium potentials of electrolytes in the cathodic and anodic half-cells determines the cell voltage, its capacity depends on the effective electrolyte concentration, which is the solubility multiplied by the number of electrons transferred in the redox reactions. Highly soluble electrolytes therefore preferably increase the energy capacity of the redox flow battery and are therefore preferred.

For instance, $-SO_3H/-SO_3^-$ and amine groups are preferably capable of increasing the solubility of the substituted compound(s) in water, which preferably provides for an electrolyte solution usable in redox flow batteries exhibiting a high capacity. The compounds or compositions according to the invention are preferably soluble in concentrations of at least 0.3 M, preferably at least 0.6 M, more preferably at least 1.0 M at 25° C.

The compounds or compositions according to the present invention and preferably obtained by the inventive method are preferably redox active. The compounds or compositions according to the present invention and preferably obtained by the inventive method are envisaged as electrolytes. Preferably, said compounds or compositions are thus provided in the form of an electrolyte solution for redox flow battery applications. Compounds and compositions according to the present invention may preferably be dissolved or suspended in a suitable solvent (e.g. water) to yield an electrolyte solution for use in redox flow batteries. Compounds and compositions according to the present invention may be provided in solid or liquid form.

Preferably, compounds and compositions according to the present invention, which are preferably provided as redox flow battery electrolytes, may be dissolved or suspended in aqueous solution, e.g. an aqueous solvent system, thereby forming an electrolyte solution.

The term "aqueous solvent system" refers to a solvent system comprising preferably at least about 20% by weight of water, relative to total weight of the solvent. In some applications, soluble, miscible, or partially miscible (emulsified with surfactants or otherwise) co-solvents may also be usefully present which, for example, extend the range of water's liquidity (e.g., alcohols/glycols). In addition to the redox active electrolytes described herein, the electrolyte solutions may contain additional buffering agents, supporting electrolytes, viscosity modifiers, wetting agents, and the like, which may be part of the solvent system.

Thus, the term "aqueous solvent system" may generally include those comprises at least about 55%, at least about 60 wt %, at least about 70 wt %, at least about 75 wt %, at least about 80%, at least about 85 wt %, at least about 90 wt %, at least about 95 wt %, or at least about 98 wt % water, relative to the total solvent. Sometimes, the aqueous solvent may consist essentially of water, and be substantially free or entirely free of co-solvents or other (non-target compound) species. The solvent system may be at least about 90 wt %, at least about 95 wt %, or at least about 98 wt % water, or may be free of co-solvents or other (non-target compound) species.

One or both electrolyte solutions may be characterized as having a pH of between about <0 and about >14. The pH of the electrolyte solution may be maintained by a buffer. Typical buffers include salts of phosphate, borate, carbonate, silicate, trisaminomethane (Tris), 4-(2-hydroxyethyl)-1-piperazineethanesulfonic acid (HEPES), piperazine-N,N'-bis (ethanesulfonic acid) (PIPES), and combinations thereof. A user may add an acid (e.g., HCl, $HNO_3$, $H_2S_4$ and the like), a base (NaOH, KOH, and the like), or both to adjust the pH of a given electrolyte solution as desired.

The pH of the first and second electrolyte solutions may be equal or substantially similar; or the pH of the two electrolytes differ by a value in the range of about 0.1 to about 2 pH units, about 1 to about 10 pH units, about 5 to about 12 pH units, about 1 to about 5 pH units, about 0.1 to about 1.5 pH units, about 0.1 to about 1 pH units, or about 0.1 to about 0.5 pH units. In this context, the term "substantially similar," without further qualification, is intended to connote that the difference in pH between the two electrolytes is about 1 pH unit or less, such as about 0.4 or less, about 0.3 or less, about 0.2 or less, or about 0.1 pH units or less.

Method for Providing Lignin-Derived Redox-Flow Battery Electrolytes

In accordance with the above, an exemplary method for providing the inventive target compounds and compositions may include the steps as described in the following, using lignocellulosic material as a starting material. The method can be performed using any suitable starting material as described herein. Accordingly, in a first step (1), a lignocellulosic material may be provided (sub-step (1.1)) and subjected to pulping (sub-step (1.2)). The lignocellulosic material may be provided in chopped form (e.g. as woodchips) and may for instance derived from wood of low silica and resin content, such as beech (or any other wood described above).

In sub-step (1.2), the lignocellulosic material may be subjected to a pulping process as described herein. Typically, said pulping process may be a Kraft process or a sulfite process as described above. In the Kraft process, the lignocellulosic material is typically wetted and pre-heated with steam, and cooked (e.g. under at least 4 bar for 3-5 hours at 150° C. or more, e.g. 170 to 180° C.) in an aqueous alkaline solution (e.g. sodium hydroxide) comprising a suitable Kraft pulping reactive agent (such as a sulfide salt, a sulfhydryl compound or salt, and a polysulfide salt, additionally, a sulfate salt may be added). Such a solution may be "white liquor" containing sodium hydroxide and sodium sulfide. The Kraft process typically yields "Kraft lignin" which may be further sulfonated to obtain "sulfonated Kraft lignin".

However, other pulping processes as described herein may be applied as well. In particular, the sulfite process may be employed. In the sulfite process, lignocellulosic material is typically wetted and preheated with steam, and cooked (e.g. under at least 4 bar for 4-6 hours at 120° C. to 170° C., e.g. 130° C.-160° C.) in an aqueous, typically acidic solution of low pH (e.g. pH 1-5) comprising a sulfite or bisulfite agent.

The pulping process preferably disintegrates wood into its components lignin, cellulose and hemicellulose, which may be separated in a subsequent step.

In sub-step (1.3), the pulp is separated from the process stream, to provide at least one process stream that is substantially free from cellulose and comprises modified lignin-derived components, hemicellulose, and the like. Separation may typically be accomplished by blowing, sieving, filtration and one or more washing steps.

Subsequently, in step (2), modified lignin-derived components may be isolated from other components of the process stream(s), e.g. by ultra- and/or nanofiltration with suitable molecular weight cut-off values (such as about kDa for ultrafiltration and 0.1-5 kDa for nanofiltration).

The isolated modified lignin-derived components are then subjected to chemical decomposition in step (3), e.g. by oxidative cracking (although other chemical decomposition methods described herein are also applicable), to break or dissociate larger molecules into their smaller fragments by dissociation of their covalent bonds. Oxidative cracking may be effected in the presence of a suitable oxidizing agent, such as air, and a suitable catalyst. The catalyst may be a homogenous catalyst, e.g. a metal salt comprising a metal ion such as Cu(II) or Fe(III), or comprising a metalloid component such as B(III), Si(IV) and Al(III). Chemical decomposition may be conducted at elevated temperatures (i.e. >30° C., e.g. 150° C.) but is typically performed at temperatures that do not induce pyrolysis of the treated materials (i.e. <350° C.). Other chemical decomposition steps as described herein may also be applied.

Step (3) of the inventive method yields decomposition products. Said decomposition products are preferably low molecular weight aromatic lignin-derived components.

In step (4) of the inventive method, the low molecular weight decomposition products are isolated from higher molecular weight aromatic lignin-derived components and/or other non-lignin-derived residual components, e.g. by ultra- or nanofiltration (sub-step (4.1)). The employed ultra- or nanofilters may have a molecular weight cut-off of 0.15 kDa to 1 kDa or less, eg. 0.5 kDa.

Step (4) may further include the oxidation (sub-step (4.2)), purification (sub-step (4.3)) and transformation (sub-step (4.4)) of the decomposition products obtained from step (3). Step (4) of the inventive method preferably yields benzoquinone, 2-hydroxyphenol, 2-methoxyphenol and o-phenylenediamine precursor compounds.

Subsequently, the precursor compounds are subjected to a condensation reaction (step (5)) to obtain condensation products according to General Formulas (1)-(6) or mixtures thereof. After an optional purification, said condensation products may further be modified to introduce one or more R substituents as defined herein (step (6)). The resulting compounds and compositions of the present invention may be further purified or directly used as redox flow battery electrolytes (step (7)).

Substituted Lignin-Derived Target Compounds

In a further aspect, the present invention provides compounds and compositions comprising the same, which are optionally obtained or obtainable by the method according to the invention. Said compounds or compositions may optionally be obtained or obtainable by step (5) (or optionally step (6) or (7)) of the inventive method.

Preferably, said compounds are lignin-derived substituted low molecular weight aromatic compounds.

More preferably, said compounds may be characterized by any one of General Formulas (1)-(6), as defined elsewhere herein.

Preferably, said compounds and compositions are redox active. Preferably, said compounds and compositions are useful or used as redox flow battery electrolytes.

Redox Flow Battery
Redox Flow Battery Setup

In a further aspect, the present invention provides a redox flow battery comprising at least one compound or composition according to the present invention.

Redox flow batteries typically comprise two parallel electrodes separated by a suitable separator, such as an ion exchange membrane, forming two half-cells. Preferably, redox flow batteries according to the invention thus comprise (1) a first half-cell comprising a first or negative electrode contacting a first (optionally aqueous) electrolyte solution comprising the first electrolyte; (2) a second half-cell comprising a second or positive electrode contacting a second (optionally aqueous) electrolyte solution comprising the second electrolyte; and (3) a separator (or "barrier") disposed between the first and second electrolytes. Preferably, the electrolytes are provided in liquid form, either in pure liquid form or dissolved in a suitable solvent, i.e. as electrolyte solutions. The electrolyte, which is in contact with the negative electrode, may also be referred to as the "negolyte". The electrolyte, which is in contact with the positive electrode, may also be referred to as the "posolyte".

The redox flow battery cell typically comprises of a first redox flow battery half-cell harbouring the positive electrode in contact with the first electrolyte solution and—separated therefrom by a suitable separator or barrier—a second half-cell harbouring a negative electrode in contact with the second electrolyte solution. Preferably, the half-cells are configured as separate reservoirs (or chambers) within the redox flow battery cell, through which the first and/or second electrolyte solutions flow so as to contact the respective electrodes disposed in the electrolyte solution, and the separator.

The negative electrode reservoir ("negolyte chamber") comprises the negative electrode immersed within the negative electrode electrolyte in a container and forms a first redox flow battery half-cell; and the positive electrode chamber ("posolyte chamber") comprises the positive electrode immersed within the positive electrode electrolyte in a container and forms the second redox flow battery half-cell. Each container and its associated electrode and electrolyte solution thus defines its corresponding redox flow battery half-cell. The containers of each redox flow battery half-cell may be composed of any preferably chemically inert material suitable to retain the respective electrolyte solutions. Each electrolyte preferably flows through its corresponding redox flow battery half-cell flow so as to contact the respective electrode disposed within the electrolyte, and the separator. The electrochemical redox reactions of the employed electrolytes occur within the redox flow battery half-cells.

Specifically, the current invention thus provides a redox flow battery comprising: a first (optionally aqueous) electrolyte solution comprising a first (redox active) electrolyte; a first electrode in contact with said first (optionally aqueous) electrolyte solution; a second (optionally aqueous) electrolyte solution comprising a second (redox active) electrolyte; a second electrode in contact with said second (optionally aqueous) electrolyte solution; wherein one or both of the first and second (redox active) electrolytes comprise at least one substituted (optionally lignin-derived) target compound as defined herein, or a composition comprising or (essentially) consisting of the same as defined herein.

The posolyte and negolyte chamber defining the corresponding redox flow battery half-cells are preferably connected to a power source. Further, each chamber may be connected, preferably via suitable ducts, to at least one separate storage tank comprising the respective electrolyte solution flowing through said chamber. The storage tank volume determines the quantity of energy stored in the system, which may be measured in kWh. The ducts may comprise transportation means (e.g. pumps, openings, valves, ducts, tubing) for transporting the electrolyte solutions from the storage tanks through the corresponding half-cell chamber.

The redox flow battery cell may further comprise control software, hardware, and optional safety systems such as sensors, mitigation equipment, meters, alarms, wires, circuits, switches, signal filters, computers, microprocessors, control software, power supplies, load banks, data recording equipment, power conversion equipment, and other devices and other electronic/hardware controls and safeguards to ensure safe, autonomous, and efficient operation of the redox flow battery. Such systems are known to those of ordinary skill in the art.

Typically, the first redox flow battery half-cell is separated from the second redox flow battery half-cell by a separator (also referred to as a "membrane" or "barrier" herein). Said separator preferably functions to (1) (substantially) prevent mixing of first and second electrolyte, i.e. physically separates the posolyte and negolyte from each other; (2) reduces or prevents short circuits between the positive and negative electrodes; and (3) enables ion (typically $H^+$) transport between the positive and negative electrolyte chambers, thereby balancing electron transport during charge and discharge cycles. The electrons are primarily transported to and from an electrolyte through the electrode contacting that electrolyte.

Suitable separator materials may be chosen by the skilled artisan from separator materials known in the art as long as they are (electro-)chemically inert and do not, for example, dissolve in the solvent or electrolyte. Separators are preferably cation-permeable, e.g. allow the passage of cations such as $H^+$ (or alkali ions, such as sodium or potassium), but is at least partially impermeable to the redox active compounds. The separator may for instance be selected from an ion conducting membrane or a size exclusion membrane.

Separators are generally categorized as either solid or porous. Solid separators may comprise an ion-exchange membrane, wherein an ionomer facilitates mobile ion transport through the body of the polymer which constitutes the membrane. The facility with which ions conduct through the membrane can be characterized by a resistance, typically an area resistance in units of ohm-cm$^2$. The area resistance is a function of inherent membrane conductivity and the membrane thickness. Thin membranes are desirable to reduce inefficiencies incurred by ion conduction and therefore can serve to increase voltage efficiency of the redox flow battery cell. Active material crossover rates are also a function of membrane thickness, and typically decrease with increasing membrane thickness. Crossover represents a current efficiency loss that must be balanced with the voltage efficiency gains by utilizing a thin membrane.

Such ion-exchange membranes may also comprise or consist of membranes, which are sometimes referred to as polymer electrolyte membranes (PEMs) or ion conductive membranes (ICMs). The membranes according to the present disclosure may comprise any suitable polymer, typically an ion exchange resin, for example comprising a polymeric anion or cation exchange membrane, or combination thereof. The mobile phase of such a membrane may comprise, and/or is responsible for the primary or preferential transport (during operation of the battery) of at least one mono-, di-, tri-, or higher valent cation and/or mono-, di-, tri-, or higher valent anion, other than protons or hydroxide ions.

Additionally, substantially non-fluorinated membranes that are modified with sulfonic acid groups (or cation exchanged sulfonate groups) may also be used. Such membranes include those with substantially aromatic backbones, e.g., poly-styrene, polyphenylene, bi-phenyl sulfone (BPSH), or thermoplastics such as polyetherketones or polyethersulfones. Examples of ion-exchange membranes comprise NAFION®.

Porous separators may be non-conductive membranes that allow charge transfer between two electrodes via open channels filled with conductive electrolyte solution. Porous membranes are typically permeable to liquid or gaseous chemicals. This permeability increases the probability of chemicals (e.g. electrolytes) passing through porous membrane from one electrode to another causing cross-contamination and/or reduction in cell energy efficiency. The degree of this cross-contamination depends on, among other features, the size (the effective diameter and channel length), and character (hydrophobicity/hydrophilicity) of the pores, the nature of the electrolyte, and the degree of wetting between the pores and the electrolyte solution. Because they contain no inherent ionic conduction capability, such membranes are typically impregnated with additives in order to function. These membranes are typically comprised of a mixture of a polymer, and inorganic filler, and open porosity. Suitable polymers include those chemically compatible with the electrolytes and electrolyte solutions described herein, including high density polyethylene, polypropylene, polyvinylidene difluoride (PVDF), or polytetrafluoroethylene (PTFE). Suitable inorganic fillers include silicon carbide matrix material, titanium dioxide, silicon dioxide, zinc phosphide, and ceria and the structures may be supported internally with a substantially non-ionomeric structure, including mesh structures such as are known for this purpose in the art.

Separators may feature a thickness of about 500 microns or less, about 300 microns or less, about 250 microns or less, about 200 microns or less, about 100 microns or less, about 75 microns or less, about 50 microns or less, about microns or less, about 25 microns or less, about 20 microns or less, about microns or less, or about 10 microns or less, for example to about 5 microns.

The negative and positive electrodes of the inventive redox flow battery provide a surface for electrochemical reactions during charge and discharge. As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to the reversible hydrogen electrode. The negative electrode is associated with the first aqueous electrolyte and the positive electrode is associated with the second electrolyte, as described herein. The inventive redox flow battery comprises a first (positive) and second (negative) electrode (cathode and anode, respectively).

The negative and positive electrodes of the inventive redox flow battery provide a surface for electrochemical reactions during charge and discharge. The first and second electrode may comprise or consist of the same or a different material(s).

Suitable electrode materials may be selected from any electrically conductive material that is chemically and electrochemically stable (i.e., inert) under the desired operating conditions. Electrodes may comprise more than one material as long as their surface is preferably covered by an electrically conductive and (electro)chemically inert material.

Exemplary electrode materials for use in the inventive redox flow battery may be selected, without limitation, from a metal, such as titanium, platinum, copper, aluminum, nickel or stainless steel; preferably a carbon material, such as glassy carbon, carbon black, activated carbon, amorphous carbon, graphite, graphene, carbon mesh, carbon paper, carbon felt, carbon foam, carbon cloth, carbon paper, or carbon nanotubes; and an electroconductive polymer; or a combination thereof. The term "carbon material" refers to materials which are primarily composed of the element carbon, and typically further contain other elements, such as hydrogen, sulfur, oxygen, and nitrogen. Carbon materials containing a high surface area carbon may be preferred due to their capability of improving the efficiency of charge transfer at the electrode.

The electrodes may take the form of a plate, which may preferably exhibit an increased surface area, such as a perforation plate, a wave plate, a mesh, a surface-roughened plate, a sintered porous body, and the like. Electrodes also may be formed by applying any suitable electrode material onto the separator.

Preferably, the electrolytes within the inventive redox flow battery are provided in liquid form, either in pure liquid form or dissolved in a suitable solvent, e.g. e.g. water, methanol, ethanol, dimethylsulfoxide, acetonitrile, acetone, glycol or mixtures thereof, i.e. as electrolyte solutions as described in greater detail elsewhere herein.

Accordingly, the redox flow battery according to the invention may comprise (1) a first half-cell comprising a first (redox active) electrolyte, optionally dissolved or suspended in suitable solution, e.g. an aqueous solution, in contact with the first electrode and (2) a second half-cell comprising a substituted, optionally lignin-derived target compound as disclosed herein as a second (redox active) electrolyte, which is preferably dissolved or suspended in aqueous solution, in contact with the second electrode, or vice versa.

Optionally, the redox flow battery according to the invention may comprise, as a first redox active electrolyte, an inorganic material, e.g. a chlorine, bromine, iodine, oxygen, vanadium, chromium, cobalt, iron, manganese, cobalt, nickel, copper, or lead, in particular, bromine or a manganese oxide, a cobalt oxide or a lead oxide, e.g. as ligand complexes, e.g. metal (e.g. Fe) complexes, e.g. iron based ligand complexes like $K_4[Fe(CN)_6]$, and, as the second redox active electrolyte, a substituted, optionally lignin-derived, target compound as described herein, or vice versa.

Alternatively, both the first and the second electrolyte may be selected from a substituted, optionally lignin-derived, target compound as described herein. The first (redox active) electrolyte may function as the anolyte, and the second (redox active) electrolyte may function as the catholyte, or vice versa.

The disclosed redox flow battery may also be characterized in terms of its half-cell reduction potentials. Both the negative and positive electrode preferably exhibit a half-cell standard reduction potential. A redox flow battery cell according to the present disclosure may exhibit a half-cell potential for the negative electrode less than about +0.3 V vs. SHE, preferably less than about +0.1 V vs. SHE. A redox flow battery cell according to the present disclosure, specifically when employing substituted target compounds as described herein as redox flow battery electrolytes, may exhibit a half-cell potential for the positive electrode at least about +0 V vs. SHE, preferably at least +0.5 V vs. SHE, most preferably at least about 0.7 V vs. SHE.

The disclosed redox flow batteries may also be characterized in terms of their energy density. Flow batteries of the present disclosure may operate with an energy density of, at least between about 10 Wh/L per side and about 20 Wh/L per side, preferably between about 20 Wh/L per side and about 50 Wh/L per side, most preferably between about 50 Wh/L per side and about 100 Wh/L per side, Operation In a charging cycle, electrical power is applied to the system. Thereby, the redox active electrolyte contained in the one (for instance the second) electrolyte solution undergoes one-or-more electron oxidation and the redox active electrolyte in the other (for instance the first) electrolyte solution undergoes one-or-more electron reduction. Similarly, in a discharge cycle one (for instance the second) electrolyte is reduced and the other (for instance the first) electrolyte is oxidized producing electrical power.

As indicated above, it is conceivable to employ different substituted (optionally lignin-derived) compounds as the first and the second electrolyte in the redox flow batteries according to the invention. Accordingly, the invention thus features a redox flow battery including first and second electrodes separated by a separator, wherein in its charged state, the redox flow battery includes a first substituted target compound in its reduced form at the first electrode and a second substituted target compound in its oxidized form at the second electrode, wherein during discharge, the first target compound is oxidized, and the second target compound is reduced. Specifically, the substituted target compounds may be dissolved or suspended in aqueous solution.

Redox Flow Battery Stacks

In some cases, a user may desire to provide higher charge or discharge voltages than available from a single battery. In such cases, and in certain embodiments, then, several batteries are connected in series such that the voltage of each cell is additive. An electrically conductive, but non-porous material (e.g., a bipolar plate) may be employed to connect adjacent battery cells in a bipolar stack, which allows for electron transport but prevents fluid or gas transport between adjacent cells. The positive electrode compartments and negative electrode compartments of individual cells are suitably fluidically connected via common positive and negative fluid manifolds in the stack. In this way, individual electrochemical cells can be stacked in series to yield a desired operational voltage.

Several redox flow batteries may be connected in series via electrically conductive, preferably non-porous material which allows for electron transport but prevents fluid or gas transport between adjacent cells (e.g., a bipolar plate) in a bipolar redox flow battery stack. Positive and negative electrode compartments of each cell are preferably connected via common positive and negative fluid manifolds in the stack. Thereby, individual electrochemical cells can be stacked in series to yield a desired operational voltage.

The term "bipolar plate" refers to an electrically conductive, substantially nonporous material that may serve to separate electrochemical cells in a cell stack such that the cells are connected in series and the cell voltage is additive across the cell stack. The bipolar plate has two surfaces such that one surface of the bipolar plate serves as a substrate for the positive electrode in one cell and the negative electrode in an adjacent cell. The bipolar plate typically comprises carbon and carbon containing composite materials.

Energy Storage Systems

Redox flow battery cells, cell stacks, or redox flow batteries as described herein comprising the substituted (optionally lignin-derived) target compounds may be incorporated in larger energy storage systems, suitably including piping and controls useful for operation of these large units. Piping, control, and other equipment suitable for such systems are known in the art, and include, for example, piping and pumps in fluid communication with the respective electrochemical reaction chambers for moving electrolytes into and out of the respective chambers and storage tanks for holding charged and discharged electrolytes.

The storage tanks contain the redox active materials; the tank volume determines the quantity of energy stored in the system, which may be measured in kWh. The control software, hardware, and optional safety systems suitably include sensors, mitigation equipment and other electronic/hardware controls and safeguards to ensure safe, autonomous, and efficient operation of the flow battery energy storage system. Such systems are known to those of ordinary skill in the art. A power conditioning unit may be used at the front end of the energy storage system to convert incoming and outgoing power to a voltage and current that is optimal for the energy storage system or the application. For the example of an energy storage system connected to an electrical grid, in a charging cycle the power conditioning unit would convert incoming AC electricity into DC electricity at an appropriate voltage and current for the electrochemical stack. In a discharging cycle, the stack produces DC electrical power and the power conditioning unit converts to AC electrical power at the appropriate voltage and frequency for grid applications.

The energy storage and generation systems described herein may also include electrolyte circulation loops, which may comprise one or more valves, one or more pumps, and optionally a pressure equalizing line. Hence, the energy storage system according to the invention may comprise at least one redox flow battery, a first chamber containing the first (preferably aqueous) electrolyte and a second chamber containing the second (preferably aqueous) electrolyte; at least one electrolyte circulation loop in fluidic communication each electrolyte chamber, said at least one electrolyte circulation loop comprising storage tanks and piping for containing and transporting the electrolytes; control hardware and software (which may include safety systems); and an optional power conditioning unit.

The energy storage and generation systems of this disclosure can also include an operation management system. The operation management system may be any suitable controller device, such as a computer or microprocessor, and may contain logic circuitry that sets operation of any of the various valves, pumps, circulation loops, and the like.

The energy storage systems of the present disclosure are preferably suited to sustained charge or discharge cycles of several hour durations. For example, redox flow batteries comprising the substituted (optionally lignin-derived) compounds of the present invention may be capable of retaining at least about 70% efficiency when subjected to 10 charge/discharge cycles. As such, the systems of the present disclosure may be used to smooth energy supply/demand profiles and provide a mechanism for stabilizing intermittent power generation assets (e.g., from renewable energy sources). It should be appreciated, then, that various embodiments, of the present disclosure include those electrical energy storage applications where such long charge or discharge durations are valuable. For example, non-limiting examples of such applications include those where systems of the present disclosure are connected to an electrical grid include, so as to allow renewables integration, peak load shifting, grid firming, baseload power generation consumption, energy arbitrage, transmission and distribution asset deferral, weak grid support, and/or frequency regulation. Cells, stacks, or systems according to the present disclosure may be used to provide stable power for applications that are not connected to a grid, or a micro-grid, for example as power sources for remote camps, forward operating bases, off-grid telecommunications, or remote sensors.

Assembly

Also disclosed herein is an assembly which is provided for conducting the inventive method and in particular steps (1.3) to (5), which are not part of a conventional pulp and/or paper manufacturing plant. With regard to step (1.3), pulp separation from the process stream originating from the pulping process (step (1.2)) is conducted as a core activity to obtain the target product of a conventional pulp and/or paper manufacturing plant. However, the separation of the process stream into at least two partial process streams as optionally devised in step (1.3) is not part of a known pulp and/or paper manufacturing plant. Hence, the assembly disclosed herein comprises (i) optionally a stream separator, (ii) an isolation unit, (iii) a decomposition unit, and (iv) a separation unit.

The provision of the process stream in step (1.3) to provide partial process streams in step (1.3(b)) is preferably conducted in a stream separation unit, comprising mechanical and/or pneumatic means known in the art. The isolation of the modified lignin may be conducted in an isolation unit, comprising, for example, means for conducting (ultra-) filtration, extraction and countercurrent flow.

Preferably, the stream separator of the assembly facilitates that the substantially pulp-free process stream of step (1.3) is divided into at least two partial process streams. By means of the stream separator, the ratio of the at least two partial process streams may be controlled, which streams may be supplied to different further processing. Typically, the fraction of modified lignin-derived components of one of the partial process streams is not isolated. Instead the stream comprising the original content of modified lignin is forwarded to a combustion and recovery unit. Using some of the fraction of modified lignin-derived components as an internal energy fuel for the energy supply for the pulp and/or paper manufacturing plant. Additionally, residual reactive agents are regained, e.g. from the black or brown liquor or from organic solvents. These reactive agents are typically salts, which withstand temperatures of, for example, at least 500° C., or even at least 750° C., or even at least 1000° C. During combustion, e.g. sodium sulfate may be reduced to sodium sulfide by the organic carbon in the mixture, which may be reused in the pulping process. In contrast, the organic material, which serves as internal fuel, such as the modified lignin, hemicellulose, residual cellulose and/or fragments thereof, are burned at temperatures of, for example, at least 500° C., or even at least 750° C., or even at least 1000° C.

The combustion and recovery process is more frequently employed in plants operating according to the Kraft process. Therein, excess black liquor typically contains about 15% (w/w) solids and may be concentrated in a multiple effect evaporator. After said concentration, the black liquor is typically enriched to about 20-30% (w/w) solids. At such a concentration of solids, a naturally comprised soap called rosin soap rises to the surface and is skimmed off. The collected soap is further processed to tall oil. Removal of the soap improves the combustion operation. Soap-depleted black liquor with about 20-30% (w/w) solids is be called weak black liquor. It may then be further evaporated to 65% or even 80% solids, which may be called "heavy black liquor", and may be burnt in a recovery boiler to provide energy and to recover the inorganic chemicals for reuse in the pulping process. Concentrated black liquor is usually appreciated for its large heating value (about 12.000 to 13.000 Btu/dry Ib). The heat released from the combustion is used to generate high pressure and power. Therefore, the high pressure steam may be fed to turbogenerators, reducing the steam pressure for the plant use and generating electricity. Some of the heat released and part of the reducing value in black liquor is used to drive the pulp and/or paper production plant's reactive agent recovery operation.

Thus, the fraction of modified lignin-derived components of the process stream coming from step (1) of the inventive method is typically an important fuel for paper and pulp manufacturing plant as it contributes heavily to a pulp and/or paper production plant's energy self-sufficiency. Moreover, the pulp and paper industry traditionally has a highly efficient infrastructure for growth, harvesting, transport, and processing of forest materials. For example, Kraft operations are highly integrated and depend on the (modified) lignin fraction from wood as a fuel to operate the incredibly expensive chemical recovery boilers that are the heart of their operation. In the past, diverting this fuel source to other uses would have required the pulping operation to supplement its energy needs by purchasing natural gas or coal, potentially upsetting the plant's economics. Therefore, the Kraft process in contrast to the sulfite process essentially did not provide a source of lignin-derived raw material.

However, modern pulp and/or paper production plants, including such running under the Kraft process, become more and more energy efficient. Additionally, bark and wood residues may be burned in a separate power boiler to generate steam. Said overflow in energy sources available to a modern pulp and/or paper manufacturing plant may provide a sufficient "safety margin" to divert lignin-derived combustible material while the plant remains self-sufficient in terms of energy supply.

The "safety margin" of overflow modified lignin available form modern pulp and/or paper production plants may be even larger considering the fact that high solid contents in the concentrated (black) liquor have the typical drawback of resulting in higher viscosity and precipitation of solids in the ducts and the combustion and recovery unit. This precipitation leads to adverse plugging and fouling of equipment, which has to be preferably avoided. Thus, controlling the isolation of the fraction of modified lignin-derived components, e.g. also by means of the stream divider of the inventive assembly, and thereby reducing the modified lignin load in the process stream supplied to the combustion and recovery unit, may advantageously contribute to avoid such adverse plugging and fouling of equipment.

In this regard, the inventive assembly provides means to balance the needs for energy supply to the Kraft process on the one hand and the diverting of lignin and derivatives thereof on the other hand. First, the flexible control of the diverting means allows to direct exactly the share of the process stream to the generation of electricity and/or steam, which is actually needed to run the pulp and/or paper manufacturing plant. Thereby, modified lignin-derived components not required in combustion may entirely be directed to other uses such as the further processing of modified lignin according to the present invention. Therefore, less or even no modified lignin is wasted anymore as fuel in excess generation of electricity and/or steam. Second, any modified lignin or lignin-derived compound or fragment thereof, which does not yield the target compound may be recycled back to the process stream feeding the energy supply of the pulp and/or paper manufacturing plant. Third, as explained herein, pulp and/or paper manufacturing plants become more and more energy efficient, thus the required modified lignin supply for energy providing purposes is about to shrink. Alternatively, energy losses could be mediated by using forest residues and/or by transferring to black liquor gasification. In that scenario, the industry could continue to generate the power they need, but because of the higher efficiency of gas turbines, could also produce a separate syngas stream that can in part for the generation of energy, and in part for the production of higher-value products.

For carrying out step (3), the assembly comprises a decomposition unit, providing means to sustain elevated temperature and/or pressure, and to provide the required reactants in solid, liquid and/or gaseous form, preferably in one reaction vessel only. Alternatively, the decomposition unit of the assembly provides a suitable electrochemical cell such as a flow cell.

For conducting step (4), the assembly comprises an isolation unit providing means for isolating low molecular weight aromatic lignin-derived compounds, such as monomers and dimers are used herein, from higher molecular weight lignin-derived components and/or other material involved in the inventive method. Preferably said means is an ultra- and/or nanofiltration unit or an extraction. All ducts and/or product and/or process stream contacting parts are preferably made from inert materials. The preferred details of said assembly are described herein with regard to the method, which is performed in said assembly. For example, valves and/or pumps or gravity assisting means may typically be employed to facilitate the required flow of the stream downwards to the next step of the inventive method.

It is even more preferred that said assembly for conducting the requires steps further comprises (v) optionally an annulation unit, (vi) an oxidizing unit, (vii) a derivatization unit and (viii) optionally a purification unit. Therein, typically step (4.2) is conducted in an annulation unit, step (4.3 (a)-(c)) in an oxidizing unit, and step (5) and step (6) in a derivatizing unit. The preferred requirements for such assembly units may be derived from the conditions and characteristics of the method steps described herein, which are performed in said assembly units.

Preferably, said assembly is directly connected to a conventional pulp and/or paper production plant. However, in an alternative embodiment, the apparatus is not directly associated or attached with the conventional pulp and/or paper manufacturing plant. Instead. The process stream originating from step (1), e.g. of a conventional pulp and/or paper manufacturing plant, is collected and then transferred to a distinct apparatus suitable to conduct the steps (2) to (5) and optionally (6). Yet, in the context of the present invention, a direct integration of the apparatus suitable to conduct the steps (2) to (5) and optionally (6) is preferred, as such direct integration provides for a flexible separation of the lignin-derived compounds in the process stream depending on the energy needs and further parameters of the pulp and/or paper manufacturing plant.

In a further aspect of the present invention, a method is provided for applying a pulp and/or paper manufacturing process using the pulping process by a plant, wherein the plant is equipped with an assembly according to the present invention. Accordingly, said method refers to modifying an existing pulp and/or paper manufacturing plant, working e.g. under the Kraft or sulfite process, wherein the plant is provided with the assembly according to the present invention. This may be of particular benefit, as an existing plant is thereby upgraded to provide potentially simultaneously (i) conventional pulp and/or paper, (ii) energy supply from lignin combustion to run the plant in a preferably self-sustaining manner, and (iii) intermediates of fine chemicals or fine chemicals such as redox active compounds based on the otherwise by-product of modified lignins. The such upgraded plant may be versatility operated depending on actual demand for pulp, energy or fine chemical. Hence, this method significantly adds flexibility and appreciation to the existing pulp and/or paper manufacturing plant.

Various Synthesis Routes

Synthesis routes for synthesizing phenazines based on monomers, e.g. vanillic acid, as e.g. obtained from lignin as the natural source are described below. However, these synthesis routes do not necessarily need to rely on lignin-based monomers, but may also employ monomers from other sources, e.g. obtained by crude oil fractionation etc. These synthesis routes Thus, the present invention discloses the following further reactions, in particular synthesis routes (1) to (23), irrespective of the source of the monomer, one or more of which may be comprised by the inventive method, e.g. may be used as step (5) or (6) of the inventive method.

More generally, the inventive method may preferably comprise one or more of the following reactions: dimerization reactions, e.g. dimerization of aminocyclohexanones, e.g. 2-aminocyclohexanones, dimerization reactions of aminocyclohexanols, e.g. 2-aminocyclohexanols, transformation reactions of a phenoxazine to a phenazine, treatment of precursor compounds, e.g. vanillic acid or vanilline, by a nitrite, e.g. sodium nitrite, treatment of a precursor compound by ammonia, in particular under pressure, transformation of vanillin to 2-methoxyhydroquinone, cyclization reactions of benzofuroxanes, dimerization reactions of aminocyclobenzoquinones, e.g. 2-aminocyclohexanones, dimerization reactions of methoxycyclohexanols, e.g. 2-methoxycyclohexanols, dimerization reactions of protocatechuic acid, dimerization reactions of nitrosophenols, e.g. 4-nitrosophenols, electrooxidation of a monomer, e.g. electrooxidation of a methoxyhydroquinone, e.g. 2-methoxyhydroquinone, and condensation reactions of a nitrophenol, e.g. 2-nitrophenol, and an aminophenol, e.g. 2-aminophenol.

Further reactions, which may preferably be used according to the inventive method with the object to modify the precursor compounds, in particular for preparing phenazines, are reactions selected from the group consisting of the following reactions: condensation of a substituted or unsubstituted 2-nitrophenol and a substituted or unsubstituted 2-aminophenol compound, a dimerization of substituted or unsubstituted 3,4-diamino-5-methoxybenzoic acid, a cyclization reaction of substituted or unsubstituted 4,4'-azanediylbis(3-methoxy-5-nitrobezoic acid), a dimerization of substituted or unsubstituted 2-aminocyclohexanones, a condensation substituted or unsubstituted 2,5-dihydroxybenzoquinone or substituted or unsubstituted 2-hydroxycyclohexa-2,5-diene-1,4-dione and substituted or unsubstituted 3,4-diaminobenzene-1-sulfonic acid, a dimerization of substituted or unsubstituted 4-nitrosophenols, a dimerization of substituted or unsubstituted methoxycyclohexanol, a dimerization of substituted or unsubstituted 3,4-dihydroxycyclohexane-1-carboxylic acid optionally in the presence of ammonia, reaction of 3,4-dioxocyclohexa-1,5-diene-1-carboxylic acid with 3,4-diaminobenzoic acid, a condensation of substituted or unsubstituted 2-aminocyclobezoquinone with substituted or unsubstituted 3,4-diaminobezene-1-sulfonic acid, a condensation reaction of substituted or unsubstituted 2-methoxybenzoquinone with an amine, e.g. 2-(methylamino)ethan-1-ol and subsequent reaction with substituted or unsubstituted 2-amino-5-methoxycyclohexa-2,5-diene-1,4-dione or subsequent reaction with substituted or unsubstituted 3,4-diaminobezene-1-sulfonic acid, a dimerization of substituted or unsubstituted 2-aminobenzoquinones or 2-amino-6-methoxycyclohexa-2,5-diene-1,4-dione, a cyclization reaction of substituted or unsubstituted benzofuroxane, e.g. by reacting 7-methoxy-3-oxo-2,1,3$\lambda^5$-benzoxadiazole-5-carboxylate with 2-methoxyhydroquinone or by reacting substituted or unsubstituted benzofuroxan with substituted or unsubstituted 2-methoxyhydroquinone or by reacting benzofuroxane with substituted or unsubstituted 3,4-dihydroxybenzoic acid or by reacting 3-oxo-2,1,3$\lambda^5$-benzoxadiazole-5-sulfonic acid with 2-methoxy-hydroquinone, reaction of substituted or unsubstituted 2-hydroxy-5-methoxycyclohexa-2,5-diene-1,4-dione and substituted or unsubstituted 3,4-diaminobenzene-1-sulfonic acid, treatment of substituted or unsubstituted vanillic acid under pressure with ammonia to yield substituted or unsubstituted 4,4'-azanediylbis(3-methoxybenzoic acid), reaction of substituted or unsubstituted 3,4-diaminobenzoic acid or substituted or unsubstituted 3,4-diamino-5-methoxy-benzoic acid with 2,5-dihydroxybenzoquinone, treatment of substituted or unsubstituted vanillic acid with sodium nitrite in the presence of acid, reaction of substituted or unsubstituted 3-(hydroxyimino)-5-methoxy-4-oxocyclohexa-1,5-diene-1-carboxylic acid with substituted or unsubstituted 3,4-diaminobenzene-1-sulfonic acid, dimerization of substituted or unsubstituted 3-amino-5-methoxy-4-oxocyclohexane-1-carboxylic acid, reaction of substituted or unsubstituted 3-amino-4-hydroxy-5-methoxybenzoic acid with substituted or unsubstituted 2,5-dihydroxybenzoquinone, reaction of substituted or unsubstituted 2-hydroxy-6-methoxy-3-oxo-3H-phenoxazine-8-carboxylic acid or 2-amino-4,6-dimethoxy-3-oxo-3H-phenoxazine-8-carboxylic acid or 1-methoxy-3H-phenoxazin-3-one with ammonia or a primary amine, dimerization of substituted or unsubstituted 5-aminovanillic acid, dimerization of substituted or unsubstituted Methyl 3-amino-4-hydroxy-5-methoxycyclohexane-1-carboxylate, dimerization of a substituted or unsubstituted 2-aminocyclohexanols, dimerization of a substituted or unsubstituted 2-aminocyclohexanones, and dimerization of substituted or unsubstituted Methyl 3-amino-5-methoxy-4-oxocyclohexane-1-carboxylate. The meaning of the term "substituted" is as defined elsewhere by the present application, in particular as defined by the "exemplary substituents" at page 8.

More specifically, the following reactions (1) to (23) may be comprised by the inventive method to further modify the precursor compounds with the object to prepare phenazines or phenazine derivatives:

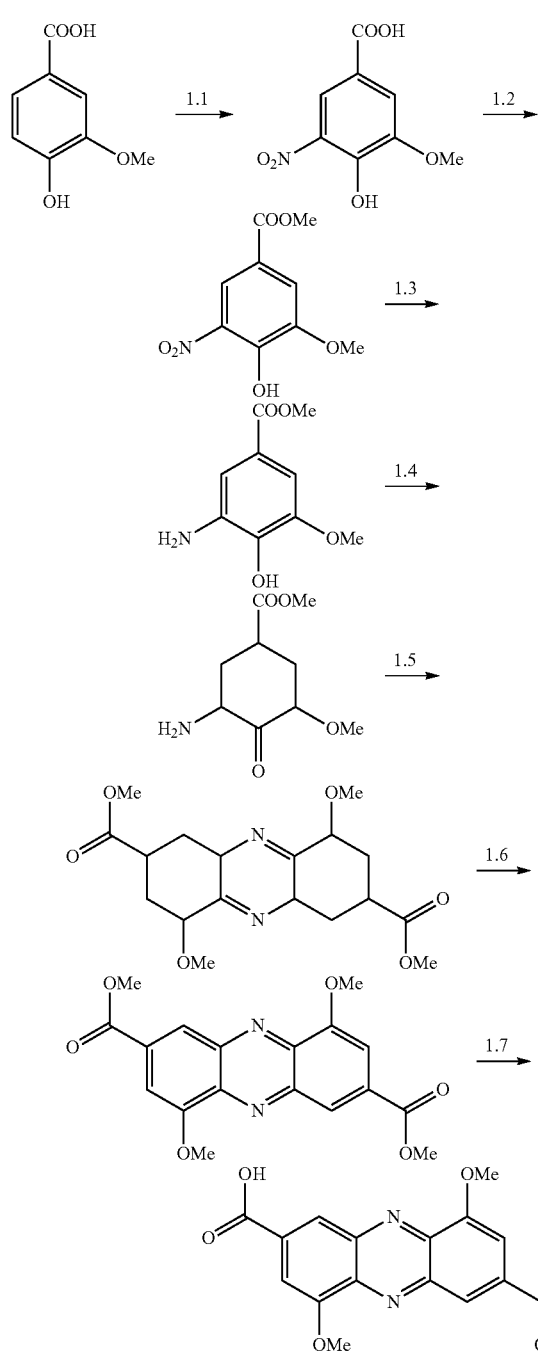

(1)

(reaction 1.2), in some embodiments, in the presence of a catalyst, such as but not limited to $H_2SO_4$, HCl, $H_3PO_4$, $CH_3COOH$ between 20-150° C., preferably between 20-100° C. most preferably between 30-70° C., to give methyl 4-hydroxy-3-methoxy-5-nitrobenzoate.

Methyl 4-hydroxy-3-methoxy-5-nitrobenzoate is reduced to methyl 3-amino-4-hydroxy-5-methoxybenzoate (reaction 1.3) by treatment with an reducing agent, such as $SnCl_2$ in water/methanol mixture, or e.g. with iron in ammonium chloride solution, or e.g. with iron in acetic acid/ethanol mixture, or e.g. with zinc in ammonium chloride solution, or by hydrogenation with a catalyst, such as but not limited to Pd, Pt, Ni, Rh or Ru between 20-150° C., preferably between 20-100° C. Methyl 3-amino-4-hydroxy-5-methoxybenzoate is hydrogenated to methyl 3-amino-5-methoxy-4-oxocyclohexane-1-carboxylate (reaction 1.4) using a doped catalyst such as but not limited to Pd, Pt, Ni, Co, Rh or Ru under 10-200 bar $H_2$, preferably 10-100 bar $H_2$ pressure between 50-250° C., preferably between 80-200° C. In some embodiments, reaction 1.3 and 1.4 are combined to a single hydrogenation reaction. Methyl 3-amino-5-methoxy-4-oxocyclohexane-1-carboxylate is then dimerized to dimethyl 4,9-dimethoxy-1,2,3,4,5a,6,7,8,9,10a-decahydrophenazine-2,7-dicarboxylate (reaction 1.5) by treatment, optionally in the presence of a catalyst, such as but not limited to trifluoroacetic acid, $H_2SO_4$, HCl, $H_3PO_4$, acetic acid, p-toluenesulfonic acid between 0-100° C., preferably 0-50° C., more preferably between 10-30° C. In some embodiments, the reaction 1.5 is spontaneously.

Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 1.6) by treatment with a catalyst such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 1.7) by treatment with aqueous alkaline solution at 20-120° C., preferably 20-90° C.

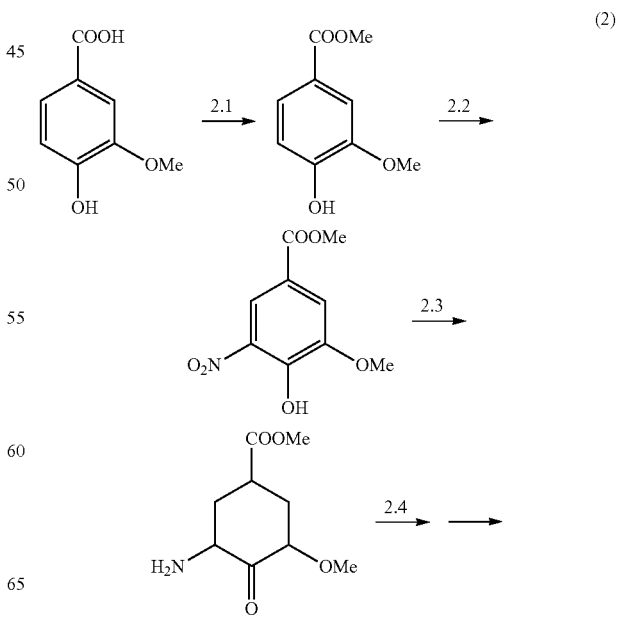

(2)

A method of obtaining phenazines or phenazine derived structures from monomers that originate from lignin, is disclosed comprising: dimerization of 2-amino cyclohexanones. In some embodiments, vanillic acid is nitrated (reaction 1.1) with but not limited to nitric acid in combination with or without nitrous acid under cooling e.g. at least at 0° C., at least at 10° C., at least 20° C. under room temperature, or e.g. under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Then, 4-hydroxy-3-methoxy-5-nitrobenzoic acid is reacted with an alcohol such as but not limited to methanol

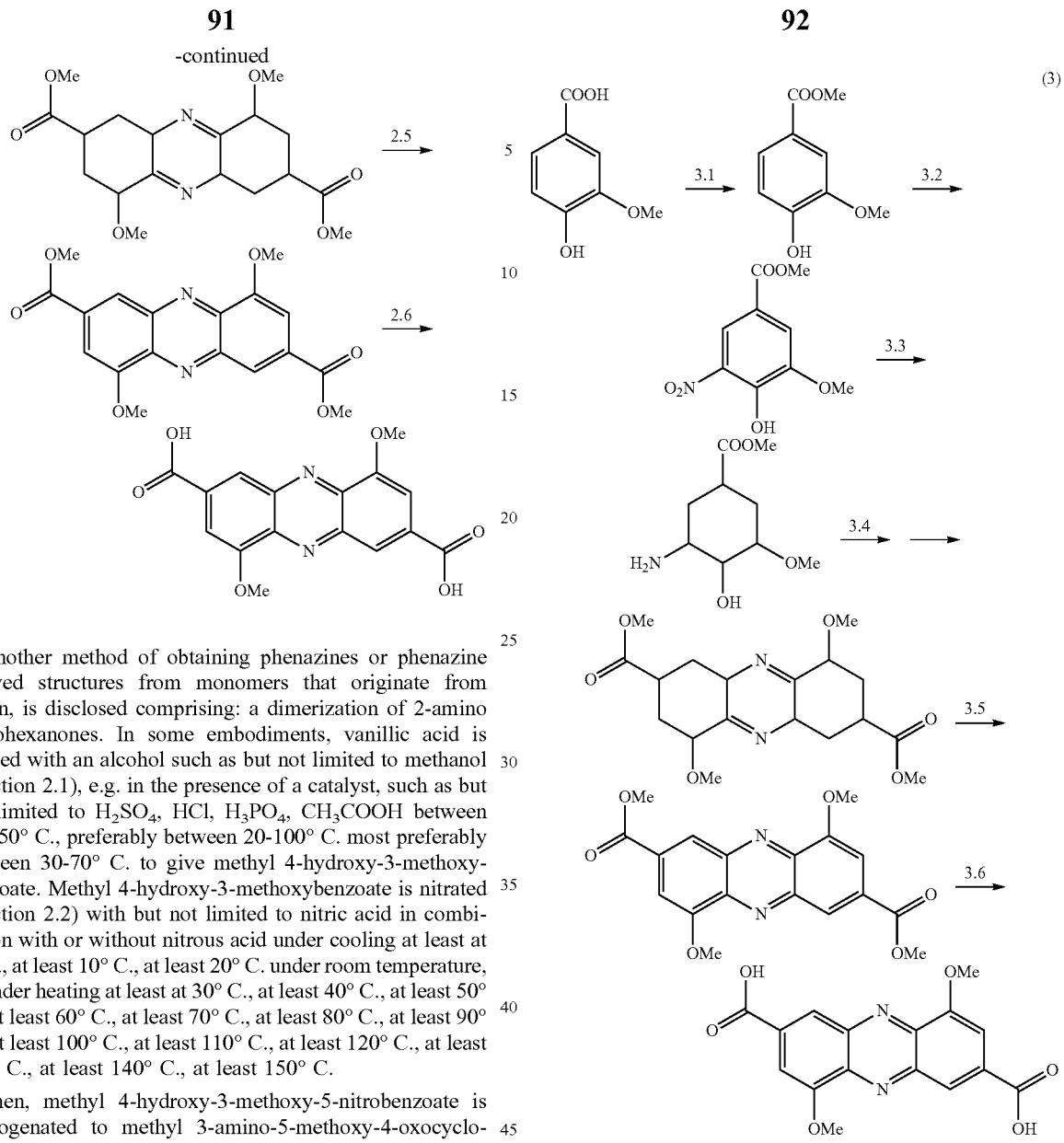

Another method of obtaining phenazines or phenazine derived structures from monomers that originate from lignin, is disclosed comprising: a dimerization of 2-amino cyclohexanones. In some embodiments, vanillic acid is reacted with an alcohol such as but not limited to methanol (reaction 2.1), e.g. in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Methyl 4-hydroxy-3-methoxybenzoate is nitrated (reaction 2.2) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C.

Then, methyl 4-hydroxy-3-methoxy-5-nitrobenzoate is hydrogenated to methyl 3-amino-5-methoxy-4-oxocyclohexane-1-carboxylate (reaction 2.3) using doped catalyst, such as but not limited to Pd, Pt, Ni, Rh or Ru under 10-200 bar $H_2$, preferably 10-100 bar $H_2$ pressure between 50-250° C., preferably between 80-200° C. Methyl 3-amino-5-methoxy-4-oxocyclohexane-1-carboxylate is then dimerized to dimethyl 4,9-dimethoxy-1,2,3,4,5a,6,7,8,9,10a-decahydrophenazine-2,7-dicarboxylate (reaction 2.4) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. In some embodiments, the reaction 1.5 is spontaneously. Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 2.5) preferably by treatment with a catalyst, such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 2.6) by treatment with aqueous alkaline solution at 20-120° C., preferably 20-90° C.

Another method of obtaining phenazines or phenazine derived structures from monomers that originate from lignin, is disclosed comprising: dimerization of 2-amino cyclohexanol. In some embodiments, vanillic acid is reacted with an alcohol, such as but not limited to methanol (reaction 3.1), in some embodiments, in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Methyl 4-hydroxy-3-methoxybenzoate is nitrated (reaction 3.2) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Then methyl 4-hydroxy-3-methoxy-5-nitrobenzoate is hydrogenated to methyl 3-amino-4-hydroxy-5-methoxycyclohexane-1-carboxylate (reaction 3.3) using a transition metal catalyst, such as but not limited to Pd, Pt, Ni, Rh or Ru under 10-200 bar H₂, preferably 10-100 bar H₂ pressure between 50-250° C., preferably between 80-200° C. Methyl 3-amino-4-hydroxy-5-methoxycyclohexane-1-carboxylate is then dimerized to dimethyl 4,9-dimethoxy-1,2,3,4,5a,6,7, 8,9,10a-decahydrophenazine-2,7-dicarboxylate (reaction 3.4) in the presence of an oxidation agent such as but not limited to O₂, H₂O₂, sodium hypochlorite, cerium ammonium nitrate or potassium permanganate and optionally an catalyst.

Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 3.5) by treatment with a catalyst such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 3.6) by treatment with aqueous alkaline solution at 20-120° C., preferably 20-90° C.

(4)

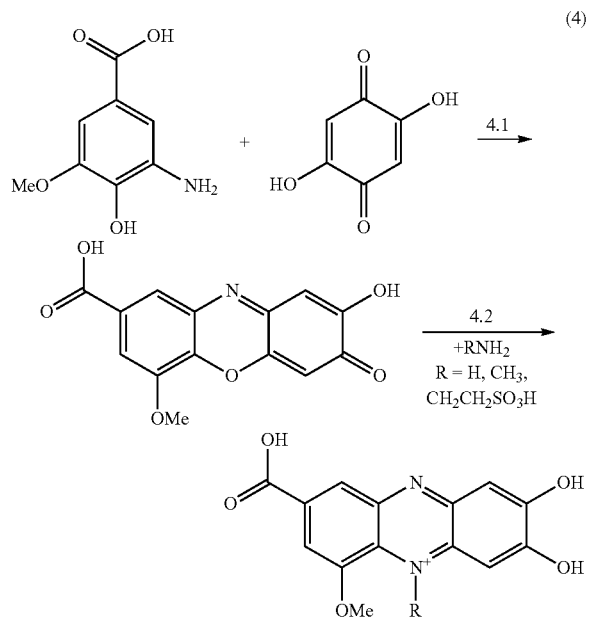

Another method of obtaining phenazines or phenazine derived structures from monomers that originate from lignin, is disclosed comprising: transformation of a phenoxazine to a phenazine. In some embodiments, 3-amino-4-hydroxy-5-methoxybenzoic acid is reacted with 2,5-dihydroxybenzoquinone (reaction 4.1) in a solvent such as but not limited to water, methanol, ethanol, acetonitrile or DMF under cooling at least at 0° C., at least 10° C., at least 20° C. under room temperature, or under heating at least at 30° C., at least 50° C., at least 80° C., at least 100° C., at least 120° C., at least 150° C. to give 2-hydroxy-6-methoxy-3-oxo-3H-phenoxazine-8-carboxylic acid. 2-hydroxy-6-methoxy-3-oxo-3H-phenoxazine-8-carboxylic acid is then reacted with ammonia (R═H) or primary amine (reaction 4.2) between 20-250° C., preferably between 50-200° C. and at 0-150 bar preferably 0-100 bar.

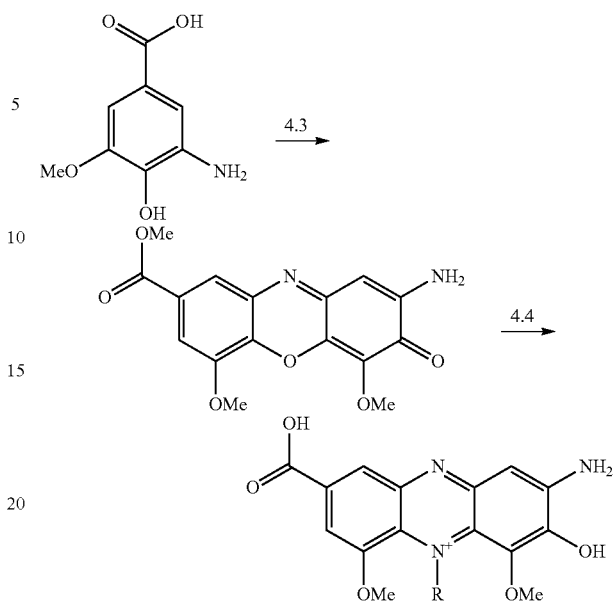

In some embodiments, 5-Aminovanillic acid is dimerized to 2-amino-4,6-dimethoxy-3-oxo-3H-phenoxazine-8-carboxylic (reaction 4.3) in the presence of an oxidant, such as but not limited to O₂, H₂O₂, sodium hypochlorite, cerium ammonium nitrate, potassium permanganate or manganese dioxide and optionally a catalyst, such as but not limited to potassium iodide, sodium tungstate, CuAlO(OH), or cupper chloride between 20-200° C. preferably 20-120° C. Subsequently, 2-amino-4,6-dimethoxy-3-oxo-3H-phenoxazine-8-carboxylic acid is reacted with ammonia (R═H) or primary amine (reaction 4.4) between 20-250° C., preferably between 50-200° C. and at 0-150 bar preferably 0-100 bar.

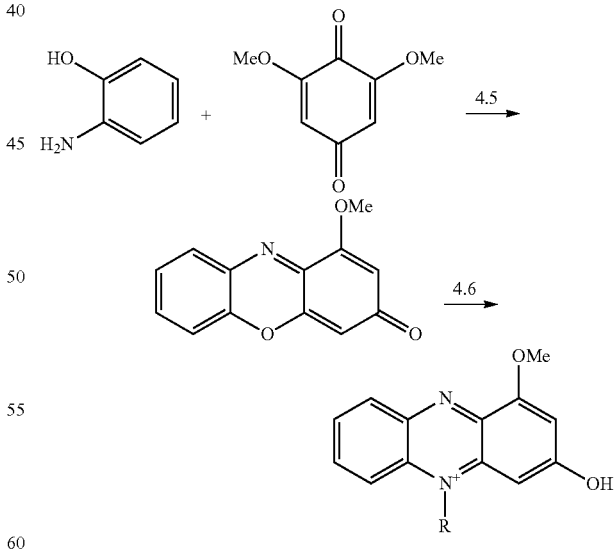

In some embodiments, 2-aminophenol acid is reacted with 2,6-dimethoxybenzoquinone (reaction 4.5) in the presence of a catalyst such as, but not limited to sulfuric acid, hydrochloric acid, phosphoric acid or organic acids such as acetic acid. At temperatures between 0-200° C. preferably between 20 to 120° C. Subsequently, 1-methoxy-3H-phenoxazin-3-one was reacted with ammonia (R=H) or primary amine (reaction 4.6) between 20-250° C., preferably between 50-200° C. and at 0-150 bar preferably 0-100 bar.

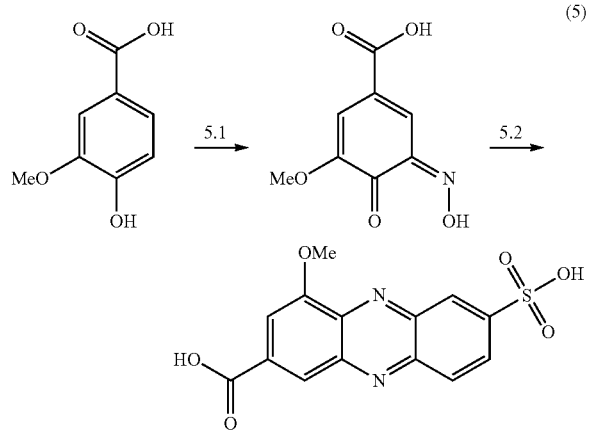

(5)

Another method of obtaining phenazines or phenazine derived structures from monomers that originate from lignin, is disclosed comprising: a treatment of monomers with sodium nitrite. In some embodiments, vanillic acid is treated with sodium nitrite (reaction 5.1) in presence of acid, such as but not limited to sulfuric acid, hydrochloric acid, phosphoric acid or organic acids such as acetic acid in water or an alcohol to yield 3-(hydroxyimino)-5-methoxy-4-oxocyclohexa-1,5-diene-1-carboxylic acid. 3-(hydroxyimino)-5-methoxy-4-oxocyclohexa-1,5-diene-1-carboxylic acid is then reacted with 3,4-diaminobenzene-1-sulfonic acid (reaction 5.2) between 0-200° C., preferably between 20-140° C. to give 4-methoxy-7-sulfophenazine-2-carboxylic acid.

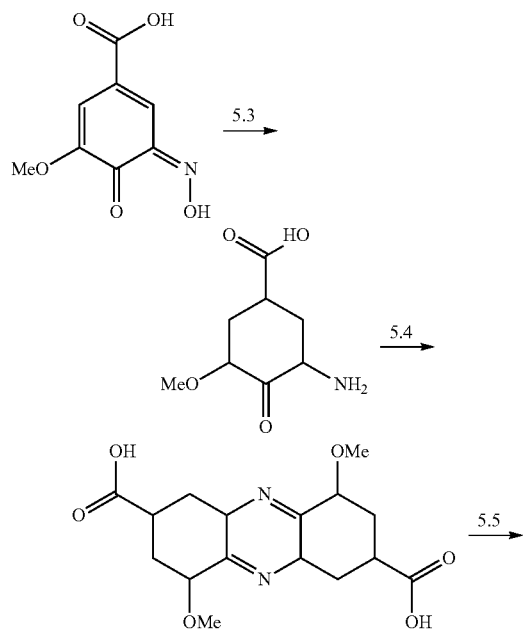

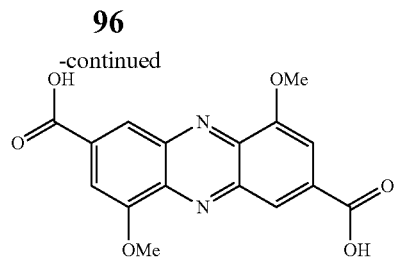

In some embodiments, 3-(hydroxyimino)-5-methoxy-4-oxocyclohexa-1,5-diene-1-carboxylic acid is hydrogenated to 3-amino-5-methoxy-4-oxocyclohexane-1-carboxylic acid (reaction 5.3) using e.g. doped catalyst, such as but not limited to Pd, Pt, Ni, Rh or Ru under 10-200 bar $H_2$, preferably 10-100 bar $H_2$ pressure between 50-250° C., preferably between 80-200° C. 3-amino-5-methoxy-4-oxocyclohexane-1-carboxylic acid is then dimerized to 4,9-dimethoxy-1,2,3,4,5a,6,7,8,9,10a-decahydrophenazine-2,7-dicarboxylic acid (reaction 5.4) by treatment optionally in the presence of a catalyst, such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. In some embodiments, the reaction 1.5 is spontaneous. 4,9-dimethoxy-1,2,3,4,5a,6,7,8,9,10a-decahydrophenazine-2,7-dicarboxylic is converted to 4,9-dimethoxyphenazine-2,7-dicarboxylic acid (reaction 5.5) by treatment with a catalyst such as but not limited to palladium on carbon between 50-300° C., preferably 100-200° C.

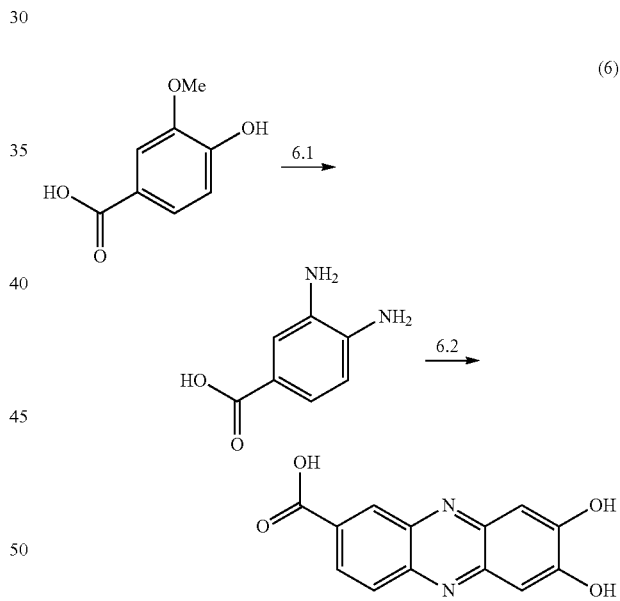

(6)

Another method of obtaining phenazines or phenazine derived structures from monomers that originate from lignin, is disclosed comprising: a treatment of monomers with ammonia under pressure. In some embodiments, vanillic acid is treated with ammonia (reaction 6.1) at 10-300 bar, preferably at 10-200 bar, more preferably at 10-50 bar, optionally in the presence of catalyst, such as but not limited to Mo, W, Ir, Ru, Pd, Pt, aluminum oxide, H-151 alumina, palladium on carbon, zeolite, copper (1) oxide at 30-400° C., preferably at 50-200° C. to give 3,4-diaminobenzoic acid. Then 3,4-diaminobenzoic acid is reacted with 2,5-dihydroxybenzoquinone (reaction 6.2) at 20-200° C., preferably at 40-120° C. to give 7,8-dihydroxyphenazine-2-carboxylic acid.

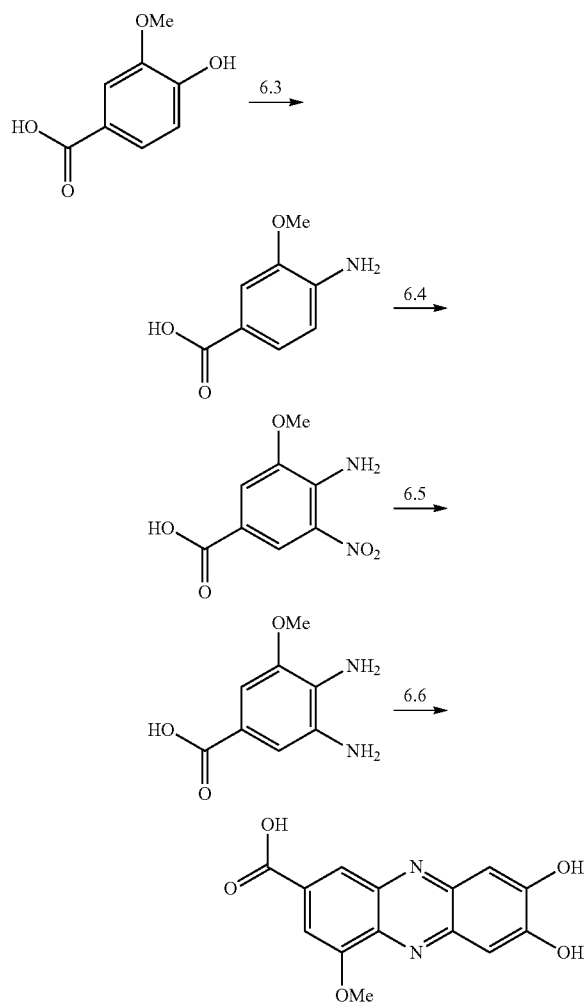

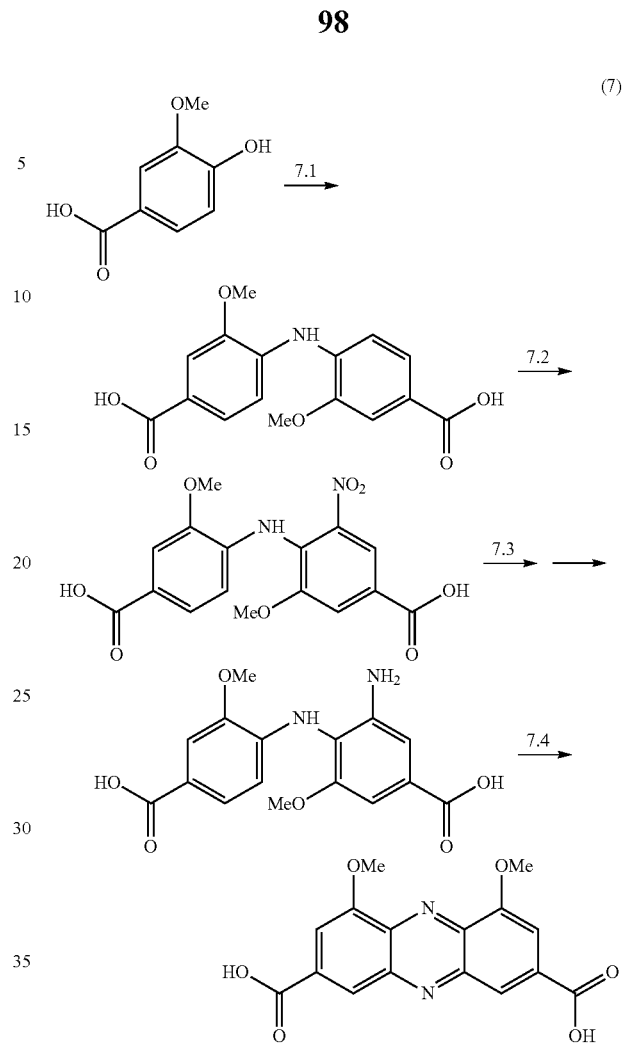

In some embodiments, vanillic acid is treated with ammonia (reaction 6.3) at 10-300 bar, preferably at 10-200 bar, more preferably at 10-50 bar, optionally in the presence of catalyst such as but not limited to Mo, W, Ir, Ru, Pd, Pt, aluminum oxide, H-151 alumina, palladium on carbon, zeolite, copper (1) oxide at 30-400° C., preferably at 40-300° C., most preferably at 50-200° C. to give 3,4-diaminobenzoic acid. Then, 4-amino-3-methoxybenzoic acid is nitrated (reaction 6.4) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-amino-3-methoxy-5-nitrobenzoic acid. 4-amino-3-methoxy-5-nitrobenzoic acid is reduced to 3,4-diamino-5-methoxybenzoic acid (reaction 6.5) by treatment with an reducing agent such as SnCl$_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3,4-diamino-5-methoxybenzoic acid is reacted with 2,5-dihydroxybenzoquinone (reaction 6.6) at 20-200° C., preferably at 40-120° C. to give 7,8-dihydroxy-4-methoxyphenazine-2-carboxylicacid.

Another method of obtaining phenazines or phenazine derived structures from monomers that originate from lignin, is disclosed comprising: treatment of monomers with ammonia under pressure. In some embodiments, vanillic acid is treated with ammonia (reaction 7.1) at 10-300 bar, preferably at 10-200 bar, more preferably at 10-100 bar, optionally in the presence of catalyst such as but not limited to Mo, W, Ir, Ru, Pd, Pt, aluminum oxide, H-151 alumina, palladium on carbon, zeolite, copper (1) oxide at 30-400° C., preferably at 50-300° C. to give 4,4-azanediylbis(3-methoxybenzoic acid). 4,4'-azanediylbis(3-methoxybenzoic acid) is then nitrated (reaction 7.2) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-(4-carboxy-2-methoxyanilino)-3-methoxy-5-nitrobenzoic acid. 4-(4-carboxy-2-methoxyanilino)-3-methoxy-5-nitrobenzoic acid is reduced to 3-amino-4-(4-carboxy-2-methoxyanilino)-5-methoxybenzoic acid (reaction 7.3) by treatment with an reducing agent such as SnCl$_2$ in water/methanol mixture, or with iron in ammonium chloride solution, or with iron in acetic acid/ ethanol mixture, or with zinc in ammonium chloride solution, or by hydrogenation with a catalyst such as but not limited to Pd, Pt, Ni, Rh or Ru between 20-150° C., preferably between 20-100° C. 3-amino-4-(4-carboxy-2- methoxyanilino)-5-methoxybenzoic acid is cyclized to 4-methoxyphenazine-2,7-dicarboxylic (reaction 7.4) acid in the presence of an oxidation reagent such as, but not limited to oxygen, hydrogen peroxide, PhI(OAc)$_2$, sodium periodate, sodium hypochlorite, cerium ammonium nitrate, MnO$_2$, KMnO$_4$, optionally with a catalyst at 20-150° C., preferably 20-100° C.

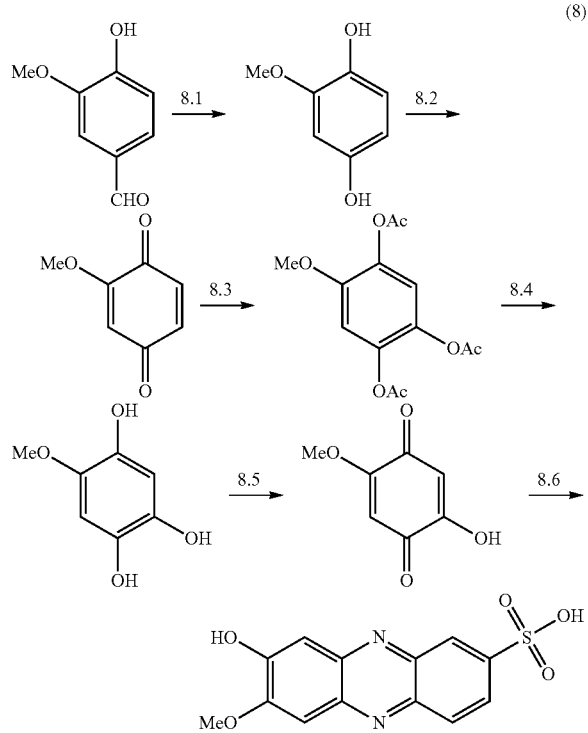

Another method of obtaining phenazines or phenazine derived structures from monomers that originate from lignin, is disclosed comprising: transformation of vanillin to 2-methoxyhydroquinone (reaction 8.1) by treatment with hydrogen peroxide and base at 0-60° C., preferably between 25-40° C. 2-methoxyhydroquinone is oxidized to 2-methoxy-5-hydroxybenzoquinone (reaction 8.2) with an oxidation agent such as but not limited to oxygen, hydrogen peroxide, manganese dioxide, sodium hypochlorite, cerium ammonium nitrate or potassium permanganate optionally in the presence of a catalyst.

In some embodiments, 2-Methoxybenzoquinone is reacted with acetic anhydride (reaction 8.3) in the presence of acid such as but not limited to sulfuric acid, hydrochloric acid, phosphorus acid, triflic acid or organic acids such as acetic acid to give 5-methoxybenzene-1,2,4-triyl triacetate. 5-methoxybenzene-1,2,4-triyl triacetate is treated with acidic or alkaline aqueous, methanolic or acetone solution to yield 5-methoxybenzene-1,2,4-triol (reaction 8.4). 5-methoxybenzene-1,2,4-triol was oxidized to 2-hydroxy-5-methoxycyclohexa-2,5-diene-1,4-dione (reaction 8.5) in the presence of oxidation agent, such as but not limited to oxygen, hydrogen peroxide, manganese dioxide, sodium hypochlorite, cerium ammonium nitrate or potassium permanganate optionally in the presence of a catalyst. Then 2-hydroxy-5-methoxycyclohexa-2,5-diene-1,4-dione was reacted with 3,4-diaminobenzene-1-sulfonic acid (reaction 8.6) at 20-200° C., preferably between 30-100° C. to give 8-hydroxy-7-methoxyphenazine-2-sulfonic acid.

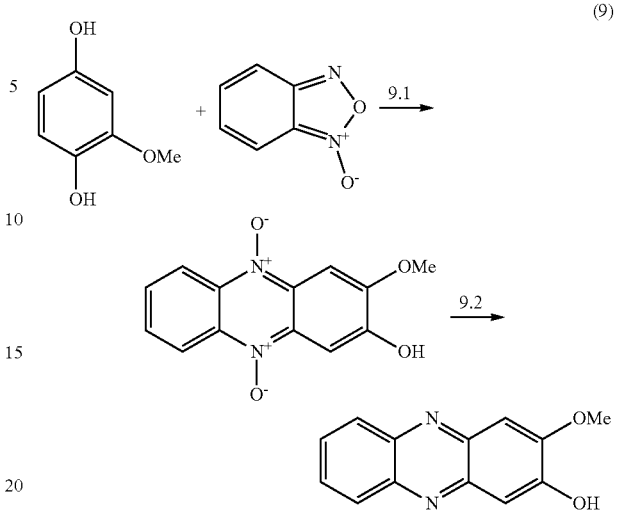

Another method of obtaining phenazines or phenazine derived structures from monomers that originate from lignin, is disclosed comprising: a cyclization reaction with benzofuroxanes. In some embodiments, Benzofuroxan is reacted with 2-methoxyhydroquinone (reaction 9.1) in the presence of a base, such as but not limited to, sodium hydroxide, potassium hydroxide, sodium carbonate, potassium carbonate, triethyl amine or sodium methylate at 0-120° C., preferably between 20-80° C. to yield 3-methoxy-5,10-dioxo-phenazin-2-ol. 3-methoxy-5,10-dioxo-phenazin-2-ol is reduced to 3-methoxyphenazin-2-ol (reaction 9.2) by treatment with reagents such as but not limited to trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

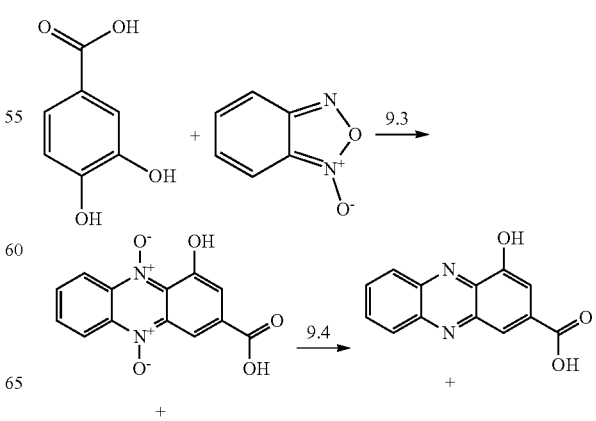

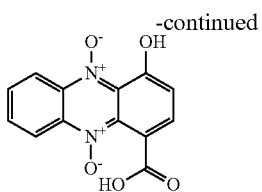
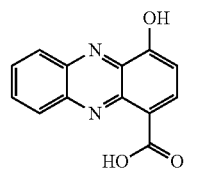
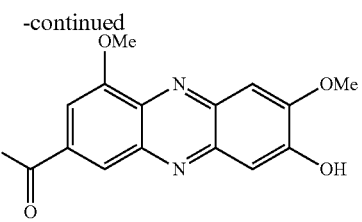

In some embodiments, benzofuroxan is reacted with 3,4-dihydroxybenzoic acid (reaction 9.3) in the presence of a base such as but not limited to, sodium hydroxide, potassium hydroxide, sodium carbonate, potassium carbonate, triethyl amine or sodium methylate at 0-120° C., preferably between 20-80° C. to yield the mixture of 4-hydroxy-5,10-dioxo-phenazine-2-carboxylic acid and 4-hydroxy-5,10-dioxo-phenazine-1-carboxylic acid. The mixture of 4-hydroxy-5,10-dioxo-phenazine-2-carboxylic acid and 4-hydroxy-5,10-dioxo-phenazine-1-carboxylic acid was reduced to 4-hydroxyphenazine-2-carboxylic acid and 4-hydroxyphenazine-1-carboxylic acid (reaction 9.4) by treatment with reagents, such as but not limited to trifluoroacetic anhydride and sodium iodide in acetonitril at rt, or titanium (IV)-chloride and tin(1)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with e.g. sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

In some embodiments, 4-amino-3-methoxy-5-nitrobenzoic acid was oxidized with an oxidation agent (reaction 9.5), such as but not limited to sodium hypochlorite in alkaline solution at 0-100° C. preferably at 10-60° C. or with PhI(OAc)$_2$ at 20-80° C. to give 7-methoxy-3-oxo-2,1,3$\lambda^5$-benzoxadiazole-5-carboxylic acid. Then 7-methoxy-3-oxo-2,1,3$\lambda^5$-benzoxadiazole-5-carboxylic acid was reacted with 2-methoxyhydroquinone (reaction 9.6) in the presence of a base such as but not limited to, sodium hydroxide, potassium hydroxide, sodium carbonate, potassium carbonate, triethyl amine or sodium methylate at 0-120° C., preferably between 20-80° C. to yield 8-hydroxy-4,7-dimethoxy-5,10-dioxo-phenazine-2-carboxylic acid. 8-hydroxy-4,7-dimethoxy-5,10-dioxo-phenazine-2-carboxylic acid was reduced to 8-hydroxy-4,7-dimethoxyphenazine-2-carboxylic acid (reaction 9.7) by treatment with reagents such as but not limited to trifluoroacetic anhydride and sodium iodide in acetonitril at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(i)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

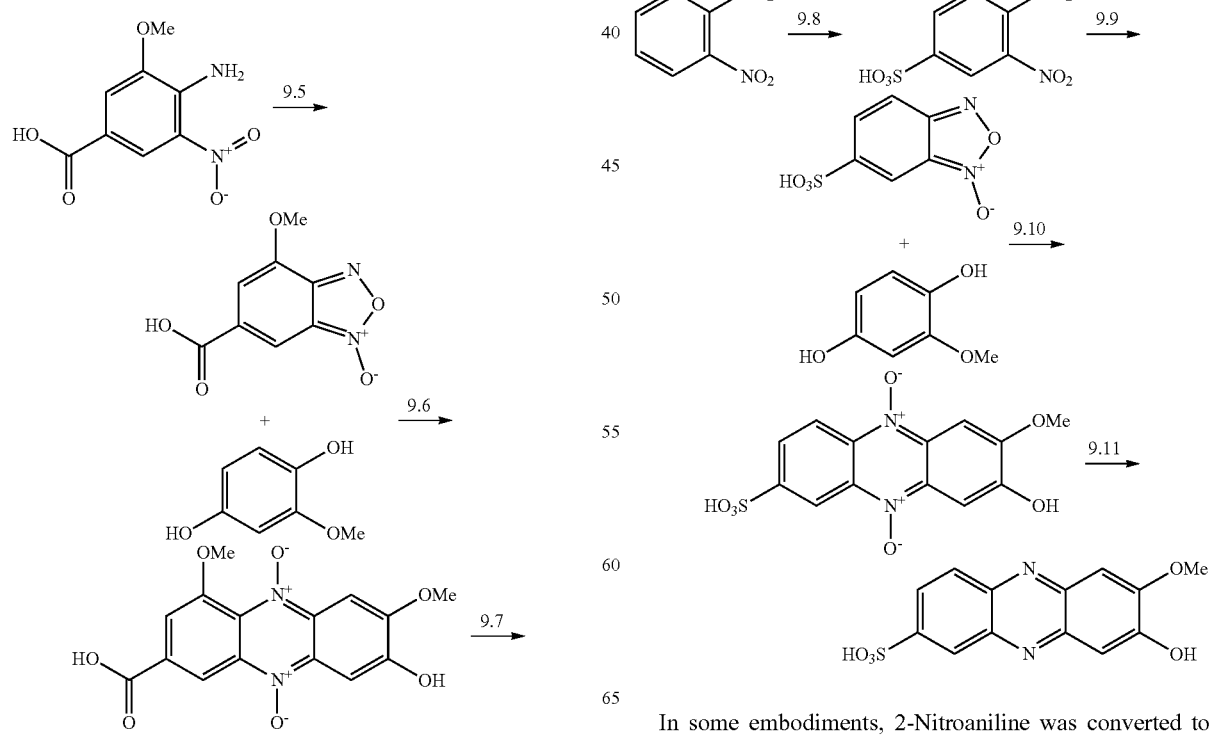

In some embodiments, 2-Nitroaniline was converted to 4-amino-3-nitrobenzene-1-sulfonic acid (reaction 9.8) by treatment with sulfuric acid or oleum at 30-200° C., preferably 50-120° C. The resulting 4-amino-3-nitrobenzene-1-sulfonic acid is oxidized with an oxidation agent (reaction 9.9) such as but not limited to sodium hypochlorite in alkaline solution at 0-100° C. preferably at 10-60° C. or with PhI(OAc)$_2$ at 20-80° C. to give 3-oxo-2,1,3λ$^5$-benzoxadiazole-5-sulfonic acid. 3-oxo-2,1,3λ$^5$-benzoxadiazole-5-sulfonic acid was reacted with 2-methoxyhydroquinone (reaction 9.10) in the presence of a base such as but not limited to, sodium hydroxide, potassium hydroxide, sodium carbonate, potassium carbonate, triethyl amine or sodium methylate at 0-120° C., preferably between 20-80° C. to yield 8-hydroxy-7-methoxy-5,10-dioxo-5λ$^5$,10λ$^5$-phenazine-2-sulfonic acid. 8-hydroxy-7-methoxy-5,10-dioxo-5λ$^5$,10λ$^5$-phenazine-2-sulfonic acid was reduced to 8-hydroxy-7-methoxy-phenazine-2-sulfonic acid (reaction 9.11) by treatment with reagents such as but not limited to trifluoroacetic anhydride and sodium iodide in acetonitril at rt, or titanium(IV)-chloride and tin(II)-chloride in acetonitrile at rt, or titanium (IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

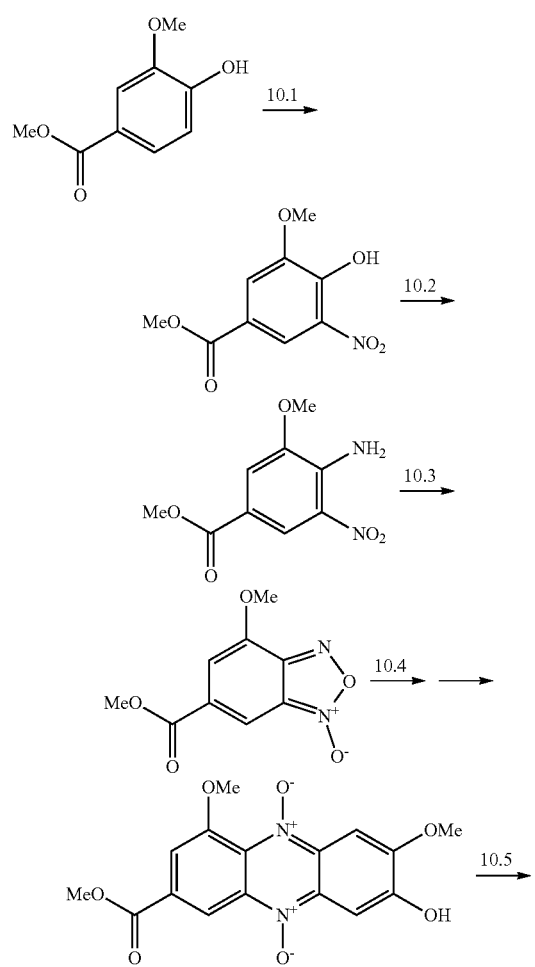

(10)

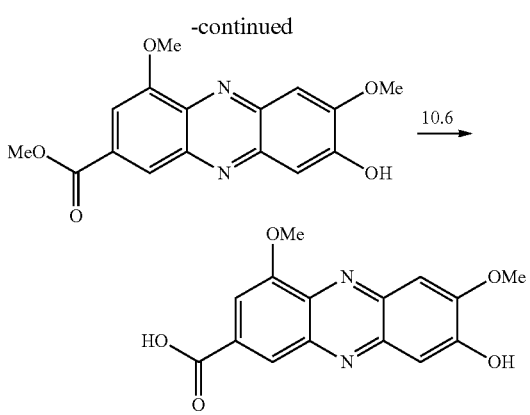

Another method of obtaining phenazines or phenazine derived structures from monomers that originate from lignin, is disclosed comprising: a cyclization reaction with benzofuroxanes. In some embodiments, Methyl 4-hydroxy-3-methoxybenzoate is nitrated (reaction 10.1) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. Methyl 4-hydroxy-3-methoxy-5-nitrobenzoate is reacted with ammonia in water or methanol at 50-300° C., preferably 100-200° C. to give methyl 4-amino-3-methoxy-5-nitrobenzoate (reaction 10.2). Methyl 4-hydroxy-3-methoxy-5-nitrobenzoate is oxidized with an oxidation agent (reaction 10.3) such as but not limited to sodium hypochlorite in alkaline solution at 0-100° C. preferably at 10-60° C. or with PhI(OAc)$_2$ at 20-80° C. to give methyl 7-methoxy-3-oxo-2,1,3λ$^5$-benzoxadiazole-5-carboxylate. Methyl 7-methoxy-3-oxo-2,1,3λ$^5$-benzoxadiazole-5-carboxylate is reacted with 2-methoxyhydroquinone (reaction 10.4) was reacted with 2-methoxyhydroquinone (reaction 10.4) in the presence of a base such as but not limited to, sodium hydroxide, potassium hydroxide, sodium carbonate, potassium carbonate, triethyl amine or sodium methylate at 0-120° C., preferably between 20-80° C. to yield methyl 8-hydroxy-4,7-dimethoxy-5,10-dioxo-5λ$^5$,10λ$^5$-phenazine-2-carboxylate. Methyl 8-hydroxy-4,7-dimethoxy-5,10-dioxo-5λ$^5$,10λ$^5$-phenazine-2-carboxylate was reduced to methyl 8-hydroxy-4,7-dimethoxyphenazine-2-carboxylate (reaction 10.5) by treatment with reagents such as but not limited to trifluoroacetic anhydride and sodium iodide in acetonitril at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH. Methyl 8-hydroxy-4,7-dimethoxyphenazine-2-carboxylate was hydrolized to 8-hydroxy-4,7-dimethoxyphenazine-2-carboxylic acid by treatment with alkaline aqueous solution at 20-100° C., preferably 20-70° C.

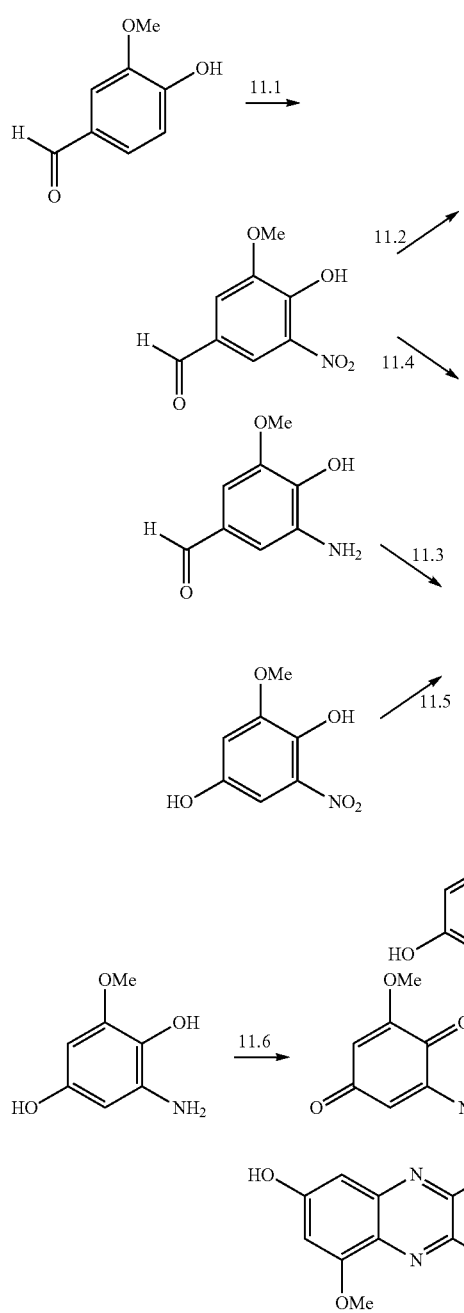

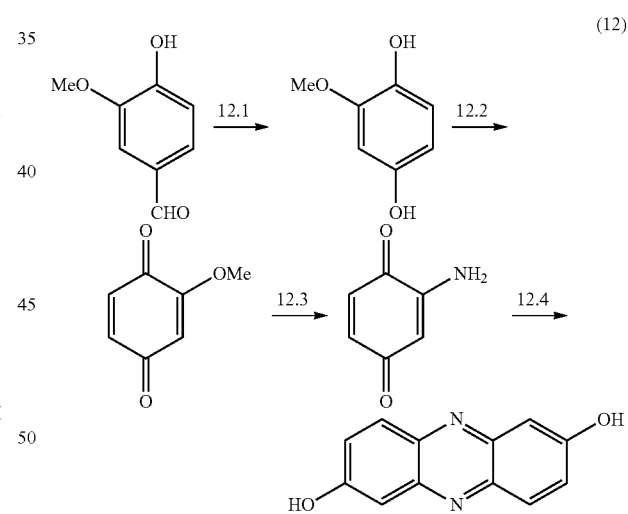

with a catalyst such as but not limited to Pd, Pt, Ni, Rh or Ru between 20-150° C., preferably between 20-100° C. 3-amino-4-hydroxy-5-methoxybenzaldehyde is oxidized to 2-amino-6-methoxybenzene-1,4-diol (reaction 11.3) with hydrogen peroxide solution in presence of base such as but not limited to sodium hydroxide or potassium hydroxide or by sodium percarbonate solution. In some embodiments, 4-hydroxy-3-methoxy-5-nitrobenzaldehyde is oxidized to 2-methoxy-6-nitrobenzene-1,4-diol (reaction 11.4) with hydrogen peroxide solution in presence of base such as but not limited to sodium hydroxide or potassium hydroxide or by sodium percarbonate solution. 2-methoxy-6-nitrobenzene-1,4-diol was reduced to 2-amino-6-methoxybenzene-1,4-diol (reaction 11.5) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then 2-amino-6-methoxybenzene-1,4-diol was oxidized to 2-amino-6-methoxycyclohexa-2,5-diene-1,4-dione (reaction 11.6) with an oxidation agent such as but not limited to oxygen, hydrogen peroxide, manganese dioxide, sodium hypochlorite, cerium ammonium nitrate or potassium permanganate optionally in the presence of a catalyst. 2-amino-6-methoxycyclohexa-2,5-diene-1,4-dione was dimerized to 4,9-dimethoxyphenazine-2,7-diol (reaction 11.7) in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C.

Another method of obtaining phenazines or phenazine derived structures from monomers that originate from lignin, comprising: a dimerization of 2-aminocyclobenzoquinones. In some embodiments, Vanillin is nitrated (reaction 11.1) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. 4-hydroxy-3-methoxy-5-nitrobenzaldehyde was reduced to 3-amino-4-hydroxy-5-methoxybenzaldehyde (reaction 11.2)) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation Another method of obtaining phenazines or phenazine derived structures from monomers that originate from lignin, is disclosed comprising: a dimerization of 2-aminocyclobenzoquinones. In some embodiments, vanillin is converted to 2-methoxyhydroquinone (reaction 12.1) by treatment with hydrogen peroxide and base at 0-60° C., preferably between 25-40° C. 2-methoxyhydroquinone is oxidized to 2-methoxy-5-hydroxybenzoquinone (reaction 12.2) with an oxidation agent such as but not limited to oxygen, hydrogen peroxide, manganese dioxide, sodium hypochlorite, cerium ammonium nitrate or potassium permanganate optionally in the presence of a catalyst. 2-Methoxybenzoquinone is reacted with ammonia to give 2-aminobenzoquinone (reaction 12.3) at 20-200° C., preferably 20-100° C. Then 2-aminobenzoquinone was dimerized to phenazine-2,7-diol (reaction 12.4) in the presence of a catalyst such as but not limited to trifluoroacetic acid, H₂SO₄, HCl, H₃PO₄, acetic acid, p-toluenesulfonic acid between 0-100° C., preferably 0-50° C., more preferably between 10-30° C.

(13)

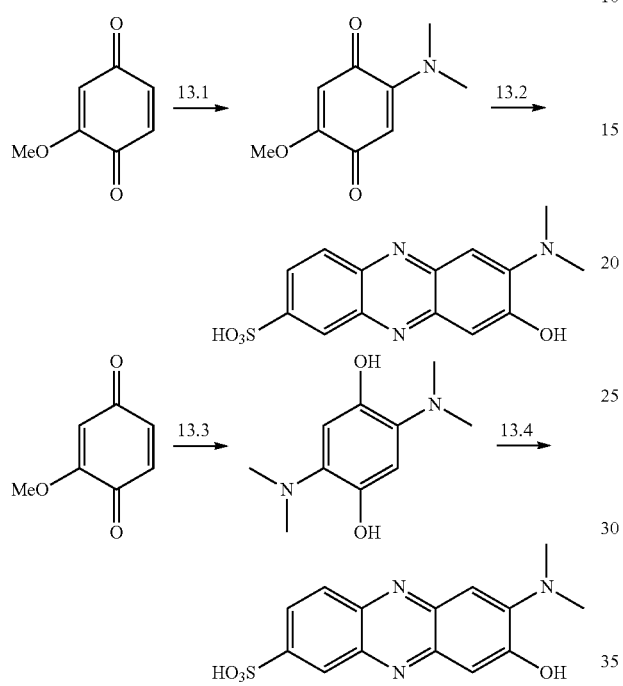

Another method of obtaining phenazines or phenazine derived structures from monomers that originate from lignin, is disclosed comprising: a condensation of 2-amino-cyclobenzoquinones with 3,4-diaminobenzene-1-sulfonic acid. In some embodiments, 2-Methoxybenzoquinone is treated with dimethylamine at 20-100° C., preferably 20-50° C. to give 2-(dimethylamino)-5-methoxycyclohexa-2,5-diene-1,4-dione (reaction 13.1). Then 2-(dimethylamino)-5-methoxycyclohexa-2,5-diene-1,4-dione is reacted with 3,4-diaminobenzene-1-sulfonic acid (reaction 13.2) at 20-200° C., preferably between 30-100° C. to give 7-(dimethylamino)-8-hydroxyphenazine-2-sulfonic acid. In some embodiments, 2-Methoxybenzoquinone is reacted with dimethylamine (reaction 13.3) at 20-100° C., preferably 20-60° C. to give 2,5-bis(dimethylamino)benzene-1,4-diol. Then 2,5-bis(dimethylamino)benzene-1,4-diol is converted to 7-(dimethylamino)-8-hydroxyphenazine-2-sulfonic acid (reaction 13.4) by a condensation reaction with 3,4-diaminobenzene-1-sulfonic acid at 20-200° C., preferably between 30-100° C.

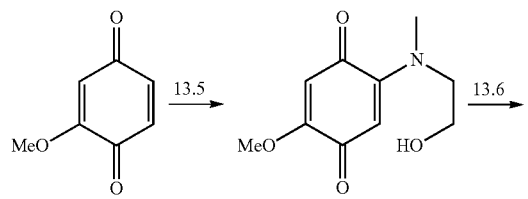

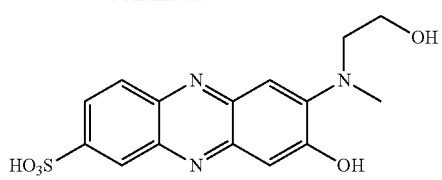

In some embodiments, 2-Methoxybenzoquinone is treated with other amines such as, but not limited to 2-(methylamino)ethan-1-ol, to give 2-amino-5-methoxycyclohexa-2,5-diene-1,4-dione (reaction 13.5) at 20-100° C., preferably 20-50° C. Then these amines are condensed e.g. with 3,4-diaminobenzene-1-sulfonic acid (reaction 13.6) at 20-200° C., preferably between 30-100° C. to give the 8-hydroxy-7-aminophenazine-2-sulfonic acid.

(14)

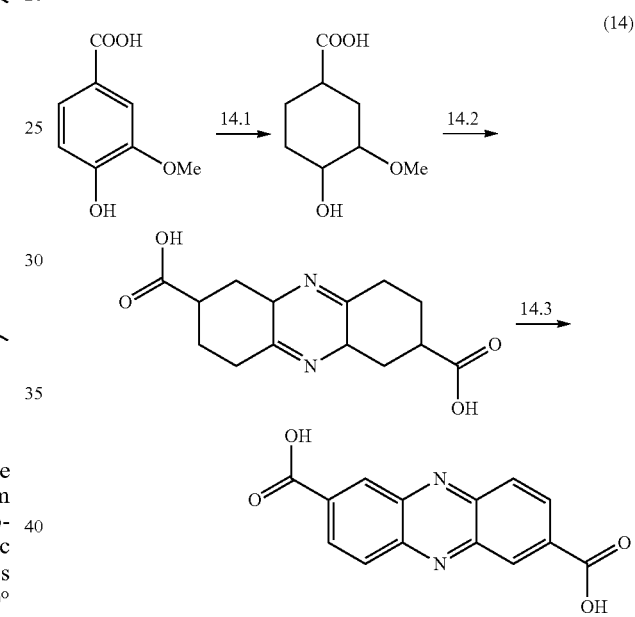

Another method of obtaining phenazines or phenazine derived structures from monomers that originate from lignin, is disclosed comprising: a dimerization of 2-methoxycyclohexanol. In some embodiments, vanillic acid is hydrogenated to 4-hydroxy-3-methoxycyclohexane-1-carboxylic acid (reaction 14.1) using a catalyst such as but not limited to Pd, Pt, Ni, Co, Rh or Ru under 10-200 bar H₂, preferably 10-100 bar H₂ pressure between 50-250° C., preferably between 80-200° C. Then 4-hydroxy-3-methoxycyclohexane-1-carboxylic acid is dimerized to 1,2,3,4,5a,6,7,8,9,10a-decahydrophenazine-2,7-dicarboxylic acid (reaction 14.2) by treatment with ammonia optionally in presence of transition metal catalyst such as but not limited to Iridium and its complexes. 1,2,3,4,5a,6,7,8,9,10a-decahydrophenazine-2,7-dicarboxylic acid is converted to phenazine-2,7-dicarboxylic acid (reaction 14.3) by treatment with a catalyst such as but not limited to palladium on carbon between 50-300° C., preferably 100-200° C.

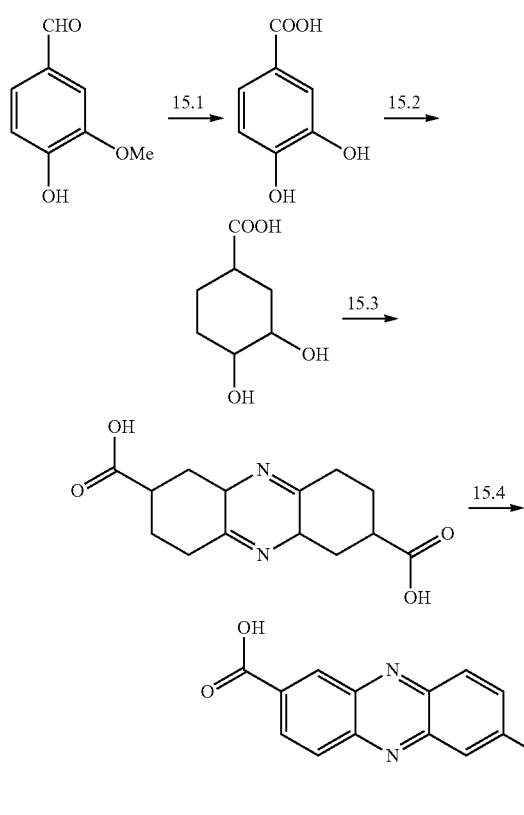

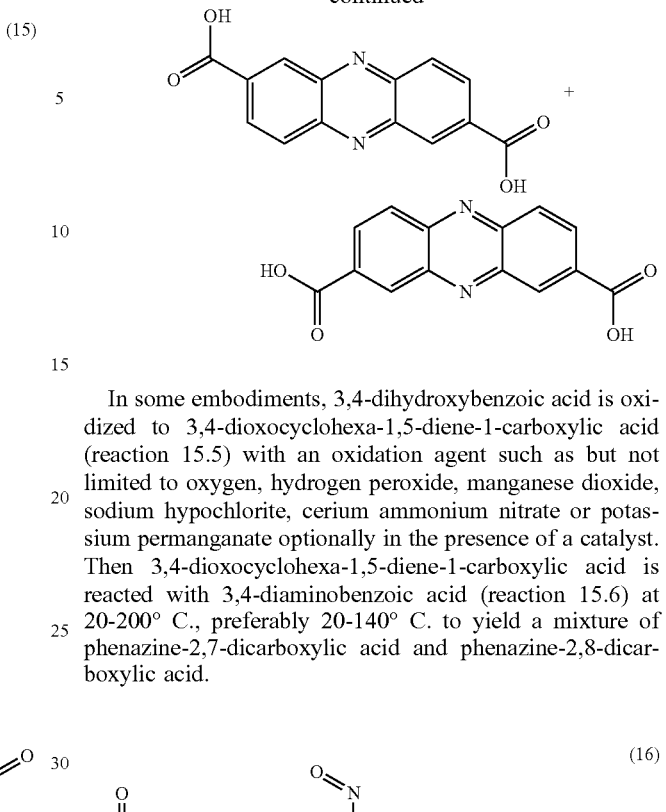

In some embodiments, 3,4-dihydroxybenzoic acid is oxidized to 3,4-dioxocyclohexa-1,5-diene-1-carboxylic acid (reaction 15.5) with an oxidation agent such as but not limited to oxygen, hydrogen peroxide, manganese dioxide, sodium hypochlorite, cerium ammonium nitrate or potassium permanganate optionally in the presence of a catalyst. Then 3,4-dioxocyclohexa-1,5-diene-1-carboxylic acid is reacted with 3,4-diaminobenzoic acid (reaction 15.6) at 20-200° C., preferably 20-140° C. to yield a mixture of phenazine-2,7-dicarboxylic acid and phenazine-2,8-dicarboxylic acid.

Another method of obtaining phenazines or phenazine derived structures from monomers that originate from lignin, is disclosed comprising: a dimerization starting from the protocatechuic acid. In some embodiments, Vanillin is converted to 3,4-dihydroxybenzoic acid (reaction 15.1) by treatment with KOH/NaOH at 150-300° C., preferably 190-245° C. under air. In the following reaction 3,4-dihydroxybenzoic acid is hydrogenated to give 3,4-dihydroxycyclohexane-1-carboxylic acid (reaction 15.2) using a catalyst such as but not limited to Pd, Pt, Ni, Co, Rh or Ru under 10-200 bar $H_2$, preferably 10-100 bar $H_2$ pressure between 50-250° C., preferably between 80-200° C. 3,4-dihydroxycyclohexane-1-carboxylic acid was dimerized to 1,2,3,4,5a,6,7,8,9,10a-decahydrophenazine-2,7-dicarboxylic acid (reaction 15.3) by treatment with ammonia optionally in presence of transition metal catalyst such as but not limited to Iridium and its complexes. 1,2,3,4,5a,6,7,8,9,10a-decahydrophenazine-2,7-dicarboxylic acid is converted to phenazine-2,7-dicarboxylic acid (reaction 15.4) by treatment with a catalyst such as but not limited to palladium on carbon between 50-300° C., preferably 100-200° C.

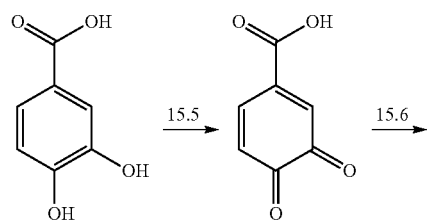

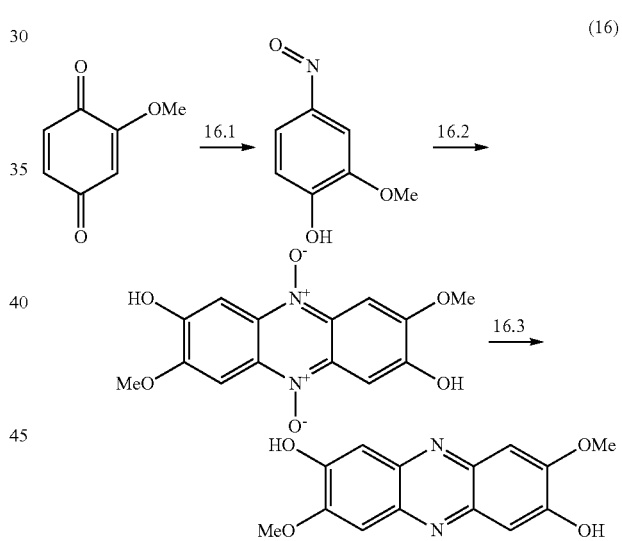

Another method of obtaining phenazines or phenazine derived structures from monomers that originate from lignin, is disclosed comprising: a dimerization of 4-nitrosophenols. In some embodiments, 2-Methoxybenzoquinone is converted to 2-methoxy-4-nitrosophenol (reaction 16.1) by treatment with hydroxylamine or its salt in presence of a base such as but not limited to sodium acetate, sodium carbonate or sodium hydroxide at temperatures from 0° C.-100° C., preferably 0° C.-60° C. Then 2-methoxy-4-nitrosophenol is dimerized to 3,8-dimethoxy-5,10-dioxophenazine-2,7-diol (reaction 16.2) optionally in the presence of a catalyst such as but not limited to trifluoroacetic acid, $H_2SO_4$, HCl, $H_3PO_4$, acetic acid, p-toluenesulfonic acid between 0-150° C., preferably 0-100° C. 3,8-dimethoxy-5,10-dioxo-phenazine-2,7-diol is reduced to 3,8-dimethoxyphenazine-2,7-diol (reaction 16.3) by treatment with reagents such as but not limited to trifluoroacetic anhydride and sodium iodide in acetonitril at rt, or titanium(IV)-chloride and tin(II)-chloride in acetonitrile at rt, or titanium (IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

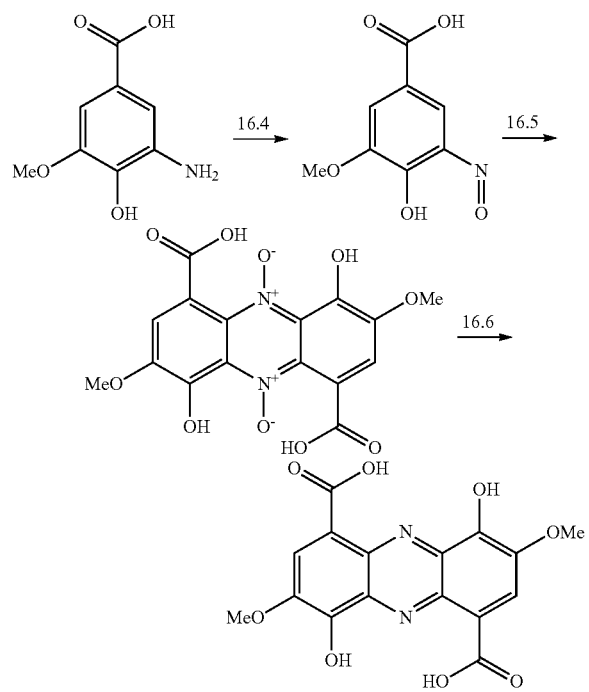

In some embodiments, 5-Aminovanillic acid is oxidized to 4-hydroxy-3-methoxy-5-nitrosobenzoic acid (reaction 16.4) using a oxidation reagent such as but not limited to hydrogen peroxide, oxone, Ph$_2$Se$_2$, oxygen, perbenzoic acid, 3-chloro-benzenecarboperoxoic acid optionally in the presence of a catalyst such as but not limited to KI, Na$_2$WO$_4$, (n-Bu$_3$Sn)$_2$WO$_4$, phosphotungstic acid, CpMo(CO)$_3$ (CCPh), MoO$_3$, methyltrioxorhenium(VII)) and additive (phosphoric acid, NBu$_4$Br) at 0° C.-150° C., preferably 0° C. to 100° C. Then 4-hydroxy-3-methoxy-5-nitrosobenzoic acid is dimerized to 4,9-dihydroxy-3,8-dimethoxy-5,10-dioxo-phenazine-1,6-dicarboxylic acid (reaction 16.5) by treatment optionally in the presence of a catalyst such as but not limited to trifluoroacetic acid, H$_2$SO$_4$, HCl, H$_3$PO$_4$, acetic acid, p-toluenesulfonic acid between 0-150° C., preferably 0-100° C. 4,9-dihydroxy-3,8-dimethoxy-5,10-dioxo-phenazine-1,6-dicarboxylic acid was reduced to 4,9-dihydroxy-3,8-dimethoxyphenazine-1,6-dicarboxylic acid (reaction 16.6) by treatment with reagents such as but not limited to trifluoroacetic anhydride and sodium iodide in acetonitril at rt, or titanium(IV)-chloride and tin(I)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

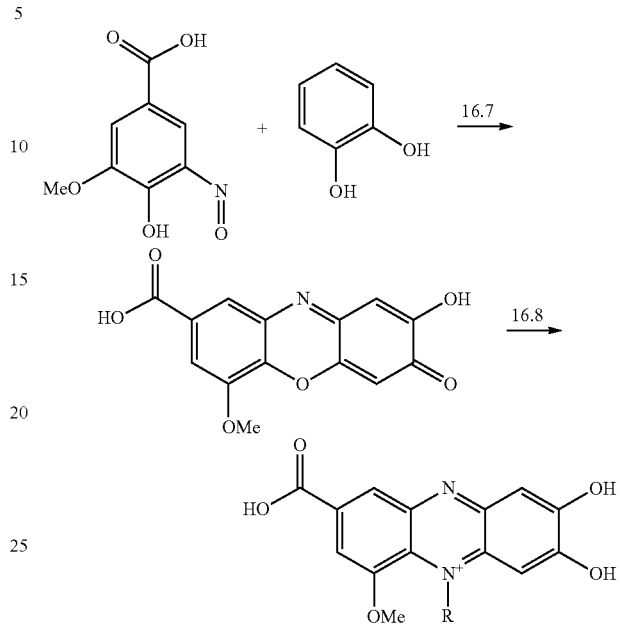

In some embodiments, 4-hydroxy-3-methoxy-5-nitrosobenzoic is reacted with catechol (reaction 16.7) by treatment optionally in the presence of a catalyst such as but not limited to trifluoroacetic acid, H$_2$SO$_4$, HCl, H$_3$PO$_4$, acetic acid, p-tolueneslfonic acid between 0-150° C., preferably 0-100° C. to yield 2-hydroxy-6-methoxy-3-oxo-3H-phenoxazine-8-carboxylic acid. Then 2-hydroxy-6-methoxy-3-oxo-3H-phenoxazine-8-carboxylic acid is reacted with ammonia (R=H) or primary amine (reaction 16.8) between 20-250° C., preferably between 50-200° C. and at 0-150 bar preferably 0-100 bar to yield the corresponding phenazine.

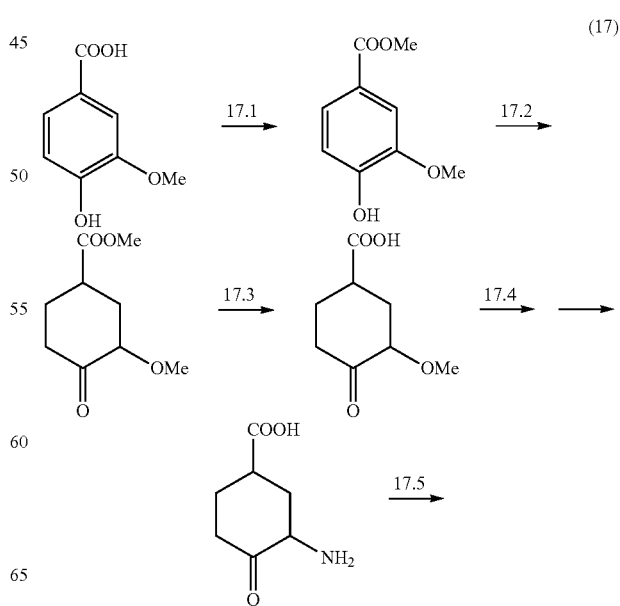

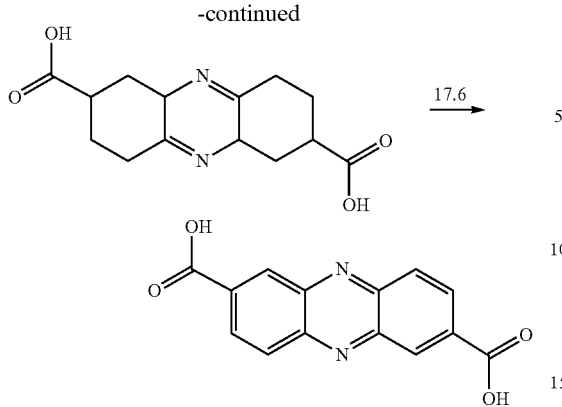

Another method of obtaining phenazines or phenazine derived structures from monomers that originate from lignin, comprising: a dimerization of 2-aminocyclohexanones. In some embodiments, vanillic acid is reacted with an alcohol such as but not limited to methanol (reaction 17.1) in some embodiments, in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Then methyl 4-hydroxy-3-methoxybenzoate is hydrogenated to methyl 3-methoxy-4-oxocyclohexane-1-carboxylate (reaction 17.2) using a doped metal catalyst such as but not limited to Pd, Pt, Ni, Co, Rh or RU under 10-200 bar $H_2$, preferably 10-100 bar $H_2$ pressure between 50-250° C., preferably between 80-200° C. Methyl 3-methoxy-4-oxocyclohexane-1-carboxylate is hydrolyzed to 3-methoxy-4-oxocyclohexane-1-carboxylic acid (reaction 17.3) by treatment with aqueous alkaline solution at 20-120° C., preferably 20-90° C. In the following step 3-methoxy-4-oxocyclohexane-1-carboxylic acid is converted to 3-amino-4-oxocyclohexane-1-carboxylic acid by treatment with ammonia (reaction 17.4) at 20-200° C., preferably 20-100° C. 3-amino-4-oxocyclohexane-1-carboxylic acid is dimerized to 1,2,3,4,5a,6,7,8,9,10a-decahydrophenazine-2,7-dicarboxylic acid (reaction 17.5) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 1,2,3,4,5a,6,7,8,9,10a-decahydrophenazine-2,7-dicarboxylic acid is converted to phenazine-2,7-dicarboxylic acid (reaction 17.6) by treatment with a catalyst such as but not limited to palladium on carbon between 50-300° C., preferably 100-200° C.

(18)

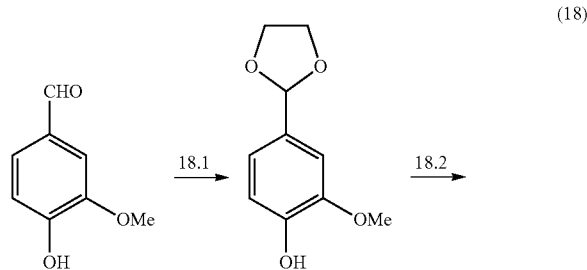

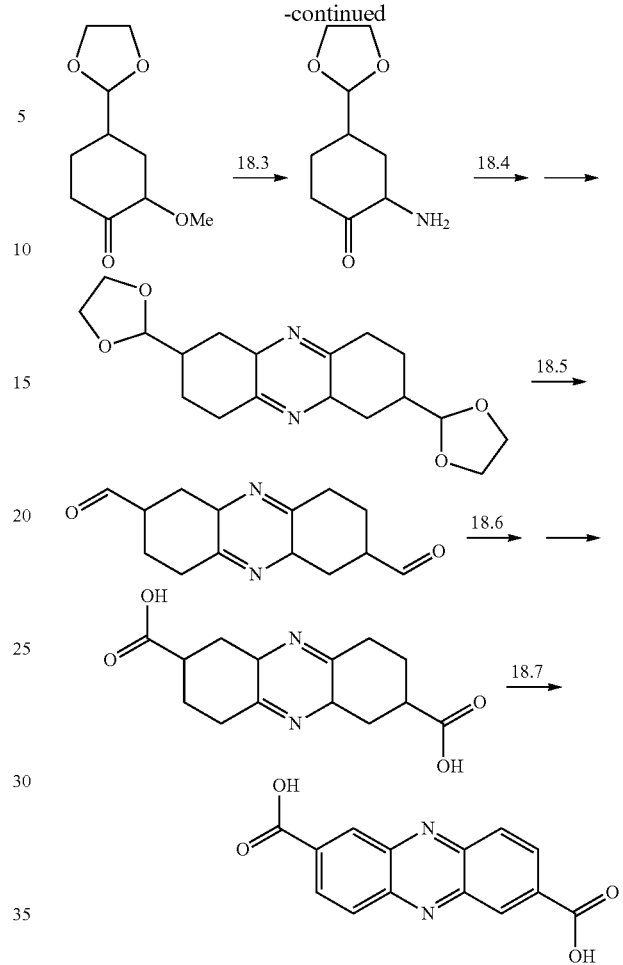

Another method of obtaining phenazines or phenazine derived structures from monomers that originate from lignin, is disclosed comprising: a dimerization of 2-aminocyclohexanones. In some embodiments, Vanillin is reacted with ethylene glycol (reaction 18.1) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 4-(1,3-dioxolan-2-yl)-2-methoxyphenol is hydrogenated to 4-(1,3-dioxolan-2-yl)-2-methoxycyclohexan-1-one (reaction 18.2) using doped catalyst such as but not limited to Pd, Pt, Ni, Co, Rh or Ru under 10-200 bar $H_2$, preferably 10-100 bar $H_2$ pressure between 50-250° C., preferably between 80-200° C. In the following step 4-(1,3-dioxolan-2-yl)-2-methoxycyclohexan-1-one is converted to 2-amino-4-(1,3-dioxolan-2-yl)cyclohexan-1-one by treatment with ammonia (reaction 18.3) at 20-200° C., preferably 20-100° C. 2-amino-4-(1,3-dioxolan-2-yl)cyclohexan-1-one is dimerized to 3,8-bis(1,3-dioxolan-2-yl)-1,2,3,4,4a,6,7,8,9,9a-decahydrophenazine (reaction 18.4) optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 3,8-bis(1,3-dioxolan-2-yl)-1,2,3,4,4a,6,7,8,9,9a-decahydrophenazine is converted to 1,2,3,4,5a,6,7,8,9,10a-decahydrophenazine-2,7-dicarbaldehyde (reaction 18.5) optionally in the presence of a catalyst such as but not limited to trifluoroacetic acid, H₂SO₄, HCl, H₃PO₄, acetic acid, p-toluenesulfonic acid between 0-100° C., preferably 0-50° C., most preferably between 10-30° C. 1,2,3,4,5a,6,7,8,9,10a-decahydrophenazine-2,7-dicarbaldehyde is oxidized to 1,2,3,4,5a,6,7,8,9,10a-decahydrophenazine-2,7-dicarboxylic acid (reaction 18.6) using an oxidation reagent such as but not limited to hydrogen peroxide, oxone, oxygen, sodium hypochlorite, potassium permanganate or manganese dioxide optionally in the presence of a catalyst at 0° C.-150° C., preferably 0° C. to 100° C. 1,2,3,4,5a,6,7,8,9,10a-decahydrophenazine-2,7-dicarboxylic acid is converted to phenazine-2,7-dicarboxylic acid (reaction 18.7) by treatment with a catalyst such as but not limited to palladium on carbon between 50-300° C., preferably 100-200° C. In some embodiments, reaction 18.6. and reaction 18.7 are done in a single step.

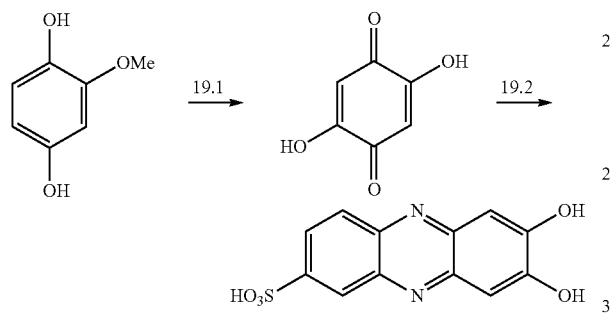

(19)

Another method of obtaining phenazines or phenazine derived structures from monomers that originate from lignin, comprising: an electrooxidation of a monomer. In some embodiments, 2-Methoxyhydroquinone is converted to 2,5-dihydroxybenzoquinone by electrochemical oxidation (reaction 19.1) with a suitable electrode, such as but not limited to PbO2/Pb as an anode and an electrolyte such as but not limited to sulfuric acid and acetic acid or a mixture thereof. 2,5-dihydroxybenzoquinone is condensed with 3,4-diaminobenzene-1-sulfonic acid (reaction 19.2) at 20-150° C., preferably 23-100° C., more preferably 40-80° C. to give 7,8-dihydroxyphenazine-2-sulfonic acid.

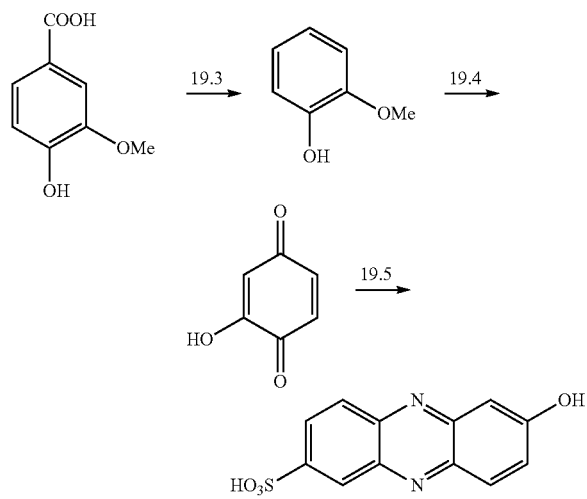

In some embodiments, vanillic acid is decarboxylated to 2-methoxyphenol (reaction 19.3) exemplary but not limited to by treatment with sodium hydroxide in 2-ethoxy-ethanol at 100-150° C., or with enzymes (e.g. decarboxylase) at 20-40° C., or with copper dichloride in water at 150-250° C., or with hydrogen chloride at 150-250° C. Then 2-methoxyphenol is converted to 2-hydroxycyclohexa-2,5-diene-1,4-dione (reaction 19.4) by electrochemical oxidation with a suitable electrode, such as but not limited to PbO2/Pb as an anode and an electrolyte such as but not limited to sulfuric acid and acetic acid or a mixture thereof. 2-hydroxycyclohexa-2,5-diene-1,4-dione is condensed with 3,4-diaminobenzene-1-sulfonic acid (reaction 19.5) at 20-150° C., preferably 23-100° C., more preferably 40-80° C. to give 7,8-dihydroxyphenazine-2-sulfonic acid.

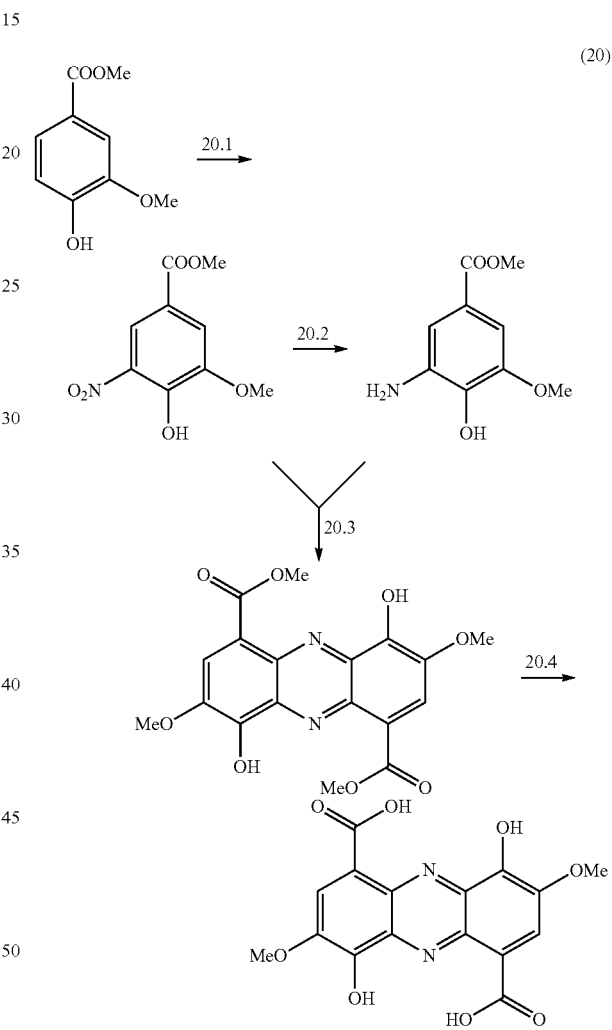

(20)

Another method of obtaining phenazines or phenazine derived structures from monomers that originate from lignin, is disclosed comprising: a condensation of a 2-nitrophenol and a 2-aminophenol, known as the Wohl-Aue-reaction. In some embodiments, methyl 4-hydroxy-3-methoxybenzoate is nitrated (reaction 20.1) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Methyl 4-hydroxy-3-methoxy-5-nitrobenzoate is reduced to methyl 3-amino-4-hydroxy-5-methoxybenzoate (reaction 20.2) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then Methyl 4-hydroxy-3-methoxy-5-nitrobenzoate is reacted with methyl 3-amino-4-hydroxy-5-methoxybenzoate at 50-300° C., preferably at 100-250° C., more preferably at 100-200° C. to give dimethyl 4,9-dihydroxy-3,8-dimethoxyphenazine-1,6-dicarboxylate (reaction 20.3). Finally, Dimethyl 4,9-dihydroxy-3,8-dimethoxyphenazine-1,6-dicarboxylate is hydrolyzed to, 9-dihydroxy-3,8-dimethoxyphenazine-1,6-dicarboxylic acid (reaction 20.4) by treatment with aqueous alkaline solution at 20-120° C., preferably 20-90° C.

nation with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-amino-3-methoxy-5-nitrobenzoic acid. 4-amino-3-methoxy-5-nitrobenzoic acid is reduced to 3,4-diamino-5-methoxybenzoic acid (reaction 21.3) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3,4-diamino-5-methoxybenzoic acid is dimerized (reaction 21.4) in the presence of an oxidation reagent such as, but not limited to iron(III) chloride, hydrogen peroxide, potassium persulfate, silver(I) oxide, oxygen, optionally with a catalyst at 20-150° C., preferably 20-100° C. to give 7,8-diamino-4,9-dimethoxyphenazine-2-carboxylicacid.

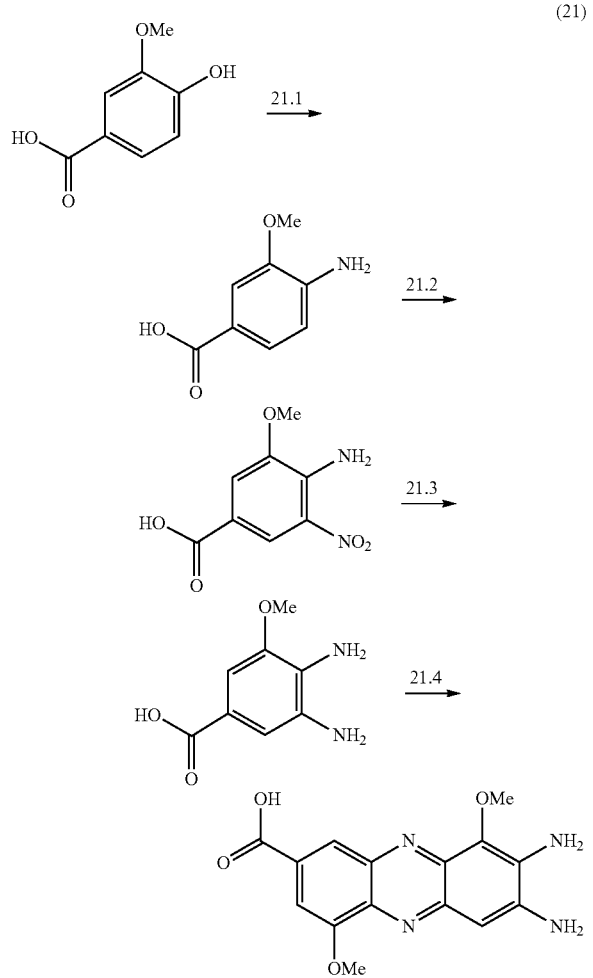

(21)

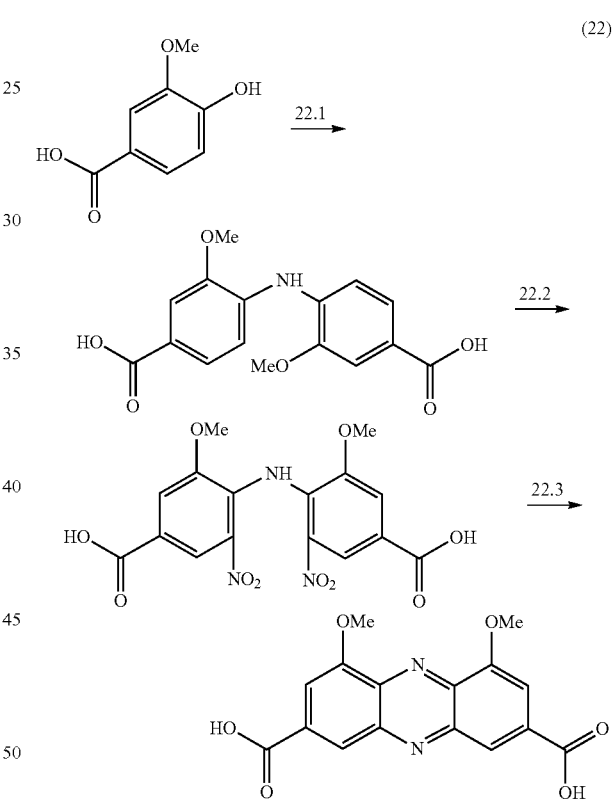

(22)

In some embodiments, vanillic acid is treated with ammonia (reaction 21.1) at 10-300 bar, preferably at 10-200 bar, more preferably at 10-50 bar, optionally in the presence of catalyst such as but not limited to Mo, W, Ir, RU, Pd, Pt, aluminum oxide, H-151 alumina, palladium on carbon, zeolite, copper (1) oxide at 30-400° C., preferably at 40-300° C., most preferably at 50-200° C. to give 3,4-diaminobenzoic acid. Then 4-amino-3-methoxybenzoic acid is nitrated (reaction 21.2) with but not limited to nitric acid in combi- Another method of obtaining phenazines or phenazine derived structures from monomers that originate from lignin, is disclosed comprising: a treatment of monomers with ammonia under pressure. In some embodiments, vanillic acid is treated with ammonia (reaction 22.1) at 10-300 bar, preferably at 10-200 bar, more preferably at 10-100 bar, optionally in the presence of catalyst such as but not limited to Mo, W, Ir, Ru, Pd, Pt, aluminum oxide, H-151 alumina, palladium on carbon, zeolite, copper (I) oxide at 30-400° C., preferably at 50-300° C. to give 4,4'-azanediylbis(3-methoxybenzoic acid). 4,4'-azanediylbis(3-methoxybenzoic acid) is then nitrated (reaction 22.2) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4,4'-azanediylbis(3-methoxy-5-nitrobenzoic acid). 4,4-azanediylbis(3-methoxy-5-nitrobenzoic acid) is cyclized to 4-methoxyphenazine-2,7-dicarboxylic acid (reaction 22.3) by treatment with an reducing agent such as but not limited to hydrazine hydrate, sodium borohydride, hydrogen, and base such as KOH or sodium ethanolate, with a catalyst such as Pd, Pt, Ni or Ru between 20-150° C., preferably between 20-100° C.

(23)

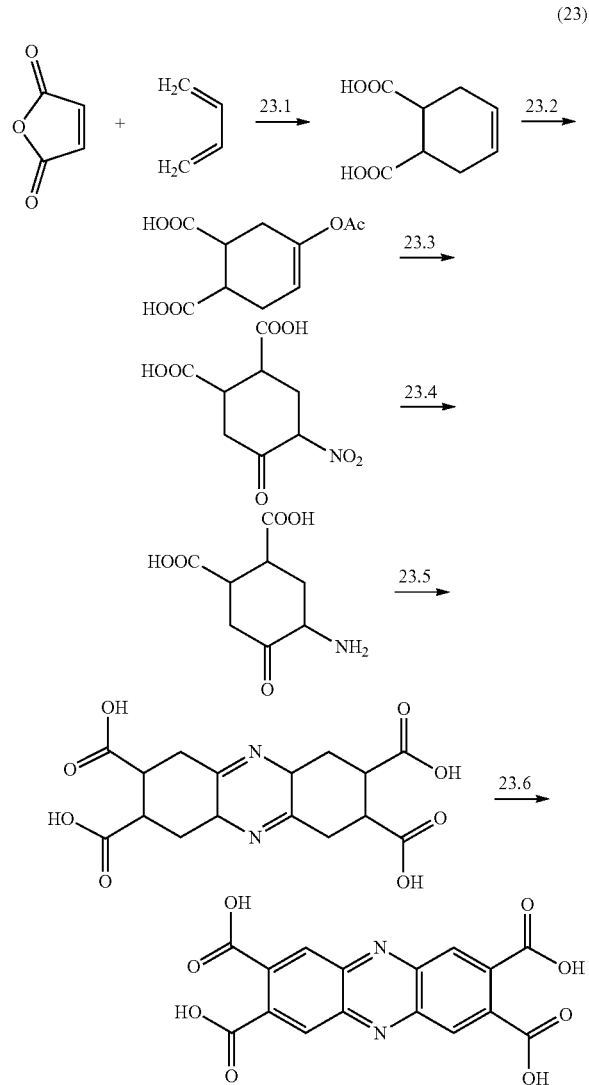

Another method of obtaining phenazines or phenazine derived structures from monomers, is disclosed comprising: a dimerization of 2-aminocyclohexanones. In some embodiments, maleic anhydride is reacted with butadiene (reaction 23.1) in presence of catalyst (Lewis acids, metal complexes) between 20-200° C., preferably 50-120° C. to give cyclohex-4-ene-1,2-dicarboxylic acid. Cyclohex-4-ene-1,2-dicarboxylic acid is converted to 4-(acetyloxy)cyclohex-4-ene-1,2-dicarboxylic acid (reaction 23.2) with acetic acid optionally in presence of catalyst (iron(III) triflate). 4-(acetyloxy)cyclohex-4-ene-1,2-dicarboxylic acid is reacted with nitric acid in acetic anhydride to give 4-nitro-5-oxocyclohexane-1,2-dicarboxylic acid (reaction 23.3) at 20-100° C. 4-nitro-5-oxocyclohexane-1,2-dicarboxylic acid is reduced to 4-amino-5-oxocyclohexane-1,2-dicarboxylic acid (reaction 23.4) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then 4-amino-5-oxocyclohexane-1,2-dicarboxylic acid was dimerized to 1,2,3,4,4a,6,7,8,9,9a-decahydrophenazine-2,3,7,8-tetracarboxylic acid (reaction 23.5) in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C. In some embodiments, the reaction 23.5 is spontaneous. 1,2,3,4,4a,6,7,8,9,9a-decahydrophenazine-2,3,7,8-tetracarboxylic acid is converted to phenazine-2,3,7,8-tetracarboxylic acid (reaction 23.6) by treatment with a catalyst such as but not limited to palladium on carbon between 50-300° C., preferably 100-200° C.

DESCRIPTION OF THE FIGURES

FIG. 3 shows electrochemical data for selected posolytes and negolytes, the negolytes being phenazin derivatives and the posolytes anorganic redox-active compounds based on.

EXAMPLES

Figure 1:
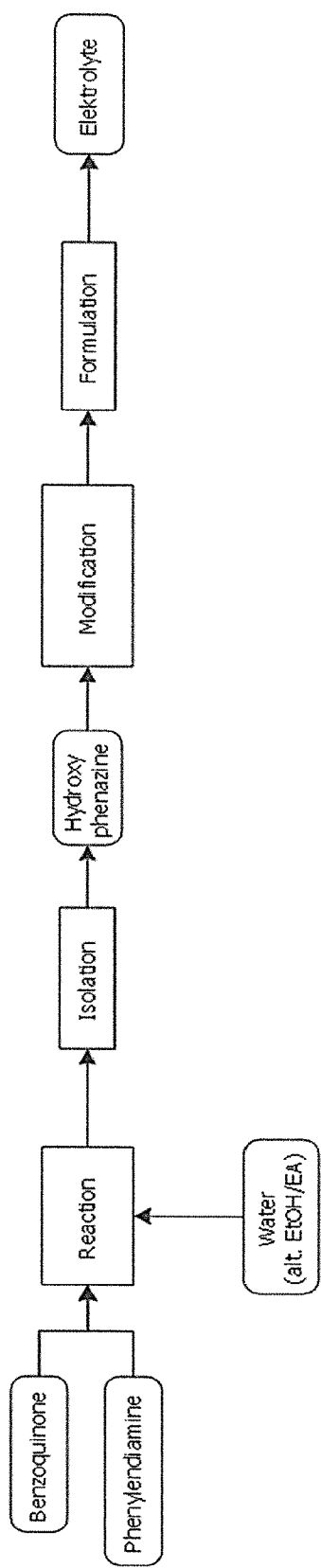
FIG. 1 shows synthesis steps of alloxazine-based electrolytes from benzoquinones.
Figure 2:
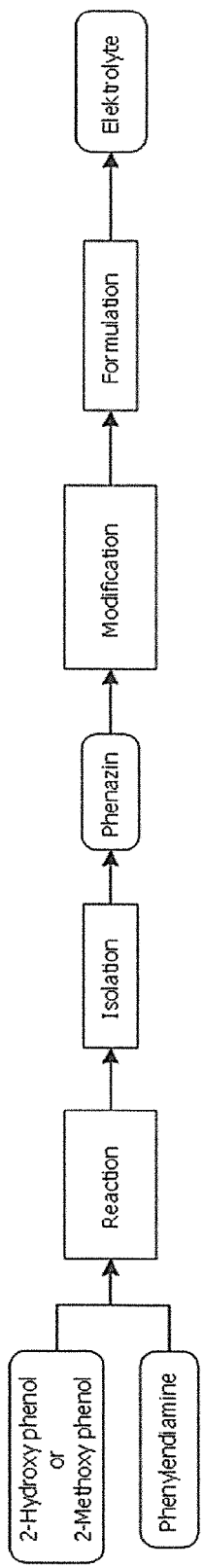
FIG. 2 shows synthesis steps of alloxazine-based electrolytes from 2-hydroxyphenols or 2-methoxyphenols.

The examples shown in the following are merely illustrative and shall describe the present invention in a further way. These examples shall not be construed to limit the present invention thereto. The following preparations and examples are given to enable those skilled in the art to more clearly understand and to practice the present invention. The present invention, however, is not limited in scope by the exemplified embodiments, which are intended as illustrations of single aspects of the invention only, and methods, which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Synthesis of 7,8-Dihydroxyphenazine-2-Sulfonic Acid 2,5-Dihydroxy-1,4-benzoquinone (8.1 g, 57.4 mmol) was added to 150 mL boiling water, then 3,4-diaminobenezenesulfonic acid (10.8 g, 57.4 mmol) was added within a few minutes. The brown suspension was stirred at 95° C. for 18 h, cooled to room temperature and 150 mL acetone were added to the reaction mixture. After filtration the product was obtained as a brown solid (14.1 g, 84%).

Example 2: Synthesis of 7,8-Dihydroxyphenazine-2-Carboxylic Acid 2,5-Dihydroxy-1,4-benzoquinone (2.8 g, 20 mmol) was added to 100 mL boiling water, then 3,4-diaminobenzoic acid (3.1 g, 20 mmol) acid was added within a few minutes. The brown suspension was stirred at 95° C. for 18 h, cooled to room temperature and 150 mL acetone was added to the reaction mixture. After filtration the product was obtained in a quantitative yield.

Example 3: Synthesis of 2,3-Dihydroxyphenazine 2,5-Dihydroxy-1,4-benzoquinone (4.0 g, 28.5 mmol) was added to 100 mL boiling water, then 1,2-phenylenediamine (3.1 g, 28.5 mmol) was added within a few minutes. The brown suspension was stirred at 80° C. for 18 h, cooled to room temperature and 130 mL acetone were added to the reaction mixture. After filtration the product was obtained in a quantitative yield.

Example 4: Synthesis of Phenazine and 2,3-Dihydroxyphenazine 1,2-Dihydoxybenzene (0.3 g, 2.8 mmol) and 1,2-phenylenediamine (0.3 g, 2.8 mmol) were heated in a microwave vial to 210° C. for 15 minutes. The melt solidified, was cooled to room temperature and washed several times with water. The insoluble product (0.2 g) contained phenazine and 2,3-dihydroxyphenazine according to HPLC and absorption spectroscopy. Washing the product mixture with 2 M aqueous sodium hydroxide yielded the desired phenazine.

Example 5

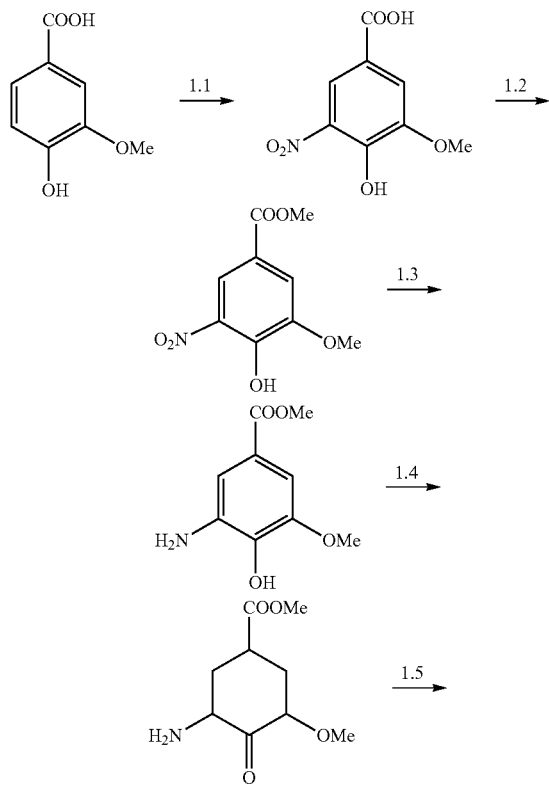

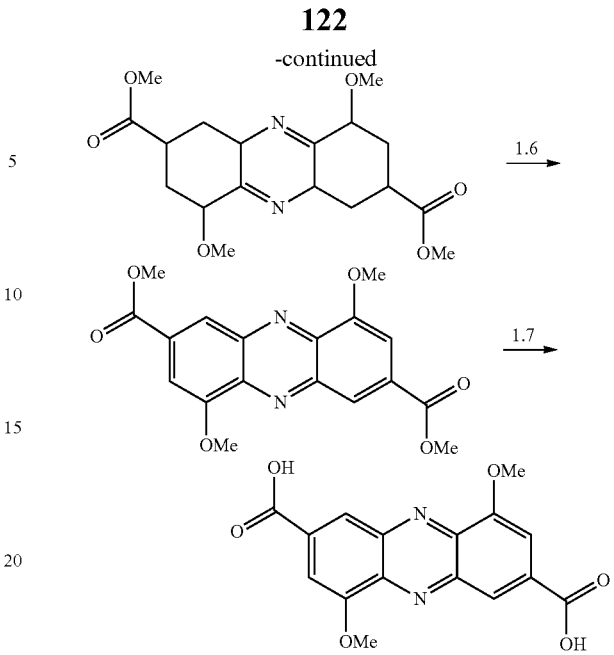

A method of obtaining phenazines or phenazine derived structures from monomers that originate from lignin, is disclosed comprising: a dimerization of 2-amino cyclohexanones. In some embodiments, vanillic acid is nitrated (reaction 1.1) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Then, 4-hydroxy-3-methoxy-5-nitrobenzoic acid is reacted with an alcohol such as but not limited to methanol (reaction 1.2) in some embodiments, in the presence of a catalyst, such as but not limited to $H_2SO_4$, HCl, $H_3PO_4$, $CH_3COOH$ between 20-150° C., preferably between 20-100° C. most preferably between 30-70° C., to give methyl 4-hydroxy-3-methoxy-5-nitrobenzoate.

Methyl 4-hydroxy-3-methoxy-5-nitrobenzoate is reduced to methyl 3-amino-4-hydroxy-5-methoxybenzoate (reaction 1.3) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Methyl 3-amino-4-hydroxy-5-methoxybenzoate is hydrogenated to methyl 3-amino-5-methoxy-4-oxocyclohexane-1-carboxylate (reaction 1.4) using doped catalyst such as but not limited to Pd, Pt, Ni, Co, Rh or Ru under 10-200 bar $H_2$, preferably 10-100 bar $H_2$ pressure between 50-250° C., preferably between 80-200° C. In some embodiments, reaction 1.3 and 1.4 are combined to a single hydrogenation reaction. Methyl 3-amino-5-methoxy-4-oxocyclohexane-1-carboxylate is then dimerized to dimethyl 4,9-dimethoxy-1,2,3,4,5a,6,7,8,9,10a-decahydrophenazine-2,7-dicarboxylate (reaction 1.5) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C. In some embodiments, the reaction 1.5 is spontaneously.

Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 1.6) by treatment with a catalyst such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 1.7) by treatment with aqueous alkaline solution at 20-120° C., preferably 20-90° C.

Example 6

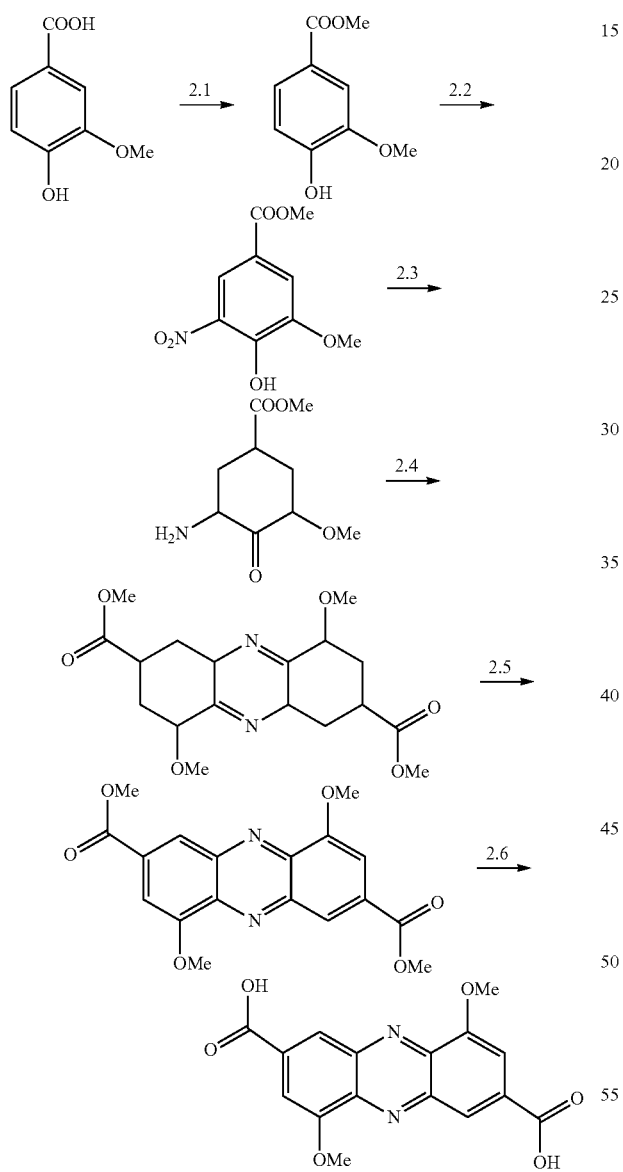

Another method of obtaining phenazines or phenazine derived structures from monomers that originate from lignin, is disclosed comprising: a dimerization of 2-amino cyclohexanones. In some embodiments, vanillic acid is reacted with an alcohol such as but not limited to methanol (reaction 2.1) in some in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Methyl 4-hydroxy-3-methoxybenzoate is nitrated (reaction 2.2) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C.

Then, methyl 4-hydroxy-3-methoxy-5-nitrobenzoate is hydrogenated to methyl 3-amino-5-methoxy-4-oxocyclohexane-1-carboxylate (reaction 2.3) using doped catalyst such as but not limited to Pd, Pt, Ni, Rh or Ru under 10-200 bar $H_2$, preferably 10-100 bar $H_2$ pressure between 50-250° C., preferably between 80-200° C. Methyl 3-amino-5-methoxy-4-oxocyclohexane-1-carboxylate is then dimerized to dimethyl 4,9-dimethoxy-1,2,3,4,5a,6,7,8,9,10a-decahydrophenazine-2,7-dicarboxylate (reaction 2.4) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. In some embodiments, the reaction 1.5 is spontaneously. Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 2.5) by treatment with a catalyst such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 2.6) by treatment with aqueous alkaline solution at 20-120° C., preferably 20-90° C.

Example 7

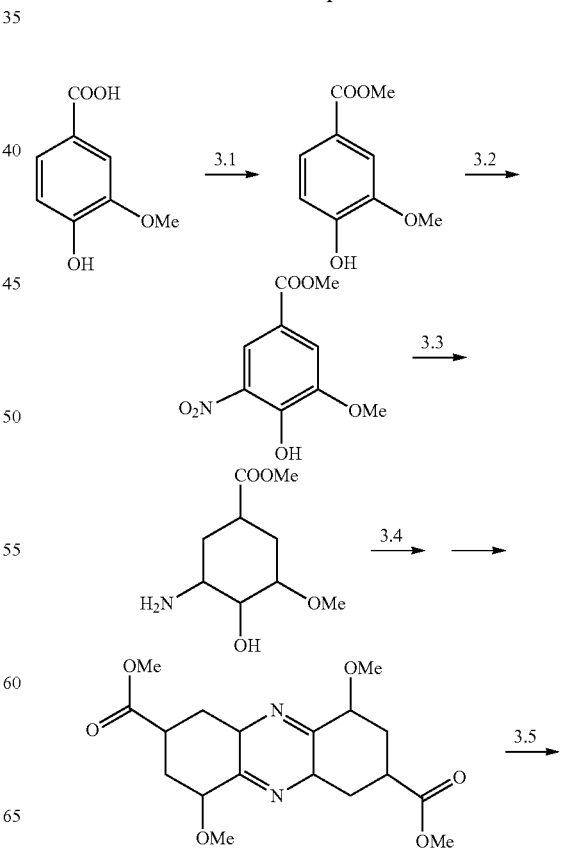

125

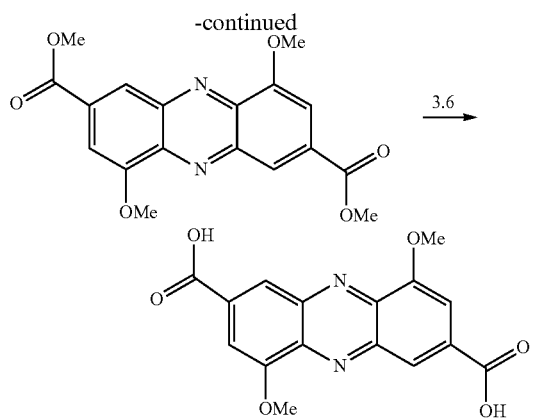

Another method of obtaining phenazines or phenazine derived structures from monomers that originate from lignin, is disclosed comprising: a dimerization of 2-amino cyclohexanol. In some embodiments, vanillic acid is reacted with an alcohol such as but not limited to methanol (reaction 3.1) in some embodiments, in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Methyl 4-hydroxy-3-methoxybenzoate is nitrated (reaction 3.2) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Then methyl 4-hydroxy-3-methoxy-5-nitrobenzoate is hydrogenated to methyl 3-amino-4-hydroxy-5-methoxycyclohexane-1-carboxylate (reaction 3.3) using a transition metal catalyst such as but not limited to Pd, Pt, Ni, Rh or Ru under 10-200 bar $H_2$, preferably 10-100 bar $H_2$ pressure between 50-250° C., preferably between 80-200° C. Methyl 3-amino-4-hydroxy-5-methoxycyclohexane-1-carboxylate is then dimerized to dimethyl 4,9-dimethoxy-1,2,3,4,5a,6,7,8,9,10a-decahydrophenazine-2,7-dicarboxylate (reaction 3.4) in the presence of an oxidation agent such as but not limited to $O_2$, $H_2O_2$, sodium hypochlorite, cerium ammonium nitrate or potassium permanganate and optionally an catalyst.

Dimethyl 4,9-dimethoxy-1,2,3,4,5a,6,7,8,9,10a-decahydrophenazine-2,7-dicarboxylate is converted to 4,9-dimethoxyphenazine-2,7-dicarboxylic acid (reaction 3.5) by treatment with a catalyst such as but not limited to palladium on carbon between 50-300° C., preferably 100-200° C. Finally, dimethyl 4,9-dimethoxyphenazine-2,7-dicarboxylate is hydrolyzed to 4,9-dimethoxyphenazine-2,7-dicarboxylic acid (reaction 3.6) by treatment with aqueous alkaline solution at 20-120° C., preferably 20-90° C.

126

Example 8

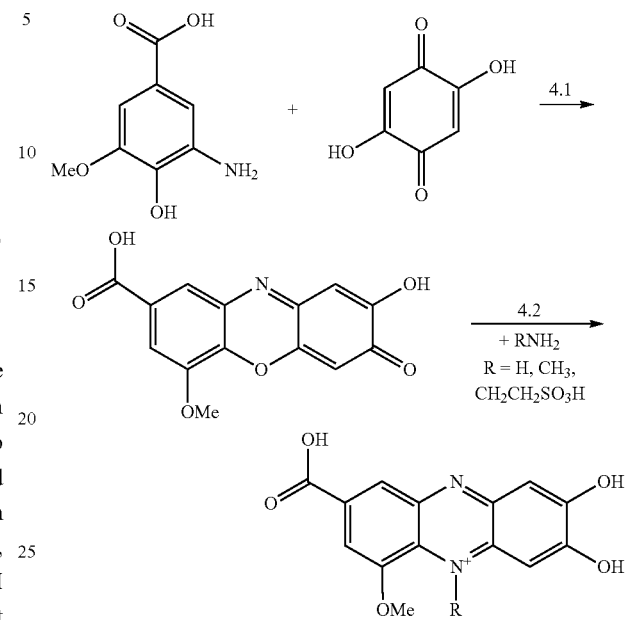

Another method of obtaining phenazines or phenazine derived structures from monomers that originate from lignin, is disclosed comprising: transformation of a phenoxazine to a phenazine. In some embodiments, 3-amino-4-hydroxy-5-methoxybenzoic acid is reacted with 2,5-dihydroxybenzoquinone (reaction 4.1) in a solvent such as but not limited to water, methanol, ethanol, acetonitrile or DMF under cooling at least at 0° C., at least 10° C., at least 20° C. under room temperature, or under heating at least at 30° C., at least 50° C., at least 80° C., at least 100° C., at least 120° C., at least 150° C. to give 2-hydroxy-6-methoxy-3-oxo-3H-phenoxazine-8-carboxylic acid. 2-hydroxy-6-methoxy-3-oxo-3H-phenoxazine-8-carboxylic acid is then reacted with ammonia (R═H) or primary amine (reaction 4.2) between 20-250° C., preferably between 50-200° C. and at 0-150 bar preferably 0-100 bar.

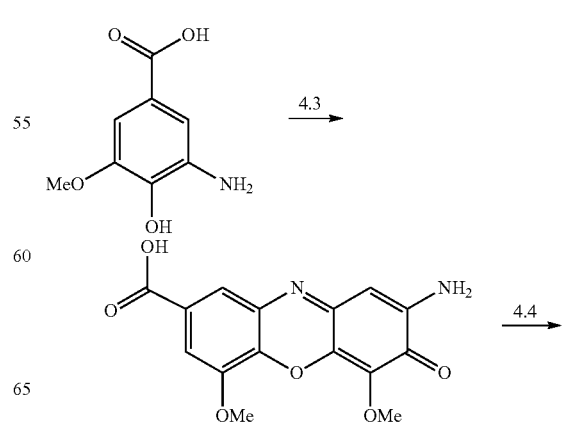

-continued

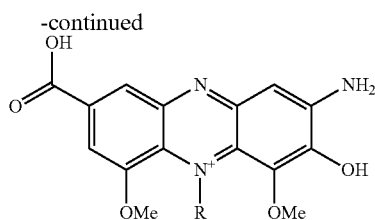

In some embodiments, 5-Aminovanillic acid is dimerized to 2-amino-4,6-dimethoxy-3-oxo-3H-phenoxazine-8-carboxylic (reaction 4.3) in the presence of an oxidant, such as but not limited to O2, $H_2O_2$, sodium hypochlorite, cerium ammonium nitrate, potassium permanganate or manganese dioxide and optionally a catalyst such as but not limited to potassium iodide, sodium tungstate, CuAlO(OH), or cupper chloride between 20-200° C. preferably 20-120° C. Subsequently 2-amino-4,6-dimethoxy-3-oxo-3H-phenoxazine-8-carboxylic acid is reacted with ammonia (R=H) or primary amine (reaction 4.4) between 20-250° C., preferably between 50-200° C. and at 0-150 bar preferably 0-100 bar.

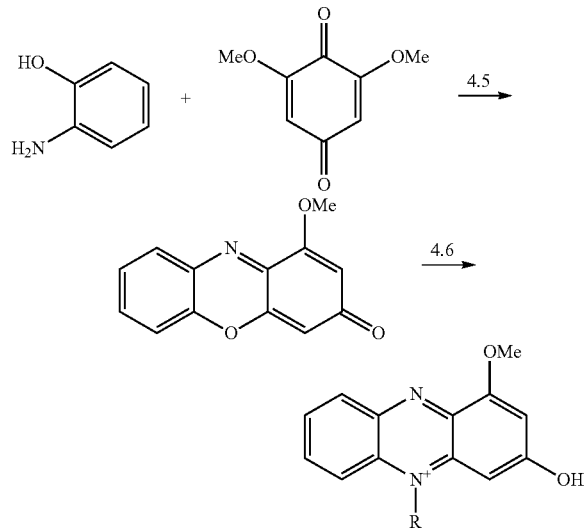

In some embodiments, 2-aminophenol acid is reacted with 2,6-dimethoxybenzoquinone (reaction 4.5) in the presence of a catalyst such as, but not limited to sulfuric acid, hydrochloric acid, phosphoric acid or organic acids such as acetic acid. At temperatures between 0-200° C. preferably between 20 to 120° C. Subsequently 1-methoxy-3H-phenoxazin-3-one was reacted with ammonia (R=H) or primary amine (reaction 4.6) between 20-250° C., preferably between 50-200° C. and at 0-150 bar preferably 0-100 bar.

Example 9

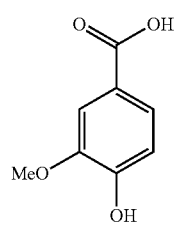

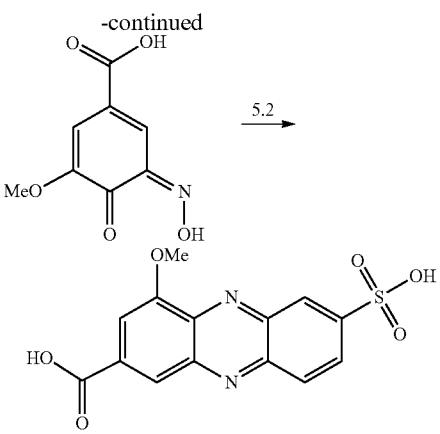

Another method of obtaining phenazines or phenazine derived structures from monomers that originate from lignin, is disclosed comprising: a treatment of monomers with sodium nitrite. In some embodiments, vanillic acid is treated with sodium nitrite (reaction 5.1) in presence of acid such as but not limited to sulfuric acid, hydrochloric acid, phosphoric acid or organic acids such as acetic acid in water or an alcohol to yield 3-(hydroxyimino)-5-methoxy-4-oxo-cyclohexa-1,5-diene-1-carboxylic acid. 3-(hydroxyimino)-5-methoxy-4-oxocyclohexa-1,5-diene-1-carboxylic acid is then reacted with 3,4-diaminobenzene-1-sulfonic acid (reaction 5.2) between 0-200° C., preferably between 20-140° C. to give 4-methoxy-7-sulfophenazine-2-carboxylic acid.

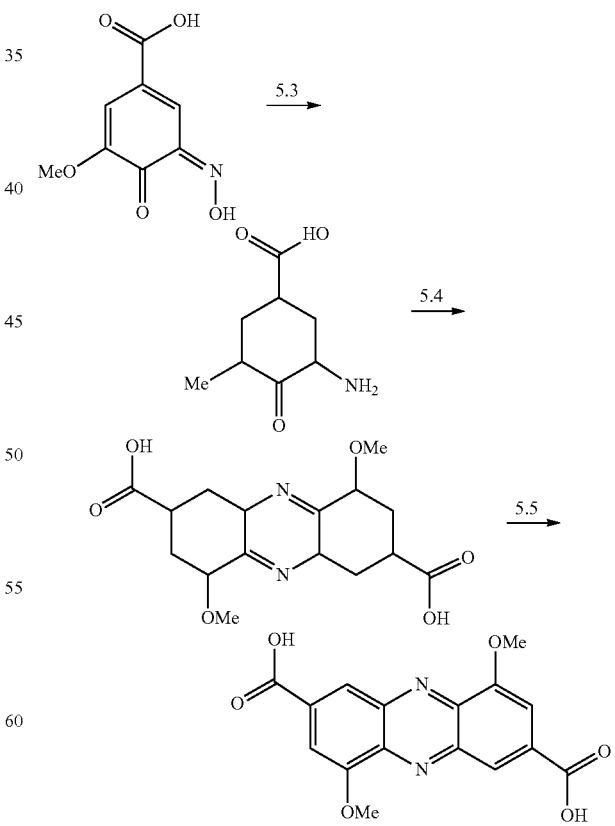

In some embodiments, 3-(hydroxyimino)-5-methoxy-4-oxocyclohexa-1,5-diene-1-carboxylic acid is hydrogenated to 3-amino-5-methoxy-4-oxocyclohexane-1-carboxylic acid (reaction 5.3) using doped catalyst such as but not limited to Pd, Pt, Ni, Rh or Ru under 10-200 bar $H_2$, preferably 10-100 bar $H_2$ pressure between 50-250° C., preferably between 80-200° C. 3-amino-5-methoxy-4-oxocyclohexane-1-carboxylic acid is then dimerized to 4,9-dimethoxy-1,2,3,4,5a,6,7,8,9,10a-decahydrophenazine-2,7-dicarboxylic acid (reaction 5.4) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. In some embodiments, the reaction 1.5 is spontaneous. 4,9-dimethoxy-1,2,3,4,5a,6,7,8,9,10a-decahydrophenazine-2,7-dicarboxylic is converted to 4,9-dimethoxyphenazine-2,7-dicarboxylic acid (reaction 5.5) by treatment with a catalyst such as but not limited to palladium on carbon between 50-300° C., preferably 100-200° C.

Example 10

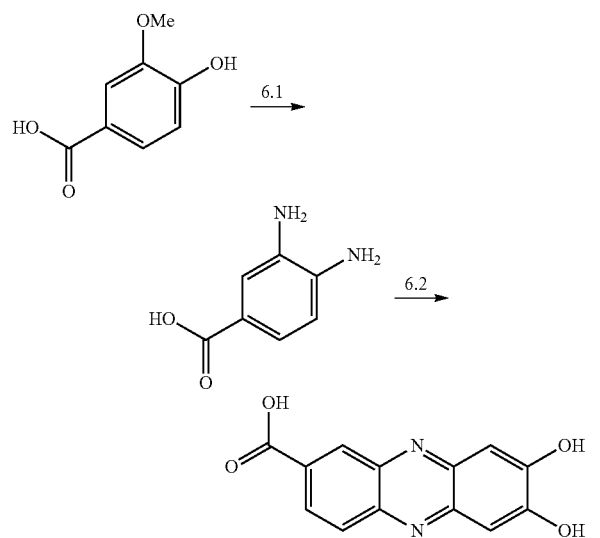

Another method of obtaining phenazines or phenazine derived structures from monomers that originate from lignin, is disclosed comprising: a treatment of monomers with ammonia under pressure. In some embodiments, vanillic acid is treated with ammonia (reaction 6.1) at 10-300 bar, preferably at 10-200 bar, more preferably at 10-50 bar, optionally in the presence of catalyst such as but not limited to Mo, W, Ir, RU, Pd, Pt, aluminum oxide, H-151 alumina, palladium on carbon, zeolite, copper (1) oxide at 30-400° C., preferably at 50-200° C. to give 3,4-diaminobenzoic acid. Then 3,4-diaminobenzoic acid is reacted with 2,5-dihydroxybenzoquinone (reaction 6.2) at 20-200° C., preferably at 40-120° C. to give 7,8-dihydroxyphenazine-2-carboxylic acid.

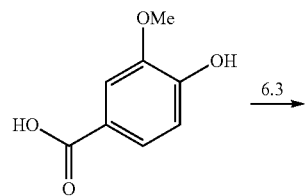

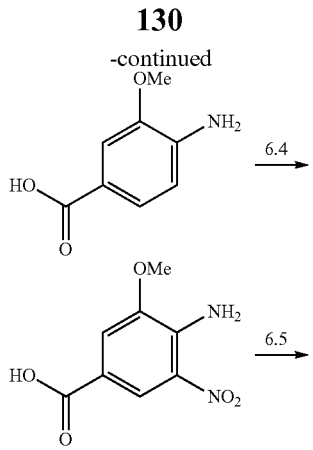

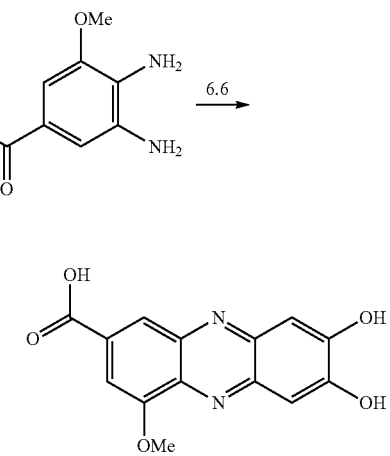

In some embodiments, vanillic acid is treated with ammonia (reaction 6.3) at 10-300 bar, preferably at 10-200 bar, more preferably at 10-50 bar, optionally in the presence of catalyst such as but not limited to Mo, W, Ir, Ru, Pd, Pt, aluminum oxide, H-151 alumina, palladium on carbon, zeolite, copper (I) oxide at 30-400° C., preferably at 40-300° C., most preferably at 50-200° C. to give 3,4-diaminobenzoic acid. Then, 4-amino-3-methoxybenzoic acid is nitrated (reaction 6.4) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-amino-3-methoxy-5-nitrobenzoic acid. 4-amino-3-methoxy-5-nitrobenzoic acid is reduced to 3,4-diamino-5-methoxybenzoic acid (reaction 6.5) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3,4-diamino-5-methoxybenzoic acid is reacted with 2,5-dihydroxybenzoquinone (reaction 6.6) at 20-200° C., preferably at 40-120° C. to give 7,8-dihydroxy-4-methoxyphenazine-2-carboxylic acid.

Example 11

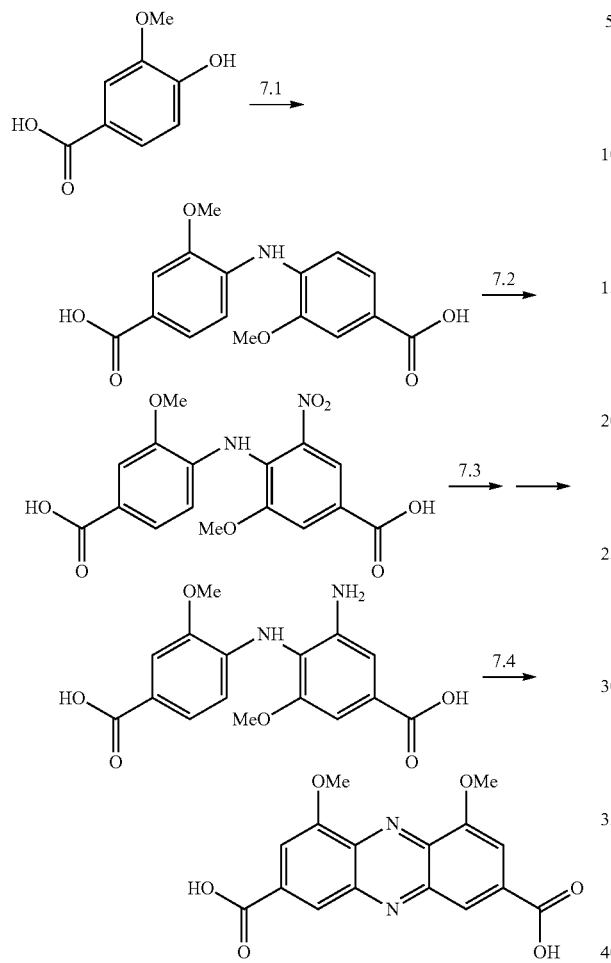

Another method of obtaining phenazines or phenazine derived structures from monomers that originate from lignin, is disclosed comprising: a treatment of monomers with ammonia under pressure. In some embodiments, vanillic acid is treated with ammonia (reaction 7.1) at 10-300 bar, preferably at 10-200 bar, more preferably at 10-100 bar, optionally in the presence of catalyst such as but not limited to Mo, W, Ir, Ru, Pd, Pt, aluminum oxide, H-151 alumina, palladium on carbon, zeolite, copper (1) oxide at 30-400° C., preferably at 50-300° C. to give 4,4'-azanediylbis(3-methoxybenzoic acid). 4,4'-azanediylbis(3-methoxybenzoic acid) is then nitrated (reaction 7.2) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-(4-carboxy-2-methoxyanilino)-3-methoxy-5-nitrobenzoic acid. 4-(4-carboxy-2-methoxyanilino)-3-methoxy-5-nitrobenzoic acid is reduced to 3-amino-4-(4-carboxy-2-methoxyanilino)-5-methoxybenzoic acid (reaction 7.3) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3-amino-4-(4-carboxy-2-methoxyanilino)-5-methoxybenzoic acid is cyclized to 4-methoxyphenazine-2,7-dicarboxylic (reaction 7.4) acid in the presence of an oxidation reagent such as, but not limited to oxygen, hydrogen peroxide, $PhI(OAc)_2$, sodium periodate, sodium hypochlorite, cerium ammonium nitrate, $MnO_2$, $KMnO_4$, optionally with a catalyst at 20-150° C., preferably 20-100° C.

Example 12

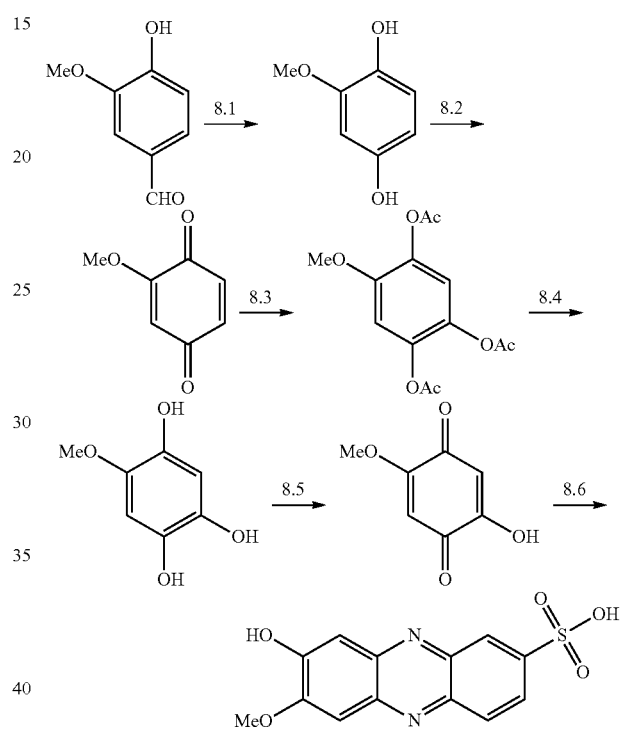

Another method of obtaining phenazines or phenazine derived structures from monomers that originate from lignin, is disclosed comprising: transformation of vanillin to 2-methoxyhydroquinone (reaction 8.1) by treatment with hydrogen peroxide and base at 0-60° C., preferably between 25-40° C. 2-methoxyhydroquinone is oxidized to 2-methoxy-5-hydroxybenzoquinone (reaction 8.2) with an oxidation agent such as but not limited to oxygen, hydrogen peroxide, manganese dioxide, sodium hypochlorite, cerium ammonium nitrate or potassium permanganate optionally in the presence of a catalyst.

In some embodiments, 2-Methoxybenzoquinone is reacted with acetic anhydride (reaction 8.3) in the presence of acid such as but not limited to sulfuric acid, hydrochloric acid, phosphorus acid, triflic acid or organic acids such as acetic acid to give 5-methoxybenzene-1,2,4-triyl triacetate. 5-methoxybenzene-1,2,4-triyl triacetate is treated with acidic or alkaline aqueous, methanolic or acetone solution to yield 5-methoxybenzene-1,2,4-triol (reaction 8.4). 5-methoxybenzene-1,2,4-triol was oxidized to 2-hydroxy-5-methoxycyclohexa-2,5-diene-1,4-dione (reaction 8.5) in the presence of oxidation agent such as but not limited to oxygen, hydrogen peroxide, manganese dioxide, sodium hypochlorite, cerium ammonium nitrate or potassium permanganate optionally in the presence of a catalyst. Then 2-hydroxy-5-methoxycyclohexa-2,5-diene-1,4-dione was reacted with 3,4-diaminobenzene-1-sulfonic acid (reaction 8.6) at 20-200° C., preferably between 30-100° C. to give 8-hydroxy-7-methoxyphenazine-2-sulfonic acid.

Example 13

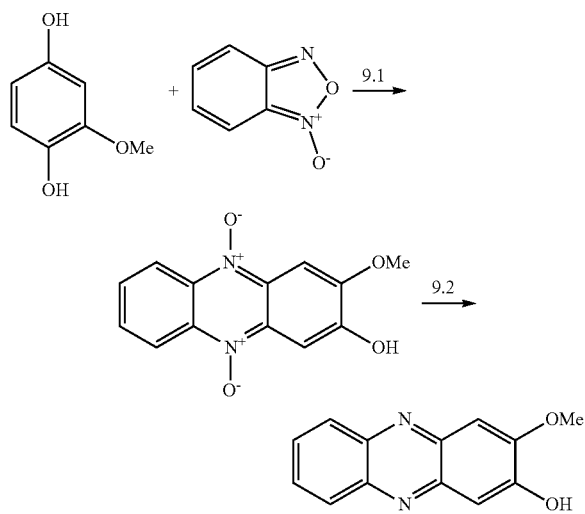

Another method of obtaining phenazines or phenazine derived structures from monomers that originate from lignin, is disclosed comprising: a cyclization reaction with benzofuroxanes. In some embodiments, Benzofuroxan is reacted with 2-methoxyhydroquinone (reaction 9.1) in the presence of a base such as but not limited to, sodium hydroxide, potassium hydroxide, sodium carbonate, potassium carbonate, triethyl amine or sodium methylate at 0-120° C., preferably between 20-80° C. to yield 3-methoxy-5,10-dioxo-phenazin-2-ol. 3-methoxy-5,10-dioxo-phenazin-2-ol is reduced to 3-methoxyphenazin-2-ol (reaction 9.2) by treatment with reagents such as but not limited to trifluoroacetic anhydride and sodium iodide in acetonitrile at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

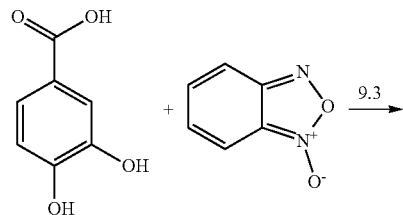

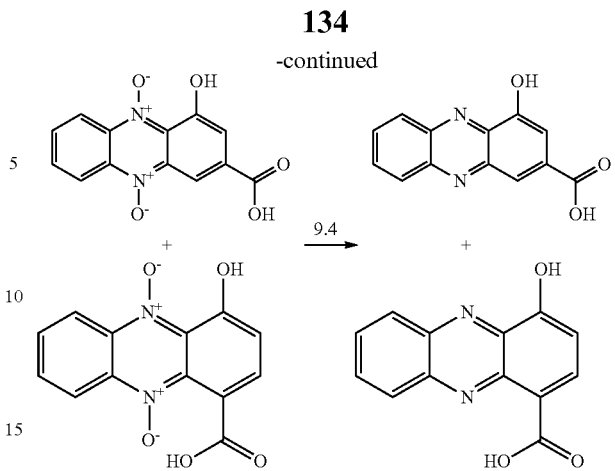

In some embodiments, benzofuroxan is reacted with 3,4-dihydroxybenzoic acid (reaction 9.3) in the presence of a base such as but not limited to, sodium hydroxide, potassium hydroxide, sodium carbonate, potassium carbonate, triethyl amine or sodium methylate at 0-120° C., preferably between 20-80° C. to yield the mixture of 4-hydroxy-5,10-dioxo-phenazine-2-carboxylic acid and 4-hydroxy-5,10-dioxo-phenazine-1-carboxylic acid. The mixture of 4-hydroxy-5,10-dioxo-phenazine-2-carboxylic acid and 4-hydroxy-5,10-dioxo-phenazine-1-carboxylic acid was reduced to 4-hydroxyphenazine-2-carboxylic acid and 4-hydroxyphenazine-1-carboxylic acid (reaction 9.4) by treatment with reagents such as but not limited to trifluoroacetic anhydride and sodium iodide in acetonitril at rt, or titanium (IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THE/water at rt, or by hydrogenation with catalytic palladium on charcoal (10% Pd) or Raney nickel (2-10%) under hydrogen (1-5 bar) in EtOH or MeOH.

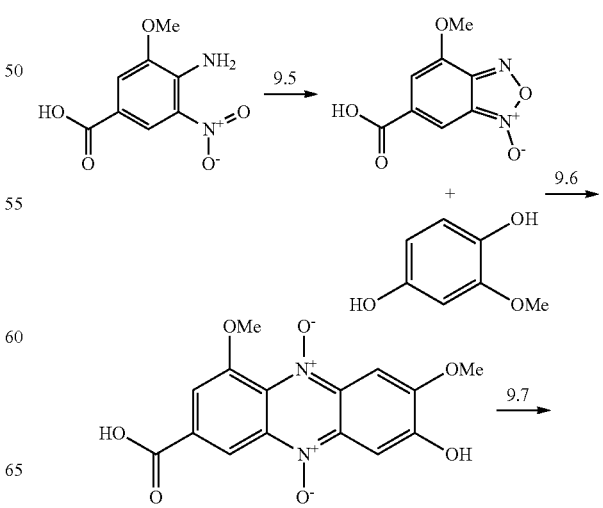

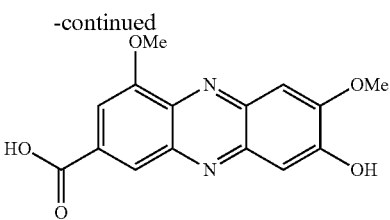

In some embodiments, 4-amino-3-methoxy-5-nitrobenzoic acid was oxidized with an oxidation agent (reaction 9.5) such as but not limited to sodium hypochlorite in alkaline solution at 0-100° C. preferably at 10-60° C. or with PhI(OAc)$_2$ at 20-80° C. to give 7-methoxy-3-oxo-2,1,3λ$^5$-benzoxadiazole-5-carboxylic acid. Then 7-methoxy-3-oxo-2,1,3λ$^5$-benzoxadiazole-5-carboxylic acid was reacted with 2-methoxyhydroquinone (reaction 9.6) in the presence of a base such as but not limited to, sodium hydroxide, potassium hydroxide, sodium carbonate, potassium carbonate, triethyl amine or sodium methylate at 0-120° C., preferably between 20-80° C. to yield 8-hydroxy-4,7-dimethoxy-5,10-dioxo-phenazine-2-carboxylic acid. 8-hydroxy-4,7-dimethoxy-5,10-dioxo-phenazine-2-carboxylic acid was reduced to 8-hydroxy-4,7-dimethoxyphenazine-2-carboxylic acid (reaction 9.7) by treatment with reagents such as but not limited to trifluoroacetic anhydride and sodium iodide in acetonitril at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(I)-chloride in hydrochloric acid, or by catalytic reduction with sodium hydrophosphite over palladium on carbon (5%) in THE/water at rt, or by hydrogenation with catalytic palladium on charcoal (10% Pd) or Raney nickel (2-10%) under hydrogen (1-5 bar) in EtOH or MeOH.

treatment with sulfuric acid or oleum at 30-200° C., preferably 50-120° C. The resulting 4-amino-3-nitrobenzene-1-sulfonic acid is oxidized with an oxidation agent (reaction 9.9) such as but not limited to sodium hypochlorite in alkaline solution at 0-100° C. preferably at 10-60° C. or with PhI(OAc)$_2$ at 20-80° C. to give 3-oxo-2,1,3λ$^5$-benzoxadiazole-5-sulfonic acid. 3-oxo-2,1,3λ$^5$-benzoxadiazole-5-sulfonic acid was reacted with 2-methoxyhydroquinone (reaction 9.10) in the presence of a base such as but not limited to, sodium hydroxide, potassium hydroxide, sodium carbonate, potassium carbonate, triethyl amine or sodium methylate at 0-120° C., preferably between 20-80° C. to yield 8-hydroxy-7-methoxy-5,10-dioxo-5λ$^5$,10λ$^5$-phenazine-2-sulfonic acid. 8-hydroxy-7-methoxy-5,10-dioxo-5λ$^5$,10λ$^5$-phenazine-2-sulfonic acid was reduced to 8-hydroxy-7-methoxy-phenazine-2-sulfonic acid (reaction 9.11) by treatment with reagents such as but not limited to trifluoroacetic anhydride and sodium iodide in acetonitril at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

Example 14

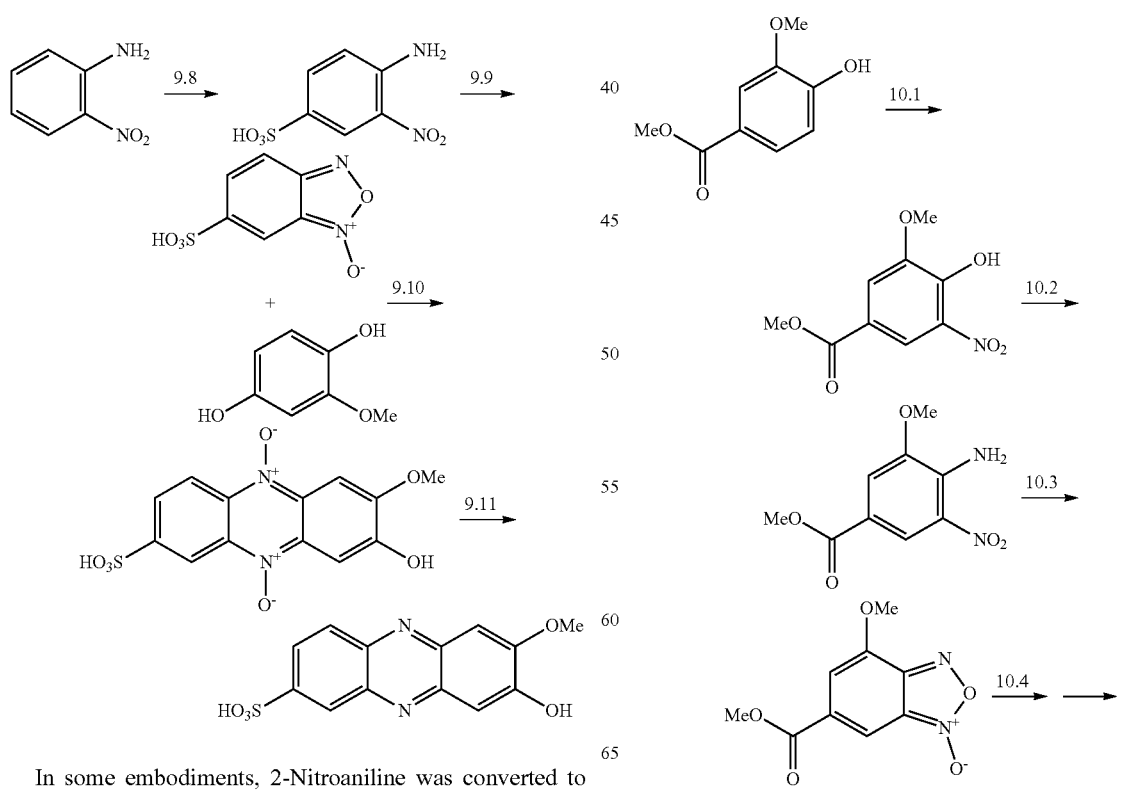

In some embodiments, 2-Nitroaniline was converted to 4-amino-3-nitrobenzene-1-sulfonic acid (reaction 9.8) by

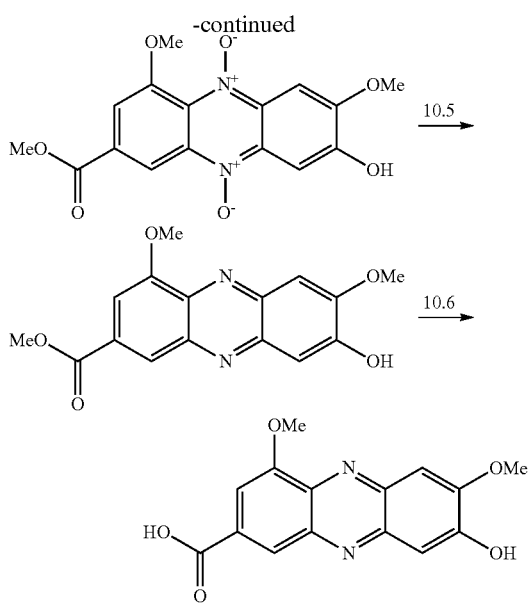

Another method of obtaining phenazines or phenazine derived structures from monomers that originate from lignin, is disclosed comprising: a cyclization reaction with benzofuroxanes. In some embodiments, Methyl 4-hydroxy-3-methoxybenzoate is nitrated (reaction 10.1) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. Methyl 4-hydroxy-3-methoxy-5-nitrobenzoate is reacted with ammonia in water or methanol at 50-300° C., preferably 100-200° C. to give methyl 4-amino-3-methoxy-5-nitrobenzoate (reaction 10.2). Methyl 4-hydroxy-3-methoxy-5-nitrobenzoate is oxidized with an oxidation agent (reaction 10.3) such as but not limited to sodium hypochlorite in alkaline solution at 0-100° C. preferably at 10-60° C. or with PhI(OAc)$_2$ at 20-80° C. to give methyl 7-methoxy-3-oxo-2,1,3$\lambda^5$-benzoxadiazole-5-carboxylate. 7-methoxy-3-oxo-2,1,3$\lambda^5$-benzoxadiazole-5-carboxylate is reacted with 2-methoxyhydroquinone (reaction 10.4) was reacted with 2-methoxyhydroquinone (reaction 10.4) in the presence of a base such as but not limited to, sodium hydroxide, potassium hydroxide, sodium carbonate, potassium carbonate, triethyl amine or sodium methylate at 0-120° C., preferably between 20-80° C. to yield methyl 8-hydroxy-4,7-dimethoxy-5,10-dioxo-5$\lambda^5$,10$\lambda^5$-phenazine-2-carboxylate. Methyl 8-hydroxy-4,7-dimethoxy-5,10-dioxo-5$\lambda^5$,10$\lambda^5$-phenazine-2-carboxylate was reduced to methyl 8-hydroxy-4,7-dimethoxyphenazine-2-carboxylate (reaction 10.5) by treatment with reagents such as but not limited to trifluoroacetic anhydride and sodium iodide in acetonitril at rt, or titanium(V)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH. Methyl 8-hydroxy-4,7-dimethoxyphenazine-2-carboxylate was hydrolized to 8-hydroxy-4,7-dimethoxyphenazine-2-carboxylic acid by treatment with alkaline aqueous solution at 20-100° C., preferably 20-70° C.

Example 15

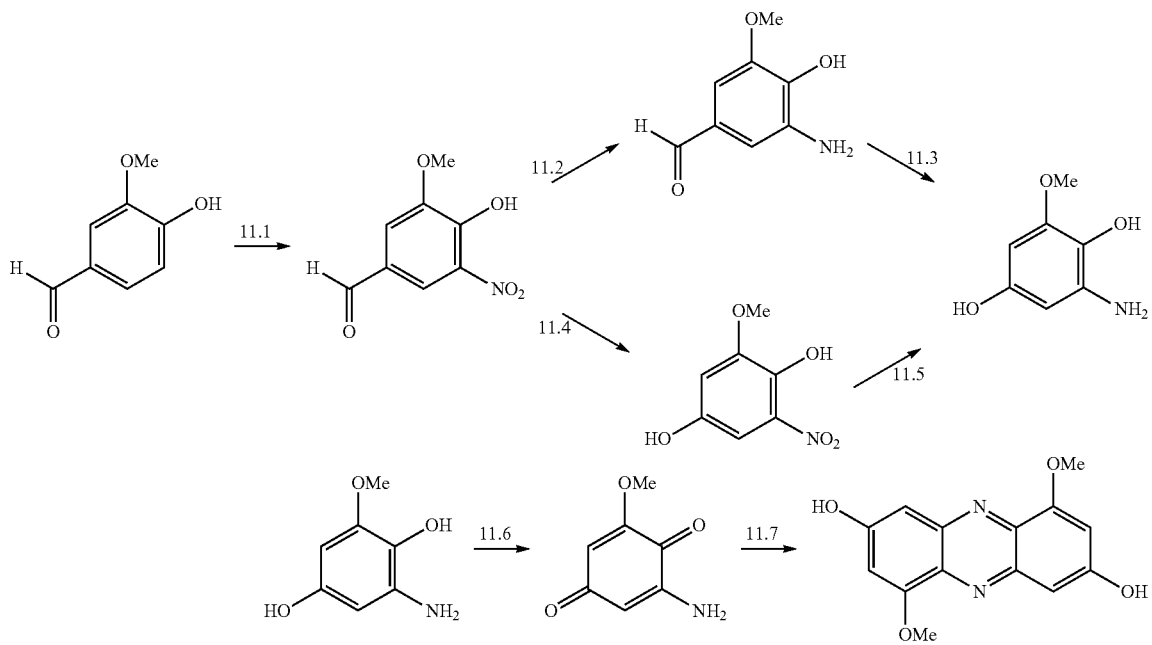

Another method of obtaining phenazines or phenazine derived structures from monomers that originate from lignin, comprising: a dimerization of 2-aminocyclobenzoquinones. In some embodiments, Vanillin is nitrated (reaction 11.1) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. 4-hydroxy-3-methoxy-5-nitrobenzaldehyde was reduced to 3-amino-4-hydroxy-5-methoxybenzaldehyde (reaction 11.2)) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3-amino-4-hydroxy-5-methoxybenzaldehyde is oxidized to 2-amino-6-methoxybenzene-1,4-diol (reaction 11.3) with hydrogen peroxide solution in presence of base such as but not limited to sodium hydroxide or potassium hydroxide or by sodium percarbonate solution. In some embodiments, 4-hydroxy-3-methoxy-5-nitrobenzaldehyde is oxidized to 2-methoxy-6-nitrobenzene-1,4-diol (reaction 11.4) with hydrogen peroxide solution in presence of base such as but not limited to sodium hydroxide or potassium hydroxide or by sodium percarbonate solution. 2-methoxy-6-nitrobenzene-1,4-diol was reduced to 2-amino-6-methoxybenzene-1,4-diol (reaction 11.5) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then 2-amino-6-methoxybenzene-1,4-diol was oxidized to 2-amino-6-methoxycyclohexa-2,5-diene-1,4-dione (reaction 11.6) with an oxidation agent such as but not limited to oxygen, hydrogen peroxide, manganese dioxide, sodium hypochlorite, cerium ammonium nitrate or potassium permanganate optionally in the presence of a catalyst. 2-amino-6-methoxycyclohexa-2,5-diene-1,4-dione was dimerized to 4,9-dimethoxyphenazine-2,7-diol (reaction 11.7) in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C.

Example 16

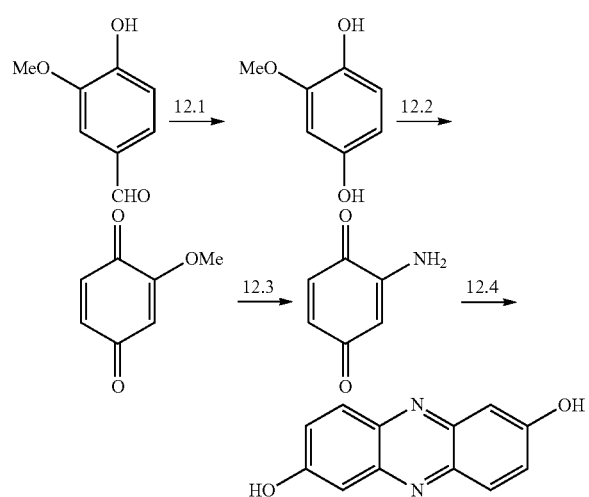

Another method of obtaining phenazines or phenazine derived structures from monomers that originate from lignin, is disclosed comprising: a dimerization of 2-aminocyclobenzoquinones. In some embodiments, vanillin is converted to 2-methoxyhydroquinone (reaction 12.1) by treatment with hydrogen peroxide and base at 0-60° C., preferably between 25-40° C. 2-methoxyhydroquinone is oxidized to 2-methoxy-5-hydroxybenzoquinone (reaction 12.2) with an oxidation agent such as but not limited to oxygen, hydrogen peroxide, manganese dioxide, sodium hypochlorite, cerium ammonium nitrate or potassium permanganate optionally in the presence of a catalyst. 2-Methoxybenzoquinone is reacted with ammonia to give 2-aminobenzoquinone (reaction 12.3) at 20-200° C., preferably 20-100° C. Then 2-aminobenzoquinone was dimerized to phenazine-2,7-diol (reaction 12.4) in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C.

Example 17

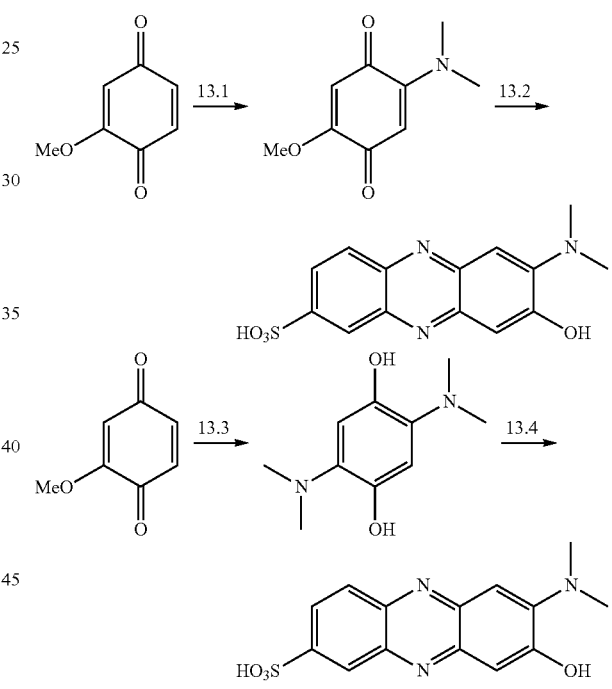

Another method of obtaining phenazines or phenazine derived structures from monomers that originate from lignin, is disclosed comprising: a condensation of 2-aminocyclobenzoquinones with 3,4-diaminobenzene-1-sulfonic acid. In some embodiments, 2-Methoxybenzoquinone is treated with dimethylamine at 20-100° C., preferably 20-50° C. to give 2-(dimethylamino)-5-methoxycyclohexa-2,5-diene-1,4-dione (reaction 13.1). Then 2-(dimethylamino)-5-methoxycyclohexa-2,5-diene-1,4-dione is reacted with 3,4-diaminobenzene-1-sulfonic acid (reaction 13.2) at 20-200° C., preferably between 30-100° C. to give 7-(dimethylamino)-8-hydroxyphenazine-2-sulfonic acid. In some embodiments, 2-Methoxybenzoquinone is reacted with dimethylamine (reaction 13.3) at 20-100° C., preferably 20-60° C. to give 2,5-bis(dimethylamino)benzene-1,4-diol. Then 2,5-bis(dimethylamino)benzene-1,4-diol is converted to 7-(dimethylamino)-8-hydroxyphenazine-2-sulfonic acid (reaction 13.4) by a condensation reaction with 3,4-diamino-benzene-1-sulfonic acid at 20-200° C., preferably between 30-100° C.

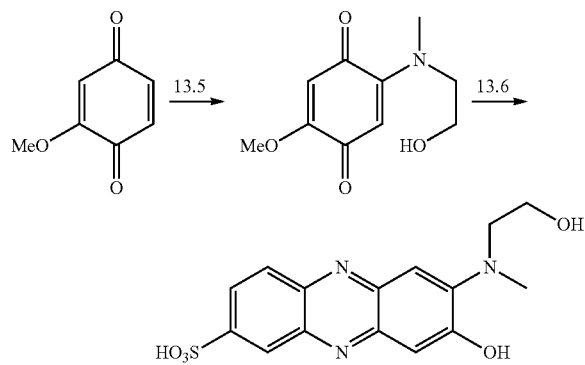

In some embodiments, 2-Methoxybenzoquinone is treated with other amines such as, but not limited to 2-(methylamino)ethan-1-ol, to give 2-amino-5-methoxycyclohexa-2,5-diene-1,4-dione (reaction 13.5) at 20-100° C., preferably 20-50° C. Then these amines are condensed with 3,4-diaminobenzene-1-sulfonic acid (reaction 13.6) at 20-200° C., preferably between 30-100° C. to give the 8-hydroxy-7-aminophenazine-2-sulfonic acid.

Example 18

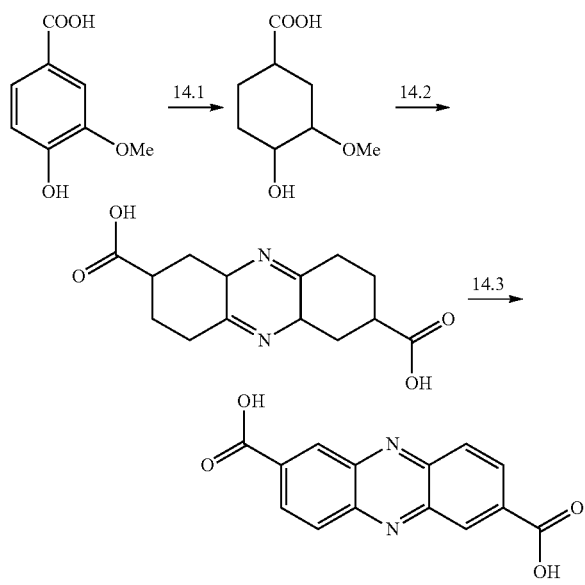

Another method of obtaining phenazines or phenazine derived structures from monomers that originate from lignin, is disclosed comprising: a dimerization of 2-methoxycyclohexanol. In some embodiments, vanillic acid is hydrogenated to 4-hydroxy-3-methoxycyclohexane-1-carboxylic acid (reaction 14.1) using a catalyst such as but not limited to Pd, Pt, Ni, Co, Rh or Ru under 10-200 bar $H_2$, preferably 10-100 bar $H_2$ pressure between 50-250° C., preferably between 80-200° C. Then 4-hydroxy-3-methoxy-cyclohexane-1-carboxylic acid is dimerized to 1,2,3,4,5a,6,7,8,9,10a-decahydrophenazine-2,7-dicarboxylic acid (reaction 14.2) by treatment with ammonia optionally in presence of transition metal catalyst such as but not limited to Iridium and its complexes. 1,2,3,4,5a,6,7,8,9,10a-decahydro-phenazine-2,7-dicarboxylic acid is converted to phenazine-2,7-dicarboxylic acid (reaction 14.3) by treatment with a catalyst such as but not limited to palladium on carbon between 50-300° C., preferably 100-200° C.

Example 19

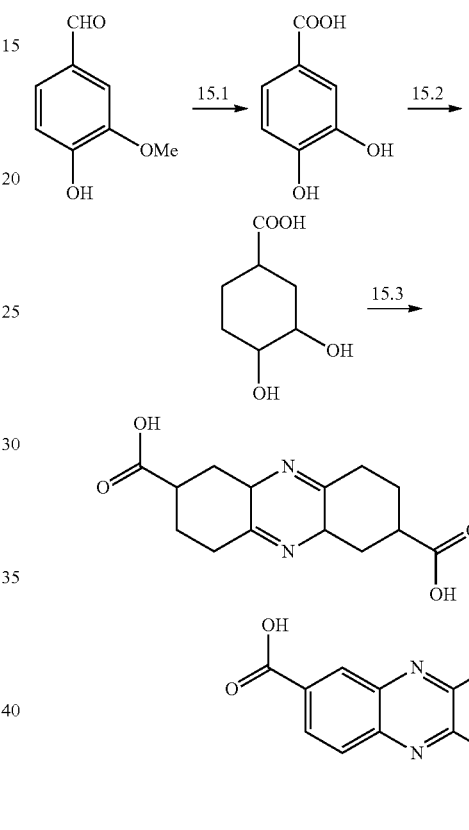

Another method of obtaining phenazines or phenazine derived structures from monomers that originate from lignin, is disclosed comprising: a dimerization starting from the protocatechuic acid. In some embodiments, Vanillin is converted to 3,4-dihydroxybenzoic acid (reaction 15.1) by treatment with KOH/NaOH at 150-300° C., preferably 190-245° C. under air. In the following reaction 3,4-dihydroxybenzoic acid is hydrogenated to give 3,4-dihydroxycyclohexane-1-carboxylic acid (reaction 15.2) using a catalyst such as but not limited to Pd, Pt, Ni, Co, Rh or Ru under 10-200 bar $H_2$, preferably 10-100 bar $H_2$ pressure between 50-250° C., preferably between 80-200° C. 3,4-dihydroxy-cyclohexane-1-carboxylic acid was dimerized to 1,2,3,4,5a,6,7,8,9,10a-decahydrophenazine-2,7-dicarboxylic acid (reaction 15.3) by treatment with ammonia optionally in presence of transition metal catalyst such as but not limited to Iridium and its complexes. 1,2,3,4,5a,6,7,8,9,10a-decahydrophenazine-2,7-dicarboxylic acid is converted to phenazine-2,7-dicarboxylic acid (reaction 15.4) by treatment with a catalyst such as but not limited to palladium on carbon between 50-300° C., preferably 100-200° C.

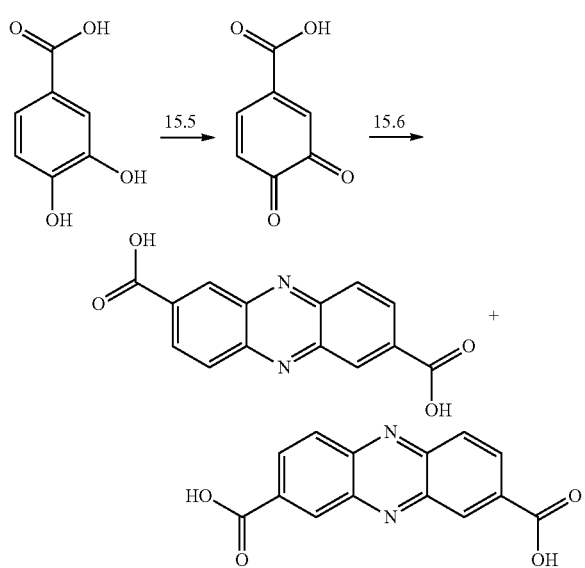

In some embodiments, 3,4-dihydroxybenzoic acid is oxidized to 3,4-dioxocyclohexa-1,5-diene-1-carboxylic acid (reaction 15.5) with an oxidation agent such as but not limited to oxygen, hydrogen peroxide, manganese dioxide, sodium hypochlorite, cerium ammonium nitrate or potassium permanganate optionally in the presence of a catalyst. Then 3,4-dioxocyclohexa-1,5-diene-1-carboxylic acid is reacted with 3,4-diaminobenzoic acid (reaction 15.6) at 20-200° C., preferably 20-140° C. to yield a mixture of phenazine-2,7-dicarboxylic acid and phenazine-2,8-dicarboxylic acid.

Example 20

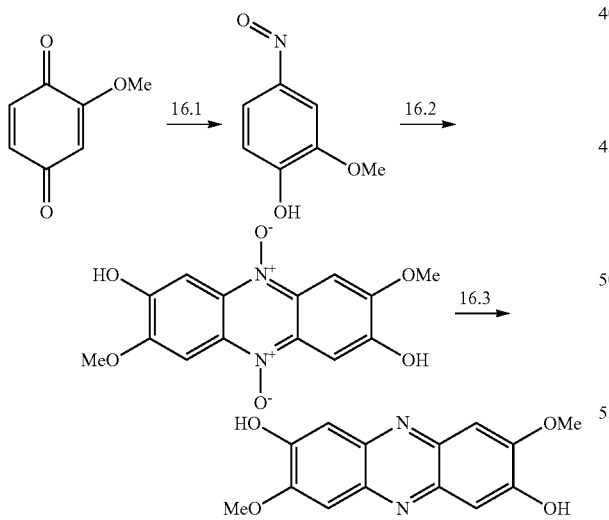

Another method of obtaining phenazines or phenazine derived structures from monomers that originate from lignin, is disclosed comprising: a dimerization of 4-nitrosophenols. In some embodiments, 2-Methoxybenzoquinone is converted to 2-methoxy-4-nitrosophenol (reaction 16.1) by treatment with hydroxylamine or its salt in presence of a base such as but not limited to sodium acetate, sodium carbonate or sodium hydroxide at temperatures from 0° C.-100° C., preferably 0° C.-60° C. Then 2-methoxy-4-nitrosophenol is dimerized to 3,8-dimethoxy-5,10-dioxo-phenazine-2,7-diol (reaction 16.2) optionally in the presence of a catalyst such as but not limited to trifluoroacetic acid, $H_2SO_4$, HCl, $H_3PO_4$, acetic acid, p-toluenesulfonic acid between 0-150° C., preferably 0-100° C. 3,8-dimethoxy-5,10-dioxo-phenazine-2,7-diol is reduced to 3,8-dimethoxy-phenazine-2,7-diol (reaction 16.3) by treatment with reagents such as but not limited to trifluoroacetic anhydride and sodium iodide in acetonitril at rt, or titanium(IV)-chloride and tin(II)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

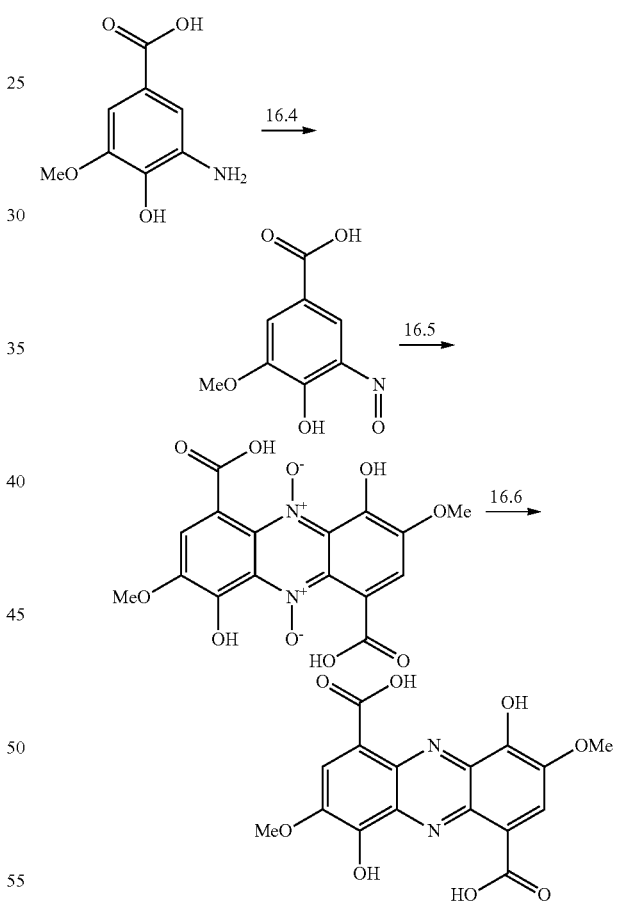

In some embodiments, 5-Aminovanillic acid is oxidized to 4-hydroxy-3-methoxy-5-nitrosobenzoic acid (reaction 16.4) using a oxidation reagent such as but not limited to hydrogen peroxide, oxone, $Ph_2Se_2$, oxygen, perbenzoic acid, 3-chloro-benzenecarboperoxoic acid optionally in the presence of a catalyst such as but not limited to KI, $Na_2WO_4$, $(n-Bu_3Sn)_2WO_4$, phosphotungstic acid, $CpMo(CO)_3$ (CCPh), $MoO_3$, methyltrioxorhenium(VII)) and additive (phosphoric acid, $NBu_4Br$) at 0° C.-150° C., preferably 0° C. to 100° C. Then 4-hydroxy-3-methoxy-5-nitrosobenzoic acid is dimerized to 4,9-dihydroxy-3,8-dimethoxy-5,10-dioxo-phenazine-1,6-dicarboxylic acid (reaction 16.5) by treatment optionally in the presence of a catalyst such as but not limited to trifluoroacetic acid, $H_2SO_4$, HCl, $H_3PO_4$, acetic acid, p-toluenesulfonic acid between 0-150° C., preferably 0-100° C. 4,9-dihydroxy-3,8-dimethoxy-5,10-dioxo-phenazine-1,6-dicarboxylic acid was reduced to 4,9-dihydroxy-3,8-dimethoxyphenazine-1,6-dicarboxylic acid (reaction 16.6) by treatment with reagents such as but not limited to trifluoroacetic anhydride and sodium iodide in acetonitril at rt, or titanium(IV)-chloride and tin(I)-chloride in acetonitrile at rt, or titanium(IV)-chloride and sodium iodide in acetonitrile at 30° C., or aqueous sodium hydrosulfite and sodium hydroxide at rt, or zinc in aqueous sodium hydroxide solution, or tin(II)-chloride in hydrochloric acid, or by catalytic reduction with sodium hydrophosphite over palladium on carbon (5%) in THF/water at rt, or by hydrogenation with catalytic palladium on charcoal (10% Pd) or Raney nickel (2-10%) under hydrogen (1-5 bar) in EtOH or MeOH.

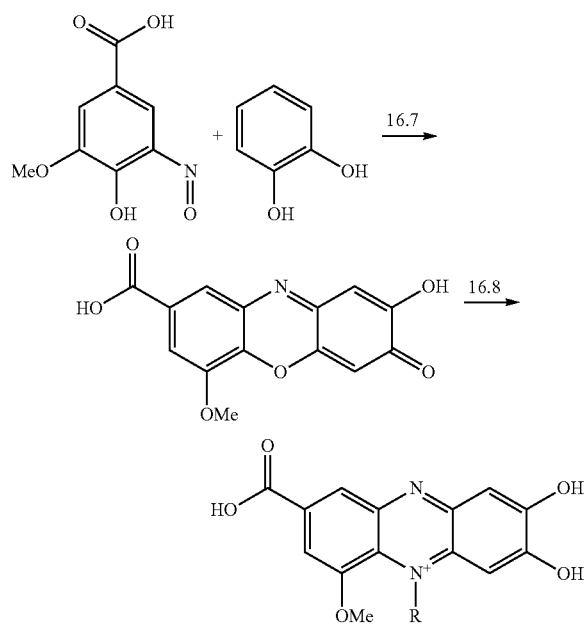

In some embodiments, 4-hydroxy-3-methoxy-5-nitrosobenzoic is reacted with catechol (reaction 16.7) by treatment optionally in the presence of a catalyst such as but not limited to trifluoroacetic acid, $H_2SO_4$, HCl, $H_3PO_4$, acetic acid, p-toluenesulfonic acid between 0-150° C., preferably 0-100° C. to yield 2-hydroxy-6-methoxy-3-oxo-3H-phenoxazine-8-carboxylic acid. Then 2-hydroxy-6-methoxy-3-oxo-3H-phenoxazine-8-carboxylic acid is reacted with ammonia (R=H) or primary amine (reaction 16.8) between 20-250° C., preferably between 50-200° C. and at 0-150 bar preferably 0-100 bar to yield the corresponding phenazine.

Example 21

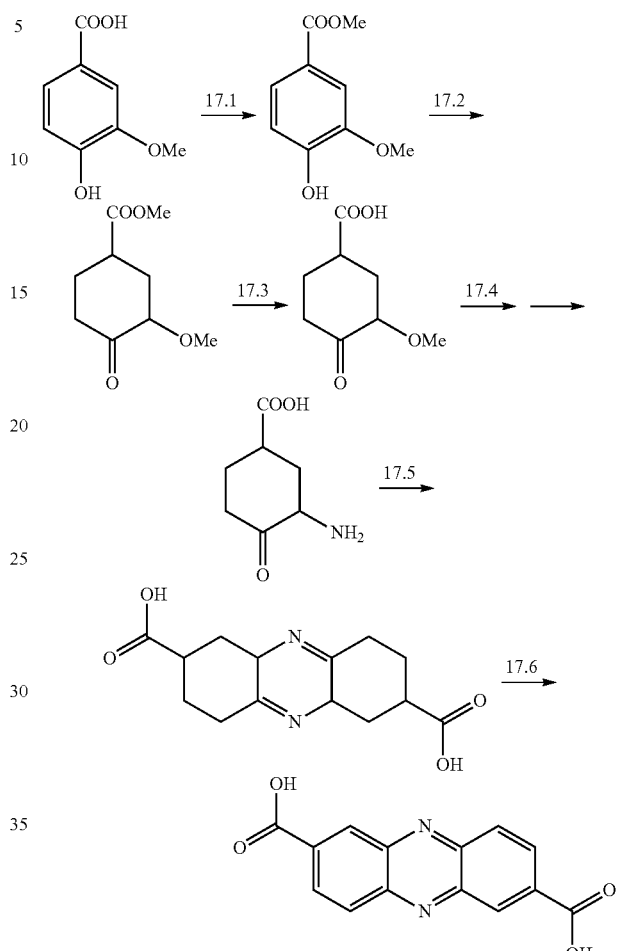

Another method of obtaining phenazines or phenazine derived structures from monomers that originate from lignin, comprising: a dimerization of 2-aminocyclohexanones. In some embodiments, vanillic acid is reacted with an alcohol such as but not limited to methanol (reaction 17.1) in some embodiments, in the presence of a catalyst, such as but not limited to $H_2SO_4$, HCl, $H_3PO_4$, $CH_3COOH$ between 20-150° C., preferably between 20-100° C. most preferably between 30-70° C. to give methyl 4-hydroxy-3-methoxybenzoate. Then methyl 4-hydroxy-3-methoxybenzoate is hydrogenated to methyl 3-methoxy-4-oxocyclohexane-1-carboxylate (reaction 17.2) using a doped metal catalyst such as but not limited to Pd, Pt, Ni, Co, Rh or Ru under 10-200 bar $H_2$, preferably 10-100 bar $H_2$ pressure between 50-250° C., preferably between 80-200° C. Methyl 3-methoxy-4-oxocyclohexane-1-carboxylate is hydrolyzed to 3-methoxy-4-oxocyclohexane-1-carboxylic acid (reaction 17.3) by treatment with aqueous alkaline solution at 20-120° C., preferably 20-90° C. In the following step 3-methoxy-4-oxocyclohexane-1-carboxylic acid is converted to 3-amino-4-oxocyclohexane-1-carboxylic acid by treatment with ammonia (reaction 17.4) at 20-200° C., preferably 20-100° C. 3-amino-4-oxocyclohexane-1-carboxylic acid is dimerized to 1,2,3,4,5a,6,7,8,9,10a-decahydrophenazine-2,7-dicarboxylic acid (reaction 17.5) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 1,2,3,4,5a,6,7,8,9,10a-decahydrophenazine-2,7-dicarboxylic acid is converted to phenazine-2,7-dicarboxylic acid (reaction 17.6) by treatment with a catalyst such as but not limited to palladium on carbon between 50-300° C., preferably 100-200° C.

Example 22

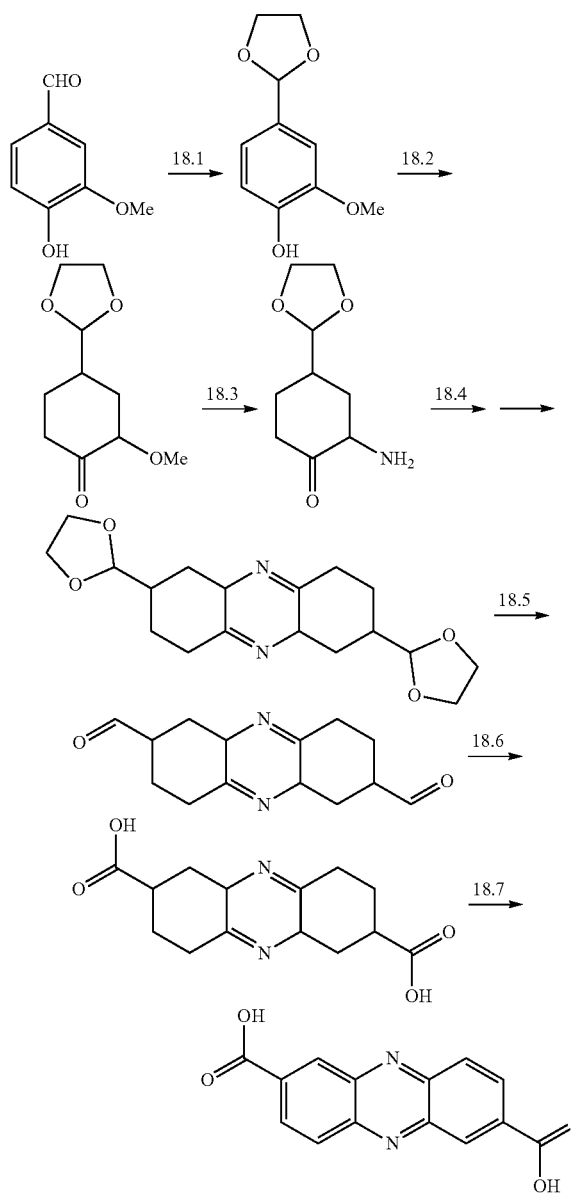

Another method of obtaining phenazines or phenazine derived structures from monomers that originate from lignin, is disclosed comprising: a dimerization of 2-aminocyclohexanones. In some embodiments, Vanillin is reacted with ethylene glycol (reaction 18.1) by treatment optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 4-(1,3-dioxolan-2-yl)-2-methoxyphenol is hydrogenated to 4-(1,3-dioxolan-2-yl)-2-methoxycyclohexan-1-one (reaction 18.2) using doped catalyst such as but not limited to Pd, Pt, Ni, Co, Rh or Ru under 10-200 bar $H_2$, preferably 10-100 bar $H_2$ pressure between 50-250° C., preferably between 80-200° C. In the following step 4-(1,3-dioxolan-2-yl)-2-methoxycyclohexan-1-one is converted to 2-amino-4-(1,3-dioxolan-2-yl)cyclohexan-1-one by treatment with ammonia (reaction 18.3) at 20-200° C., preferably 20-100° C. 2-amino-4-(1,3-dioxolan-2-yl)cyclohexan-1-one is dimerized to 3,8-bis(1,3-dioxolan-2-yl)-1,2,3,4,4a,6,7,8,9,9a-decahydrophenazine (reaction 18.4) optionally in the presence of a catalyst such as but not limited to trifluoroacetic acid, $H_2SO_4$, HC, $H_3PO_4$, acetic acid, p-toluenesulfonic acid between 0-100° C., preferably 0-50° C., most preferably between 10-30° C. 3,8-bis(1,3-dioxolan-2-yl)-1,2,3,4,4a,6,7,8,9,9a-decahydrophenazine is converted to 1,2,3,4,5a,6,7,8,9,10a-decahydrophenazine-2,7-dicarbaldehyde (reaction 18.5) optionally in the presence of a catalyst such as but not limited to trifluoroacetic acid, $H_2SO_4$, HCl, $H_3PO_4$, acetic acid, p-toluenesulfonic acid between 0-100° C., preferably 0-50° C., most preferably between 10-30° C. 1,2,3,4,5a,6,7,8,9,10a-decahydrophenazine-2,7-dicarbaldehyde is oxidized to 1,2,3,4,5a,6,7,8,9,10a-decahydrophenazine-2,7-dicarboxylic acid (reaction 18.6) using an oxidation reagent such as but not limited to hydrogen peroxide, oxone, oxygen, sodium hypochlorite, potassium permanganate or manganese dioxide optionally in the presence of a catalyst at 0° C.-150° C., preferably 0° C. to 100° C. 1,2,3,4,5a,6,7,8,9,10a-decahydrophenazine-2,7-dicarboxylic acid is converted to phenazine-2,7-dicarboxylic acid (reaction 18.7) by treatment with a catalyst such as but not limited to palladium on carbon between 50-300° C., preferably 100-200° C. In some embodiments, reaction 18.6. and reaction 18.7 are done in a single step.

Example 23

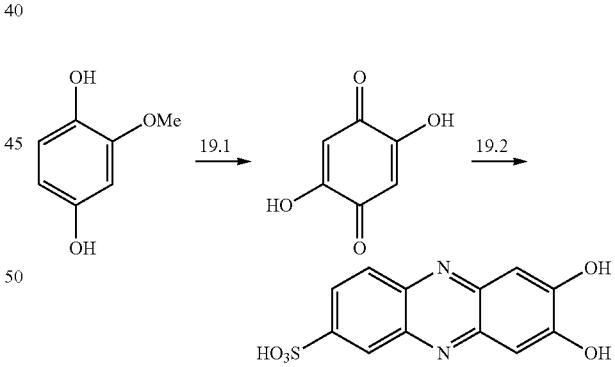

Another method of obtaining phenazines or phenazine derived structures from monomers that originate from lignin, comprising: an electrooxidation of a monomer. In some embodiments, 2-Methoxyhydroquinone is converted to 2,5-dihydroxybenzoquinone by electrochemical oxidation (reaction 19.1) with a suitable electrode, such as but not limited to PbO2/Pb as an anode and an electrolyte such as but not limited to sulfuric acid and acetic acid or a mixture thereof. 2,5-dihydroxybenzoquinone is condensed with 3,4-diaminobenzene-1-sulfonic acid (reaction 19.2) at 20-150° C., preferably 23-100° C., more preferably 40-80° C. to give 7,8-dihydroxyphenazine-2-sulfonic acid.

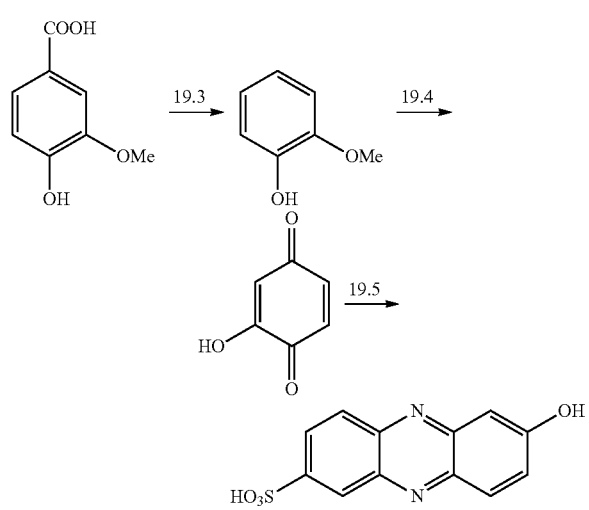

In some embodiments, vanillic acid is decarboxylated to 2-methoxyphenol (reaction 19.3) exemplary but not limited to by treatment with sodium hydroxide in 2-ethoxy-ethanol at 100-150° C., or with enzymes (e.g. decarboxylase) at 20-40° C., or with copper dichloride in water at 150-250° C., or with hydrogen chloride at 150-250° C. Then 2-methoxyphenol is converted to 2-hydroxycyclohexa-2,5-diene-1,4-dione (reaction 19.4) by electrochemical oxidation with a suitable electrode, such as but not limited to PbO2/Pb as an anode and an electrolyte such as but not limited to sulfuric acid and acetic acid or a mixture thereof. 2-hydroxycyclohexa-2,5-diene-1,4-dione is condensed with 3,4-diaminobenzene-1-sulfonic acid (reaction 19.5) at 20-150° C., preferably 23-100° C., more preferably 40-80° C. to give 7,8-dihydroxyphenazine-2-sulfonic acid.

Example 24

Another method of obtaining phenazines or phenazine derived structures from monomers that originate from lignin, is disclosed comprising: a condensation of a 2-nitrophenol and a 2-aminophenol, known as the Wohl-Aue-reaction. In some embodiments, methyl 4-hydroxy-3-methoxybenzoate is nitrated (reaction 20.1) with but not limited to nitric acid in combination with or without nitrous acid under cooling at least at 0° C., at least 10° C., at least 20° C. under room temperature, or under heating at least at 30° C., at least 40° C., at least 50° C., at least 60° C., at least 70° C., at least 80° C., at least 90° C., at least 100° C., at least 110° C., at least 120° C., at least 130° C., at least 140° C., at least 150° C. Methyl 4-hydroxy-3-methoxy-5-nitrobenzoate is reduced to methyl 3-amino-4-hydroxy-5-methoxybenzoate (reaction 20.2) by treatment with an reducing agent such as SnCl2 in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then Methyl 4-hydroxy-3-methoxy-5-nitrobenzoate is reacted with methyl 3-amino-4-hydroxy-5-methoxybenzoate at 50-300° C., preferably at 100-250° C., more preferably at 100-200° C. to give dimethyl 4,9-dihydroxy-3,8-dimethoxyphenazine-1,6-dicarboxylate (reaction 20.3). Finally, Dimethyl 4,9-dihydroxy-3,8-dimethoxyphenazine-1,6-dicarboxylate is hydrolyzed to, 9-dihydroxy-3,8-dimethoxyphenazine-1,6-dicarboxylic acid (reaction 20.4) by treatment with aqueous alkaline solution at 20-120° C., preferably 20-90° C.

Example 25

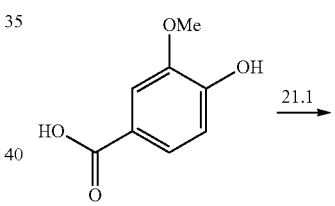

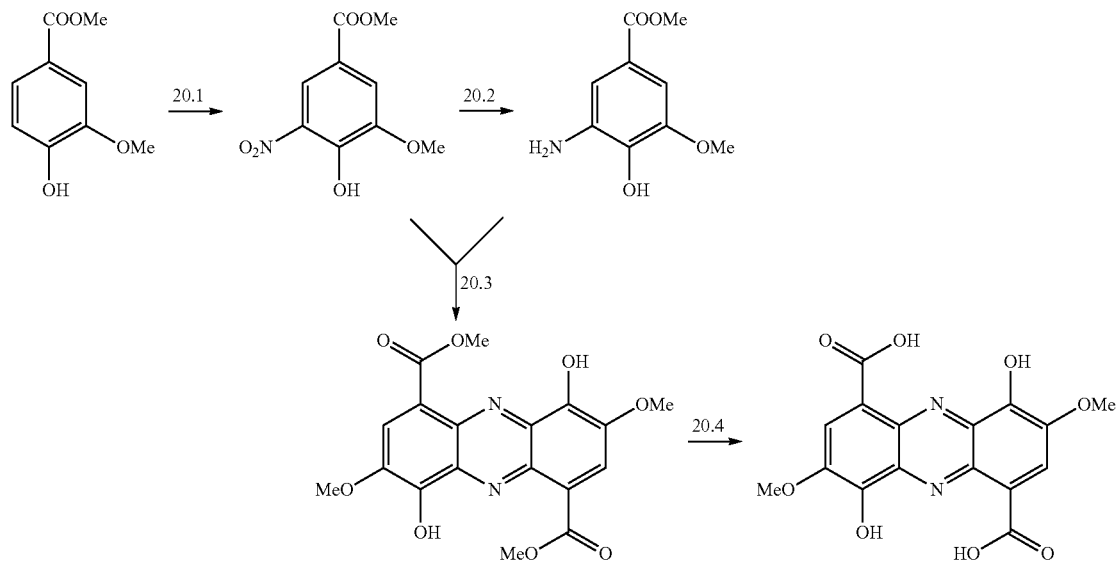

151

-continued

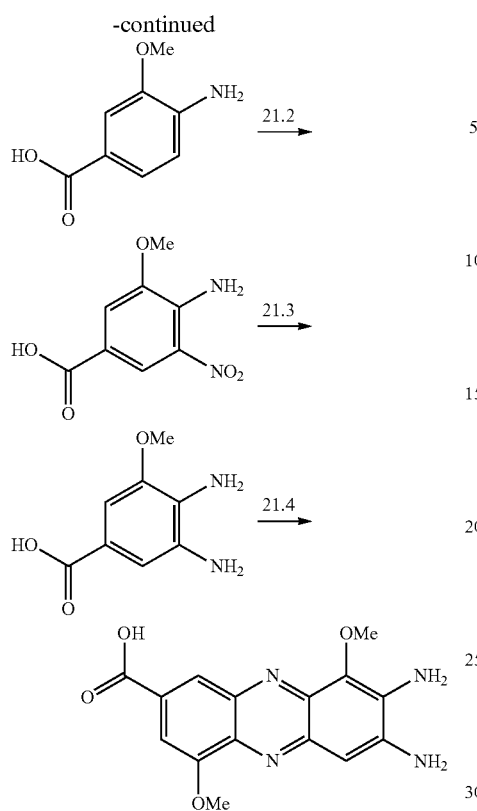

In some embodiments, vanillic acid is treated with ammonia (reaction 21.1) at 10-300 bar, preferably at 10-200 bar, more preferably at 10-50 bar, optionally in the presence of catalyst such as but not limited to Mo, W, Ir, Ru, Pd, Pt, aluminum oxide, H-151 alumina, palladium on carbon, zeolite, copper (1) oxide at 30-400° C., preferably at 40-300° C., most preferably at 50-200° C. to give 3,4-diaminobenzoic acid. Then 4-amino-3-methoxybenzoic acid is nitrated (reaction 21.2) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4-amino-3-methoxy-5-nitrobenzoic acid. 4-amino-3-methoxy-5-nitrobenzoic acid is reduced to 3,4-diamino-5-methoxybenzoic acid (reaction 21.3) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. 3,4-diamino-5-methoxybenzoic acid is dimerized (reaction 21.4) in the presence of an oxidation reagent such as, but not limited to iron(III) chloride, hydrogen peroxide, potassium persulfate, silver(I) oxide, oxygen, optionally with a catalyst at 20-150° C., preferably 20-100° C. to give 7,8-diamino-4,9-dimethoxyphenazine-2-carboxylic acid.

152

Example 26

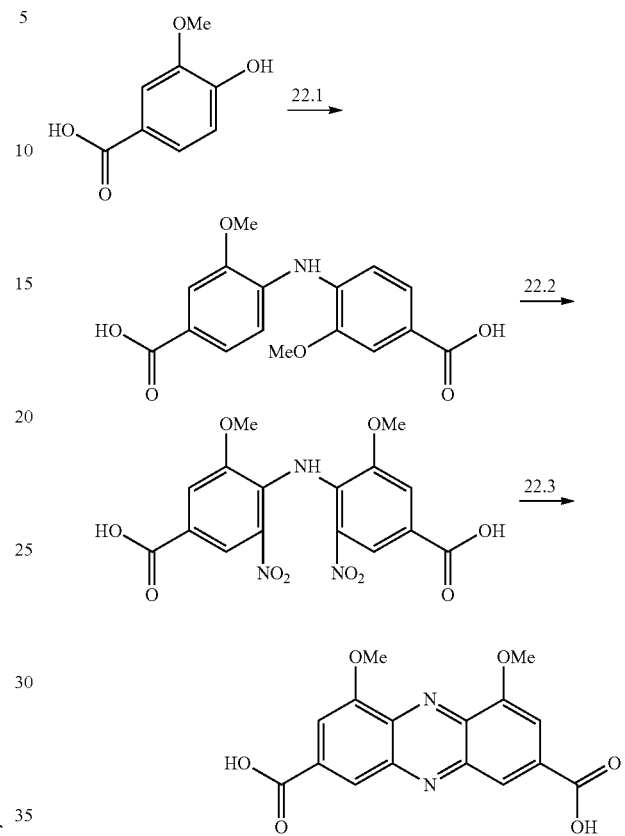

Another method of obtaining phenazines or phenazine derived structures from monomers that originate from lignin, is disclosed comprising: a treatment of monomers with ammonia under pressure. In some embodiments, vanillic acid is treated with ammonia (reaction 22.1) at 10-300 bar, preferably at 10-200 bar, more preferably at 10-100 bar, optionally in the presence of catalyst such as but not limited to Mo, W, Ir, Ru, Pd, Pt, aluminum oxide, H-151 alumina, palladium on carbon, zeolite, copper (1) oxide at 30-400° C., preferably at 50-300° C. to give 4,4'-azanediylbis(3-methoxybenzoic acid). 4,4'-azanediylbis(3-methoxybenzoic acid) is then nitrated (reaction 22.2) with but not limited to nitric acid in combination with or without nitrous acid under cooling at least at 0° C., at least 10° C., at least 20° C. under room temperature, or under heating at least at 30° C., at least 50° C., at least 70° C., at least 100° C., at least 120° C., at least 150° C. to give 4,4'-azanediylbis(3-methoxy-5-nitrobenzoic acid). 4,4'-azanediylbis(3-methoxy-5-nitrobenzoic acid) is cyclized to 4-methoxyphenazine-2,7-dicarboxylic acid (reaction 22.3) by treatment with an reducing agent such as but not limited to hydrazine hydrate, sodium borohydride, hydrogen, and base such as KOH or sodium ethanolate, with a catalyst such as Pd, Pt, Ni or Ru between 20-150° C., preferably between 20-100° C.

Example 27

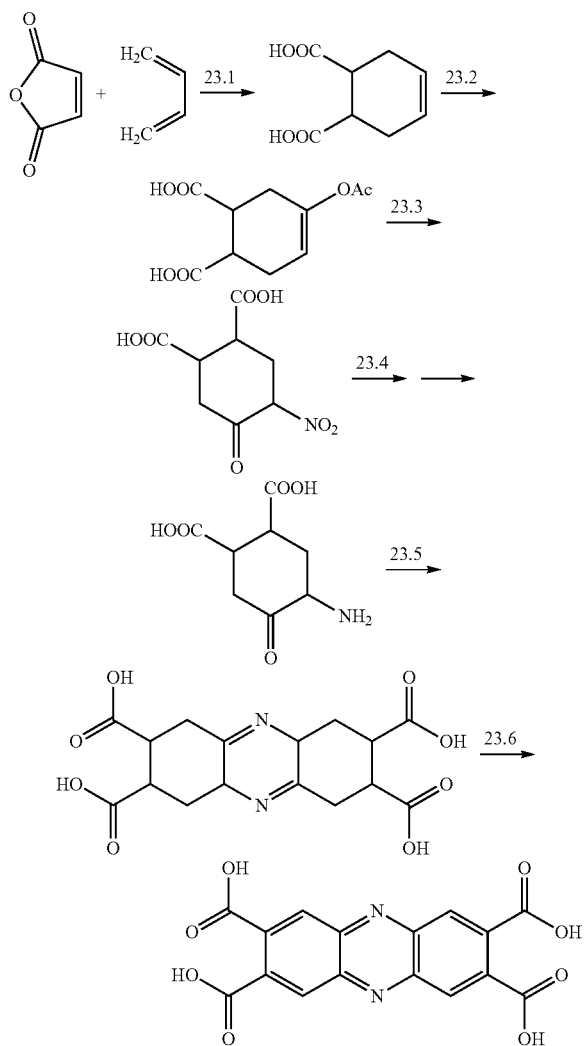

Another method of obtaining phenazines or phenazine derived structures from monomers, is disclosed comprising: a dimerization of 2-aminocyclohexanones. In some embodiments, maleic anhydride is reacted with butadiene (reaction 23.1) in presence of catalyst (Lewis acids, metal complexes) between 20-200° C., preferably 50-120° C. to give cyclohex-4-ene-1,2-dicarboxylic acid. Cyclohex-4-ene-1,2-dicarboxylic acid is converted to 4-(acetyloxy)cyclohex-4-ene-1,2-dicarboxylic acid (reaction 23.2) with acetic acid optionally in presence of catalyst (iron(III) triflate). 4-(acetyloxy)cyclohex-4-ene-1,2-dicarboxylic acid is reacted with nitric acid in acetic anhydride to give 4-nitro-5-oxocyclohexane-1,2-dicarboxylic acid (reaction 23.3) at 20-100° C. 4-nitro-5-oxocyclohexane-1,2-dicarboxylic acid is reduced to 4-amino-5-oxocyclohexane-1,2-dicarboxylic acid (reaction 23.4) by treatment with an reducing agent such as $SnCl_2$ in water/methanol mixture, or with iron in ammonium chloride solution, or with iron in acetic acid/ethanol mixture, or with zinc in ammonium chloride solution, or by hydrogenation with a catalyst such as but not limited to Pd, Pt, Ni, Rh or Ru between 20-150° C., preferably between 20-100° C. Then 4-amino-5-oxocyclohexane-1,2-dicarboxylic acid was dimerized to 1,2,3,4,4a,6,7,8,9,9a-decahydrophenazine-2,3,7,8-tetracarboxylic acid (reaction 23.5) in the presence of a catalyst such as but not limited to trifluoroacetic acid, $H_2SO_4$, HCl, $H_3PO_4$, acetic acid, p-toluenesulfonic acid between 0-100° C., preferably 0-50° C., more preferably between 10-30° C. In some embodiments, the reaction 23.5 is spontaneous. 1,2,3,4,4a,6,7,8,9,9a-decahydrophenazine-2,3,7,8-tetracarboxylic acid is converted to phenazine-2,3,7,8-tetracarboxylic acid (reaction 23.6) by treatment with a catalyst such as but not limited to palladium on carbon between 50-300° C., preferably 100-200° C.

Example 28

For electrochemical characterization, a small laboratory cell is used. A graphite felt (with an area of 6 cm², 6 mm in thickness, supplier: SGL GFA 6EA) is employed as both the positive and negative electrode, and a cation exchange membrane (630K or 620PE, supplier: fumatech) is used to separate the positive and negative electrolytes. The membrane is conditioned in 0.5 M KOH/NaOH (50/50) for at least 150 h prior to each test. Electrolyte volumes range from 12 to 50 mL. The electrolytes are pumped by peristaltic pumps (Drifton BT100-1L, Cole Parmer Ismatec MCP and BVP Process IP 65) at a rate of 24 mL/min to the corresponding electrodes, respectively. Electrochemical testing is performed on a BaSyTec (BaSyTec GmbH, 89176 Asselfingen, Germany) or a Bio-Logic (Bio-Logic Science Instruments, Seyssinet-Pariset 38170, France) battery test system by polarization curves, which are recorded in the charged state by galvanostatic holds and constant-current charge-discharge cycles. For cycling, the cell is charged at a current density of 25 mA/cm² up to 1.7 V and discharged at the same current density down to 0.8 V cut-off.

Figure 3:
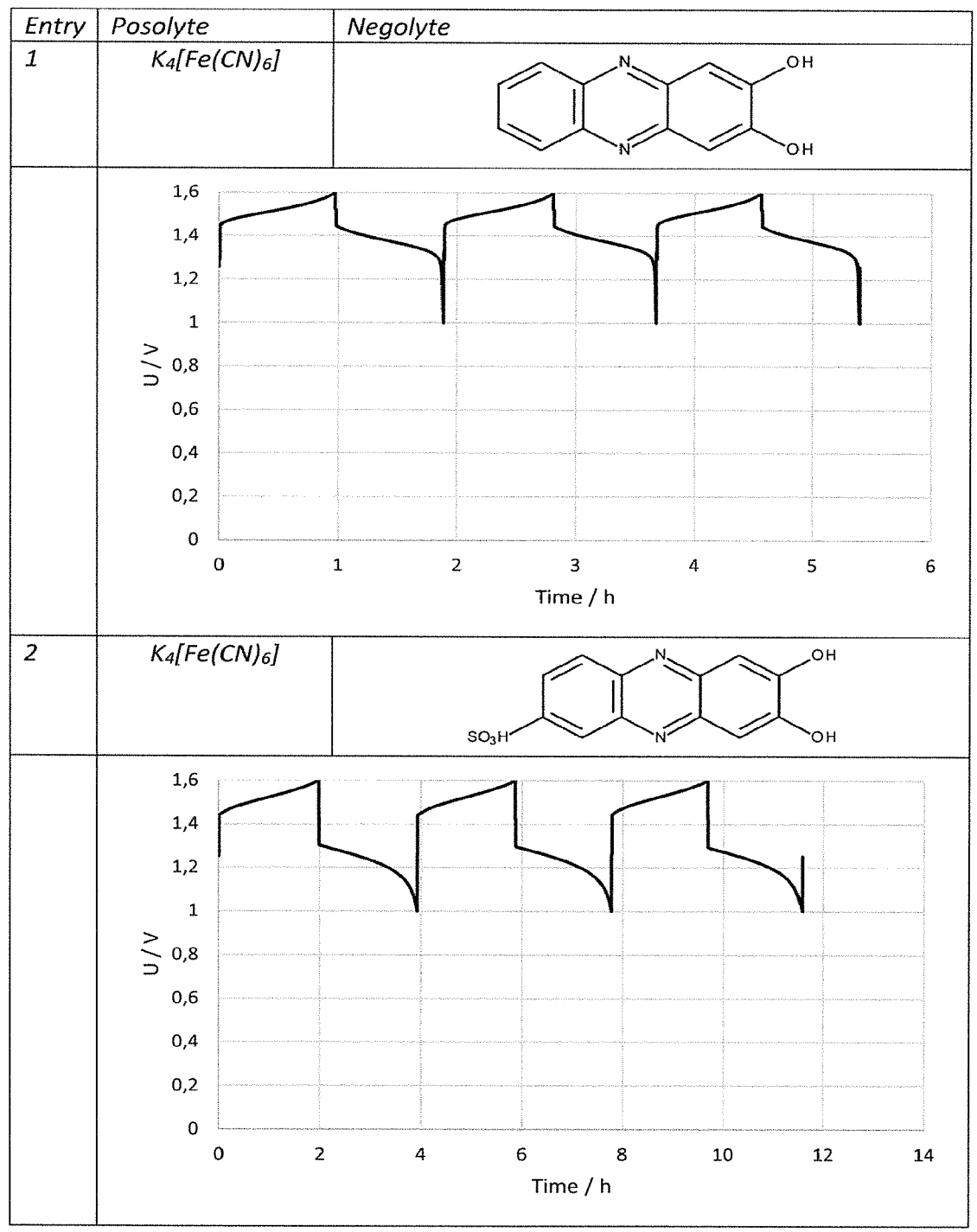
Figure 3:
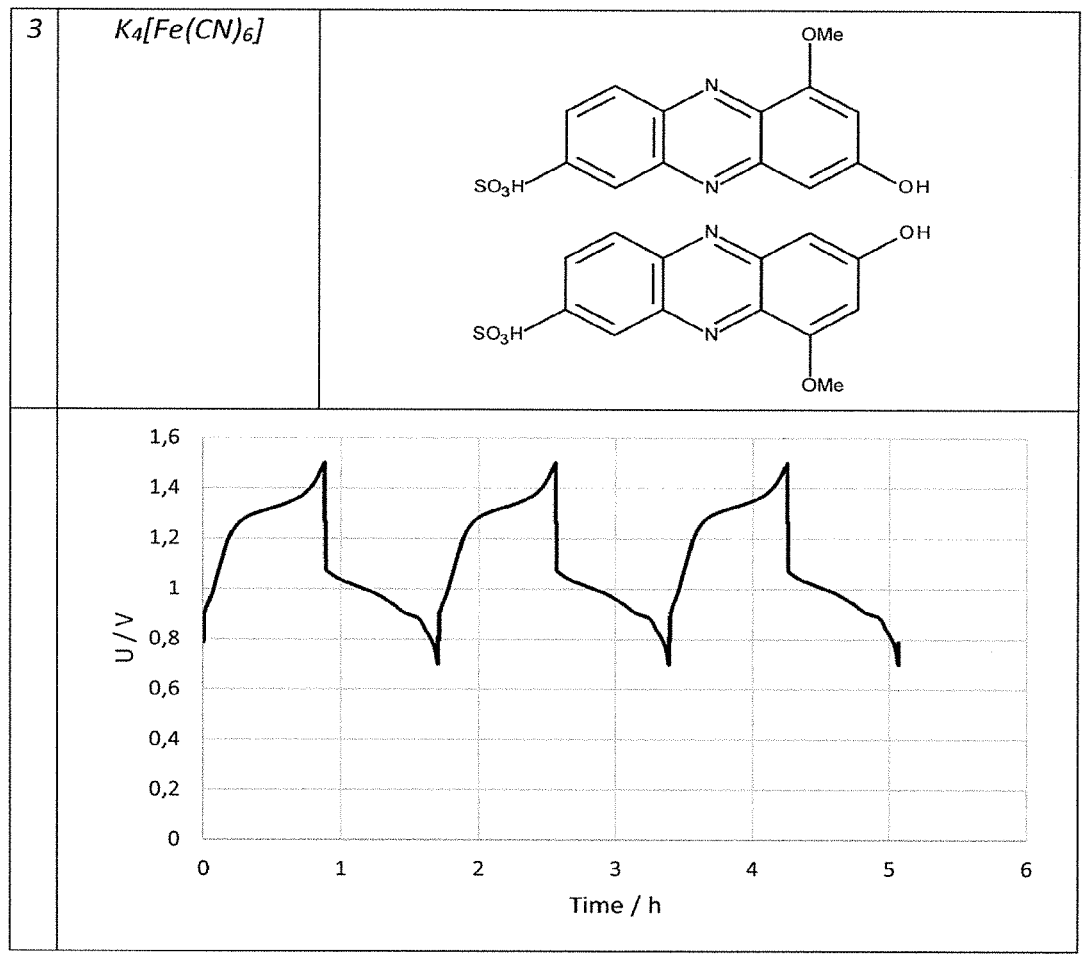
Figure 3:
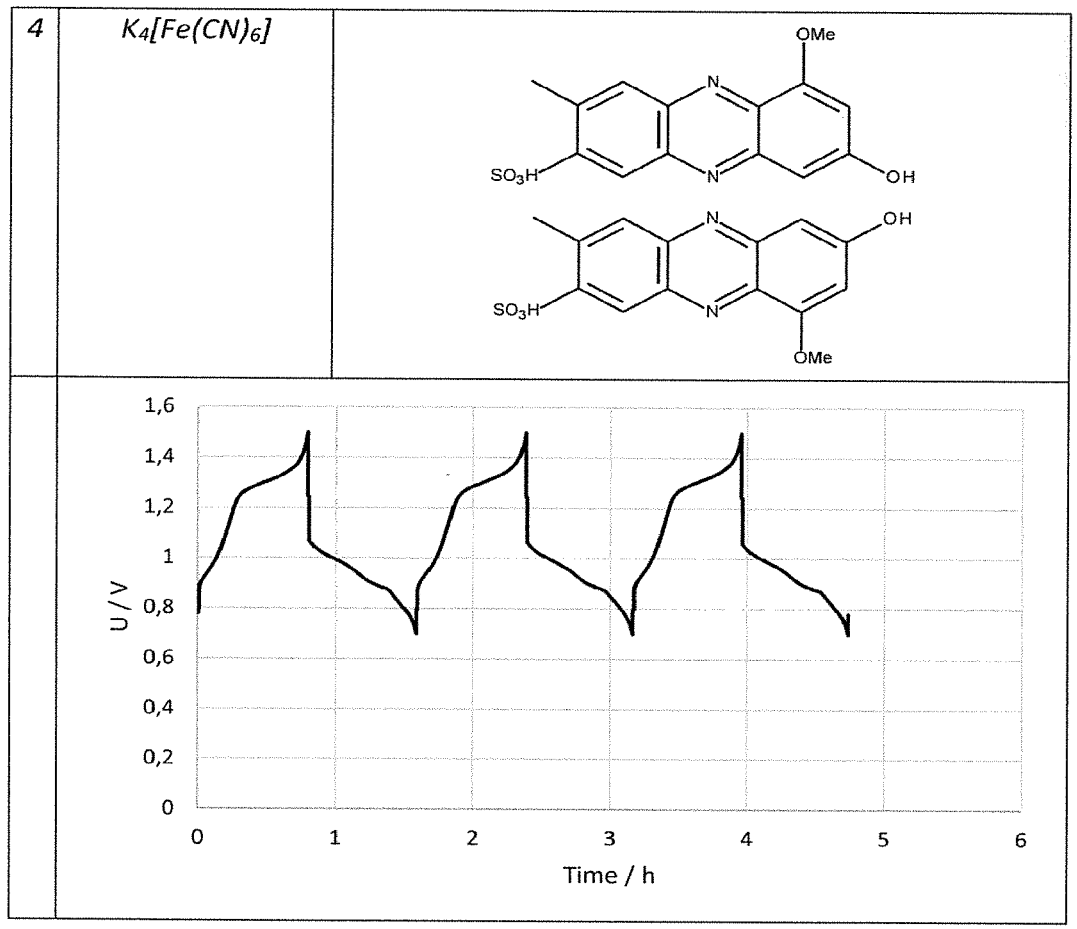

The results of the electrochemical experiments using [$K_4Fe(CN)_6$] as a posolyte and a phenazine derivative (phenazine derivatives substituted by hydroxyl, methoxysulfonic acid and/or sulfonated alkoxy groups) are shown by FIG. 3. The voltage is shown as a function of time (over various charge/discharge cycles). Peak voltage values of up to 1.6 V are observed.

The invention claimed is:

1. A redox flow battery, comprising a substituted low molecular weight aromatic compound or a composition comprising the compound, wherein the compound is characterized by any one of General Formulas (3)-(6);

General Formula (3)

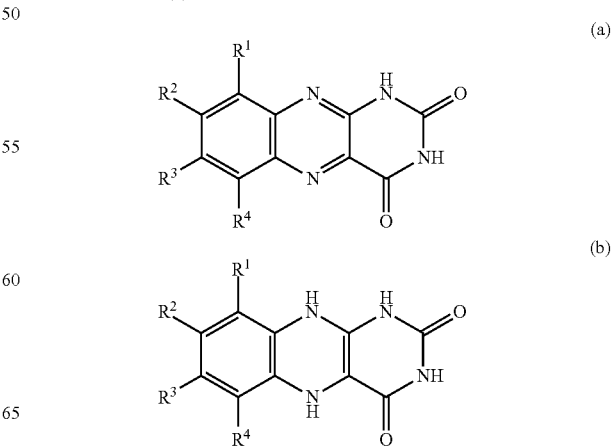

-continued

General Formula (4)

(a)
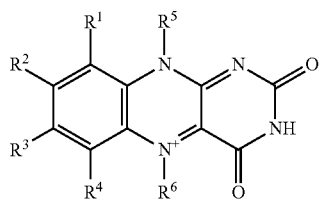

(b)
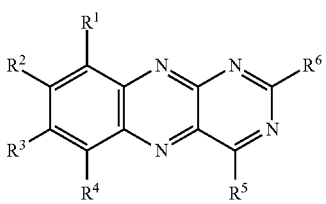

General Formula (5)

(a)
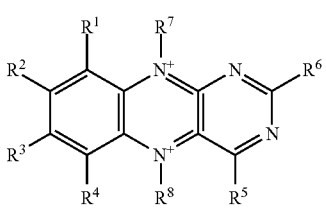

(b)
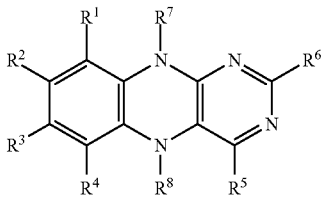

General Formula (6)

(a)
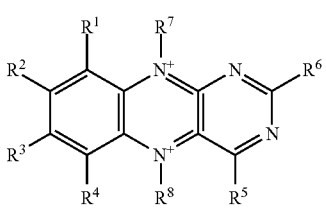

(b)
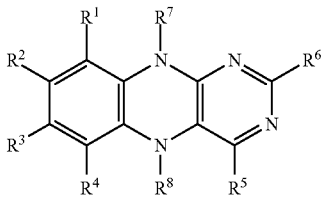

wherein,
each $R^1$-$R^4$ in General Formula (3),
each $R^1$-$R^6$ in General Formula (4),
each $R^1$-$R^6$ in General Formula (5), and
each $R^1$-$R^8$ in General Formula (6)
is independently selected from
—H, -Alkyl, -AlkylG$^a$, -Aryl, —SO$_3$H, —SO$_3^-$, —SO$_3$H/—SO$_3^-$, —PO$_3$H$_2$, —OH, —OG$^a$, —SH, -Amine, —NH$_2$, —CHO, —COOH, —COOG$^a$, —CN, —CONH$_2$, —CONHG$^a$, —CONG$^a{}_2$, -Heteroaryl, -Heterocycyl, NOG$^a$, —N$^+$OG$^a$, —F, —Cl, and —Br, or are joined together to form a saturated or an unsaturated carbocycle;

wherein each G$^a$ is independently selected from
—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b{}_2$, —NG$^b{}_3^+$, —CHO, —COOH, —COOAlkyl, —CN, —CONH$_2$, —CONHAlkyl, —CONAlkyl$_2$, -Heteroaryl, -Heterocycyl, —NOG$^b$, —N$^+$OAlkyl, —F, —Cl, and —Br;

wherein each G$^b$ is independently selected from
—H, -Alkyl, -Aryl, —SO$_3$H, —SO$_3^{-1}$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br;

wherein the compound comprises a —SO$_3$H/—SO$_3^-$ group and at least one other substituent selected from the group consisting of an alkoxy group, a hydroxyl group, an amino group, and a carboxyl group.

2. The redox flow battery of claim 1, wherein the redox flow battery further comprises:
(a) a first electrolyte solution, comprising a first redox active electrolyte;
(b) a first electrode in contact with the first electrolyte solution;
(c) a second electrolyte solution, comprising a second redox active electrolyte;
and
(d) a second electrode in contact with the second electrolyte solution;
wherein one or both of the first and the second redox active electrolytes comprise at least one substituted low molecular weight aromatic compound or the composition comprising the at least one compound.

3. The redox flow battery of claim 1, wherein 1-5; 2-5; 1, 3, or 4; or 3-4 substituents of:
$R^1$-$R^4$ in General Formula (3),
$R^1$-$R^6$ in General Formula (4),
$R^1$-$R^6$ in General Formula (5), and
$R^1$-$R^8$ in General Formula (6)
are independently selected from
Alkyl, -AlkylG$^a$, -Aryl, —SO$_3$H, —SO$_3^-$, —SO$_3$H/—SO$_3^-$, —PO$_3$H$_2$, —OH, —OG$^a$, —SH, -Amine, —NH$_2$, —CHO, —COOH, —COOG$^a$, —CN, —CONH$_2$, —CONHG$^a$, —CONG$^a{}_2$, -Heteroaryl, -Heterocycyl, NOG$^a$, —N$^+$OG$^a$, —F, —Cl, and —Br, or are joined together to form a saturated or an unsaturated carbocycle;

wherein each G$^a$ is independently selected from
—H, -Alkyl, -AlkylG$^b$, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —NHG$^b$, —NG$^b{}_2$, —NG$^b{}_3^+$, —CHO, —COOH, —COOAlkyl, —CN, —CONH$_2$, —CONHAlkyl, —CONAlkyl$_2$, -Heteroaryl, Heterocycyl, —NOG$^b$, —N$^+$OAlkyl, —F, —Cl, and —Br;

wherein each G$^b$ is independently selected from
—H, -Alkyl, -Aryl, —SO$_3$H, —SO$_3^-$, —PO$_3$H$_2$, —OH, —OAlkyl, —OOH, —OOAlkyl, —SH, —SAlkyl, —NH$_2$, —NHAlkyl, —NAlkyl$_2$, —NAlkyl$_3^+$, —CHO, —COOH, —COOAlkyl, —CN, —CONH$_2$, —CONHAlkyl, —CONAlkyl$_2$, -Heteroaryl, -Heterocycyl, —N$^+$OAlkyl, —F, —Cl, and —Br.

4. The redox flow battery of claim 1, wherein the composition comprises at least one or at least two compounds.

5. The redox flow battery of claim 1, wherein the composition is an aqueous composition.

6. The redox flow battery of claim 4, wherein the composition comprises:
   (a) at least one compound according to Formula (3);
   (b) at least one compound according to Formula (4);
   (c) at least one compound according to Formula (5); and/or
   (d) at least one compound according to Formula (6).

7. The redox flow battery of claim 6, wherein the composition comprises:
   (a) at least one compound of Formula (3)(b) (reduced state) and at least one corresponding compound of Formula (3) (a) (oxidized state);
   (b) at least one compound of Formula (4) (b) (reduced state) and at least one corresponding compound of Formula (4) (a) (oxidized state);
   (c) at least one compound of Formula (5) (b) (reduced state) and at least one corresponding compound of Formula (5) (a) (oxidized state); and/or
   (d) at least one compound of Formula (6) (b) (reduced state) and at least one corresponding compound of Formula (6) (a) (oxidized state).

8. The redox flow battery of claim 1, wherein the compound comprises at least one $—SO_3H/—SO_3^-$ group.

9. The redox flow battery of claim 1, wherein the compound comprises at least one hydroxyl group.

10. The redox flow battery of claim 1, wherein the compound comprises at least one alkyl group.

11. The redox flow battery of claim 1, wherein the compound comprises at least one alkoxy group.

12. The redox flow battery of claim 1, wherein the compound comprises at least one carboxyl group.

13. The redox flow battery of claim 1, wherein the compound comprises at least one amine group.

14. The redox flow battery of claim 1, wherein the compound by their substitution pattern comprises at least one hydroxyl group and at least one substituent selected from the group consisting of an carboxyl group, a $—SO_3H/—SO_3^-$ group, and an alkoxy group.

15. The redox flow battery of claim 1, wherein the compound comprises as substituents at least one alkoxy group and at least one hydroxyl group.

16. The redox flow battery of claim 1, wherein the compound comprises as substituents at least one carboxyl group and at least one $—SO_3H/—SO_3^-$ group.

17. The redox flow battery of claim 1, wherein the compound comprises as substituents at least one $—SO_3H/—SO_3^-$ group and at least one hydroxyl group.

18. The redox flow battery of claim 1, wherein the compound comprises as substituents at least one $—SO_3H/—SO_3^-$ group and at least one alkoxy group.

19. The redox flow battery of claim 1, wherein the compound comprises as substituents at least one carboxyl and at least one hydroxyl group.

20. The redox flow battery of claim 1, wherein the compound comprises as substituents at least one $—SO_3H/—SO_3^-$ group, at least one hydroxyl and at least one methoxy group.

21. The redox flow battery of claim 1, wherein the compound comprises as substituents at least one $—SO_3H/—SO_3^-$ group, at least one hydroxyl, and at least one carboxyl group.

22. The redox flow battery of claim 1, wherein the compound comprises as substituents at least one alkoxy group, at least one hydroxyl, and at least one carboxyl group.

23. The redox flow battery of claim 1, wherein the compound comprises a methoxy, a hydroxyl, and a $—SO_3H/—SO_3^-$ group.

24. The redox flow battery of claim 1, wherein the compound comprises as substituents at least one alkoxy group, wherein the alkoxy group is a methoxy group.

* * * * *